United States Patent
Smith et al.

(10) Patent No.: US 12,427,023 B1
(45) Date of Patent: Sep. 30, 2025

(54) JOINT IMPLANTS WITH INTERFACE SURFACES HAVING REGISTRATION FEATURES

(71) Applicant: Djit Medtech, Inc., Baltimore, MD (US)

(72) Inventors: Fraser M. Smith, Baltimore, MD (US); Marcia Andrews Hart, Baltimore, MD (US); Ryan David Katz, Baltimore, MD (US); Allan C. Doyle, Baltimore, MD (US)

(73) Assignee: Djit Medtech, Inc., Baltimore, MD (US)

( * ) Notice: Subject to any disclaimer, the term of this patent is extended or adjusted under 35 U.S.C. 154(b) by 0 days.

(21) Appl. No.: 18/826,096

(22) Filed: Sep. 5, 2024

(51) Int. Cl.
*A61F 2/30* (2006.01)
*A61F 2/42* (2006.01)

(52) U.S. Cl.
CPC ...... *A61F 2/30771* (2013.01); *A61F 2002/30433* (2013.01); *A61F 2002/30462* (2013.01); *A61F 2002/30523* (2013.01); *A61F 2002/3085* (2013.01); *A61F 2002/3093* (2013.01);
(Continued)

(58) Field of Classification Search
CPC ...... A61F 2002/4243; A61F 2002/4251; A61F 2002/4228; A61F 2002/4233; A61F 2002/4238
See application file for complete search history.

(56) References Cited

U.S. PATENT DOCUMENTS

| | | | |
|---|---|---|---|
| 3,932,045 | A | 1/1976 | Hillberry et al. |
| 3,945,053 | A | 3/1976 | Hillberry et al. |
| 3,969,773 | A | 7/1976 | Menschik |

(Continued)

FOREIGN PATENT DOCUMENTS

| | | |
|---|---|---|
| EP | 2117471 B1 | 4/2017 |
| FR | 2927529 A1 | 8/2009 |

(Continued)

OTHER PUBLICATIONS

Hong et al., Novel implant design of the proximal interphalangeal joint using an optimized rolling contact joint mechanism, Journal of Orthopaedic Surgery and Research, Jul. 12, 2019, 13 pages, Springer Nature, Germany.

(Continued)

*Primary Examiner* — Javier G Blanco
(74) *Attorney, Agent, or Firm* — Christopher L. Johnson

(57) ABSTRACT

A joint implant can include a proximal joint implant element having a proximal curved interface surface with a plurality of proximal registration features. A distal joint implant element can be rotatably coupled to the proximal joint implant element, and can have a distal curved interface with a plurality of distal registration features that are complementary to the proximal registration features such that the registration features interface together to maintain registration between the proximal and distal joint implant elements. A joint implant element connector can include a proximal pin supporting the proximal joint implant element and a distal pin supporting the distal joint implant element. At least one of the curved interface surfaces can include a protrusion that prevents rotation of the joint implant elements when the protrusion contacts the opposite curved interface surface.

29 Claims, 76 Drawing Sheets

(52) U.S. Cl.
CPC ............... *A61F 2002/4228* (2013.01); *A61F 2002/4243* (2013.01)

(56) References Cited

U.S. PATENT DOCUMENTS

| | | | |
|---|---|---|---|
| 4,267,608 A | 5/1981 | Bora, Jr. | |
| 4,438,983 A | 3/1984 | Davis | |
| 4,558,911 A | 12/1985 | Ruoff | |
| 4,770,663 A | 9/1988 | Hanslik et al. | |
| 4,790,850 A | 12/1988 | Dunn et al. | |
| 4,815,911 A | 3/1989 | Bengtsson et al. | |
| 5,108,433 A | 4/1992 | May et al. | |
| 5,171,284 A | 12/1992 | Branemark | |
| 5,526,760 A | 6/1996 | Ok | |
| 5,674,297 A | 10/1997 | Lane et al. | |
| 5,702,397 A | 12/1997 | Goble et al. | |
| 5,749,916 A | 5/1998 | Richelsoph | |
| 5,769,852 A | 6/1998 | Branemark | |
| 6,183,255 B1 | 2/2001 | Oshida | |
| 6,187,009 B1 | 2/2001 | Herzog et al. | |
| 6,447,532 B1 | 9/2002 | Herder et al. | |
| 8,308,801 B2 | 11/2012 | Halverson et al. | |
| 8,376,974 B2 * | 2/2013 | Nace ................ | A61F 5/0123 601/35 |
| 8,951,254 B2 | 2/2015 | Mayer et al. | |
| 10,368,914 B2 | 8/2019 | Serbousek et al. | |
| 10,376,367 B2 | 8/2019 | Fallin et al. | |
| 10,683,085 B2 | 6/2020 | Foster et al. | |
| 10,925,658 B2 | 2/2021 | Hopkins | |
| 2001/0011191 A1 | 8/2001 | Kohrs | |
| 2005/0165486 A1 | 7/2005 | Trieu | |
| 2007/0156241 A1 | 7/2007 | Reiley et al. | |
| 2007/0185583 A1 | 8/2007 | Branemark | |
| 2008/0306604 A1 | 12/2008 | Parenti Castelli | |
| 2009/0287314 A1 | 11/2009 | Rifkin | |
| 2010/0241232 A1 | 9/2010 | Halverson et al. | |
| 2011/0015762 A1 | 1/2011 | Rifkin | |
| 2011/0208322 A1 | 8/2011 | Rifkin et al. | |
| 2012/0150309 A1 | 6/2012 | Marissen | |
| 2013/0152724 A1 | 6/2013 | Mozeika et al. | |
| 2013/0197653 A1 | 8/2013 | Hawkins et al. | |
| 2013/0218275 A1 | 8/2013 | Caballes | |
| 2014/0052265 A1 * | 2/2014 | Slocum, Jr. ........... | A61F 5/0123 623/20.24 |
| 2014/0116165 A1 | 5/2014 | Baudasse et al. | |
| 2014/0243910 A1 | 8/2014 | Weiner et al. | |
| 2014/0309691 A1 | 10/2014 | Brown et al. | |
| 2015/0223942 A1 | 8/2015 | Merle et al. | |
| 2016/0177605 A1 | 6/2016 | Howell et al. | |
| 2017/0219007 A1 | 8/2017 | Lang et al. | |
| 2017/0231778 A1 * | 8/2017 | Overes .................. | A61F 2/4425 623/17.16 |
| 2017/0273775 A1 | 9/2017 | Rocco et al. | |
| 2017/0333193 A1 | 11/2017 | Miura et al. | |
| 2017/0354509 A1 | 12/2017 | Finley et al. | |
| 2018/0325681 A1 * | 11/2018 | Lee ......................... | A61F 2/384 |
| 2020/0069434 A1 | 3/2020 | Mimnaugh et al. | |
| 2020/0078185 A1 | 3/2020 | Marks et al. | |
| 2020/0222206 A1 | 7/2020 | Elliot | |
| 2020/0315810 A1 | 10/2020 | Petranto | |
| 2021/0322001 A1 | 10/2021 | Prandi et al. | |
| 2022/0305676 A1 * | 9/2022 | Sun ......................... | B25J 9/1085 |
| 2024/0423677 A1 | 12/2024 | Hart et al. | |

FOREIGN PATENT DOCUMENTS

| | | |
|---|---|---|
| RU | 2115382 C1 | 7/1998 |
| RU | 2636207 C1 | 11/2017 |
| SU | 1335276 A1 | 9/1987 |
| WO | WO 8909579 A | 10/1989 |
| WO | WO 98/11833 A2 | 3/1998 |
| WO | WO 2007/074387 A2 | 7/2007 |
| WO | WO 2017/136612 A1 | 8/2017 |

OTHER PUBLICATIONS

Kim et al., Biomechanical comparative finite element analysis between a conventional proximal interphalangeal joint flexible hinge implant and a novel implant design using a rolling contact joint mechanism, Journal of Orthopaedic Surgery and Research, Dec. 19, 2023, 14 pages, Springer Nature, Germany.

International Search Report for International Application No. PCT/US2023/016369 dated Jun. 15, 2023, 21 pages.

* cited by examiner

A

B

JOINT IMPLANTS WITH INTERFACE SURFACES HAVING REGISTRATION FEATURES

BACKGROUND

Millions of people worldwide over the age of 45 are affected by arthritis of the interphalangeal joints due to osteoarthritis, rheumatoid arthritis, or traumatic injury. In cases of osteoarthritis, the degeneration of the joint can lead to bone-on-bone contact, which can cause severe pain. Bone-on-bone contact can also lead to inefficient joint mechanics, impair digital range of motion, accelerate degenerative processes, and may ultimately lead to an ankylosis or complete loss of motion of the joint. Currently available solutions for arthritis of the interphalangeal joints include arthroplasty, also known as joint replacement surgery, and fusion of the joint. Fusion has been the prevailing treatment for chronic pain in interphalangeal joints due to the lack of durable and reliable interphalangeal joint replacements. However, fusion of the joint results in permanent functional loss of movement of the joint. Hinge joints within the body, in addition to interphalangeal joints, such as knee joints and elbow joints, can have similar or other problems.

SUMMARY

An initial overview of the inventive concepts is provided below and then specific examples are described in further detail later. This initial summary is intended to aid readers in understanding the examples of the present technology more quickly, but is not intended to identify key features or essential features of the examples, nor is it intended to limit the scope of the present technology or the claimed subject matter.

In one example, a joint implant can comprise a proximal joint implant element having a proximal curved interface surface, wherein the proximal curved interface surface comprises a plurality of proximal registration features. A distal joint implant element can be rotatably coupled to the proximal joint implant element, and can have a distal curved interface surface facing the proximal curved interface surface, wherein the distal curved interface surface comprises a plurality of distal registration features that are complementary to the proximal registration features such that the distal registration features and the proximal registration features interface together to maintain registration between the proximal and distal joint implant elements through a range of motion of the proximal and distal joint implant elements relative to one another. A joint implant element connector can comprise a proximal pin supporting the proximal joint implant element and a distal pin supporting the distal joint implant element such that the distal curved interface surface interfaces with the proximal curved interface surface through the range of motion of the proximal and distal joint implant elements relative to one another. At least one of the proximal curved interface surface or the distal curved interface surface can comprise a protrusion that prevents rotation of the proximal joint implant element with respect to the distal joint implant element upon the protrusion contacting the other of the proximal curved interface surface or the distal curved interface surface, such that the protrusion restricts a range of motion of the relative rotation of the proximal joint implant element and the distal joint implant element.

In another example, a joint implant can include a proximal joint implant element having a proximal curved interface surface and a proximal base portion, wherein the proximal curved interface surface comprises a plurality of proximal registration features. A distal joint implant element can be rotatably coupled to the proximal joint implant element, and can have a distal curved interface surface facing the proximal curved interface surface, wherein the distal curved interface surface comprises a plurality of distal registration features that are complementary to the proximal registration features such that the distal registration features and the proximal registration features interface together to maintain registration between the proximal and distal joint implant elements through a range of motion of the proximal and distal joint implant elements relative to one another, wherein the distal joint implant element further comprises a distal base portion. A proximal bone interface connector can be connected to the proximal base portion. A distal bone interface connector can be connected to the distal base portion.

In another example, a joint implant can include a proximal joint implant element having a proximal curved interface surface, wherein the proximal curved interface surface comprises a first area having a plurality of proximal registration features. A distal joint implant element can be rotatably coupled to the proximal joint implant element, and can have a distal curved interface surface facing the proximal curved interface surface, the distal joint implant element being supported such that the distal curved interface surface interfaces with the proximal curved interface surface through a range of motion of the proximal and distal joint implant elements relative to one another, wherein the distal curved interface surface comprises a first area having a plurality of distal registration features that are complementary to the proximal registration features such that the distal registration features and the proximal registration features interface together to maintain registration between the proximal and distal joint implant elements through the range of motion. A first filament segment can extend from an attachment point on the proximal joint implant element, across a second area of the proximal curved interface surface without overlapping the proximal registration features, to an attachment point on the distal joint implant element. A second filament segment can extend from an attachment point on the distal joint implant element, across a second area of the distal curved interface surface without overlapping the distal registration features, to an attachment point on the proximal joint implant element. The second filament segment can cross the first filament segment at a location between the proximal joint implant element and the distal joint implant element.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein.

Figure 1A:
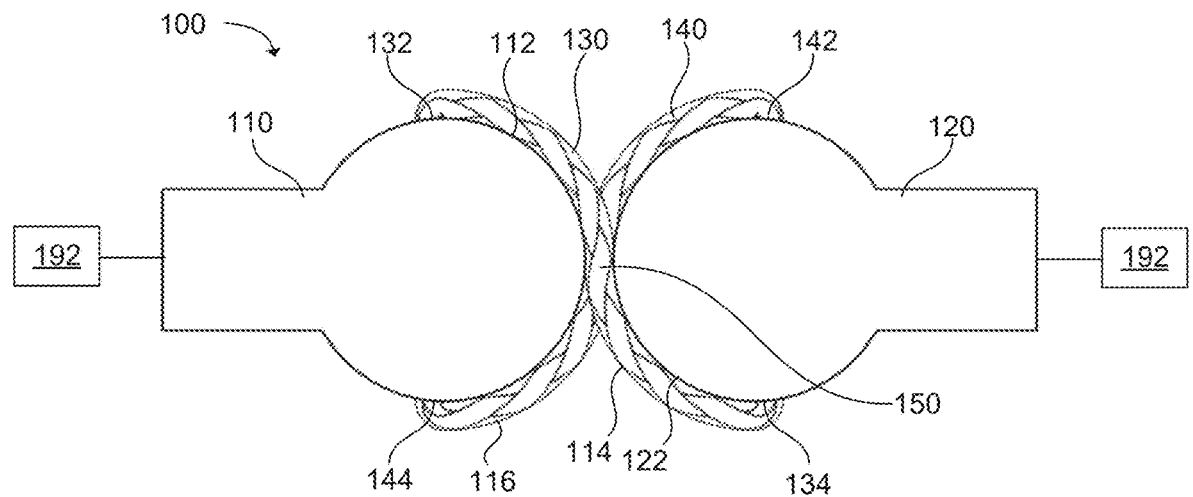
FIGS. 1A-1D illustrate an example joint implant in accordance with the present technology.

Reference will now be made to the examples illustrated, and specific language will be used herein to describe the same. It will nevertheless be understood that no limitation of scope is thereby intended.

DETAILED DESCRIPTION

The following detailed description of exemplary embodiments of the present technology refers to the accompanying drawings, which form a part hereof and in which are shown, by way of illustration, examples in which the present technology may be practiced. While these exemplary embodiments are described in sufficient detail to enable those skilled in the art to practice the present technology, it should be understood that other embodiments may be realized and that various changes to the present technology may be made without departing from the spirit and scope of the present technology. Thus, the following more detailed description of the embodiments of the present technology is not intended to limit the scope of the invention, as claimed, but is presented for purposes of illustration only to describe the features and characteristics of the present technology, and to sufficiently enable one skilled in the art to practice the invention.

Description of Terms

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

The term "joint implant" refers to an apparatus configured to be implanted in a joint of a subject to replace or repair the joint. The joint implant can provide a range of motion at least partially mimicking the natural range of motion of the physiologic joint, and the joint can constrain motion that would be uncharacteristic of the natural physiologic joint. In particular, the joint implants described herein can mimic the range of motion of a joint of the human body that flexes about a single axis, i.e., a hinge joint. The joint implant can comprise two joint implant elements and multiple filaments that couple the joint implant elements together. The filaments can couple the joint implant elements together in a way that allows the joint implant elements to rotate with respect to one another. Each joint implant element can rotate about an axis of rotation that is parallel to a hinge axis of the joint implant as a whole. As described herein, the two joint implant elements can be referred to as a "proximal joint implant element" and a "distal joint implant element." The multiple filaments can include at least a first filament that extends from an attachment point on the proximal joint implant element to an attachment point on the distal joint implant element, and a second filament that extends from an attachment point on the distal joint implant element to an attachment point on the proximal joint implant element, where the first and second filaments cross each other at a location between the proximal joint implant element and the distal joint implant element. The term "cross each other at a location between the proximal joint implant element and the distal joint implant element" refers to the first and second filaments appearing to cross when the joint implant is viewed from the side. Additional components that can be included in the joint implant comprise tensioning elements, bone interface connectors, bone anchors, and connectors for connecting the various components together such as screws, pins, or bolts.

The term "joint implant element" refers to a component of the joint implant that is coupled to another joint implant element by filaments, so that the two joint implant elements can rotate with respect to each other. The joint implant can comprise a curved interface surface and a base portion. In a joint implant, the two joint implant elements are oriented with their curved interface surfaces facing one another. The filaments that couple the joint implant elements together wrap partially around each of the curved interface surfaces. When the two joint implant elements rotate with respect to each other, the curved interface surfaces can roll on each other, either with the curved interface surface directly contacting one another or with the curved interface surfaces being separated by the filaments. The base portion of the joint implant element refers to all parts of the joint implant element other than the curved interface surface. The shape of the joint implant element is not particularly limited as long as the joint implant element has a curved surface that can interface with the curved interface surface of another joint implant element, and as long as the joint implant can be connected to a bone either directly or indirectly. Direction connection to the bone refers to the joint implant element being in direct contact with the bone. Indirect connection to the bone refers to the joint implant element connecting to the bone through one or more additional components, such as a bone interface connector or bone anchor. The joint implant element can be a solid or hollow cylinder, a solid or hollow partial cylinder, non-cylindrical three-dimensional shape having a curved surface, or any of these shapes further having protrusions on the curved interface surface or on the base portion. Depending upon its configuration, the joint implant element can also be referred to as a cylinder, a curved body, a roller, a hinging element.

The term "curved interface surface" refers to the surface of the joint implant element that faces a second curved interface surface of a second joint implant element and which rolls on the second curved interface surface, either in direct contact with the second curved interface surface or separated from the second curved interface surface by the filaments coupling the joint implant elements together. The curved surface can curve about a single axis of curvature. This can allow two curved interface surfaces to roll on each other to allow the joint implant elements to rotate about a single axis of rotation, but not allowing rotation about multiple axes such as is provided by a ball and socket joint. The curved interface surface can comprise any features of the surface that interfaces with the curved interface surface of another joint implant element. Some example features that can be included comprise grooves for accommodating the filaments, attachment points for the filaments, holes through which the filaments can extend, protrusions that can stop rotation of the joint implant elements, raised or recessed features that can interlock with other raised or recessed features of another curved interface surface, and others.

The term "base portion" refers to the remainder of the joint implant element besides the curved interface surface. This includes the volume within the joint implant element, surfaces of the joint implant element other than the curved interfaces surfaces, and any features of the joint implant element other than features on the curved interface surface. The base portion can have any shape as long as it can connect, either directly or indirectly, to a bone of a joint into which the joint implant is implanted. The base portion can also comprise one or more grooves to receive a filament therein.

The term "tensioning element" refers to a component of the joint implant that applies tension to a filament of the joint implant. The tensioning element can be a component that fits at least partially within a joint implant element. The tensioning element can be a cylinder that is smaller than the joint implant element so that the tensioning element fits inside the hollow interior of joint implant element. The tensioning element can have other shapes, such as a partial cylinder, or a non-cylindrical three-dimensional shape that fits at least partially within the joint implant element. The tensioning element can be an insert that can be positioned inside the hollow interior of a joint element and push against a filament to increase tension in the filament. The tensioning element can be a spool, screw, bolt, or other turnable component and a filament can be wrapped at least partially around the tensioning element, then the tensioning element can be turned to increase the tension in the filament.

The term "bone interface connector" refers to a component that is separate from the joint implant element, but which can connect to the joint implant element and to the bone of a subject. The bone interface connector can connect directly or indirectly to the joint implant element and can connect directly or indirectly to the bone. The bone interface connector can connect directly to the joint implant element, or the bone interface connector can connect directly to a tensioning element and the tensioning element can connect directly to the joint implant element. The bone interface connector can connect directly to a bone or the bone interface connector can connect directly to a bone anchor and the bone anchor can be connected directly to a bone. The bone interface connector can be or comprise a stem, a shaft, a bulged portion for retention in a slot formed in a bone, a bulged portion for retention in a bone anchor, or a combination thereof. In some cases, a single component can act as both a tensioning element and a bone interface connector. The bone interface connectors as described herein can comprise one or more features and/or configurations to facilitate and increase osseointegration. For example, a bone interface connector can comprise at least one of an osseointegration coating, an osseointegration surface texture, a sintered surface, barbs, flanges, protrusions for bone in-growth, recesses for bone in-growth, an open lattice configuration, or a combination thereof.

The term "bone anchor" refers to a component that directly connects to a bone of a subject. The bone anchor can be directly implanted into the bone. In some cases, the bone anchor can include a stem, a screw, a slotted screw, a slotted tube, or another shape adapted to be implant directly into a bone.

The term "joint span" refers to a portion of a joint implant that extends from a bone anchor or bone interface connector that is connected to a first bone, to a bone anchor or bone interface connector that is connected to a second bone. The joint span can include the movable parts of the joint that allow the joint to bend in a constrained fashion. In particular, the joint span can include the joint implant elements and filament segments that couple the joint implant elements together as described herein. In some examples, the joint implant can include a modular joint span, meaning that the joint span can be detached from bone anchors or bone interface connectors. This can allow the joint span to be removed for repair or to be replaced with a different joint span, for example.

The term "filament" refers to a thin, elongated, flexible strand. Filaments used in the present technology can be sufficiently flexible to wrap at least partially around the curved interfaces surfaces of the joint implant elements described herein. The filaments are not limited in terms of their material of construction, other than sufficient flexibility to operate as described in the present technology. The filaments can be made of any material, including metal, polymer, natural fibers, synthetic fibers, or other materials. A filament can be a single unitary strand of a continuous material, or a filament can also include multiple sub-filaments that have been braided, woven, twisted, or otherwise combined together to form a filament. Filaments can also have a variety of shapes, including threads and cords, which, for example, have an approximately circular cross-section (taken along an axis orthogonal to a longitudinal axis of the filament), and ribbons, which, for example, have a wider, substantially rectangular cross-section (again, taken along an axis orthogonal to a longitudinal axis of the filament).

Examples of the Technology

The present technology includes joint implants that can be used in arthroplasty. The joint implants can provide flexing motion in a single plane similar to a hinge. Thus, the joint implants can be used as a replacement for hinge joints in the body. For example, the joint implants can be adapted as replacements for a finger joint, a toe joint (i.e., interphalangeal joints), an elbow joint, or a knee joint. The joint implants described herein can closely mimic the kinematics of flexion and extension of physiologic joints in the body. The design of the joint implants can prevent or reduce unwanted lateral bending and shearing motion in the joint. At the same time, the joint implants can have a very low actuation force to flex and extend the joint in the desired direction. Moreover, the joint implants can be configured with non-slip interfacing surfaces between proximal and distal joint implant elements. Thus, a joint that has been replaced using a joint implant can be flexed and extended easily without increased fatigue or unexpected motion of the joint. The joint implants can also be designed to have a range of motion equivalent to a normal physiologic range of motion. Alternatively, the joint implants can have a much greater range of motion compared to a natural physiologic joint. In some cases, the overall range of motion of a replaced joint in a subject can be limited by other tissues, such as soft tissue or bone around the joint implant, and not by the joint implant itself. These and a variety of other characteristics of the joint implants can be adjusted to increase comfort and usability of the joint implants.

The joint implants described herein can include two joint implant elements that can rotate in relation to one another, and that also interface with one another in a non-slip manner during rotation. The joint implant elements can be coupled together by filaments. The filaments can be attached to the joint implant elements and arranged in a way that allows the joint implant elements to rotate relative one to another while also constraining lateral bending of the joint, shearing motion, and pulling apart of one joint implant element from the other. FIG. 1A shows a schematic side view of an example joint implant 100 to illustrate this design. The joint implant 100 includes a proximal joint implant element 110 and a distal joint implant element 120. The proximal joint implant element 110 comprises a structural configuration having curved interface surface 112 (otherwise referred to as a proximal curved interface surface 112 as it is located on the proximal joint implant element 110). Likewise, the distal joint implant element 120 comprises a structural configuration having curved interface surface 122 (otherwise referred to as a distal curved interface surface 122 as it is located on the distal joint implant element 120) facing toward the proximal curved interface surface 112. The joint implant 100 can further comprise a first filament 114. The first filament 114 can comprise a first filament segment 130 that extends from an attachment point 132 on the proximal joint implant element 110 to an attachment point 134 on the distal joint implant element 120. The joint implant 100 can further comprise a second filament 116. The second filament 116 can comprise a second filament segment 140 that extends from an attachment point 142 on the distal joint implant element 120 to an attachment point 144 on the proximal joint implant element 110. The locations of the attachment points are such that the first and second filament segments 130,140 cross each other at a location 150 between the proximal joint implant element 110 and the distal joint implant element 120. The first and second filament segments 130,140 can be supported between the proximal and distal joint implant elements 110,120 such that they do not interfere with one another, such as being adjacent one another. FIG. 1A also shows boxes 192, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

Figure 1B:
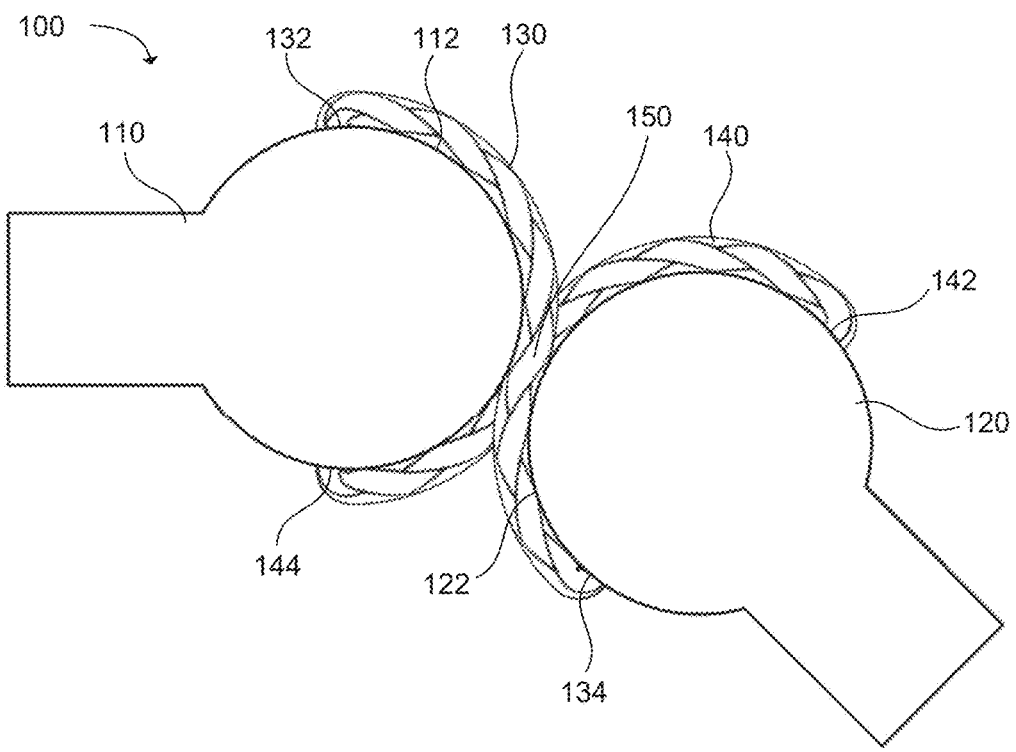

FIG. 1B shows another side view of the example joint implant 100 in a partially flexed position. In this figure, the proximal joint implant element 110 remains in the same position as in FIG. 1A, but the distal joint implant element 120 has rotated. As the distal joint implant element 120 rotates downward, the first filament segment 130 simultaneously unwinds from the distal curved interface surface 122 and winds onto the proximal curved interface surface 112. The second filament segment 140 winds and unwinds in an opposite fashion. As the distal joint implant element 120 rotates downward, the second filament segment 140 simultaneously unwinds from the proximal curved interface surface 112 and winds onto the distal curved interface surface 122. The distal curved interface surface 122 moves with a rolling motion relative to the proximal curved interface surface 112. In other words, the distal curved interface surface 122 moves relative to the proximal curved interface surface 112 such that there is no relative slipping between these surfaces (i.e., a non-slip rolling motion) with little to no friction or drag between them except rolling friction. The filaments also assist in reducing or eliminating slippage between the distal and proximal curved interface surfaces 122,112. In this example, the distal curved interface surface 122 is not in direct contact with the proximal curved interface surface 112, but instead is in contact with and rolls on the filament segments 130,140. The filament segments 130,140 are positioned between the curved interface surfaces 112, 122, and in this example the curved interface surfaces 112,122 are separated one from another by the filament segments 130,140. In other examples, the curved interfaces surfaces 112,122 can have a shape that allows the proximal and distal curved interface surfaces 112,122 to directly contact one another. In these examples, the distal curved interface surface 122 can move with a rolling motion relative to the proximal curved interface surface 112, with these being in direct contact.

Figure 1C:
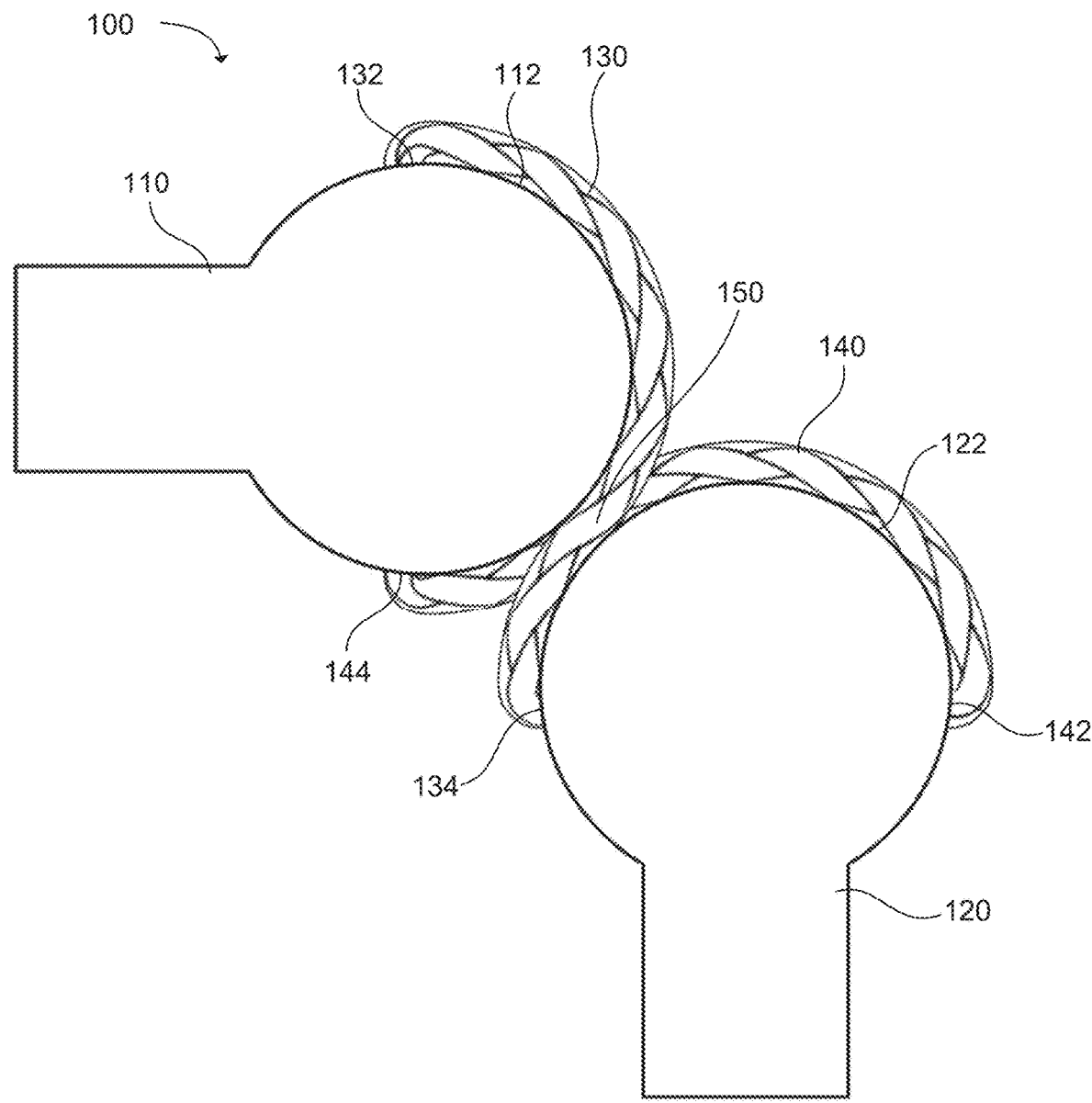
Figure 1D:
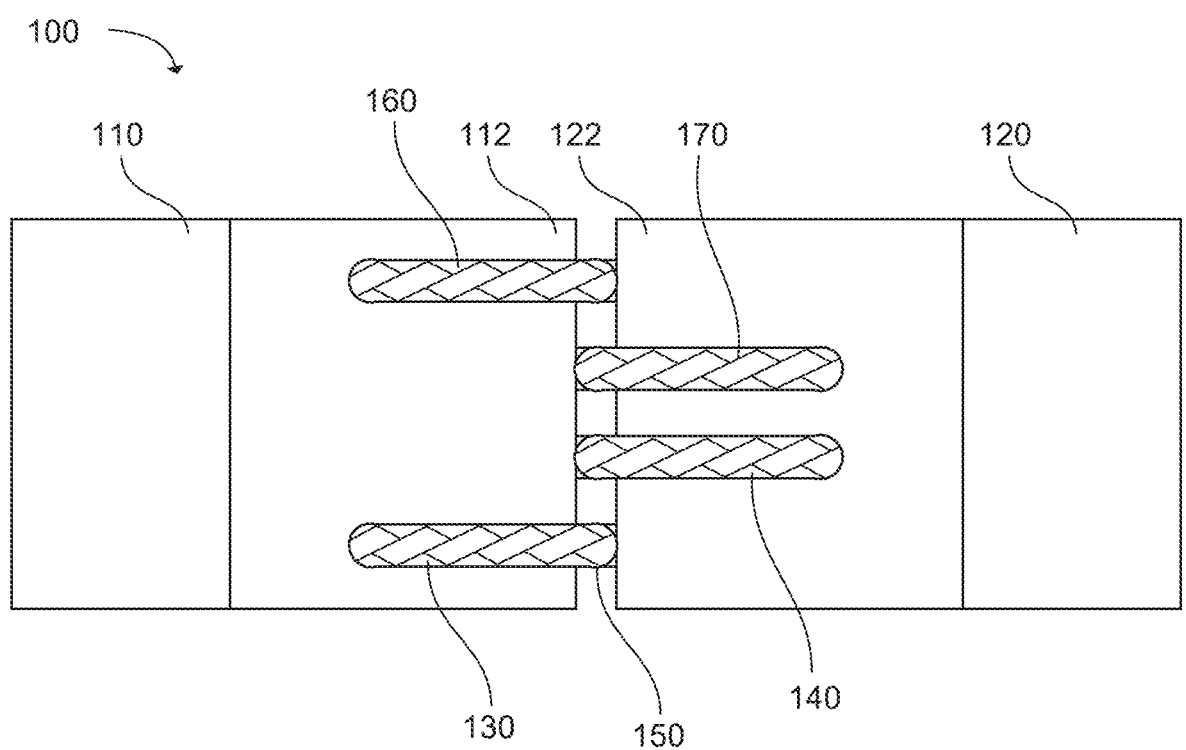

FIG. 1C shows another side view of the joint implant 100 in a further flexed position. In this position, the distal joint implant element 120 has rotated still further. In this position, the first filament segment 130 has unwound further from the distal curved interface surface 122 and wound more onto the proximal curved interface surface 112. Thus, a majority of the first filament segment 130 is now wound on the proximal curved interface surface 112. The opposite occurs with the second filament segment 140. The second filament segment 140 has unwound further from the proximal curved interface surface 112 and wound more onto the distal curved interface surface 122, so that a majority of the second filament segment 140 is now wound on the distal curved interface surface 122. The location 150 at which the filament segments 130,140 cross is the same location where each filament switches from unwinding to winding around the opposite curved interface surface. This crossing location 150 moves as the joint flexes because of the rolling motion of the distal joint implant element 120 relative to the proximal joint implant element 110. This location 150 is the point where the first filament segment 130 separates from the distal curved interface surface 122 and begins to wind onto the proximal curved interface surface 112 as the joint flexes. This location 150 is also the point where the second filament segment 140 separates from the proximal curved interface surface 112 and begins to wind onto the distal curved interface surface 122. It is also noted that the crossing location 150 can be the location where the proximal and distal curved interface surfaces 112,122 are closest to one another. In this example, the filament segments 130,140 are between the proximal and distal curved interface surfaces 112,122 and prevent the curved interface surfaces 112,122 from touching. However, in other examples the curved interfaces surfaces 112,122 can have portions that directly contact one another. The point at which the curved interface surfaces 112,122 touch can also be at the crossing location 150. When stating that the crossing location 150 is the "same" as the location where the curved interface surfaces 112, 122 are closest to one another, and the "same" as the location where the filament segments start to wind on the opposite curved interface surface, the intended meaning is that these points are at the same location when viewed from a side view, as in FIGS. 1A-1C. These various locations may be in different places in three-dimensional space, such as spaced apart from side to side across the joint implant 100, but the locations can be aligned so that they coincide when viewed from the side.

The joint implant elements are referred to as "proximal" and "distal" for convenience to easily differentiate between the joint implant elements. When a joint in the body is replaced using a joint implant as described herein, one of the joint implant elements can be located proximally, i.e., closer to the point of origin of the limb of the joint. The other joint implant element can be located distally, i.e., farther from the point of origin of the limb. In some examples the proximal and distal joint implant elements can be identical or mirror images of each other, while in other examples the proximal and distal joint implant elements can have differing designs or sizes. In any of these examples, the joint implant can be implanted in either direction, so the "proximal joint implant element" may be located distally and the "distal joint implant element" may be located proximally. Thus, the terms "proximal" and "distal" are not to be considered limiting, and the proximal and distal directions can be switched in any of the embodiments described herein.

Additionally, the example above is described as having a proximal joint implant element that remains stationary while the distal joint implant element moves. However, in other examples, the proximal joint implant element can move while the distal joint implant element remains stationary. In further examples, both the proximal and the distal joint implant elements can move at the same time.

The above example is described as comprising a first filament with a first filament segment and a second filament with a second filament segment, but this is not intended to be limiting in any way. Indeed, in some examples, the joint implant can comprise more than two filaments, each comprising respective filament segments (see the example joint implant 100 of FIGS. 1A-1D). One or more of the filament segments can extend from the proximal joint implant element to the distal joint implant element in one direction, and one or more other filament segments can extend from the proximal joint implant element to the distal joint implant in an opposite direction, such that the filament segments cross at a crossing location between the joint implant elements. In the example shown in FIG. 1A, the first filament segment of the first filament is attached to the top of the proximal joint implant element and to the bottom of the distal joint implant element. Therefore, the first filament segment extends from the proximal joint implant element to the distal joint implant element in a top-down direction. The second filament segment of the second filament attaches to the bottom of the proximal joint implant element and to the top of the distal joint implant element. Therefore, the second filament segment extends from the proximal joint implant element to the distal joint implant element in a bottom-up direction. Thus, the first and second filament segments can be described as extending between the joint implant elements in opposite directions. In further examples, the joint implant can include one or more additional filament segments that extend in the same direction as the first filament segment or the second filament segment. It is also noted that the attachment points for the filament segments may not always be on the bottom or top of a joint implant element. However, in some examples the attachment points can be in higher and lower positions (or in closer and further away positions) relative one to another as compared with the example of FIGS. 1A-1D, and the filament segments can extend in a relatively upward direction or a relatively downward direction so that the filament segments extending in the upward direction cross the filament segments extending in the downward direction.

In some examples, the joint implant can include at least three filaments, each having respective filament segments. A first filament segment of a first filament and a second filament segment of a second filament can extend in opposite directions so that they cross at a crossing location between the proximal and distal joint implant elements. A third filament segment of a third filament can extend in a parallel direction to the first filament segment. Thus, the third filament segment can cross the second filament segment in the same direction that the first filament segment crosses the second filament segment. In further examples, the joint implant can also include a fourth filament having a fourth filament segment that extends parallel to the second filament segment. Thus, the joint implant can have two filament segments extending in each direction. In many examples, the filaments can be arranged in a symmetrical arrangement across the width of the joint implant. The example joint implant 100 of FIGS. 1A-1D illustrates this specific arrangement of four filaments and four filament segments, which is not intended to be limiting. The first filament segment 130 attaches at the top of the proximal joint implant element 110 and wraps around the proximal joint implant element, then wraps under the bottom of the distal joint implant element 120. The second filament segment 140 attaches at the top of the distal joint implant element 120 and wraps around the distal joint implant 120 element and then under the bottom of the proximal joint implant element 110. A third filament segment 160 is also attached to the top of the proximal joint implant element 110. The third filament segment 160 is parallel to the first filament segment 130 and wraps in the same direction as the first filament segment 130. A fourth filament segment 170 is attached to the top of the distal joint implant element 120. The fourth filament segment 170 is parallel to the second filament segment 140, and wraps in the same direction as the second filament segment 140. In this example, the first and third filament segments 130, 160 are located near the sides of the joint implant 100. The second and fourth filament segments 140,170 are located near the middle of the joint implant 100, between the first and third filament segments 130,160. Thus, the filaments have a symmetrical arrangement from side to side when the joint implant is viewed from the top (see FIG. 1D). A variety of alternative arrangements can also be used. For example, the joint implant can have two outer filament segments near the sides of the joint implant, and a single inner filament segment between the outer filament segments. Alternatively, the joint implant can have more than two inner filament segments, more than two outer filament segments, or any combination thereof. The joint implant can also have multiple alternating filament segments that alternate in the direction that they wrap around the joint implant elements, either in a downward direction or in an upward direction.

In some examples, the filament segments in the joint implant can be separate filaments, such as described above. The filaments can have one end attached to the proximal joint implant element at one attachment point, and the opposite end of the filament can be attached to the distal joint implant element at another attachment point. In other examples, the filament segments can be multiple segments of a single longer filament. For example, a single strand of filament can loop through a hole in the proximal joint implant element or the distal joint implant element, and the segments of the filament that are exposed outside the joint implant element can act as the first and second filament segments. In some examples, all the filament segments in the joint implant can be segments of a single long filament, or multiple long filaments can each have multiple segments, or some filament segments can be separate filaments while other filament segments can be segments of a longer filament, or any combination thereof can be included. It is noted that, although described above as having four separate filaments, FIGS. 1A-1D alternatively illustrate these examples as the ends of the filament or filaments are not shown. Indeed, the joint implant 100 can be configured as shown in FIGS. 1A-1D to alternatively comprise multiple long filaments, each having one or more of the four filament segments shown, or a single long filament that comprises the four filament segments shown. Essentially, it is contemplated that the number of filament segments operable within the joint implant 100, such as those shown, can be part of a single filament or part of two or more filaments.

As mentioned above, the proximal and distal joint implant elements can rotate relative one to another with a rolling motion. This rolling motion is consistent with wrapping and unwrapping the filament segments from the curved interface surfaces as described above. Because of this rolling motion, the joint implant moves somewhat different from a typical hinge. In a typical hinge, such as door hinge, the two halves of the hinge rotate about a single axis of rotation. In the example of a door hinge, the hinge includes two flat plates known as leafs, a knuckle, and a pin. The knuckle is a cylindrical-shaped tube formed when the leafs are joined together. The pin is a rod that is inserted into the knuckle. In this type of hinge, the leafs both rotate around an axis of rotation that is at the center of the pin. In contrast, the joint implants described herein do not have a single axis of rotation. The proximal and distal joint implant elements may each rotate about its own axis of rotation. However, that axis of rotation can move due to the translation component inherent in a rolling motion as the joint implant elements roll against each other. In some joint implant element examples, particularly those having a curved interface surface based on circular geometry, although also undergoing translation, the axis of rotation of a rotating joint implant element can be at the center of the radius of curvature of the curved interface surface of that joint implant element.

In certain examples, the proximal and distal joint implant elements can rotate relative to one another with a rolling motion without any slipping between the respective proximal and distal curved interface surfaces. Even when the curved interface surfaces are in direct contact, the surfaces can roll on each other without slipping. Furthermore, the joint implant elements can rotate with substantially no slipping or sliding of the filaments on or relative to the curved interface surfaces. This can be useful because eliminating slipping and rubbing between the components of the implant can significantly decrease wear on the joint implant and thus increase the useable lifetime of the implant. In other types of prior implants, rubbing between the components can be a major source of wear over time. This can lead to the need for replacement of worn implants. Rubbing between implant components can also lead to small shards or other particles of material breaking off the implant, which can damage surrounding tissue. These issues of prior implants can be avoided by configuring the joint implants described herein to bend or rotate (i.e., undergo a flex/extend movement) without slipping or rubbing between the joint implant elements, or other components of the joint implant 100. Additionally, the lack of rubbing can expand the range of possible materials that can be used to make the joint implant elements to include materials that would not withstand the repeated rubbing experienced in other prior implant designs. The design of the joint implants also constrains the motion of the joint implant elements to a rolling motion.

The interface of the proximal joint implant element and the distal joint implant element as constrained to a rolling motion, in conjunction with the motion of rolling without slipping can be referred to as "registration" of the proximal joint implant element with the distal joint implant element. Registration of the proximal joint implant element with the distal joint implant element can be achieved and maintained through rotation of the joint implant in several different ways. In one example, he filaments described above can facilitate and help maintain registration of the proximal joint implant element with the distal joint implant element. In other examples, registration can also be achieved and maintained using registration features on the proximal and distal curved interface surfaces. Registration features can comprise mating features or interfaces, such as those shaped as gear teeth, those having a sinusoidal profile, or any other shape, that can function to register the proximal joint implant element with the distal joint implant element, and prevent the proximal joint implant element from sliding relative to or on the surface of the distal joint implant element. These registration features are described in more detail below. It is noted that any of the example joint implant elements described herein can comprise and utilize registration features instead of filaments or in addition to filaments to achieve and maintain the registration between the proximal and distal joint implant elements.

With respect to the curved interface surfaces and their configuration, in some examples, the curved interface surfaces can have a circular profile. The term "profile" refers to the shape or configuration of the curved interface surface (or other structure, component, or element (e.g., a "profile" of a groove formed in a curved interface surface) when the joint implant is viewed from the side. A circular profile can comprise a full circle or any portion of a circle, i.e., an arc of a circle. For example, the proximal and distal joint implant elements of the joint implant 100 shown in FIG. 1A each have curved interface surfaces with a circular profile. In other examples, the proximal curved interface surface, or the distal curved interface surface, or both can have a circular profile. The circular profile can have a radius of curvature, which is the radius of the circle. In some examples, the proximal and distal curved interface surfaces can have the same radius of curvature, while in other examples the proximal and distal curved interface surfaces can have different radii of curvature.

Other profiles can also be used for the curved interface surfaces. In various examples, not to be limiting in any way, the curved interface surfaces can have a circular profile, a non-circular profile, an elliptical profile, a parabolic profile, a hyperbolic profile, a piriform profile, or an oval profile. In some examples, the proximal curved interface surface and the distal curved interface surface can have congruent profiles, meaning that the surfaces match one another and are mirror images of each other. In other examples, the proximal and distal curved interface surfaces can have differing profiles.

Figure 2A:
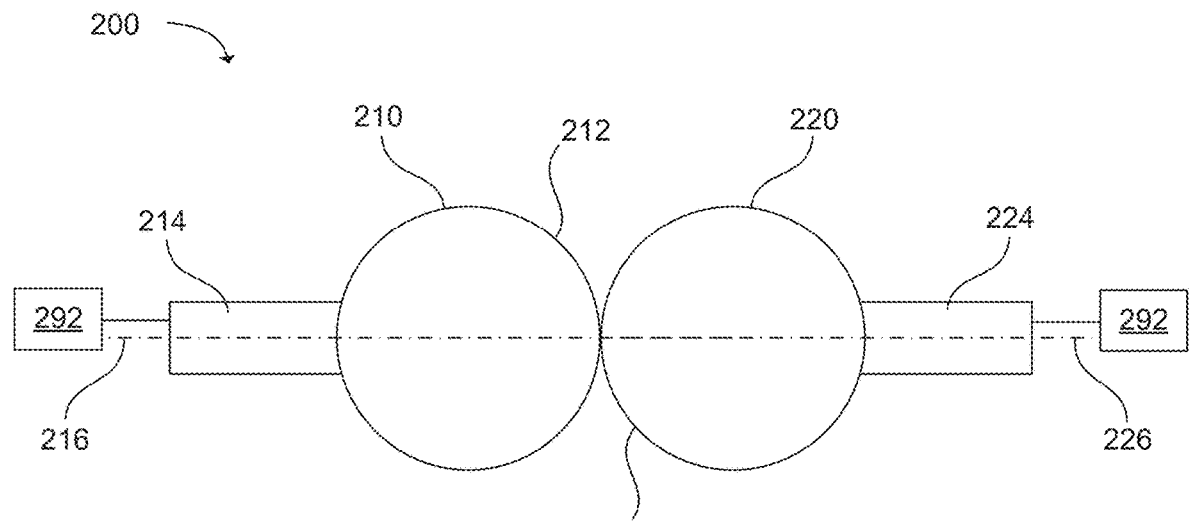
FIGS. 2A-2D illustrate another example joint implant in accordance with the present technology.
Figure 2B:
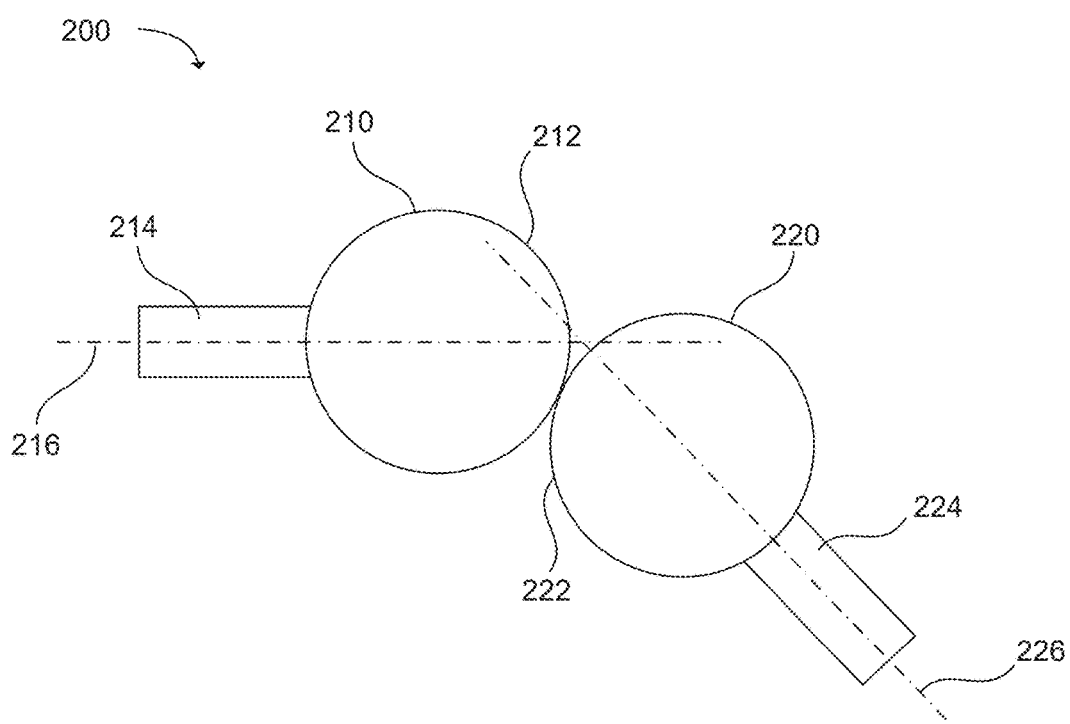
Figure 2C:
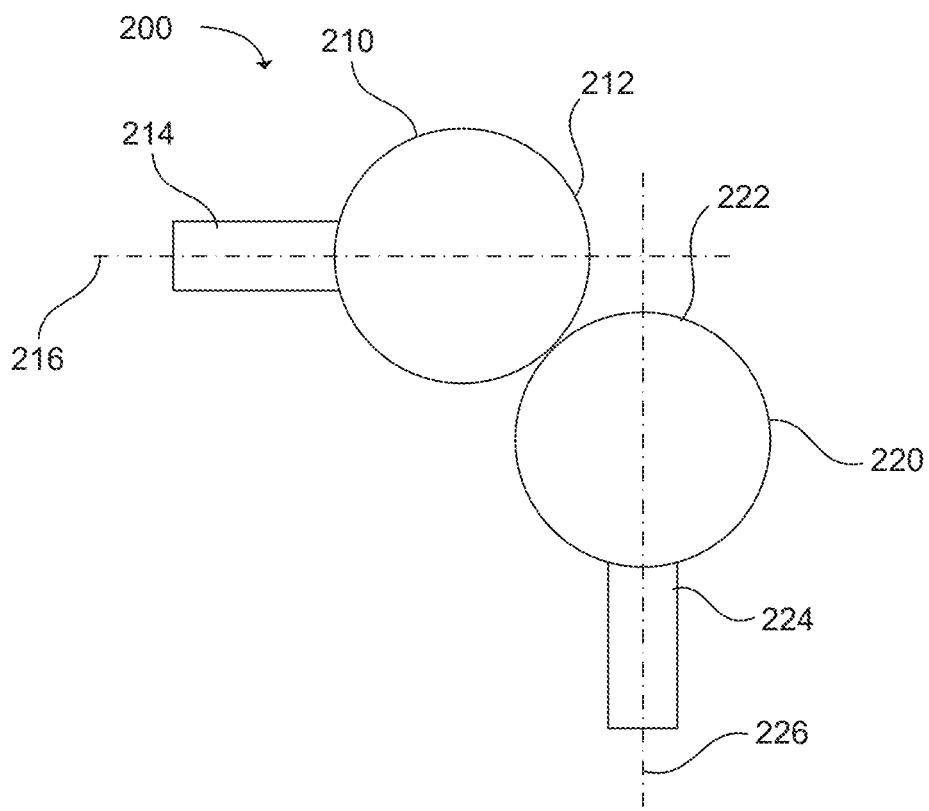
Figure 2D:
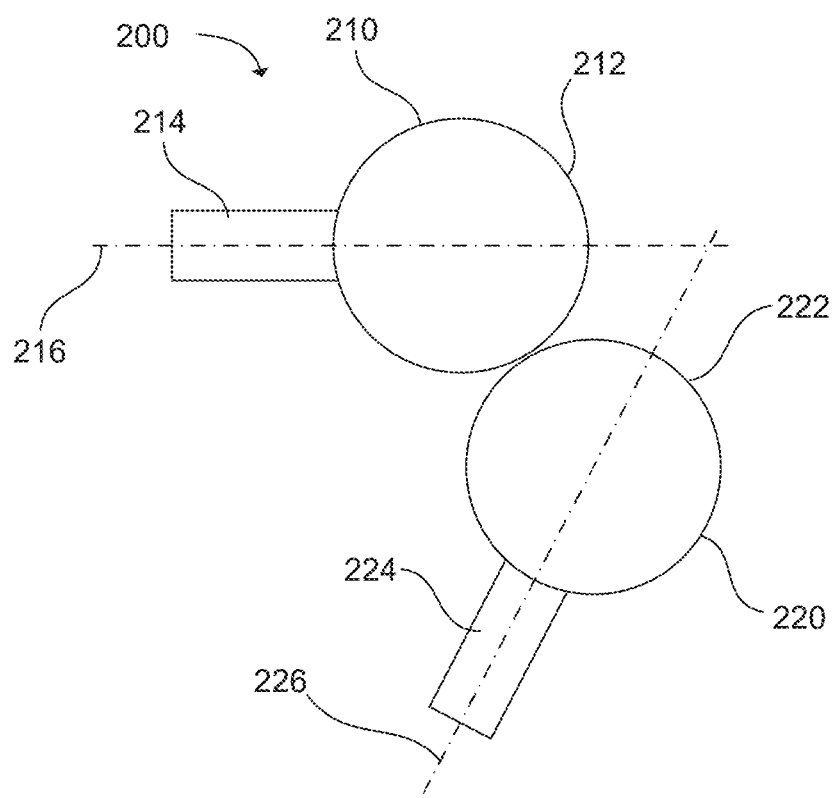

Using different curve profiles can affect the rotation characteristics of the joint implant and the joint implant elements. In one example, when the proximal and distal curved interface surfaces have a congruent circular profile, the joint implant elements can have a uniform ratio of rotation to rolling distance when the curved interface surfaces roll on each other. In other examples, certain curved interface surfaces can provide increasing or decreasing rotation of a given joint element over a given rolling distance as the joint elements roll on each other. As used herein, the "rolling distance" refers to a distance that either joint implant element has rolled over the curved interface surface of the other joint implant element, as measured along either of the curved interface surfaces (the distance will be the same on both curved interface surfaces). The "rotation" refers to the change in angular orientation of a joint implant element. To clearly illustrate the rotation of a joint implant element in a joint implant with two circular curved interfaces surfaces, similar to the joint implant 100 of FIGS. 1A-1D, FIG. 2A shows a schematic side view of another example joint implant 200. This example includes a proximal joint implant element 210 having a proximal curved interface surface 212 and a proximal base portion 214. A distal joint implant element 220 has a distal curved interface surface 222 and a distal base portion 224. The proximal and distal curved interface surfaces 212,222 both have a circular profile with the same radius of curvature, and are shown as being in direct contact with one another. This figure also shows a proximal longitudinal axis 216 of the proximal joint implant element 210 and a distal longitudinal axis 226 of the distal joint implant element 220 in order to more clearly show the rotating motion of the joint implant elements relative to one another. The filaments are omitted in this figure to more clearly show how the profile of the curved interface surfaces affects the rotation of the joint implant elements. FIG. 2A also shows boxes 292, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. FIGS. 2B, 2C, and 2D show this example as the distal joint implant element 220 rotates relative to the proximal joint implant element 210 progressively further from the extended position to the flexed position. Throughout this movement, the ratio of rotation of the distal joint implant element to the rolling distance is uniform. These figures show that the joint implant 200 does not flex about a single hinge axis like a typical hinge. The hinge axis of the joint can be considered to be the point where the longitudinal axes cross. However, this point moves as the joint implant 200 flexes and extends.

Figure 3A:
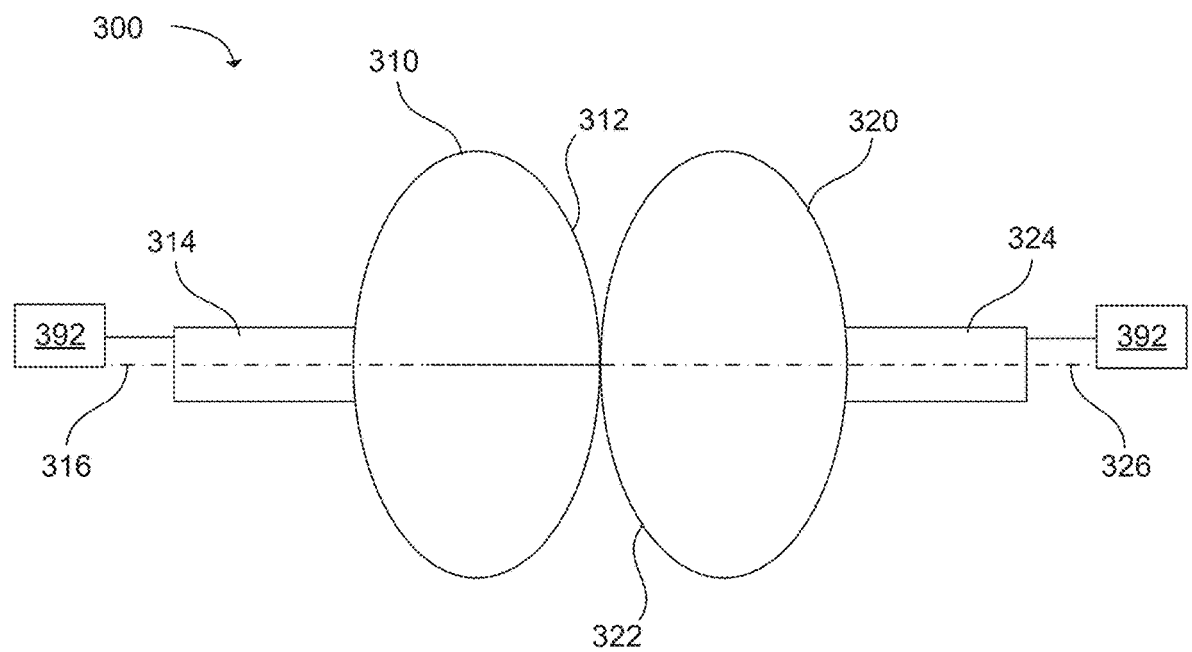
FIGS. 3A-3D illustrate another example joint implant in accordance with the present technology.
Figure 3B:
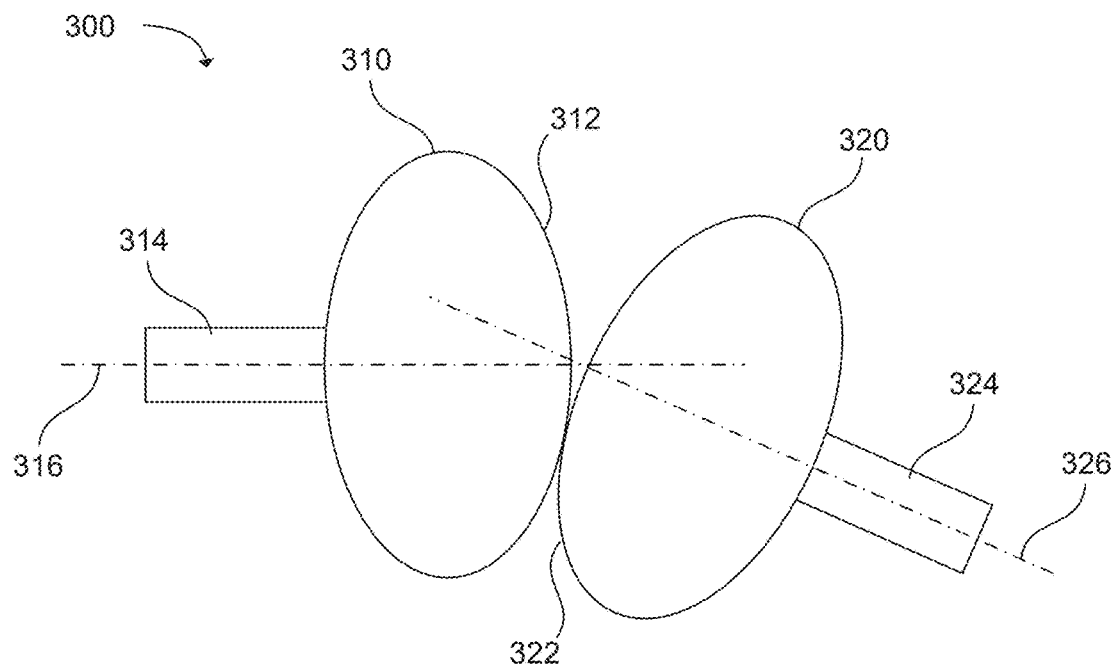
Figure 3C:
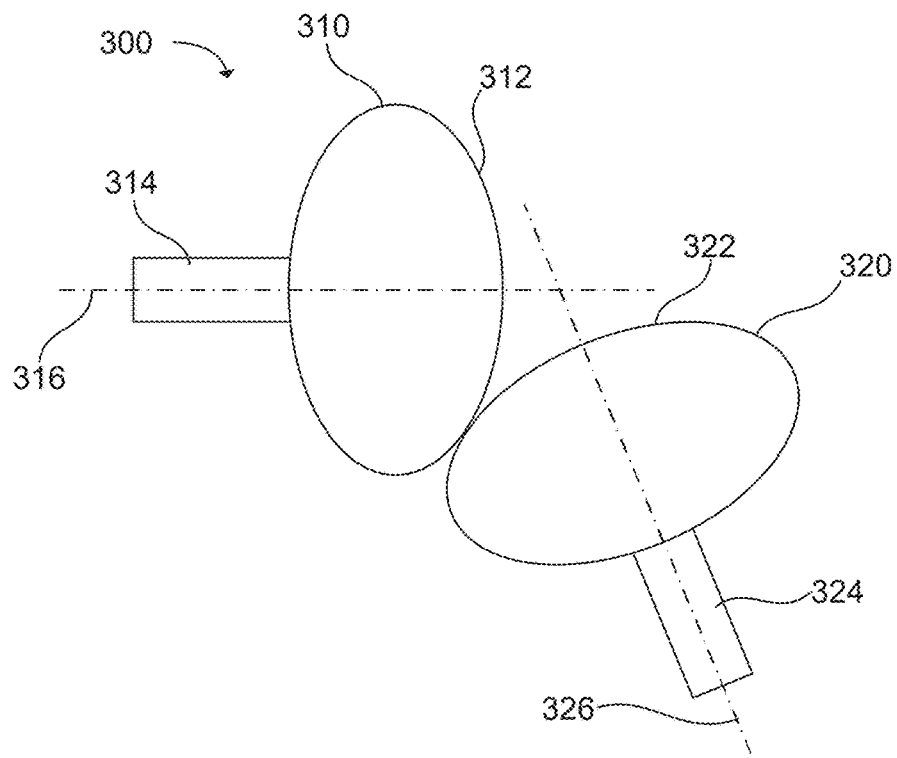
Figure 3D:
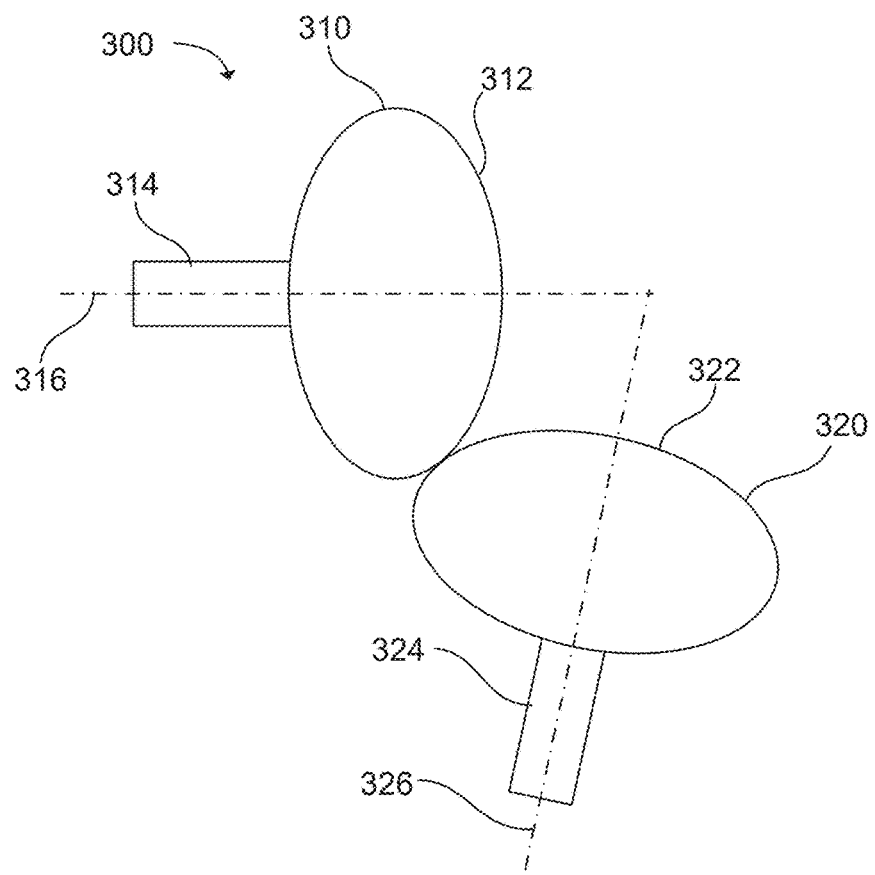

FIG. 3A shows a schematic view of another joint implant 300. This example also has a proximal joint implant element 310 with a proximal curved interface surface 312, a proximal base portion 314, and a proximal longitudinal axis 316, and a distal joint implant element 320 with a distal curved interface surface 322, a distal base portion 324, and a distal longitudinal axis 326. In this example, the curved interface surfaces 312,322 have an elliptical profile. When the joint implant 300 is in the extended position, shown in FIG. 3A, the elliptical curved interface surfaces 312,322 touch at the point where the ellipse has a large radius of curvature. FIG. 3A also shows boxes 392, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. When the distal joint implant element 320 rotates into a flexed position, the ellipses roll on each other as shown in FIGS. 3B, 3C, and 3D. The point where the elliptical curved interface surfaces 312,322 touch will move along the surfaces as the surfaces roll on each other, and the radius of curvature at this point gets progressively smaller. As the elliptical curved interface surfaces 312,322 roll farther from the extended position, the ratio of rotation of the distal joint implant element (and thus the joint implant 300) to the rolling distance will increase as the contact point moves to locations with a smaller radius of curvature. In other words, with this particular surface configuration, the rate of rotation of the distal joint element relative to the proximal joint implant element increases and is not uniform as the curved interface surfaces 312, 322 roll farther from the extended position. Thus, the relationship between the rotation and the rolling distance is different for the elliptical curved interface surfaces than for circular curved interface surfaces.

Figure 4A:
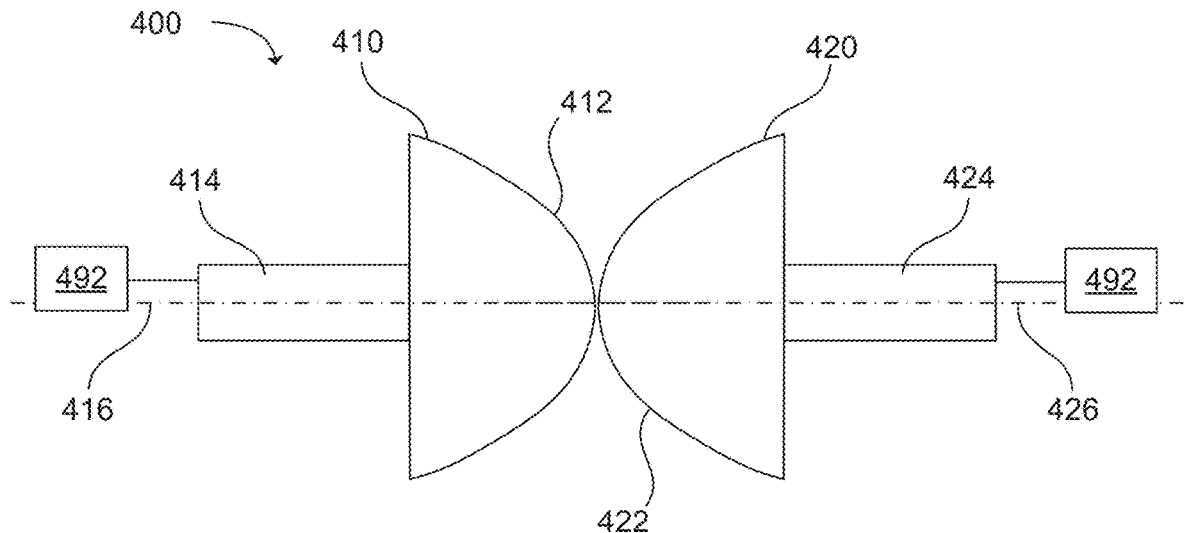
FIGS. 4A-4D illustrate a further example joint implant in accordance with the present technology.
Figure 4B:
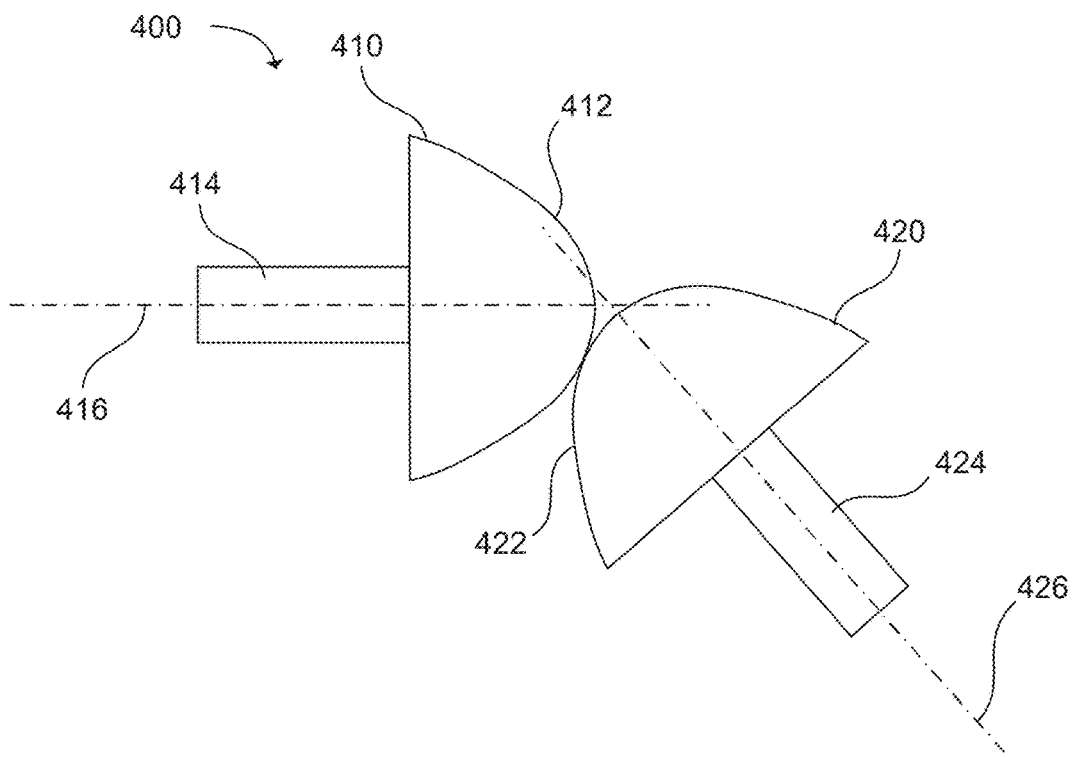
Figure 4C:
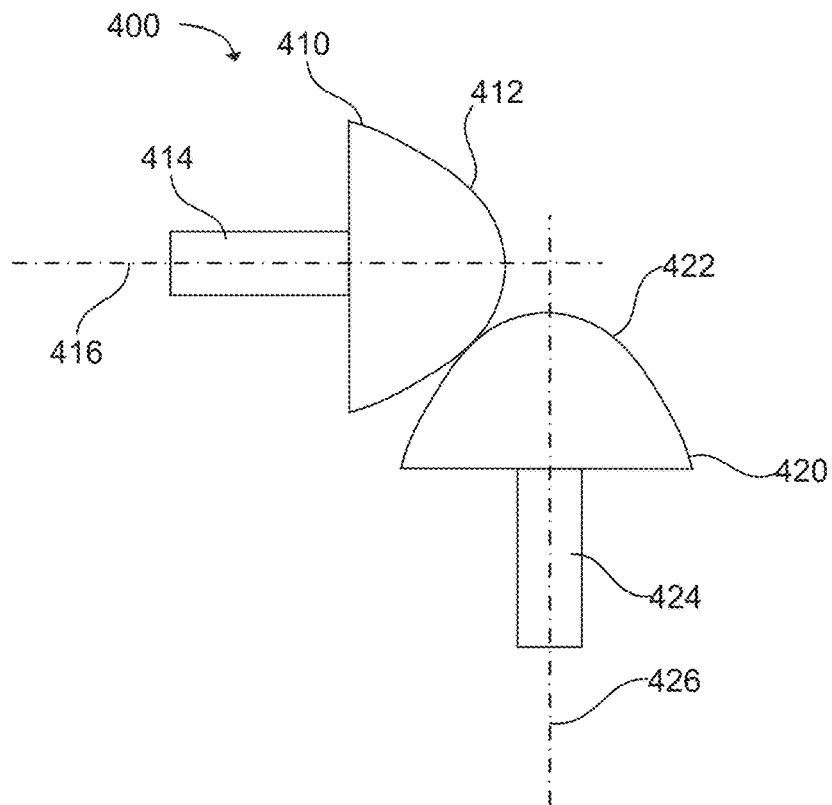
Figure 4D:
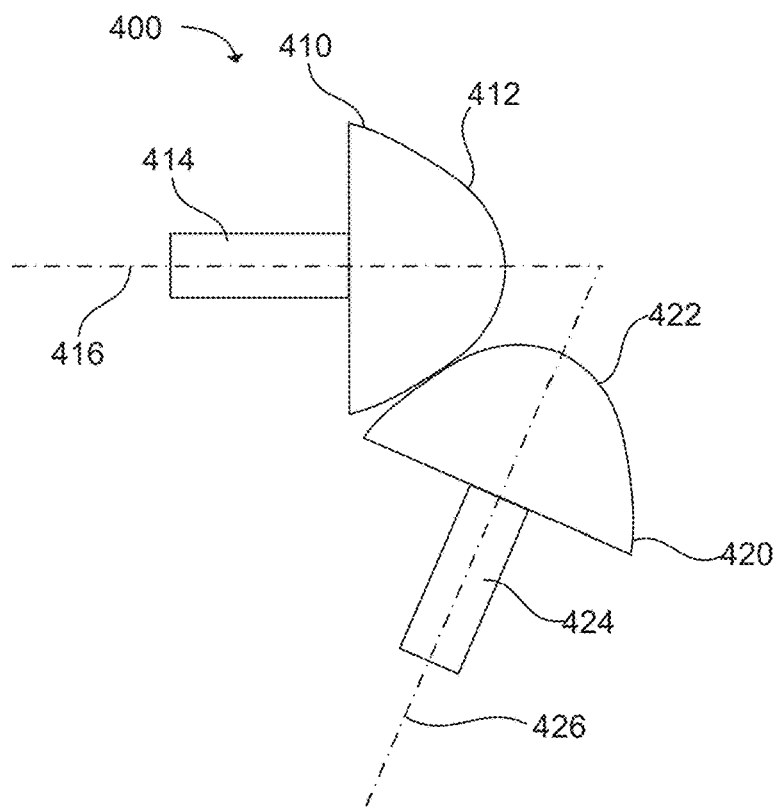

FIGS. 4A-4D show schematic side views of another joint implant 400. This example also has a proximal joint implant element 410 with a proximal curved interface surface 412, a proximal base portion 414, and a proximal longitudinal axis 416, and a distal joint implant element 420 with a distal curved interface surface 422, a distal base portion 424, and a distal longitudinal axis 426. In this examples, the curved interface surfaces have a parabolic profile. FIG. 4A also shows boxes 492, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. When the joint implant is in the extended position, as shown in FIG. 4A, the contact point between the curved interface surfaces is at the location where the curves have their smallest radius of curvature. Therefore, the rotation to rolling distance ratio of the distal joint implant element (and the joint implant) will be greatest when it starts rotating from the extended position (see FIG. 4B). As the distal joint implant element rotates farther, as shown in FIGS. 4C-4D, the radius of curvature at the contact point decreases. Thus, the rotation to rolling distance ratio will decrease. It is noted that the above example curved interface surface profiles are merely examples and used to illustrate the ability of the joint implant of the present disclosure to be configured to comprise different rotation to rolling distance ratios within the components that make up the joint implant. These certainly are not meant to be limiting in any way. Indeed, other types of curved interface surfaces can also be used, which can also affect the bending (i.e., flex/extend) movement characteristics of the joint implant.

Figure 12:
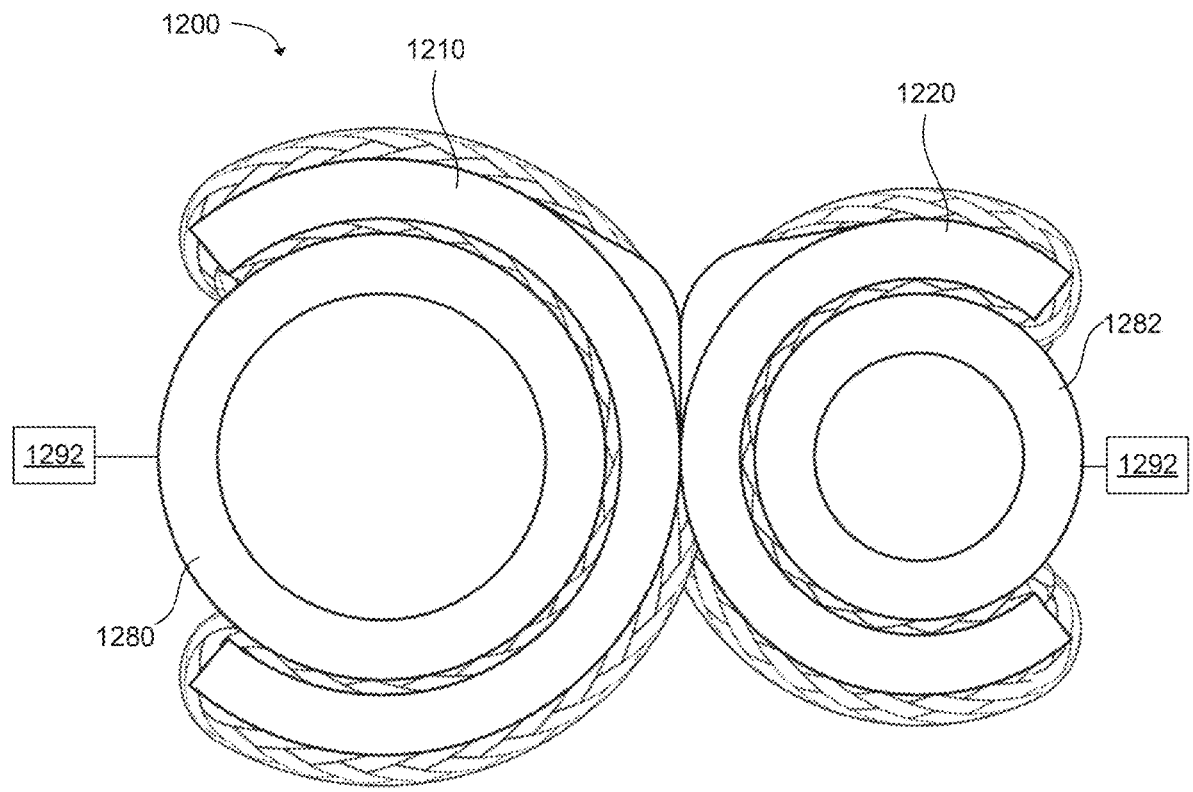
FIG. 12 is a side view of another example joint implant in accordance with the present technology.

The examples of FIGS. 2-4 illustrate how the rotation to rolling distance ratio can change throughout the range of motion of a joint implant when one or both of the curved interface surfaces have a non-circular profile. In contrast, a joint implant with two curved interface surfaces that have circular profiles will have a uniform ratio of rotation to rolling distance throughout the range of motion of the joint implant. It is noted that the ratio of rotation to rolling distance can also be changed by changing the radius of one or both of the curved interface surfaces having a circular profile. For example, a joint implant that has two curved interface surfaces with a circular profile that is relatively small will have a greater rotation to rolling distance ratio than a joint implant that has two curved interface surfaces with a circular profile that is relatively larger. Additionally, some example joint implants can have two curved surfaces with circular profiles of differing radii. Reducing the radius of either curved interface surface will also have the effect of increasing the ratio of rotation to rolling distance. This is because the joint implant element having the smaller circular profile will rotate more with a given rolling distance than a joint implant element having a larger circular profile. FIG. 12 shows one example joint implant element 1200 that has a distal joint implant element 1220 with a smaller circular profile and a proximal joint implant element 1210 with a larger circular profile. This example is described in more detail below.

The joint implants described herein can be designed to control the actuation force used to flex the joint implant. When a joint implant is implanted into a patient, the actuation force can be provided by the patient's own muscles and tendons. In certain examples, the joint implant can be configured to have an actuation force approximately equal to the normal actuation force of a physiologic joint. In certain examples, the joint implant can be configured to flex with no actuation force or a negligible actuation force. The joint implant can be designed so that tension in the filaments does not affect the actuation force of the joint implant. In order to accomplish this, the curved interface surfaces can be designed so that tension in the filaments does not change when the joint implant flexes. Even if the filaments are under very high tension, the joint can still be configured to flex with no actuation force or very little actuation force because, as configured as described in examples herein, flexing the joint does not stretch the filaments any further. The actuation force can also be constant through the range of motion of the joint. In these examples, the only motion that occurs in the filament is that of the filament segments unwinding from one curved interface surface and winding on the other curved interface surface as the joint implant elements are caused to move relative to one another.

Alternatively, the joint implant can be designed to change tension in the filaments when the joint implant is flexed or extended. In some examples, one or both of the curved interface surfaces can have a contact portion with a radius of curvature that increases at the location where the joint implant elements contact one another when the joint implant elements rotate relative to one another from the extended position to a flexed position, and the increasing radius of curvature causes the joint implant elements to pull on the filaments connecting the joint implant elements and thereby increase the tension in the filaments. The increased tension in the filaments can create a returning or restoring force, that will tend to pull the joint implant back to the extended position, and assist in moving from a flexed position to an extended position. Configuring the joint implant in this way can be useful for patients that are extensor tendon deficient, which would make it difficult for the patient to extend the joint implant. The increase in tension in the filaments can stay within the elastic range of the filaments. In other words, the filaments can stretch, but they do not stretch so much that plastic deformation of the filaments occurs. This can allow the filaments to return to their lower tension elastically when the joint is extended. In certain examples, one or both of the curved interface surfaces can include a raised contact portion that directly contacts the opposite curved interface surface, and the raised portion can have the increasing radius that causes the tension to increase in the filaments as the opposing curved interface surface rolls along the raised portion. The filaments can be located at or within a non-raised portion, such as a groove formed in one or more of the curved interface surfaces. In further examples, the groove where the filaments are positioned can have a constant radius while the raised portion of the curved interface surface has an increasing radius when the joint is flexed. It is noted that the one or more grooves formed in the one or more curved interface surfaces can have the same or a different profile as the curved interface surface (i.e., can comprise the same or a different configuration in terms of, for example, curvature, radius, etc.). The surfaces defining or making up the one or more grooves may or may not be parallel to the surfaces defining or making up one of more of the curved interface surfaces.

Another example can provide increased tension in the filaments when the joint is extended, which can create a force tending to pull the joint into a flexed position. In this example, one or both of the curved interface surfaces can have a contact portion with a radius of curvature that decreases as the joint implant elements rotate with respect to one another from the extended to the flexed position, and this can cause tension in the filaments to decrease when the joint flexes. This configuration can be useful for patients that are flexor tendon deficient, because the joint implant can provide a force to flex the joint without requiring force from the patient's flexor tendons.

The filaments used in the joint implants can be made from a wide variety of materials. The filaments can also have a thin, elongated shape to allow the filaments to be attached to both joint implant elements and to extend along the respective curved interface surfaces of the joint implant elements while crossing at a point between the joint implant elements. Any material that is sufficiently flexible to wind around the curved interface surface can be used. In some examples, the filaments can include polyethylene fibers such as Dyneema® fibers from Avient Corporation (USA), Spectra® fibers from Honeywell International Inc. (USA), aramid fibers, nylon fibers, other polymeric fibers, natural fibers, woven fabrics made of these fibers, metal wires, metal cables, or combinations thereof. The filaments can have a variety of forms. In some examples, the filaments can include monofilaments, fibers, twisted strands, braided strands, rope, string, cord, cable, ribbon, tape, or other form factors.

Figure 5:
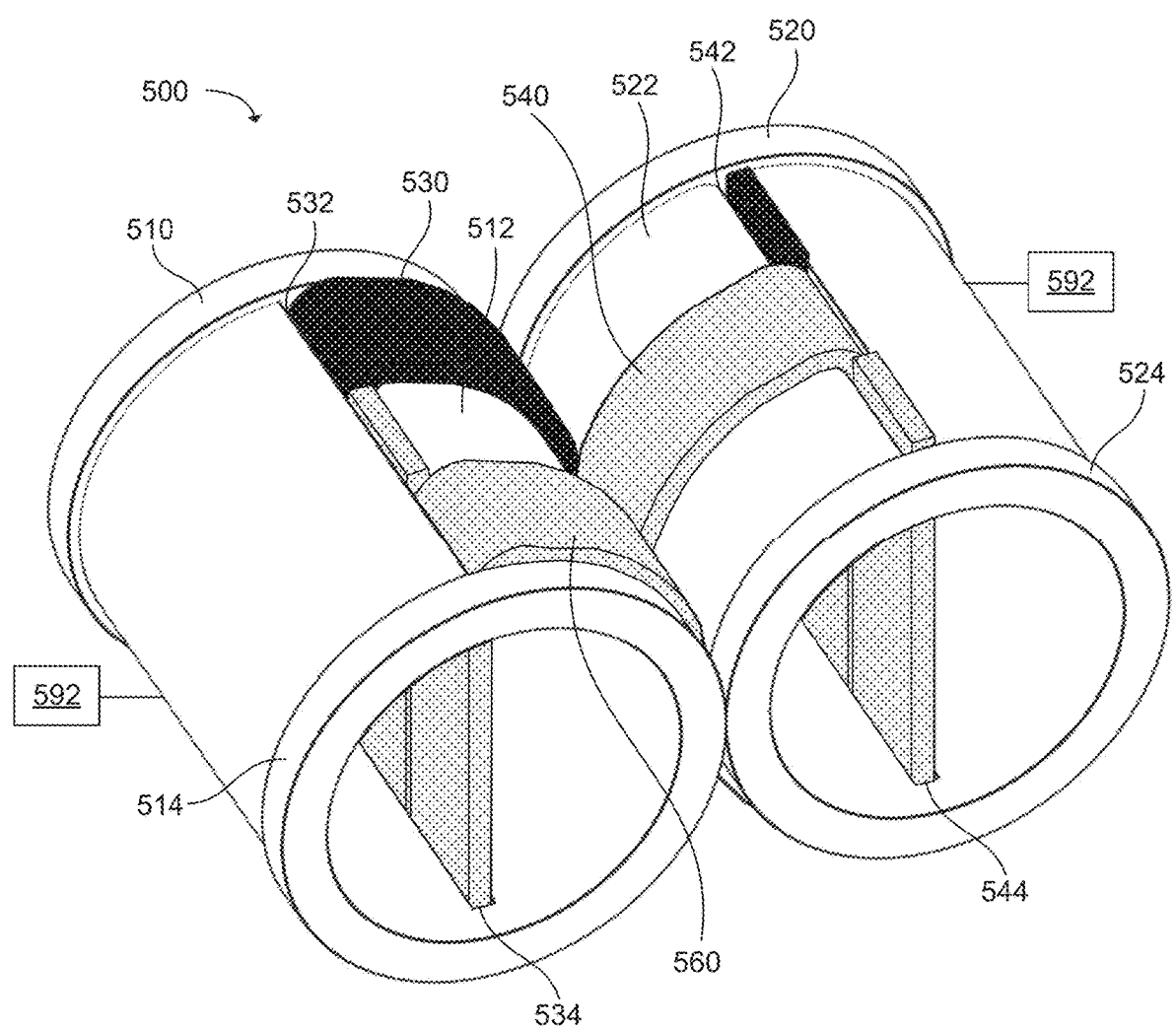
FIG. 5 is a perspective view of another example joint implant in accordance with the present technology.

In some examples, the filaments can be ribbons. As used herein, the term "ribbon" refers to filaments that have a wide, flat shape with a width (measured along an axis orthogonal to a longitudinal axis of the filament) significantly larger than the thickness of the ribbon. FIG. 5 shows a perspective view of an example joint implant 500 that includes ribbons as the filaments. In this example, the proximal joint implant element 510 and the distal joint implant element 520 have a hollow cylindrical shape. A first filament segment 530 extends from a slot 532 formed in the proximal curved interface surface 512 of the proximal joint implant element. The first filament segment extends from this slot and then extends along a portion of the proximal curved interface surface until reaching a location between the proximal joint implant element and the distal joint implant element. The first filament segment then switches to extending along the distal curved interface surface 522 of the distal joint implant element. The first filament segment then extends to a slot 544 formed in the distal curved interface surface. The slots act as the attachment points for the ribbon-shaped filaments in this example. The first filament segment is a portion of longer ribbon-shaped filament; specifically, the first filament segment refers to the segment of the filament extending from the slot 532 to the slot 544. The ends of the filament extend through the slots into the hollow interiors of the proximal and distal joint implant elements. The tips of the filament are then secured in slots on the opposite interior surfaces of the proximal and distal joint implant elements. A second filament segment 540 extends from another slot 534 on the proximal curved interface surface, then along the proximal curved interface surface to the location between the joint implant elements. At this location, the second filament segment crosses the first filament segment. Specifically, when the joint implant is viewed from the side, the filament segments cross at this location between the proximal and distal joint implant elements. The second filament segment then extends along the distal curved interface surface to a slot 542. Similar to the first filament segment, the second filament segment is also a portion of a longer filament that extends inside the hollow interiors of the of the proximal and distal joint implant elements and is secured in slots on the opposite interior surfaces of the hollow interiors. This example also includes a third filament segment 560. The third filament segment extends parallel to the first filament segment and attaches to slots in the same way as the first filament segment. The third filament segment also crosses the second filament in the same direction as the first filament segment. The filament segments are arranged symmetrically from side-to-side of the joint implant, with the first and third filaments being outer filaments near the sides of the implant. The second filament is an inner filament located between the first and third filaments. The filaments in this example are in direct lateral contact with adjacent filaments. The curved interface surfaces also include raised portions 514, 524 that can contact each other and roll against each other. The space between the raised surfaces forms a wide groove or channel that accommodates the filament segments. FIG. 5 also shows boxes 592, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

In further examples, the filaments can be cords, meaning any elongated shape that has a width and a thickness that are approximately equal. Whereas ribbons can have a width that is many times greater than their thickness, cords can have a width that is about the same as their thickness. In some cases, cords can have an aspect ratio of width to thickness from about 1:2 to about 2:1. In contrast, ribbons can have an aspect ratio of width to thickness from more than 2:1 to about 200:1 or more. Cords can include monofilaments, fibers, twisted strands, braided strands, ropes, strings, cables, threads, etc.

Figure 6A:
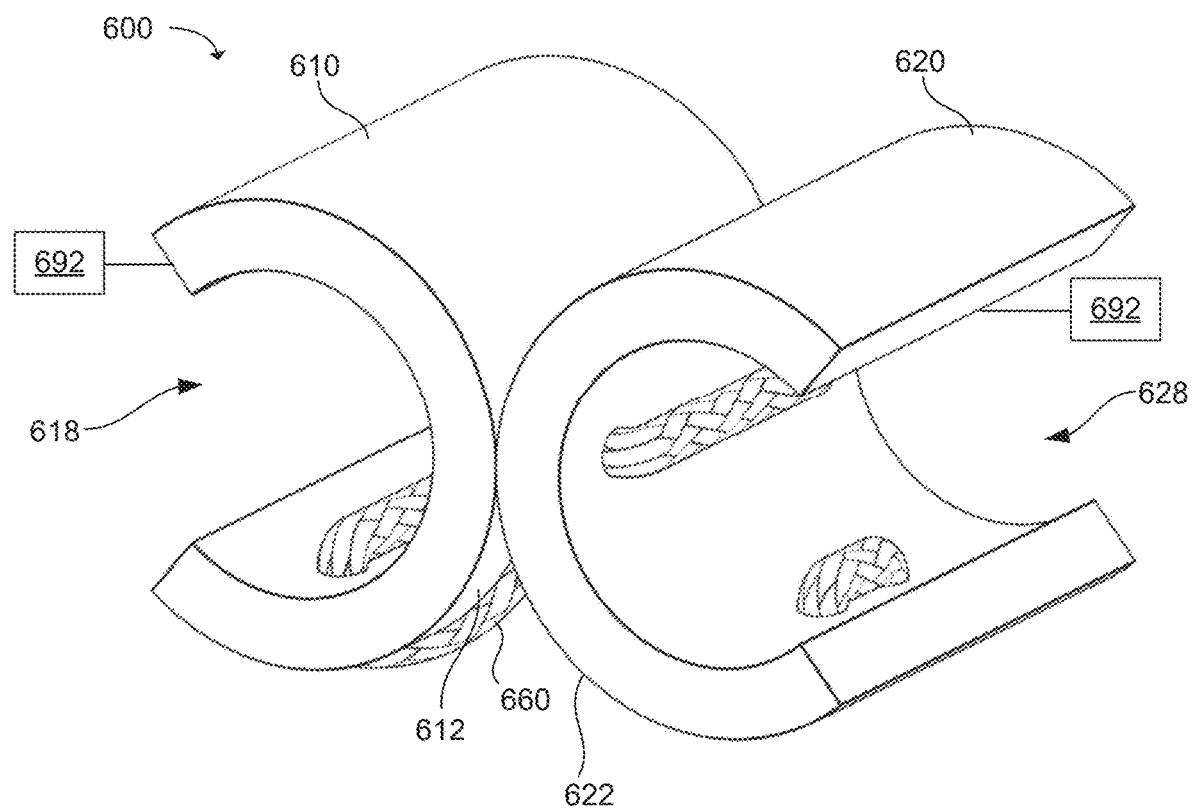
FIGS. 6A-6D illustrate another example joint implant in accordance with the present technology.
Figure 6B:
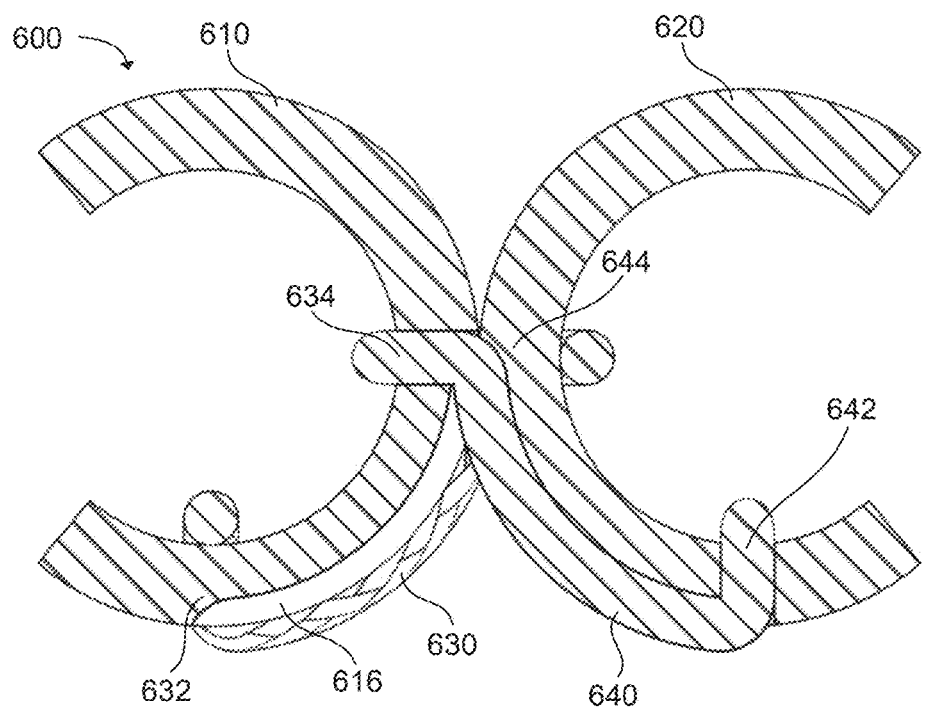
Figure 6C:
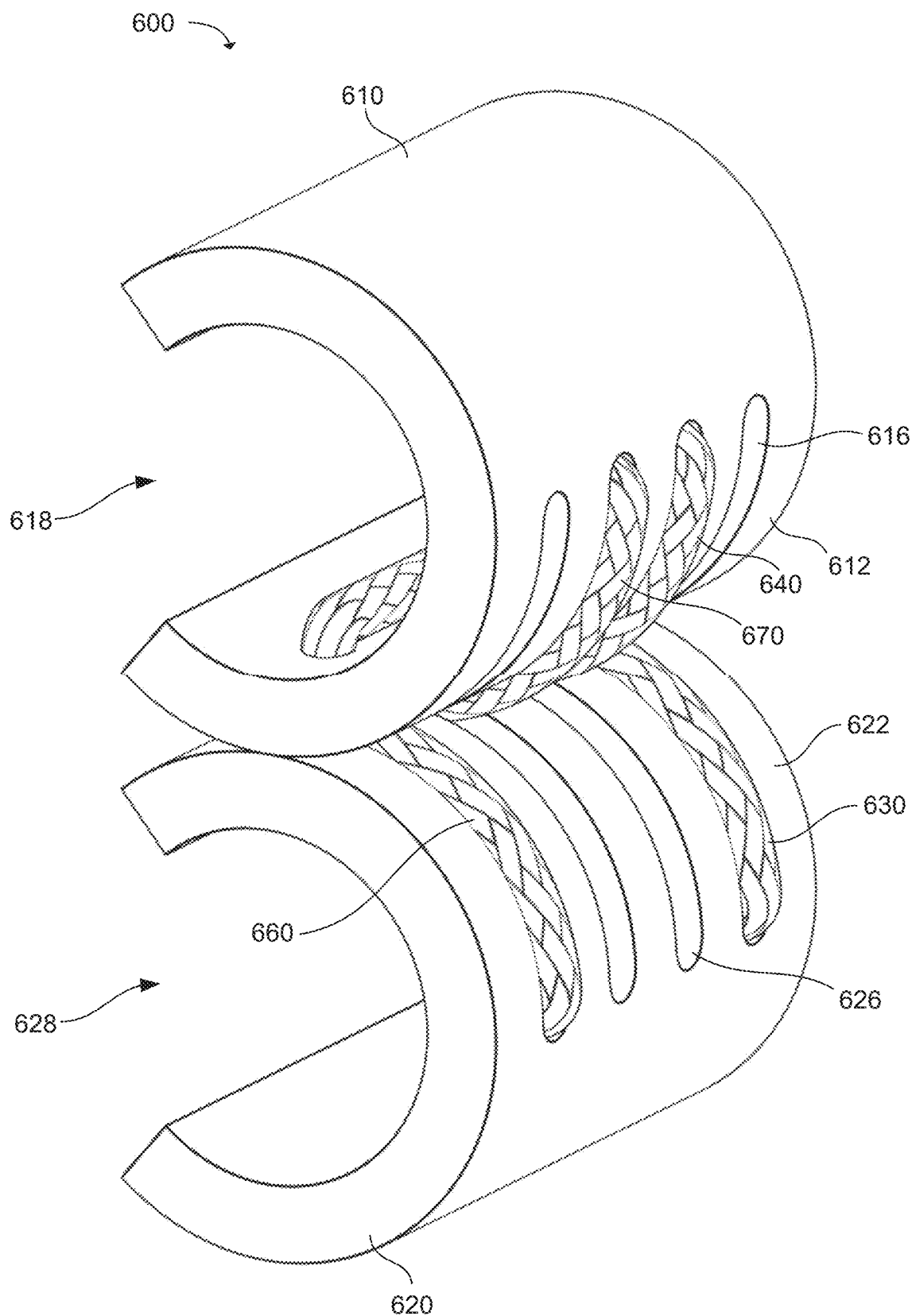
Figure 6D:
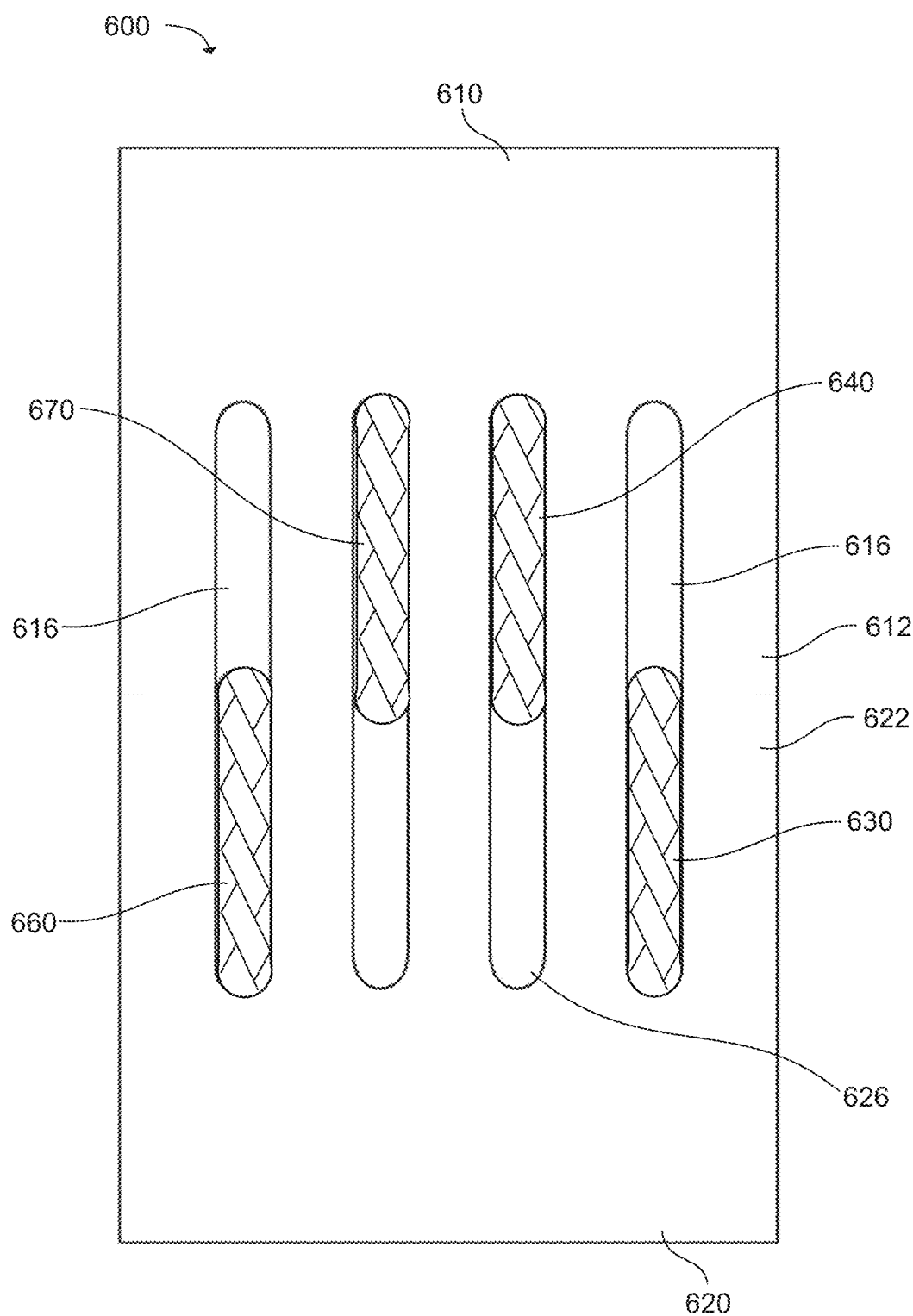

FIG. 6A shows a perspective view of an example joint implant 600 that has cord-shaped filaments. This example includes a proximal joint implant element 610 and a distal joint implant element 620, which are both shaped as cylinders having a gap 618, 628 in the cylinder facing away from the curved interface surfaces 612, 622. FIG. 6B shows a side cross-sectional view of the joint implant 600, to more clearly show how the filaments are configured to extend along the curved interface surfaces 612, 622. A first filament segment 630 extends from an attachment point 632 on the proximal joint implant element 610 to an attachment point 644 on the distal joint implant element 620. In this example, the attachment points are holes formed in the cylinder-shaped joint implant elements, leading to the hollow interiors of the joint implant elements. In this example, the first filament segment 630 extends from the proximal joint implant element 610 to the distal joint implant element 620 in a bottom-up direction. A second filament segment 640 extends in a top-down direction, from an attachment point 634 on the proximal joint implant element 610 to an attachment point 642 on the distal joint implant element 620. In this example, the filament segments are portions of longer filaments shaped as loops. The first filament segment 630 is a portion of a wide filament loop that forms two outer filament segments, and the second filament segment 640 is a portion of a narrow filament loop that forms two inner filament segments, as shown in FIGS. 6B-6D. The proximal curved interface surface comprises proximal grooves 616, and the distal curved interface surface comprises distal grooves 626. In this example, the proximal grooves and distal grooves have a depth that is about half the thickness of the filament segments, or a little more than half the thickness of the filament segments. These grooves are aligned so that the filament segments can be accommodated within the grooves while surrounding areas of the curved interface surfaces 612, 622 contact one another direction. The areas of the proximal and distal curved interface surfaces that directly contact one another can be referred to as a proximal contact portion and a distal contact portion. One proximal groove made to accommodate the second filament segment is visible in FIGS. 6B-6C. The other grooves can be seen more easily in FIG. 6C, which shows the joint implant element in a flexed position. It is noted that the grooves are not visible in FIG. 6A because the grooves do not extend all the way around the circumference of the joint implant elements, but rather extend along an approximately 90° pathway, which occupies about a quarter of the circumference. FIG. 6C also clearly all of the filament segments. FIG. 6D also shows a front view of the joint implant in the flexed position. The first filament segment is nearest to one side of the joint implant. A third filament segment 660 is nearest to the opposite side of the joint implant. The first filament segment 630 and the third filament segment 660 are both portions of the wide filament loop, which loops through the holes and across the interior surfaces of the hollow interior of the proximal and distal joint implant elements. A fourth filament segment 670 is positioned adjacent to the second filament segment. The second and fourth filament segments 640, 670 are inner filament segments, positioned between the outer filament segments. The second and fourth filament segments 640, 670 extend in the same direction, crossing the first and third filament segments 630, 660 at a location between the proximal and distal joint implant elements 610, 620. The second and fourth filament segments are both portions of a narrow inner filament loop, which also extends through the holes in the joint implant elements and across a portion of the interior surfaces of the proximal and distal joint implant elements 610, 620. Although the filament segments are portions of loops of two filaments in this example, a similar joint implant element can be made with four separate filaments, where each filament segment comprises a portion of one of the four separate filaments. Another example can also be made with a single larger filament loop that is configured to go through all the holes and form all four of the filament segments. FIG. 6A also shows boxes 692, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. Again, it is noted that the grooves formed in the curved interface surfaces can comprise the same or a different profile (i.e., size, shape and/or configuration of surfaces) than that of the curved interface surfaces. In addition, the depth of the grooves measured from the face of the respective curved interface surfaces can vary along the length of the grooves. Still further, one or more surfaces of the grooves can comprise texturing or objects or elements formed with or otherwise supported from the surface(s), such as protrusions (e.g., bumps, barbs, etc.), to enhance the engagement of the filaments with the surface(s) of the grooves.

In some examples, the filament segments used in a joint implant can all be the same type of filament, while in other examples, multiple different types of filaments can be combined. The example shown in FIG. 5 includes ribbon-shaped filaments, and the example shown in FIGS. 6A-6D includes braided cord-shaped filaments. The size and shape of the filaments can be selected to fit the particular joint implant. In some examples, the filaments can have a width from about 0.1 mm to about 2 cm. Widths above a few millimeters can be useful for ribbon-shaped filaments in some examples. In further examples, the width of the filaments can be from about 0.1 mm to about 1 cm, or from about 0.1 mm to about 5 mm, or from about 0.1 mm to about 3 mm, or from about 0.1 mm to about 2 mm, or from about 0.1 mm to about 1 mm, or from about 0.1 mm to about 0.5 mm, or from about 0.5 mm to about 5 mm, or from about 0.5 mm to about 3 mm, or from about 0.5 mm to about 2 mm, or from about 0.5 mm to about 1 mm, or from about 1 mm to about 5 mm, or from about 1 mm to about 3 mm, or from about 1 mm to about 2 mm. In further examples, the thickness of the filaments can be from about 0.1 mm to about 3 mm, or from about 0.1 mm to about 2 mm, or from about 0.1 mm to about 1 mm, or from about 0.1 mm to about 0.5 mm, or from about 0.5 mm to about 3 mm, or from about 0.5 mm to about 2 mm, or from about 0.5 mm to about 1 mm, or from about 1 mm to about 3 mm, or from about 1 mm to about 2 mm.

The filaments can be spaced apart over the curved interface surfaces in some examples. The spacing distance can be from about 0.5 mm to about 10 mm, or from about 0.5 mm to about 5 mm, or from about 0.5 mm to about 2.5 mm, or from about 1 mm to about 2.5 mm, or from about 1 mm to about 5 mm in some examples. The spacing distance can be a lateral distance between adjacent filaments at the location where the filaments cross between the curved interface surfaces.

In other examples, the filaments can be positioned in direct contact with one or more adjacent filaments. In certain examples, all of the filaments can be positioned to contact each adjacent filament at least in the location where the filaments cross between the curved interface surfaces. The filaments can provide resistance to shearing motion of the joint implant elements relative to one another when the filaments are in direction contact one with another, as the filaments do not have any empty space to slide laterally.

Non-limiting examples of materials that can be included in the filaments can include polyethylene, low density polyethylene, high density polyethylene, ultra-high molecular weight polyethylene, Dyneema® fibers from Avient Corporation (USA), Ulteeva Purity™ fibers from DSM Biomedical (Netherlands), Spectra® fibers from Honeywell International Inc. (USA), aramid fibers, nylon fibers, medical grade biocompatible fibers, radiopaque fibers, natural fibers, steel, stainless steel, surgical steel, titanium, and combinations thereof.

In certain examples, radiopaque filaments can be useful because these filaments can be visible by X-ray or other imaging methods. This can allow the position and condition of the filaments to be inspected non-invasively. However, in some cases radiopaque filaments can obscure the bones of a joint in X-ray images, which can make it difficult to inspect the bones noninvasively. In certain examples, the filaments can have a radiopaque portion in the space between the curved interface surfaces of the joint implant elements, while other portions of the filaments can be radio transparent. In some examples, the radiopaque portions of the filaments can be formed by dyeing the portion of the filaments with a radiopaque dye.

The filaments can have an elastic modulus from about 1 GPa to about 200 GPa, or from about 1 GPa to about 100 GPa, or from about 1 GPa to about 50 GPa, or from about 1 GPa to about 20 GPa, or from about 1 GPa to about 5 GPa, or from about 5 GPa to about 200 GPa, or from about 5 GPa to about 100 GPa, or from about 5 GPa to about 50 GPa, or from about 5 GPa to about 20 GPa, or from about 20 GPa to about 200 GPa, or from about 20 GPa to about 100 GPa, or from about 20 GPa to about 50 GPa, or from about 50 GPa to about 200 GPa, or from about 50 GPa to about 100 GPa, or from about 100 GPa to about 200 GPa, or from about 80 GPa to about 120 GPa, in some examples.

The filaments can have a maximum extension at break from about 0.5% to about 15%, or from about 0.5% to about 10%, or from about 0.5% to about 5%, or from about 0.5% to about 2%, or from about 0.5% to about 1%, or from about 1% to about 15%, or from about 1% to about 10%, or from about 1% to about 5%, or from about 1% to about 2%, or from about 2% to about 15%, or from about 2% to about 10%, or from about 2% to about 5%, or from about 5% to about 15%, or from about 5% to about 10%. In some examples, the joint implant can include at least three filament segments. The filament segments can be arranged with a pair of the filament segments nearer to the sides of the joint implant (the outer filament segments) extending parallel to one another. Thus, the pair of outer filament segments can both extend in the same direction from the proximal joint implant element to the distal joint implant element. In some examples, the pair of outer filament segments can both extend in a top-down direction. In other examples, both of the outer filament segments can extend in a bottom-up direction. One or more inner filament segments can be positioned between the outer filament segments (i.e., between the outer filament segments in a side-to-side direction). At least one of the inner filament segments can extend between the proximal and distal joint implant elements in the opposite direction to the outer filament segments. In further examples, if there are multiple inner filament segments then some of the inner filament segments can also extend parallel to the outer filament segments, as long as at least one inner filament segment extends in the opposite direction. In some examples, multiple inner filament segments can alternate in the direction that they extend between the proximal and distal joint implant elements.

The curved interface surfaces can include grooves to receive and to provide space for the filament segments. Grooves on the proximal curved interface surface can be referred to as proximal grooves, and grooves on the distal curved interface surface can be referred to as distal grooves. In some examples, a single wide groove can receive and accommodate multiple filament segments side by side, as in the example of FIG. 5. In other examples, individual grooves can receive and accommodate individual filament segments, as in the example of FIGS. 6A-6D. The grooves can have a width equal to or greater than the filament segment. In some examples a groove that is sized to accommodate a single filament segment can have a width that is from about 100% to about 150%, or from about 100% to about 130%, or from about 100% to about 120%, or from 100% to about 110% of the width of the filament segment. In further examples, the grooves can have a depth of at least half the thickness of the filament. If the grooves on the proximal and distal curved interface surfaces are aligned, and if both grooves have a depth of at least 50% of the thickness of the filament segment, the grooves will have enough space together to accommodate the filament segment. In some examples, the grooves can have a depth from about 50% to about 100%, or from about 50% to about 80%, or from about 50% to about 70%, or from about 50% to about 60% of the thickness of the filament segments. In some examples, both of the curved interface surfaces can include grooves. In certain examples, the grooves on each curved interface surface can be aligned with each other. In other examples, grooves can be present on one curved interface surface but not on the other curved interface surface. Alternatively, grooves can be present on both curved interface surfaces, but the grooves can be offset instead of aligned.

The joint implant can be designed so that the curved interface surfaces contact each other directly and roll on each other when the joint flexes and/or extends. In some examples, the filament segments can be received and accommodated in grooves as explained above, and this can allow portions of the curved interface surfaces around the grooves to directly contact each other. In other examples, the curved interface surfaces may not directly contact one another, and the filament segments can separate the curved interface surfaces from each other. In these examples, a curved interface surface can roll on the filaments instead of directly rolling on the opposite curved interface surface. However, in these examples the rolling motion of the joint implant elements can be very similar to the rolling motion when the curved interface surfaces roll directly on each other. In some examples, the curved interface surfaces can roll without slipping, whether the surfaces are directly contacting the opposite curved interface surface or the filament segments.

In further detail regarding the attachment points for the filament segments, the examples of FIG. 5 and FIGS. 6A-6D show attachment points that are formed as holes in the proximal and distal joint implant elements. The filament segments can be inserted into the holes so that the ends of the filament segments are tensioned and retained in the holes. In some examples, the filament segments can be part of filament loops like in FIGS. 6A-6D, and the filament loops can be looped through multiple holes. In other examples, the filament segments can be part of filaments that are tensioned and retained in the holes by tying a knot in a portion of the filament adjacent the opposite side of the hole, or by melting and fusing a portion of the end of the filament extending through the hole to the interior of the joint implant element, or a combination thereof. In some examples, the end of the filament can pass through a hole, and then a knot and/or fused portion can be formed on the end inside the interior portion of the joint implant on the opposite side of the hole. In other examples, the filament can extend through a hole and across an interior portion of the join implant element. The filament can then extend through a second hole in the joint implant element, and then a knot and/or a fused portion can be formed to hold the end of the filament in place. In all of these examples, the filaments are secured to the proximal and distal joint implant elements under tension.

In some examples, the attachment points for the filament segments can be on the curved interface surfaces of the joint implant elements. However, in other examples, the attachment points can be on the base portion of a joint implant element. The base portion of the joint implant element can include any portion of the joint implant element other than the curved interface surface. Therefore, if an attachment point is located anywhere on a joint implant element that is not on the curved interface surface, then the attachment point can be considered to be on the base portion of the joint implant element.

Figure 7A:
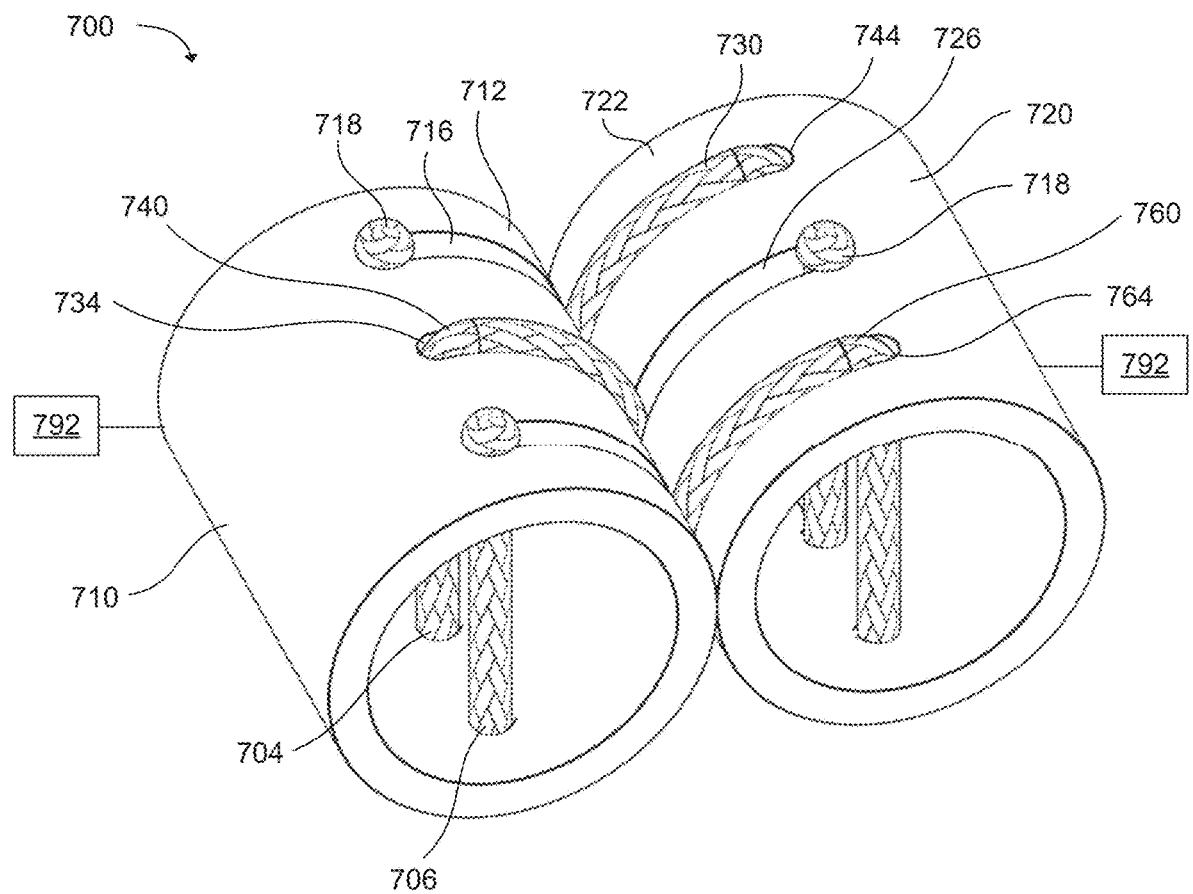
FIGS. 7A-7B illustrate a further example joint implant in accordance with the present technology.
Figure 7B:
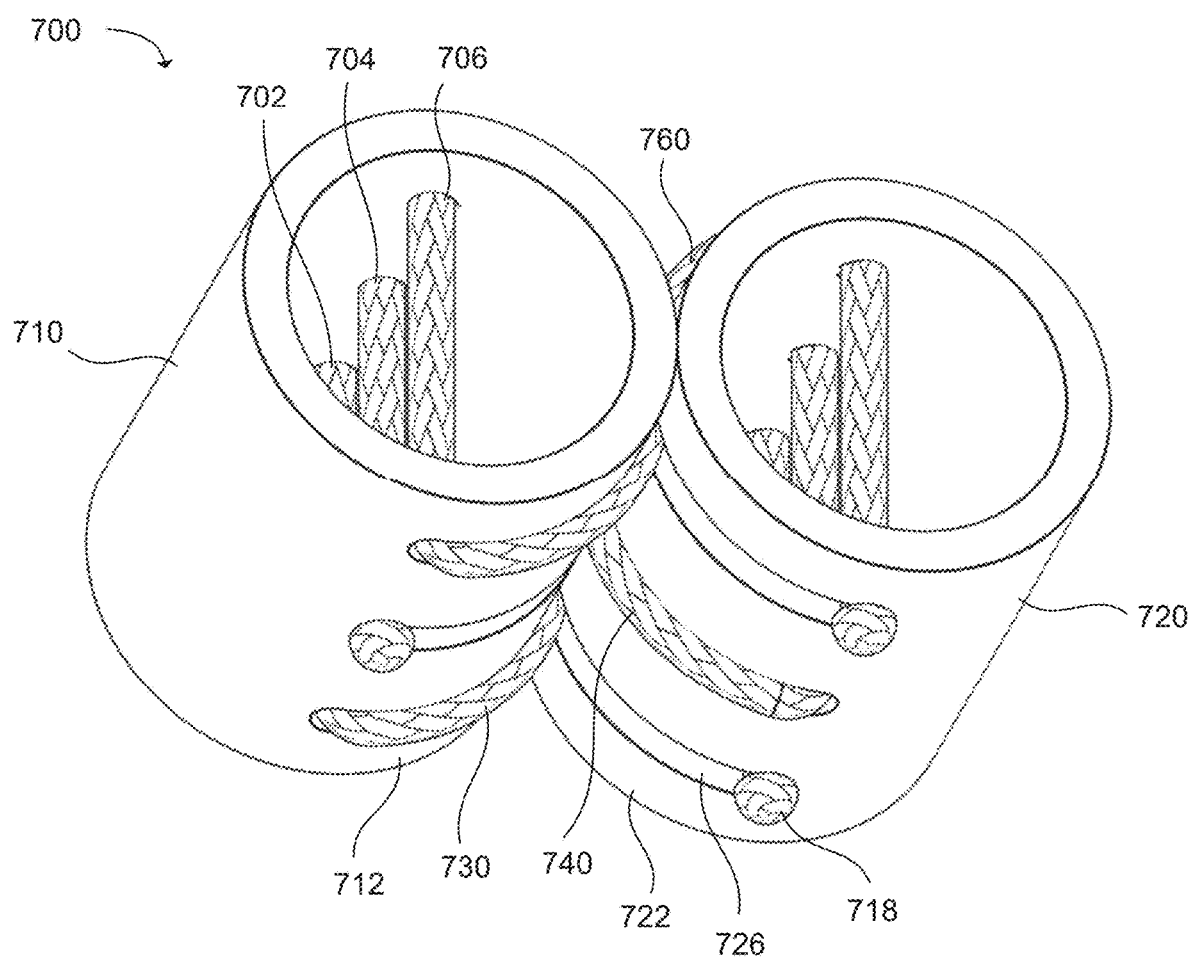

FIG. 7A shows a perspective view of another example joint implant 700. FIG. 7B shows another perspective view of the joint implant 700 from a lower angle. This example includes a proximal joint implant element 710 and a distal joint implant element 720 that are both shaped as hollow cylinders. The proximal joint implant element 710 includes a proximal curved interface surface 712 that faces towards a distal curved interface surface 722 on the distal joint implant element 720. The joint implant elements are coupled together by three filaments 702, 704, and 706. The first filament 702 includes a first filament segment 730 that extends from an attachment point 732 on the proximal joint implant element 710 to an attachment point 744 on the distal joint implant element 720. The second filament 704 includes a second filament segment 740 that extends from an attachment point 734 on the proximal joint implant element 710 to an attachment point 742 on the distal joint implant element 720. The second filament segment 740 extends in an opposite direction to the first filament segment 730, so that the first and second filament segments cross. The third filament 706 includes a third filament segment 760 that extends from an attachment point 762 on the proximal joint implant element 710 to an attachment point 764 on the distal joint implant element 720. The third filament segment 760 is parallel to the first filament segment 730, so it crosses the second filament segment 740 in same direction as the first filament segment 730. Additionally, the first and third filament segments are outer filament segments that are close to the sides of the joint implant 700. The filament segments are received and accommodated in proximal grooves 716 and distal grooves 726 formed in the curved interface surfaces. The attachment points for the filament segments are holes in the joint implant elements. The ends of the filament segments are held in the holes. The filaments that include the filament segments extend through the holes into the hollow interiors of the joint implant elements. The filaments then extend across to an opposite surface of the joint implant element, through another hole, and are secured by a knot 718 outside the other hole. In this example, the knots can serve as stoppers or stopping points to define the end point of motion of the joint. If one of the joint implant elements rotates to the point that one of the knots contacts the filament segment on the opposite joint implant element, then the rotation will stop because the knot prevents any further rotation. In some examples, the knots can be melted or fused if the filament is made of a meltable or fusable material. This can help ensure that the knots will not come undone. In other examples, the end of the filament can be melted or fused without tying a knot, but the melted or fused portion can have a width wider than the hole so that the filament is secured in the hole by the melted or fused portion. The melted or fused portion can also act as a stop to define the end point of the motion of the joint. FIG. 7A also shows boxes 792, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

With respect to any of the example joint implants discussed herein and shown in the drawings, the joint implant can be configured to provide a specific range of motion. The range of motion of the joint implant can be approximately the same as the range of motion of a physiologic joint to be replaced with the joint implant in some examples. For example, a proximal interphalangeal (PIP) joint can have a range of motion from about 0° at an extended position to about 110° at a flexed position in some examples. In one example, a joint implant as described herein can have a range of motion from about 0° at an extended position to between about 100° and 120° at a flexed position to match the natural range of motion of the PIP joint. In further examples, a joint implant configured to replace a distal interphalangeal (DIP) joint can have a range of motion from about 0° at an extended position to between about 60° and 80° at a flexed position. A joint implant configured to replace a metacarpophalangeal (MCP) joint can have a range of motion from about 0° at an extended position to between about 50° and 70° at a flexed position. A joint implant configured to replace an elbow joint can have a range of motion from about 0° at an extended position to between about 130° and 160° at a flexed position. A joint implant configured to replace a knee joint can have a range of motion from about 0° at an extended position to between 120° and 140° at a flexed position. Thus, the joint implant itself can be configured to approximately match the natural range of motion of the joint.

In other examples, the joint implant can be configured to have a range of motion greater than the natural range of motion of the joint that is to be replaced. In certain examples, the joint implant can be implanted in a patient so that other tissues of the patient can constrain the motion of the joint. For example, the joint implant can be implanted into bones of a joint in such a way that the heads of the bones provide a stopping point to stop movement of the joint at a desired position. In one example, the bones can stop the motion of the joint when the joint reaches a fully extended position, to prevent hyperextension of the joint. In another example, the bones can be shaped in a way that blocks the flexing motion of the joint when the joint reaches a certain degree of flexure. Alternatively, soft tissues of the patient can constrain the range of motion of the joint. The soft tissues can include muscles, tendons, ligaments, skin, etc. For example, the flexing motion of a joint can be stopped when the soft tissues between the bones of joint become compressed and prevent any further flexing of the joint.

The joint implant can be configured to have a specific range of motion by selecting appropriate locations for the attachment points of the filament segments. As explained above, the filament segments unwind from one curved interface surface and wind onto the opposite curved interface surface when the joint implant is moving. The filament segments switch from one curved interface surface to the other at the crossing point, where the first filament segment crosses the second filament segment. This crossing point moves as the joint implant rolls and rotates. Eventually, the crossing point can reach one of the attachment points where the filament segment ends. The filament segment runs out and the joint implant elements cannot rotate anymore, so the motion stops. Thus, the attachment points of the filament segments can act as stopping points to define the range of motion of the joint implant. As an example, the joint implant shown in FIG. 1A-1D has filament attachment points that are about 180° apart from one another on the curved interface surfaces. Specifically, the attachment point for the first filament segment and the attachment point for the second filament segment are located 180° apart on the circular curve interface surface of each joint implant element. With the attachment points at these locations, the distal joint implant element is able to rotate 180° clockwise or 180° counterclockwise, starting at the fully extended position in FIG. 1A. If the distal joint implant element rotates 180° clockwise, then the distal joint implant element will be positioned under the proximal joint implant element and facing the opposite direction. If the distal joint implant element rotates 180° counterclockwise, then the distal joint implant element will be positioned above the proximal joint implant element and facing the opposite direction. The distal joint implant element will not be able to rotate any farther than 180° in either direction because the point where the filament segments cross will reach one of the attachment points, and there will be no more filament left to wind around the distal joint implant element.

In some examples, the range of motion of the joint implant can be about twice the angular difference between the attachment point of the first filament segment and the attachment point of the second filament segment on a given joint implant element. In the example shown in FIGS. 1A-1D, the attachment point of the first filament segment and the attachment point of the second filament segment are 180° apart, and the joint implant has a range of motion of 360° (i.e., 180° in both directions starting from the extended position). In another example, the attachment points of the first and second filament segments can be 90° apart, and the joint implant can have a range of motion of 180°. In another example, the attachment points can be 45° apart and the joint implant can have a range of motion of 90°. In various examples, attachment points of the first and second filament segments can be anywhere from 45° to 180° apart from each other on the curved interface surface of either the proximal or the distal joint implant element. The total range of motion of the joint implant can be from 0° to 360°, or from 30° to 210°, or from 30° to 160°, or from 30° to 130°, or from 30° to 110°, or from 30° to 90°, or from 30° to 70°, or from 30° to 50°, or from 45° to 160°, or from 45° to 130°, or from 45° to 110°, or from 45° to 90°, or from 45° to 70°, or from 70° to 160°, or from 70° to 130°, or from 70° to 110°, or from 70° to 90°, in some examples. These ranges refer to the total number of degrees through the which the joint can flex. When a joint is fully extended, the joint can be considered to be at a position of 0°, and the joint can be capable of flexing to a fully flexed position, and the number of degrees of the fully flexed position can be used to described the range of motion of the joint. As an example, a joint with a range of motion of 90° can move from a fully extended position at 0° to a fully flexed position at 90°. As another example, if the joints can have a "range of motion from 70° to 90°" then the fully flexed position can be anywhere from 70° to 90°, and the joints can be fully extended to a position of 0°.

In other examples, the joint implant can further comprise a feature that acts as a stopper defining a stopping point to constrain the range of motion. In certain examples, a knot, melted portion, or fused portion of the filaments can act as a stopper defining a stopping point. In the example shown in FIGS. 7A and 7B, the knots can act as a stopper defining a stopping point because the knots protrude farther from the curved interface surfaces than the filament segments. Therefore, when the joint implant elements rotate far enough so that the knots contact the filament segments or curved interface surface on the opposite joint implant element, the knots will get in the way of any further rotation. In other examples, the curved interface surfaces can be formed with protrusions that function as stoppers and that will stop rotation of the joint implant elements at a desired point. One or more protrusions can be present on either the proximal curved interface surface, the distal curved interface surface, or both. Such protrusions can be used to restrict the range of motion of the joint implant to any of the ranges of motion described above.

Figure 8:
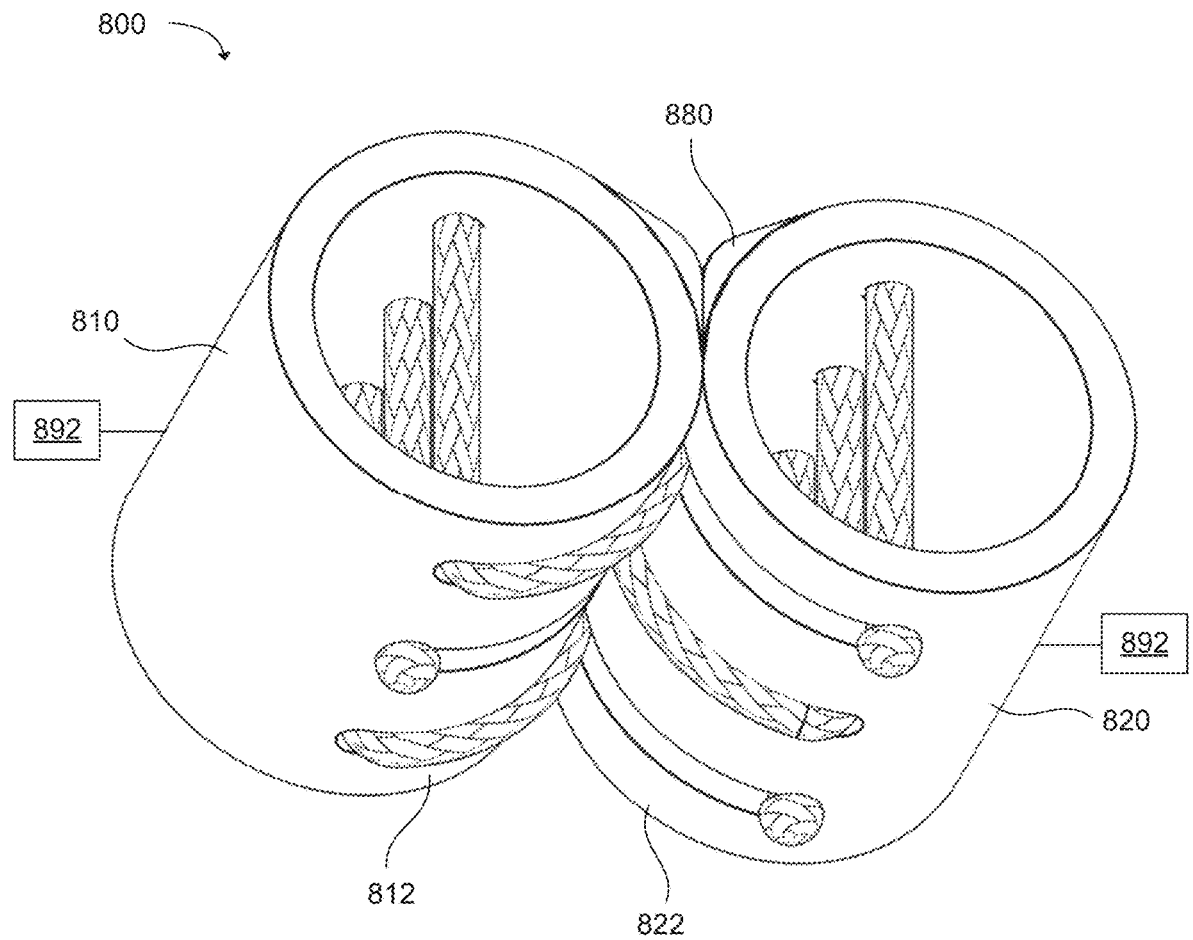
FIG. 8 is a perspective view of a different example joint implant in accordance with the present technology.

FIG. 8 shows a perspective view of another example joint implant 800 that is similar to the joint implant shown in FIGS. 7A-7B. However, this example includes protrusions 880 on the proximal curved interface surface 812 and on the distal curved interface surface 822 that function as stoppers to prevent rotation within the joint implant 800 beyond a certain number of rotational degrees, or in other words to limit the rotation within the joint implant. When the distal joint implant element 820 and the proximal joint implant element 810 rotate relative to one another, for example when the distal joint implant element is caused to rotate counterclockwise relative to the proximal joint implant element, the protrusions are caused to contact and butt up against one another, wherein any further rotation in this direction is stopped. FIG. 8 also shows boxes 892, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

The joint implants described herein can be configured to prevent or minimize shearing, or lateral, movement of the joint implant elements. In some examples, the filament segments can help prevent shearing. As used herein, "shear"

and "lateral" movement refers to sideways motion of one joint implant element with respect to the other joint implant element. When the filament segments are held in grooves that are sized at about the same width or slightly larger than the filament segments, then the presence of the filament segment in the grooves can prevent shearing movement of the joint implant elements. In examples where there are no grooves or where multiple filament segments are in a single groove, the filament segments can be spaced closed together so the filament segments are touching or nearly touching. This can also prevent shearing movement of the joint implant elements.

Figure 21:
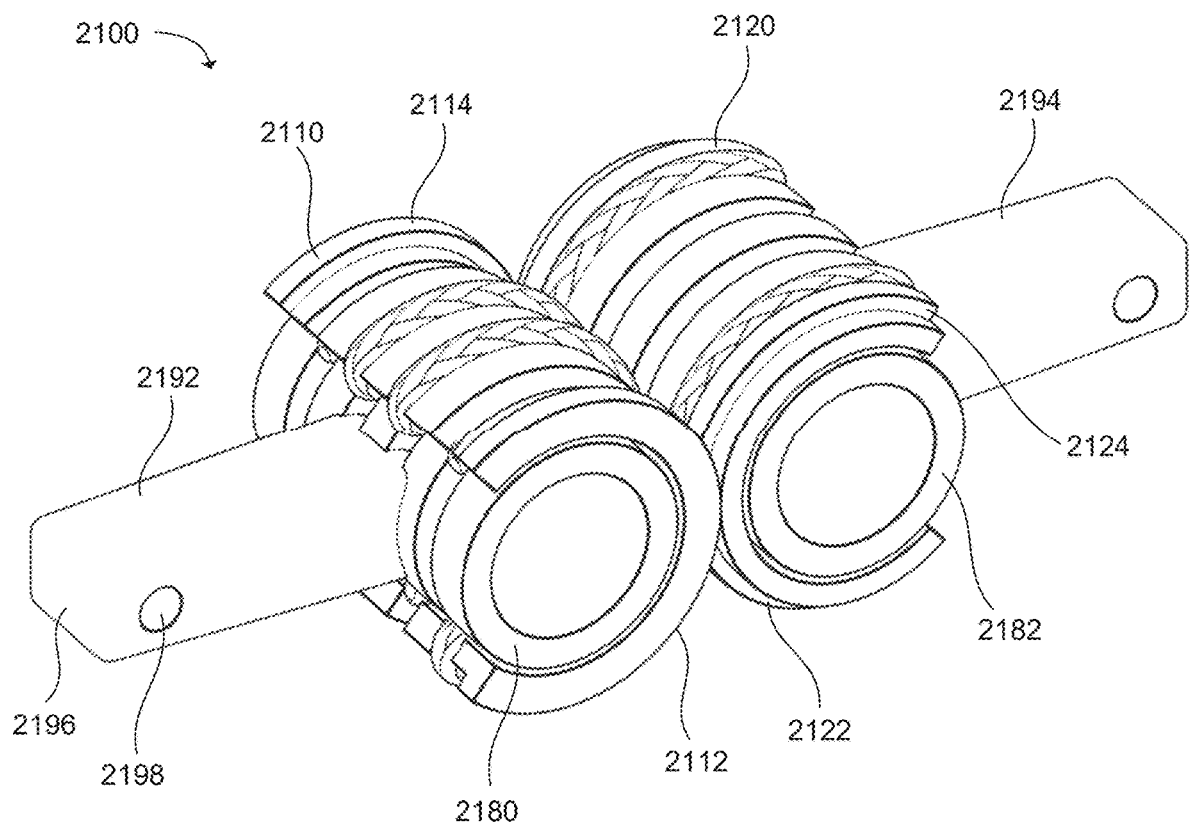
FIG. 21 is a perspective view of another example joint implant in accordance with the present technology.

The curved interface surfaces can also be designed to prevent shearing. In some examples, the curved interface surfaces can include interlocking features that can prevent lateral movement of the joint implant elements with respect to one another. In certain examples, the interlocking features can include a lip or ridge extending from one curved interface surface, and a groove or recess on the opposite curved interface surface that is configured to receive the lip or ridge. These features can be present along the entire curved interface surface or a portion of the curved interface surface. The interlocking features can be configured to allow the joint implant elements to rotate freely while also preventing lateral movement of the joint implant elements with respect to each other. An example of such interlocking features is shown in FIG. 21, which is described in more detail below. In this example, the joint implant 2100 includes a proximal joint implant 2110 with a ridge 2114 at the outer edge of the proximal curved interface surface 2112. The distal joint implant element 2120 includes a recess 2124 at the outer edge of the distal curved interface surface 2122. The ridge pits into this recess so that the curved interface surfaces interlock on with another.

The present disclosure also describes methods of making joint implants that can be used to make any of the joint implants described herein. One example method can include configuring a proximal joint implant element to comprise a proximal curved interface surface, and configuring a distal joint implant element to comprise a distal curved interface surface. The proximal joint implant element can be rotatably coupled to the distal joint implant element to cause the proximal and distal curved interface surfaces to face and interface with one another through a range of motion of the proximal and distal joint implant elements relative to one another. The rotatable coupling step can be accomplished using filaments with one or more filament segments as described above. A first filament segment can be attached to the proximal joint implant element and to the distal joint implant element. A second filament segment can be attached to the proximal joint implant element and the distal joint implant element such that the first filament segment crosses the second filament segment at a location between the proximal and distal joint implant elements.

Controlling the tension in one or more filaments with their one or more filament segments can also be useful in some examples of the present joint implants. When making a joint implant, it can be useful to remove any slack from the filament(s) and filament segments, and to place these in tension. This can help the filament(s) and filament segments to couple the proximal and distal joint implant elements together securely. It can also be useful to use filaments that have low stretchability, so that the length of the filaments can remain about the same even when different amounts of tension are applied to the filament. When the filament(s) and filament segments are configured without slack, and when the filaments and filament segments do not stretch easily, the joint implant elements will be held together securely and the filaments and filament segments will prevent lateral bending and twisting of the joint.

In practice, all filaments can be made of materials that have at least some elasticity. In some examples, a desired amount of tension can be applied to the filament(s) and filament segments to ensure that there is no slack in them and that the proximal and distal joint implant elements will not pull away from each other or twist with respect to each other. The amount of tension applied to the filament(s) and filament segments can be less than an amount that would cause permanent deformation of the filament(s). In particular, and in some examples, the tension on the filament(s) can be within the elastic regime of the filament(s) and not the plastic regime. However, in certain other examples, it can be useful to apply a degree of tension that causes some plastic deformation of the filament(s). For example, inducing a certain degree of plastic deformation can take the filament(s) through the primary creep regime and into the secondary creep regime, which secondary creep regime is less sensitive to creep at a given applied load. In certain examples, the filament(s) can be pre-stretched before being installed in the joint implant. The pre-stretching can take the filament(s) through the primary creep regime and into the secondary creep regime. Because the rate of creep in the secondary creep regime is lower than in the primary creep regime for a given applied load, this pre-stretching can reduce any loss of tension over time due to creep after the filament(s) have been installed in the joint implant. The amount of tension in the filament(s) to achieve this can vary depending upon the configuration of the proximal and distal joint implant elements, the type and configuration of the filament(s) themselves, and other factors. In certain examples, the tension on the filament(s) can be from zero up to 100% of the rated working load of the filament(s). Different filaments can have different rated working loads depending on the material of the filament, the thickness of the filament, etc. For a given filament, the rate working load can be a fraction of the peak or breaking load. The rated working load can be determined based on tests yielding fatigue lives that are consistent with what is desired for the joint implants described herein. As an example, a 2 mm diameter Dyneema® filament (available from Dyneema, Netherlands) can have a breaking load of about 3,000 N. In certain examples, the breaking load can be from about 1,300 N to about 2,300 N, or from about 1,550 N to about 1,800 N. The rated working load can be a fraction of the breaking load, such as 80% of the breaking load, for example. The filament(s) in the joint implants described herein can be under a tension from zero to 100% of this rated working load. The specific tension forces can vary widely depending on the particular filament(s) used. In some examples, the tension applied to the filament(s) can be from 0 N to about 10,000 N, or from 0 N to about 5,000 N, or from 0 N to about 3,000 N, or from 0 N to about 2,000 N, or from 0 N to about 1,000, or from 0 N to about 500 N, or from 0 N to about 100 N, or from 0 N to about 10 N.

In further examples, the joint implants can include a tensioning element. The tensioning element can be any component that applies tension within the filament and filament segments. In some examples, at least one of the proximal joint implant element or the distal joint implant element can have a base portion with a hollow interior. The tensioning element can be positioned within the hollow interior. In some examples, both the proximal and distal joint implant elements can have a base portion with a hollow interior. In further examples, the joint implant can include one tensioning element, two tensioning elements, or more tensioning elements. The one or more tensioning elements can be used to apply tension to all the filaments present in the joint implant. Moreover, the interior surface of the base portion can comprise one or more grooves sized and configured to receive a filament, such as one that is engaged or positioned between the tensioning element and the interior surface of the base portion inside the hollow interior. As such, the grooves formed in the tensioning element can be aligned with the grooves formed in the interior surface of the base portion. The grooves formed in the interior surface of the base portion can be sized and configured in a similar manner as other grooves described herein.

Figure 9:
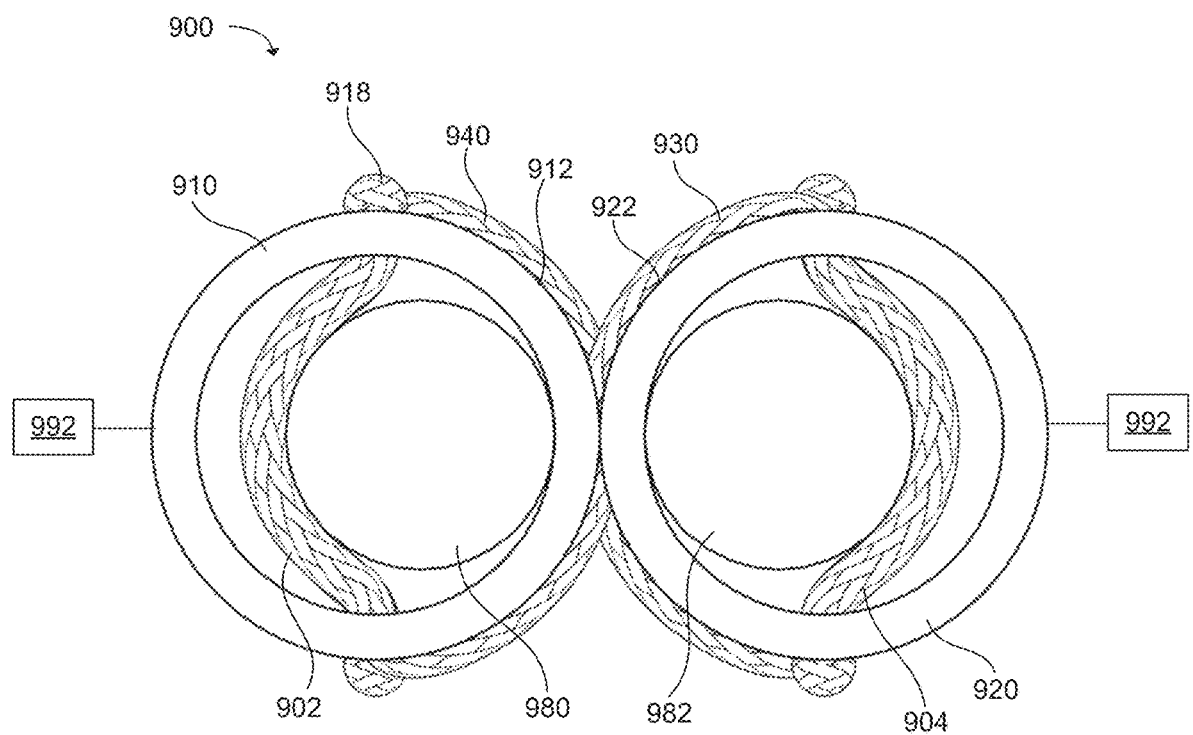
FIG. 9 is a side view of a further example joint implant in accordance with the present technology.

The tensioning elements can have a variety of forms. FIG. 9 shows a side view of one example joint implant 900 that includes tensioning elements 980, 982 inside the hollow interiors of the proximal joint implant element 910 and the distal joint implant element 920. In this example, the first filament segment 930 is a portion of a first filament 902 and the second filament segment 940 is a portion of a second filament 904. The first and second filaments both extend from the proximal joint implant element to the distal joint implant element, and they enter the hollow interiors of the joint implant elements and extend across the hollow interiors to the opposite surfaces of the hollow interiors, where they are held in place with knots 918. This joint implant can be made by threading the filaments through the holes in the joint implant elements in this arrangement, and then the tensioning elements can be placed inside the hollow interiors of the joint implant elements to apply tension to the filaments. In some cases, the tensioning elements can be tapered cylinders. The narrow end of the tapered cylinders can be inserted into the hollow interiors of the joint implant elements next to the filaments, and then the tapered cylinders can be pushed in farther until a desired amount of tension is applied to the filaments. In particular, the tensioning elements are wedged between the filaments and the interior surfaces of the hollow interiors. The tensioning elements apply a force to the filaments in a direction transverse to the longitudinal axis of the filaments. This will create tension along the entire filament, including the filament segments that wrap around the proximal curved interface surface 912 and the distal curved interface surface 922. The tensioning elements can be held in place by compressive force between the filaments and the interior surface of the hollow interior. In certain examples, the tensioning elements can include surface features such as ribs or barbs that can allow the tensioning elements to be pushed in in one direction, but which resist being pulled out in the opposite direction. FIG. 9 also shows boxes 992, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

In another example, the tensioning element can be a spool that can rotate within the hollow interior of the joint implant element to apply tension to the filament. The spool can be a cylinder, a screw, or another shape that can be turned to apply tension to the filament. In some examples, the filament can be secured to the spool in any suitable way before the spool is turned to apply the tension. In certain examples, friction can hold the filament between the spool and the interior surface of the hollow interior of the joint implant element. In further examples, the filament can be at least partially wrapped around the spool.

Figure 10A:
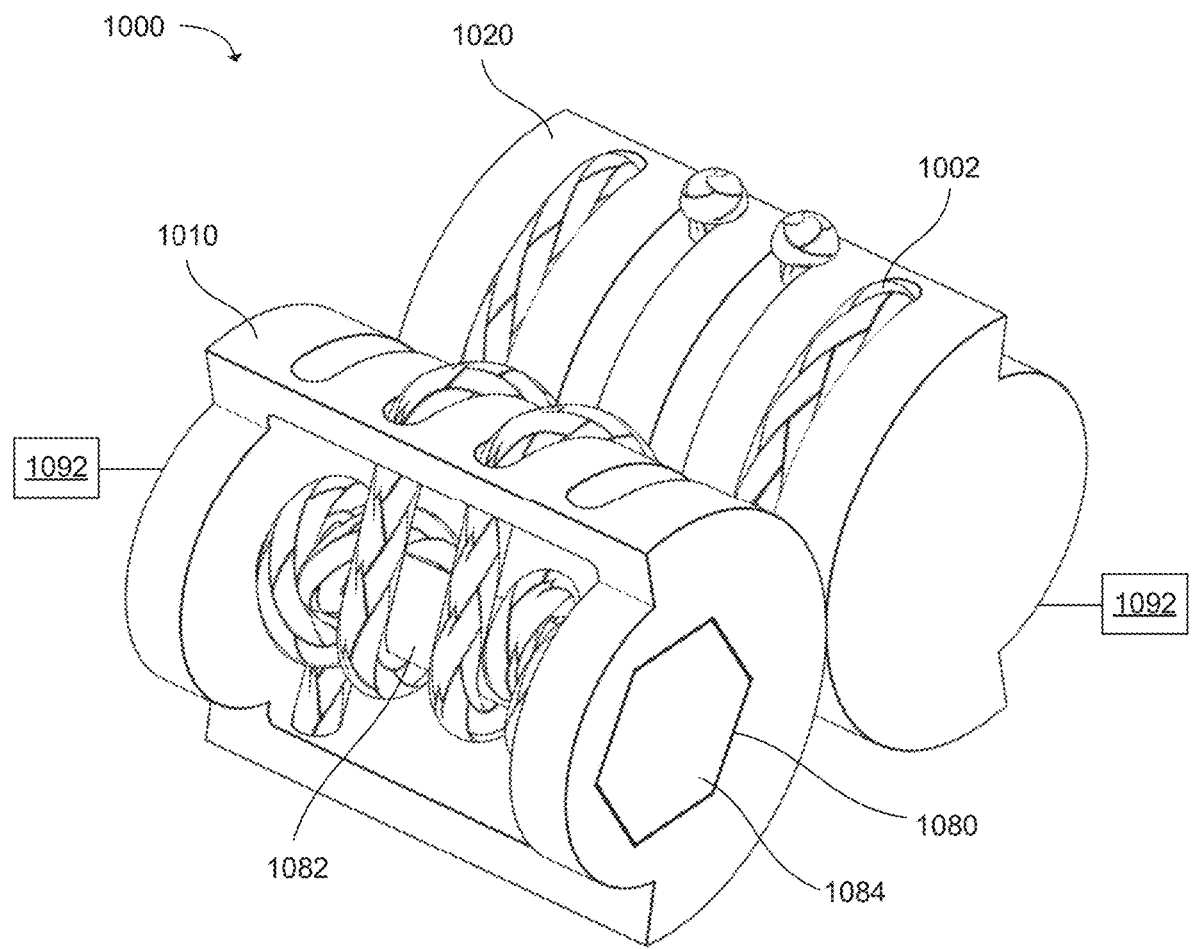
FIGS. 10A-10C illustrate another example joint implant in accordance with the present technology.
Figure 10B:
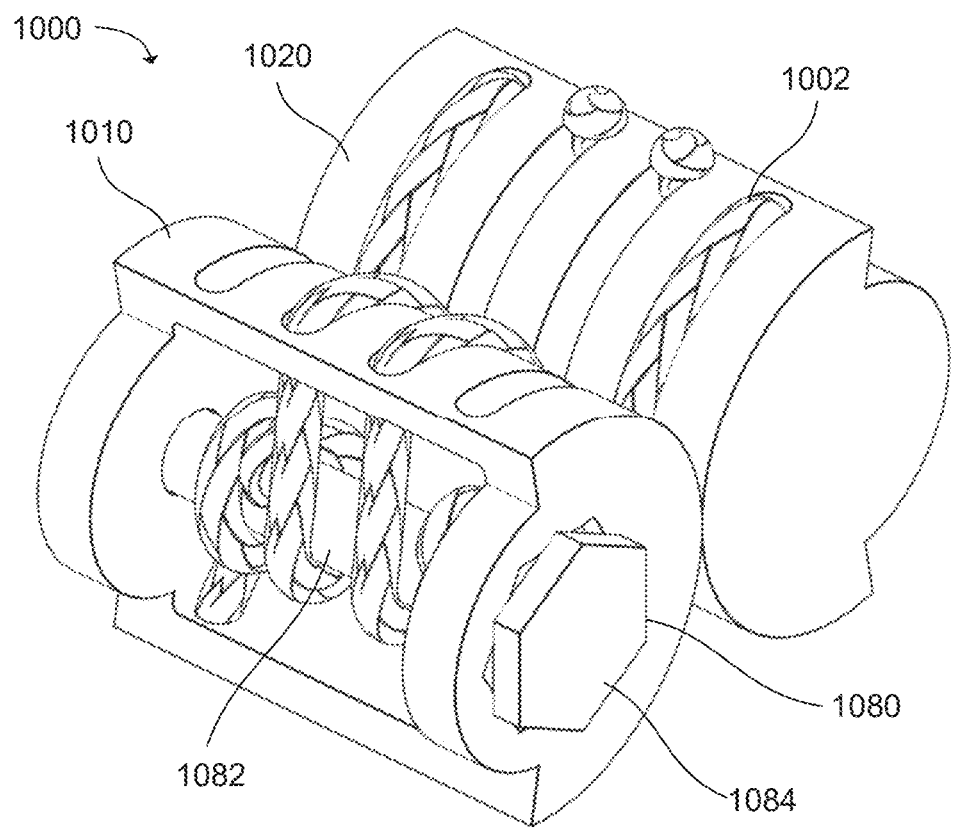
Figure 10C:
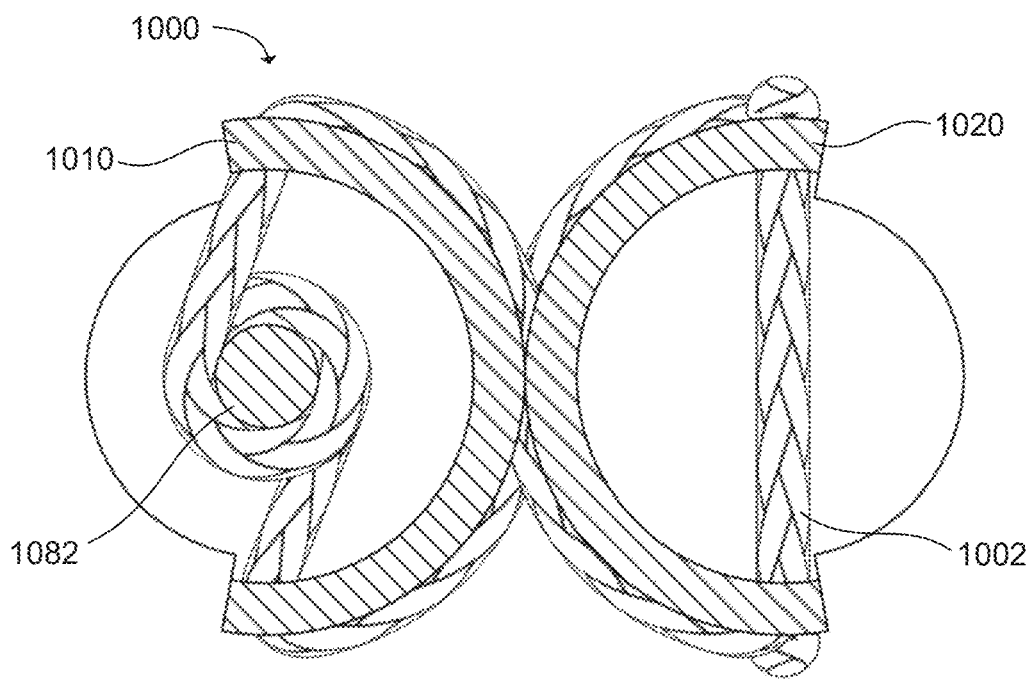

In certain examples, the tensioning element can include a spool and a lock to prevent the spool from rotating relative to the hollow interior to maintain the tension force. In some examples, the lock can include a non-circular shape on a side of the spool, and the joint implant element can include a recess having the same shape or a shape configured accept the non-circular shape such that the spool is prevented from rotating. As one example, the spool can have a hexagonal shaped head formed on one side, and the joint implant element can have a matching hexagonal recess on the side where the spool is inserted into the hollow interior of the joint implant element. The filament can be wrapped around the spool inside the hollow interior, the spool can be rotated to apply tension to the filament, and then the spool can be pushed in farther so that the hexagonal shaped head fits into the hexagonal recess. This can prevent the spool from rotating back, and thereby maintain the tension on the filament. A variety of other arrangements can also be used to lock the spool in place after tightening the filament. FIG. 10A is a perspective view of one example joint implant 1000 having such a tensioning element 1080. The tensioning element comprises a spool 1082 and a lock 1084. The lock is a hexagonal head that fits into a matching hexagonal recess in the proximal joint implant element 1010. The filaments 1002 have one end wrapped around the spool 1082 inside the hollow interior of the proximal joint implant element 1010. The other ends of the filaments 1002 are secured to the distal joint implant element 1020 by knots. FIG. 10A also shows boxes 1092, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. FIG. 10B shows the tensioning element 1080 in another position with the hexagonal head outside the hexagonal recess. In this position, the tensioning element can be rotated by applying torque to the hexagonal head to increase tension in the filaments 1002. When the desired amount of tension has been applied to the filaments, the hexagonal head can be inserted into the hexagonal recess to hold the tensioning element 1080 in place. FIG. 10C is a side cross-sectional view of the joint implant 1000. This view shows how the filaments 1002 are wrapped around the tensioning element 1080 in the hollow interior of the proximal joint implant element 1010, with the other ends of the filaments secured to the distal joint implant element 1020.

Another example can include a tensioning element with a slot or hole that allows the filament to pass through. The filament can be secured after passing through the slot or hole, such as using a knot or melting the end of the filament to form a nub to retain the filament in the slot or hole. The tensioning element can also be made up of two parts that are inserted into the hollow interior of the joint implant element from either side, and each part can have a half-slot that forms a slot when the two parts are inserted and attached together. In this case, the filament can be passed through the hollow interior first, and then the two parts of the tensioning element can be inserted so that the filament is in the slot that is formed of the two half-slots. Once the filament is positioned in the slot, the tensioning element can then be rotated to at least partially wrap the filament around the tensioning element to apply tension to the filament.

In further examples, the tensioning element can attach to the joint implant element without being placed inside a hollow interior of the joint implant element. In one example, a joint implant element can have a flat back side (referring to the side of the joint implant opposite from the curved interface surface). Filaments can be wrapped around the curved interface surface and then across the flat back side. A tensioning element can then be attached to the flat back side to sandwich the filaments between the tensioning element and the joint implant element. The filaments can have tension applied by a manufacturer, machine, or other tool while the tensioning element is being attached. Then, once the tensioning element has been attached to the joint implant element, the tensioning element can retain the tension that was applied to the filaments. The filaments can also be terminated with knots or fused nubs to prevent the filaments from pulling out of the space between the tensioning element and the joint implant element. The tensioning element and/or the joint implant element can have a roughened surface to increase retention of the filaments. The tensioning element can also have one or more grooves to accommodate the filaments. The surface of the joint implant element, instead of being flat, can also be designed with grooves to accommodate the filaments. Any other features, such as ridges or grooves that are not used to accommodate the filaments, can also be included to help the tensioning element mate with the joint implant element.

Figure 11A:
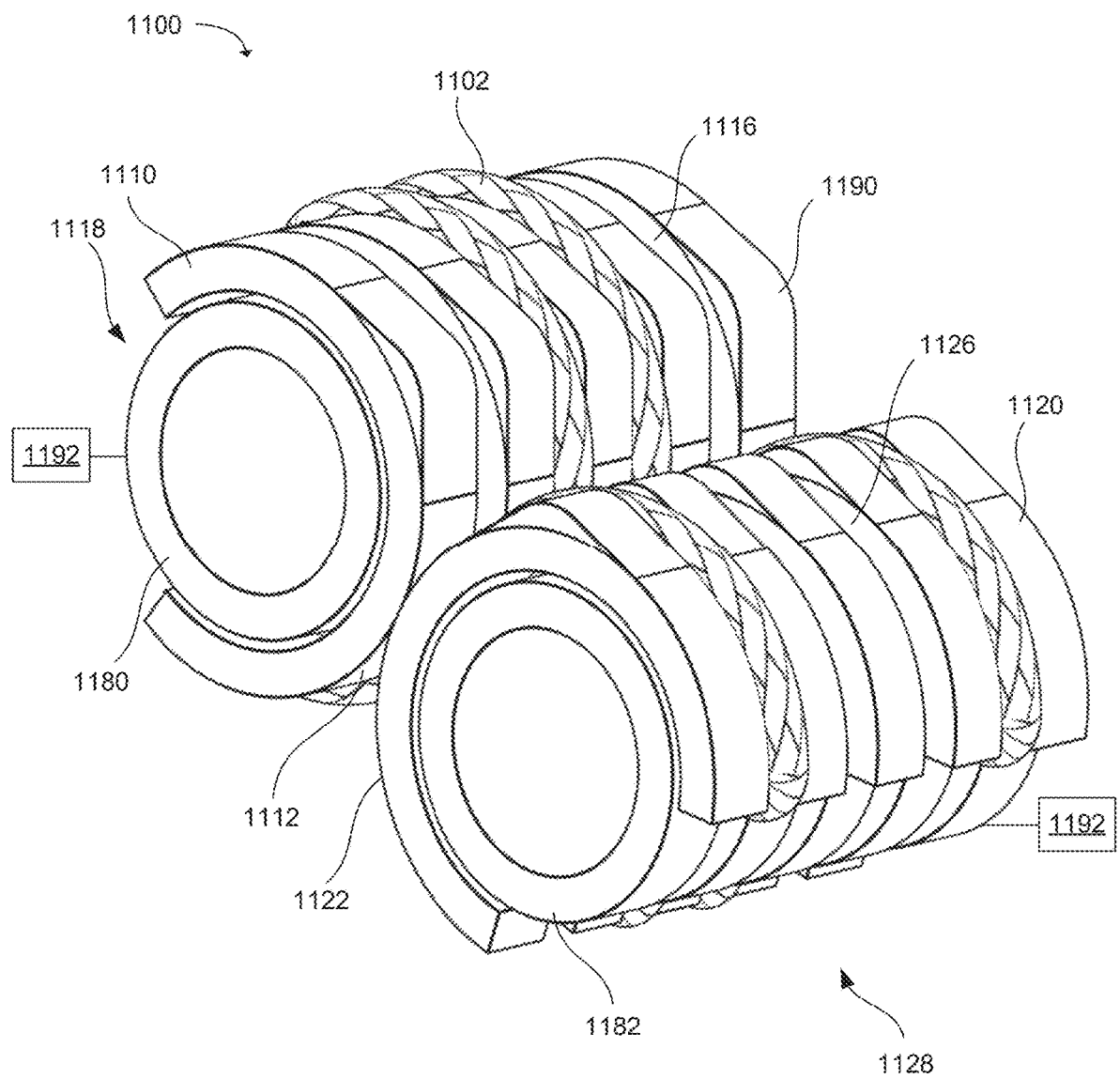
FIGS. 11A-11F illustrate yet another example joint implant in accordance with the present technology.
Figure 11B:
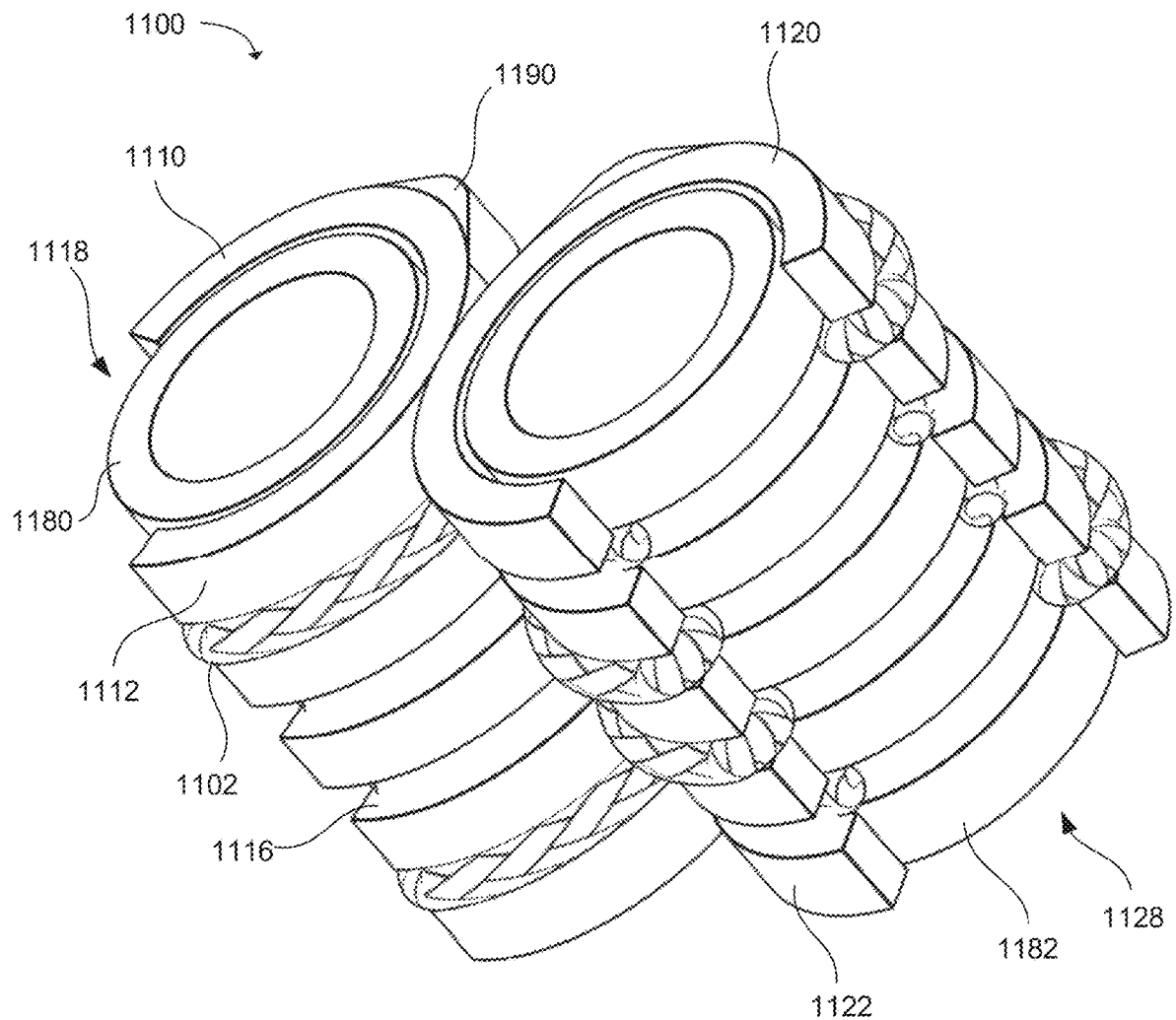

In other examples, a joint implant element can include a gap leading into the hollow interior, and the tensioning element can be pressed into the hollow interior through the gap. FIG. 11A shows a perspective view of an example joint implant 1100 with this type of design. This example includes a proximal joint implant element 1110 and a distal joint implant element 1120 that have the overall shape of a cylinder with a gap 1118, 1128 in the cylinder leading into a hollow interior. In this example, a proximal tensioning element 1180 is pressed through the proximal gap 1118 into the hollow interior of the proximal joint implant element 1110. Similarly, a distal tensioning element 1182 is pressed through the distal gap 1128 into the hollow interior of the distal joint implant element 1120. The filaments 1102 can be arranged in their desired locations on the proximal curved interface surface 1112 and the distal curved interface surface 1122, and then the ends of the filaments can be wrapped inside the hollow interiors of the joint implant elements or merely laid across the gaps. Then, the tensioning elements 1180, 1182 can be pressed through the gaps 1118, 1128. The friction between the tensioning elements 1180, 1182 and the filaments 1102 can cause the filaments to be pulled into the hollow interior along with the tensioning elements. This can apply tension to the filaments 1102. Once the tensioning elements 1180,1182 are fully inside the hollow interiors of the joint implant elements 1110, 1120, the filaments are held securely between the tensioning elements and the interior surfaces of the joint implant elements. Thus, the filaments 1102 are secured and tensioned simultaneously. The gaps 1118, 1128 can be slightly smaller than the diameter of the tensioning elements 1180, 1182. However, the joint implant elements 1110,1120 can be made from a material that has some elasticity, so that the joint implant elements can flex slightly when the tensioning elements 1180,1182 are pressed through the gaps 1118, 1128 to allow the gaps to be slightly and temporarily enlarged. The elasticity of the material can then allow the gap to return to its original size after the tensioning element has been pressed through the gap, and the tensioning element can be held securely inside the hollow interior of the joint implant element. In particular, the tensioning element can be held in compression within the hollow interior by pressure applied by the joint implant element and the filaments that are compressed between the interior surface of the joint implant element and the tensioning element. FIG. 11A also shows that this design includes proximal grooves 1116 and distal grooves 1126 to accommodate the filament segments, and protrusions 1190 on the curved interface surfaces to stop and limit rotation of the joint implant elements at a specific point. FIG. 11A also shows boxes 1192, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. FIG. 11B shows another perspective view from a lower angle of the same example joint implant.

The joint implant elements can generally be made of a rigid material. The material can have sufficient rigidity for the joint implant element to function as described herein. However, as mentioned above, the joint implant element can have some elasticity, especially in examples that include a gap and a tensioning element that is to be pressed through the gap. Some example materials that can be used to form the joint implant elements include steel, stainless steel, surgical steel, titanium, cobalt, chromium, molybdenum, alloys of these metals, polyethylene, low density polyethylene, high density polyethylene, high molecular weight polyethylene, ultra-high molecular weight polyethylene, nylon, biocompatible polymers, PEEK (polyether ethyl ketone), polytetrafluoroethylene (PTFE), Teflon, ceramics, and combinations thereof. In certain examples, joint implant elements can be made of a metal coated with a biocompatible polymer or ceramic to provide the strength of the metal while avoiding contact between the metal and bodily tissues. In some examples, tensioning elements, bone interface connectors, bone anchors, and other components of the joint implants can also be made of any of these materials.

Figure 11C:
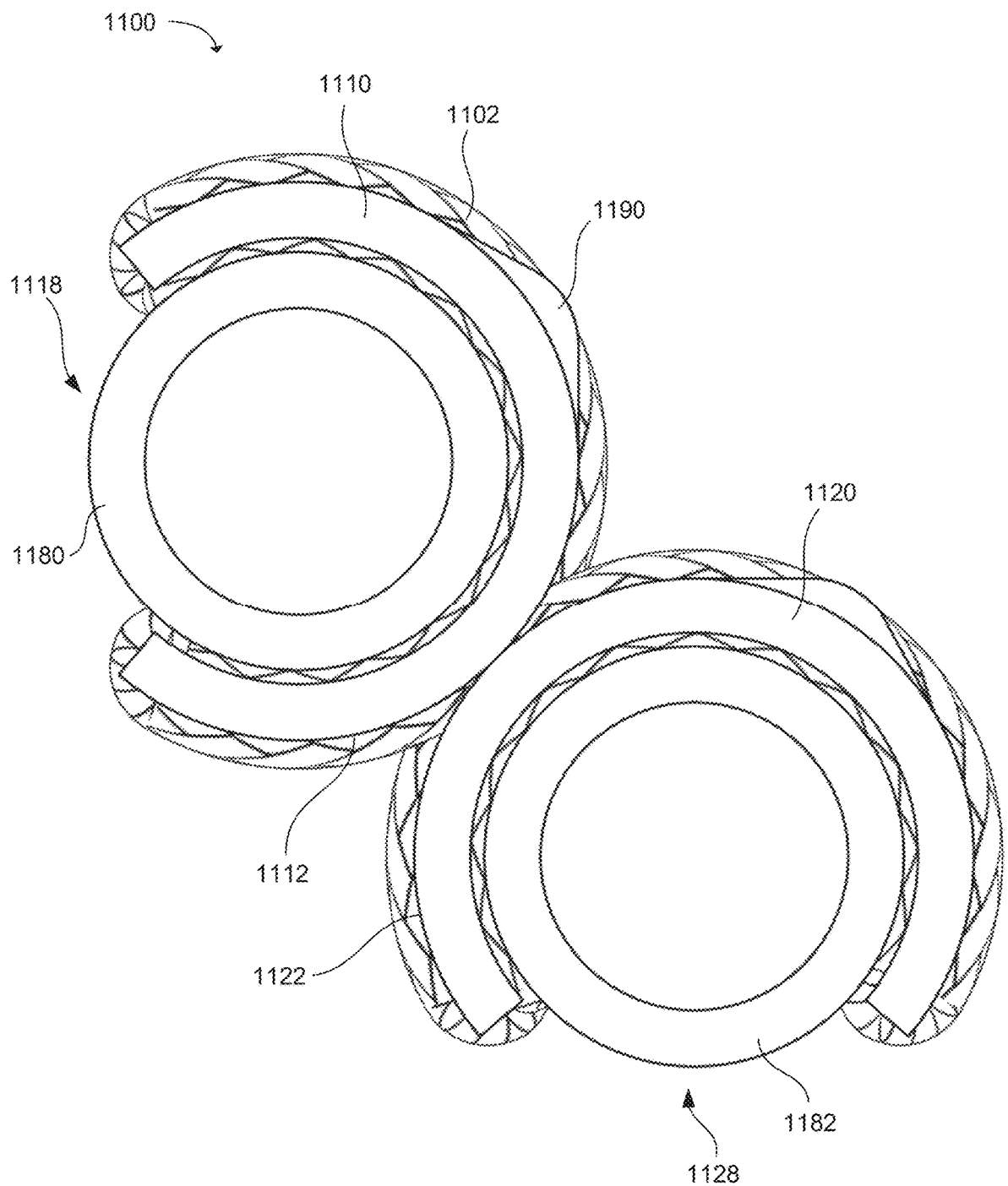

FIG. 11C shows a side view of the joint implant 1100 in a flexed position. This view shows how the filaments 1102 extend along the curved interface surfaces 1112, 1122 of the joint implant elements 1110, 1120 and then extend through the gaps 1118,1128 into the hollow interiors of the joint implant elements. It is noted all parts of the joint implant elements 1110, 1120 other than the curved interface surface can be referred to collectively as the "base portion." Therefore, the interior surface of the hollow interior is a surface of the base portion of the joint implant elements. The filaments are held in place by the tensioning elements 1180, 1182 that have been pressed into the hollow interiors. A portion of the filaments are held immobile by compression in the space between the tensioning element and the interior surface of the hollow interior. Therefore, the point where the filaments enter the space between the tensioning element and the interior surface of the hollow interior can act as an attachment point for the filaments.

Figure 11D:
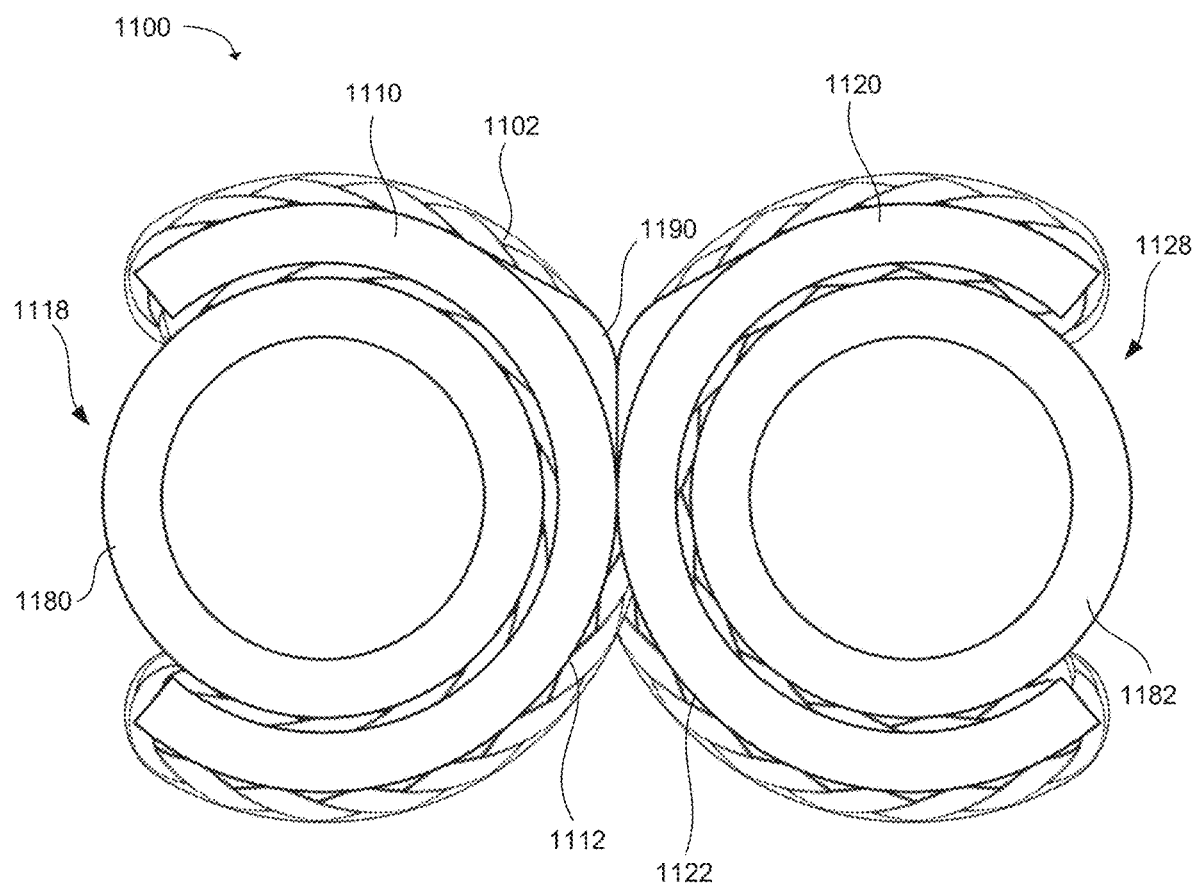

FIG. 11D shows another side view of the joint implant 1100 in an extended position. This example includes protrusions 1190 on the curved interface surfaces to act as a stopping point for rotation of the joint implant elements 1110, 1120. When the joint implant elements 1110,1120 have rotated to the fully extended position, the protrusions 1190 butt up against each other and do not allow the joint implant elements to rotate any farther.

Figure 11E:
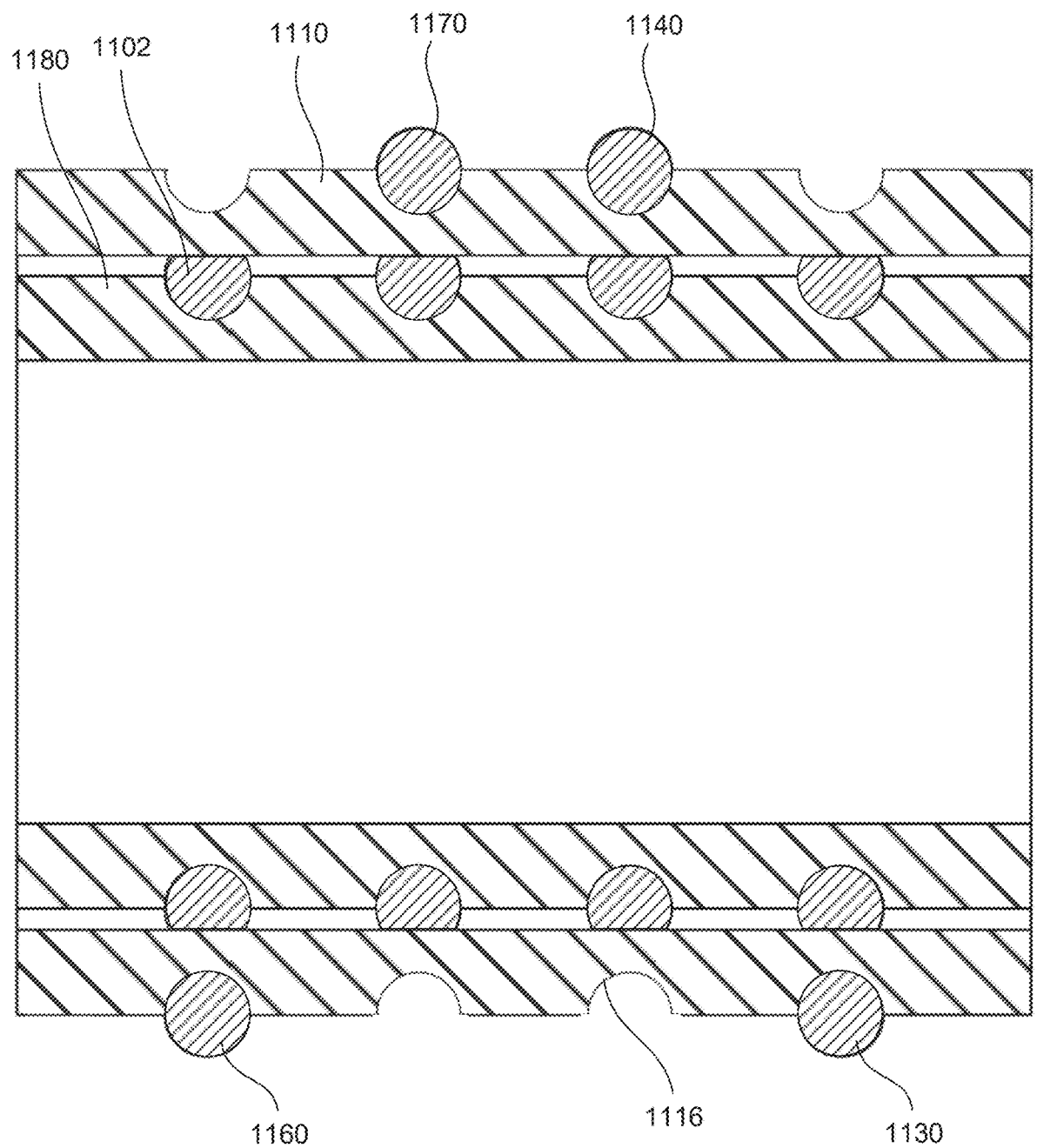

FIG. 11E shows a cross-sectional view of the proximal joint implant element 1110 view from a front-on direction, where the cross section is taken on a plane that bisects the joint implant element as if the joint implant element has been cut in half. In this example, a first filament segment 1130 and a third filament segment 1160 are in grooves 1116 on the bottom of the proximal joint implant element. These are the outer filament segments, closest to the sides of the joint implant. A second filament segment 1140 and a fourth filament segment 1170 are the inner filament segments, closer to the middle of the joint implant between the outer filament segments. The second and fourth filament segment 1140, 1170 are in grooves 1116 on the top of the proximal joint implant element. The proximal tensioning element 1180 is inside the hollow interior of the proximal joint implant element 1110. It can be seen in this figure that the tensioning element 1180 also has grooves to help align the filaments 1102 in and hold the filaments securely between the tensioning element and the interior surface of the hollow interior. Portions of all the filaments are held in this way by the tensioning element 1180. Again, it is noted that the grooves formed in the joint implant elements can comprise the same or a different profile (i.e., size, shape and/or configuration of surfaces) than that of the curved interface surfaces. In addition, the depth of the grooves measured from the face of the respective curved interface surfaces can vary along the length of the grooves. Still further, one or more surfaces of the grooves can comprise texturing or objects or elements formed with or otherwise supported from the surface(s), such as protrusions (e.g., bumps, barbs, etc.), to enhance the engagement of the filaments with the surface(s) of the grooves. Similarly, the grooves formed in the tensioning elements can comprise the same or a different profile as/than that of the outer surfaces of the tensioning elements. Moreover, the depth of the grooves in the tensioning elements can vary along their length, and the surfaces of the grooves can comprise texturing or objects or elements formed with or otherwise supported from the surface(s) of the grooves to enhance the engagement of the filaments with the surfaces of the grooves.

Figure 11F:
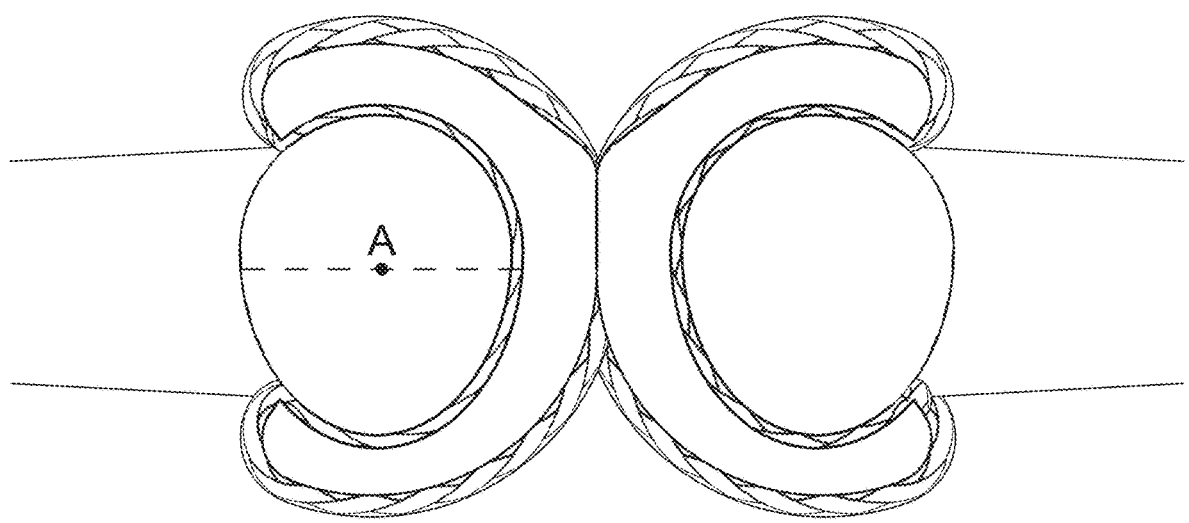

FIG. 11F illustrates another configuration of the joint implant 1100 with just the proximal joint implant element 1110 and the proximal tensioning element 1180 being shown. In this example, the proximal tensioning element 1180 can comprise a nonsymmetrical configuration, such as with a volar side of the proximal tensioning element being at a greater distance from an axis that extends through a center point A of the proximal joint implant element 1110 than a dorsal side of the tensioning element. The hollow or interior of the proximal joint implant element 1110 can likewise comprise a nonsymmetrical configuration that corresponds to the nonsymmetrical configuration of the proximal tensioning element 1180, or the proximal joint implant 1110 can comprise a hollow interior having a symmetrical configuration like the ones shown in FIGS. 11A-11E. In practice, the volar side can be inserted first into the hollow interior of the proximal joint implant element 1110, and then rotated to then insert the dorsal side of the proximal tensioning element 1180 into the hollow interior of the proximal joint implant element 1110, with the dorsal side essentially snapping into place within the hollow interior of the proximal joint implant element. FIG. 11 F illustrates the proximal tensioning element 1180 inside the hollow interior of the proximal joint implant element 1110. Although not shown, the dorsal tensioning element 1128 can also be configured in a similar manner with a nonsymmetrical configuration.

FIG. 12 shows a side view of a different example joint implant 1200. This example also includes tensioning elements 1280, 1282 inside proximal joint implant element 1210 and the distal joint implant element 1220. However, in this example, the distal joint implant element 1220 has a smaller diameter, and thus a curved interface surface having a smaller radius of curvature, than the proximal joint implant element. Therefore, the distal joint implant element 1220 will rotate more with a given rolling distance when the distal joint implant element rolls against the proximal joint implant element 1210, compared to the amount of rotation that would occur if the distal joint implant element were the same diameter with the same size of curved interface surface as the proximal joint implant element. The distal tensioning element 1282 is also smaller than the proximal tensioning element 1280 to fit within the distal joint implant element 1220. FIG. 12 also shows boxes 1292, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

If the proximal joint implant element and the distal joint implant element have different diameters or radii of curvature, this can affect the bending of the joint. If the proximal joint implant element has a larger radius of curvature and the distal joint implant element has a smaller radius of curvature, then a higher torque can be exerted by the tendons of a subject to exert a given force at the end of the digit compared to an arrangement where the joint implant elements have an equal radius of curvature. This sacrifice can be useful in scenarios where tendon extension and contraction are less than normal, such as when tendons are shorter than normal. In the alternative, the proximal joint implant element can have a smaller radius of curvature and the distal joint implant element can have a larger radius of curvature. In this case, torque at the joint can increase but may require longer tendon extension and retraction. If there is sufficient tendon available, then this arrangement can create a larger force application at the end of the digit.

Figure 13:
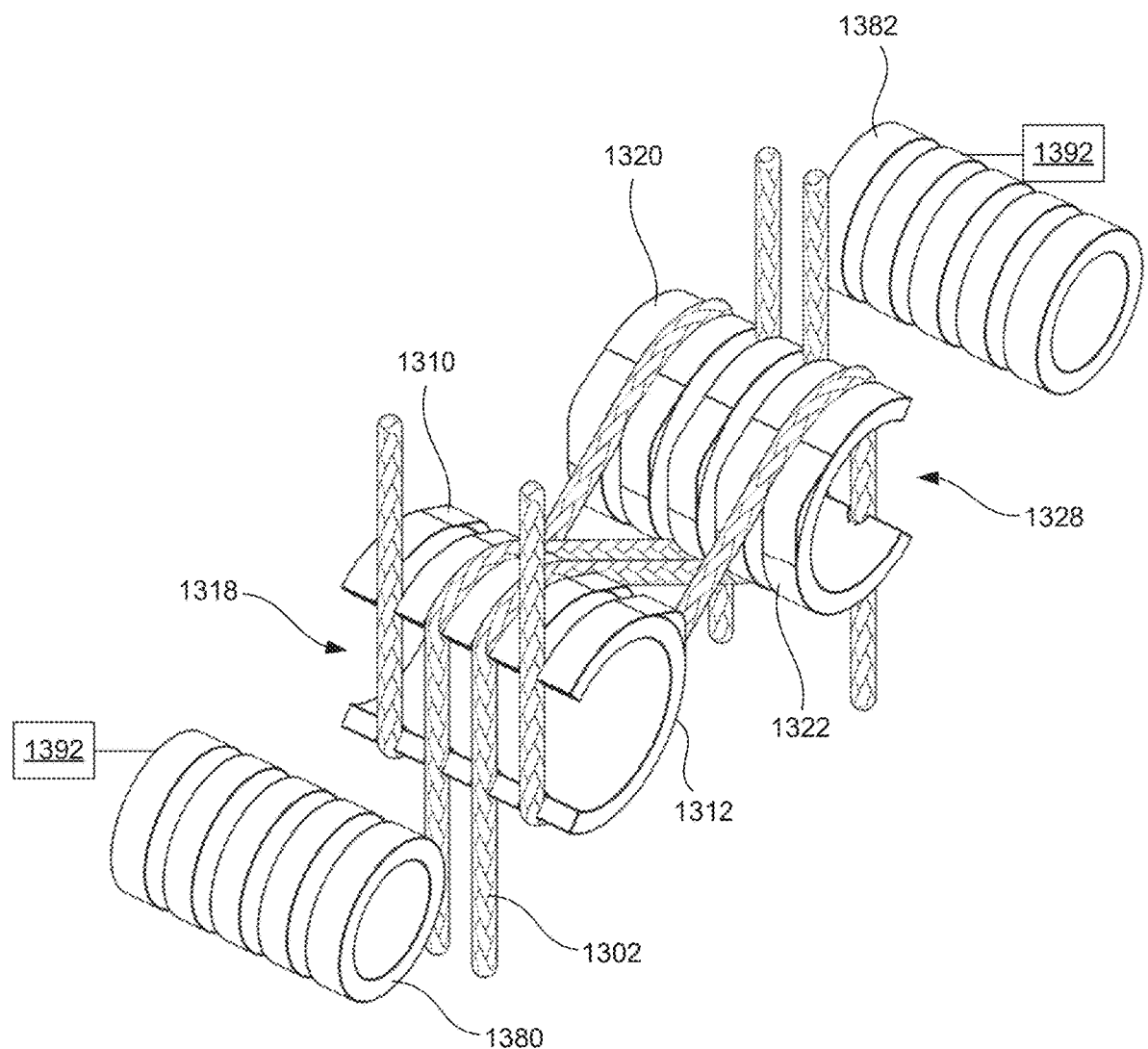
FIG. 13 is an exploded view of an example joint implant in accordance with the present technology.

FIG. 13 shows a perspective view of one step in an example method of making an example joint implant, such as the joint implant 1100 of FIGS. 11A-11D. A proximal joint implant element 1310 and a distal joint implant element 1320 can be arranged with the proximal curved interface surface 1312 facing toward the distal curved interface surface 1322. Filaments 1302 can then be wrapped around the joint implant elements to make a pair of outer filaments and a pair of inner filaments that cross the outer filaments at a location between the proximal and distal joint implant elements 1310,1320. The ends and other portions of the filaments can be positioned or extend across gaps 1318, 1328 as shown in the figure. A proximal tensioning element 1380 and a distal tensioning element 1382 can then be pressed into the gaps, thereby applying tension to the filaments 1302 while simultaneously securing the filaments in the space between the tensioning elements and the interior surface of the joint implant elements 1310,1320. FIG. 13 also shows boxes 1392, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

Figure 14A:
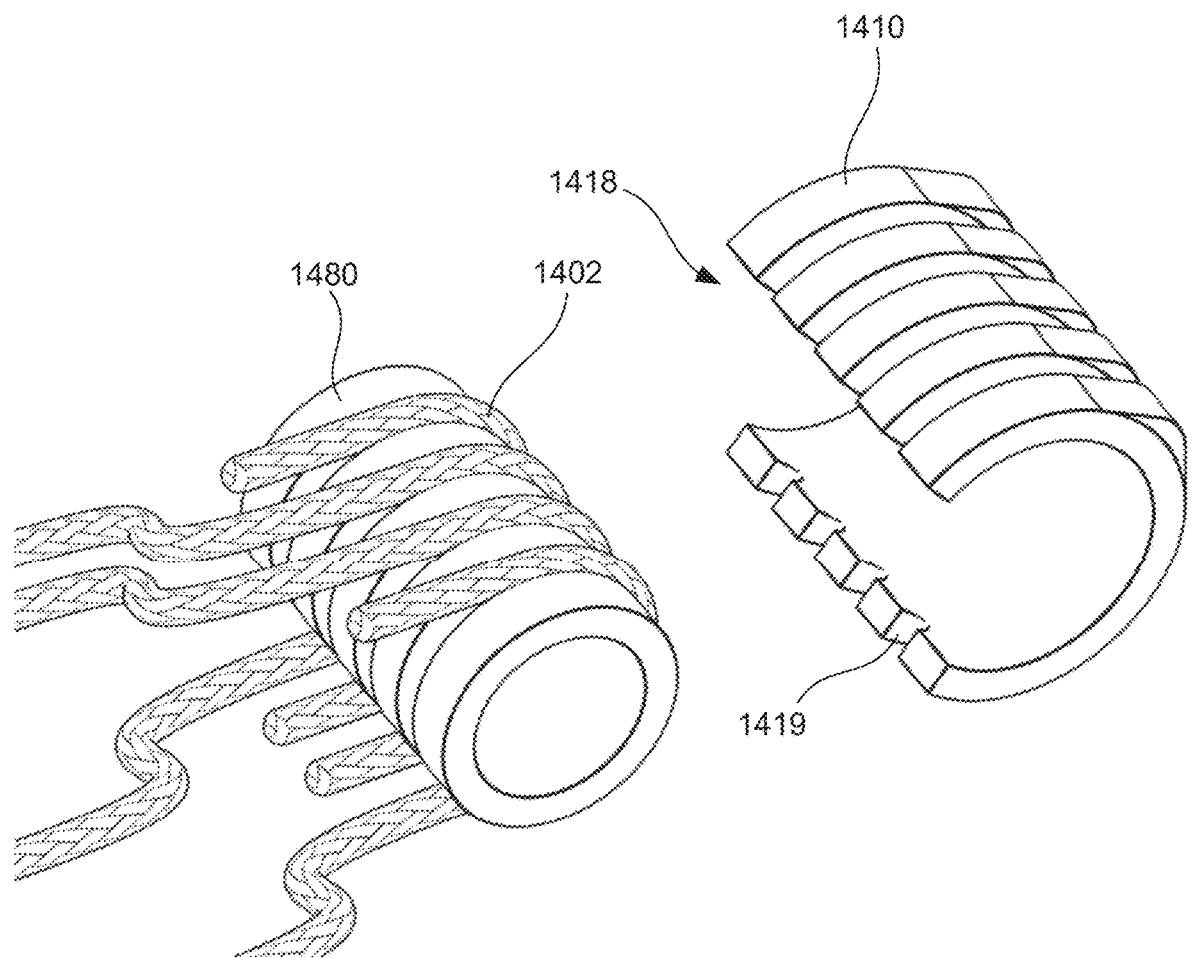
FIGS. 14A-14H illustrate steps in a method of making a joint implant in accordance with the present technology.
Figure 14B:
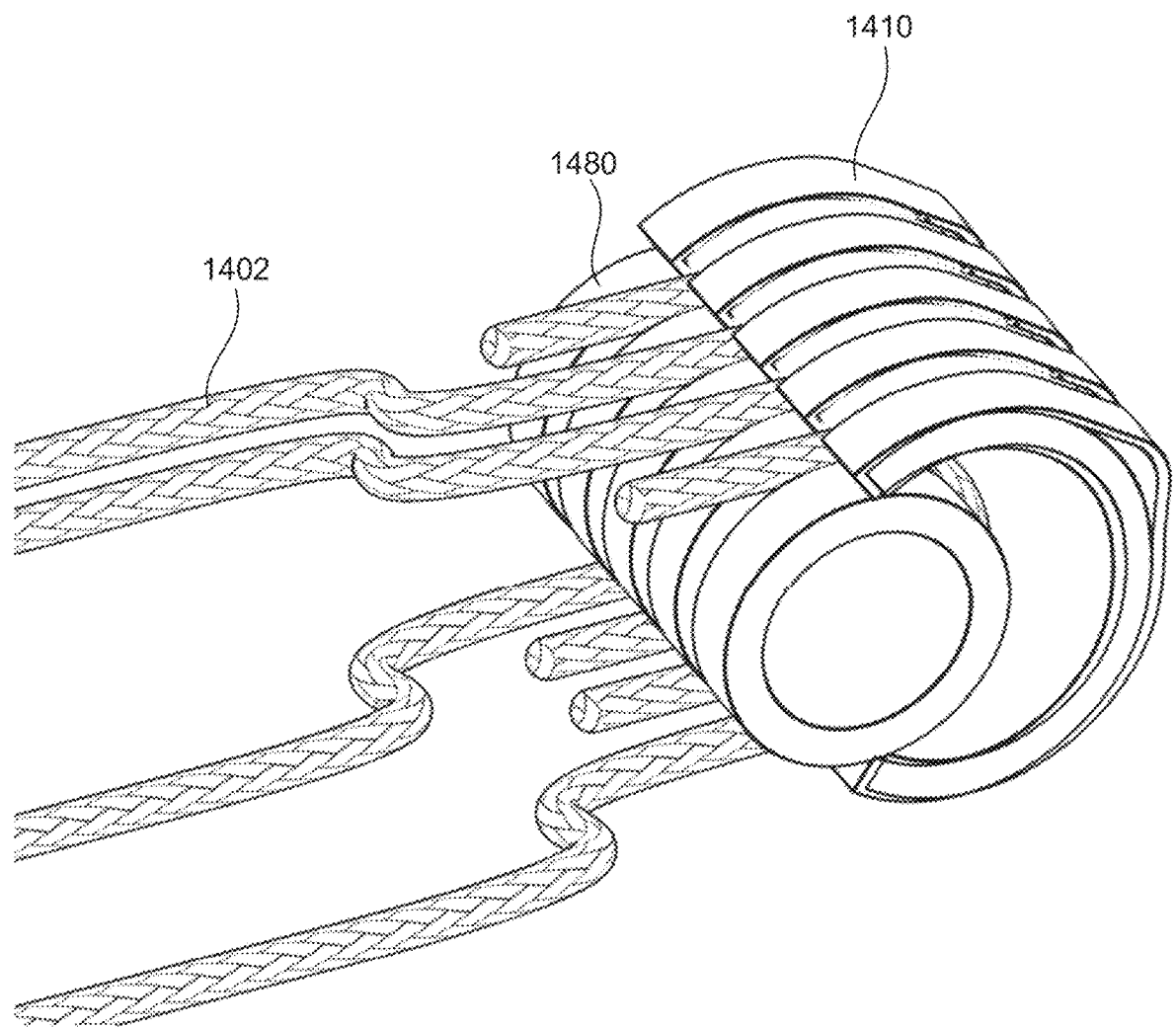
Figure 14C:
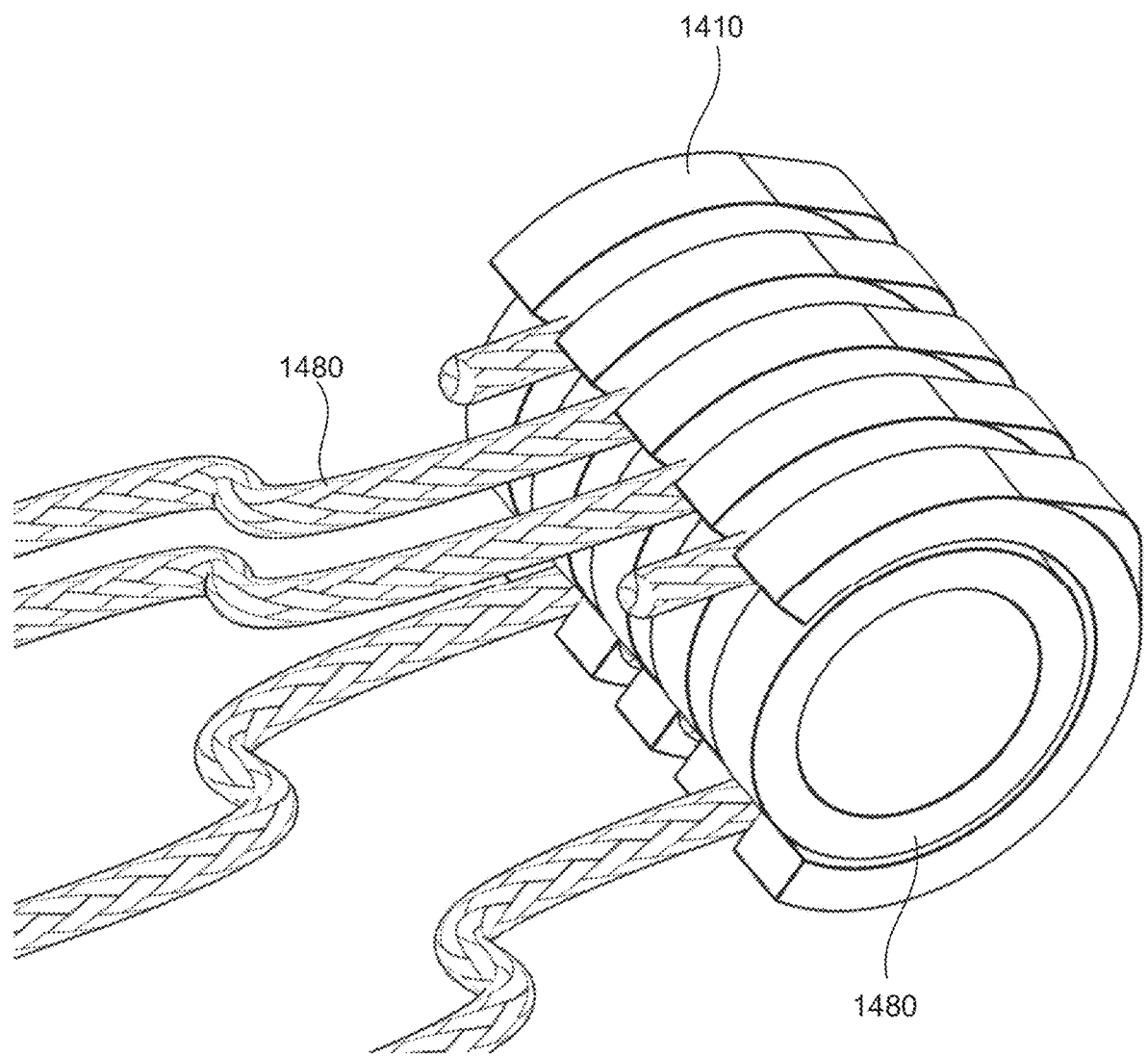
Figure 14D:
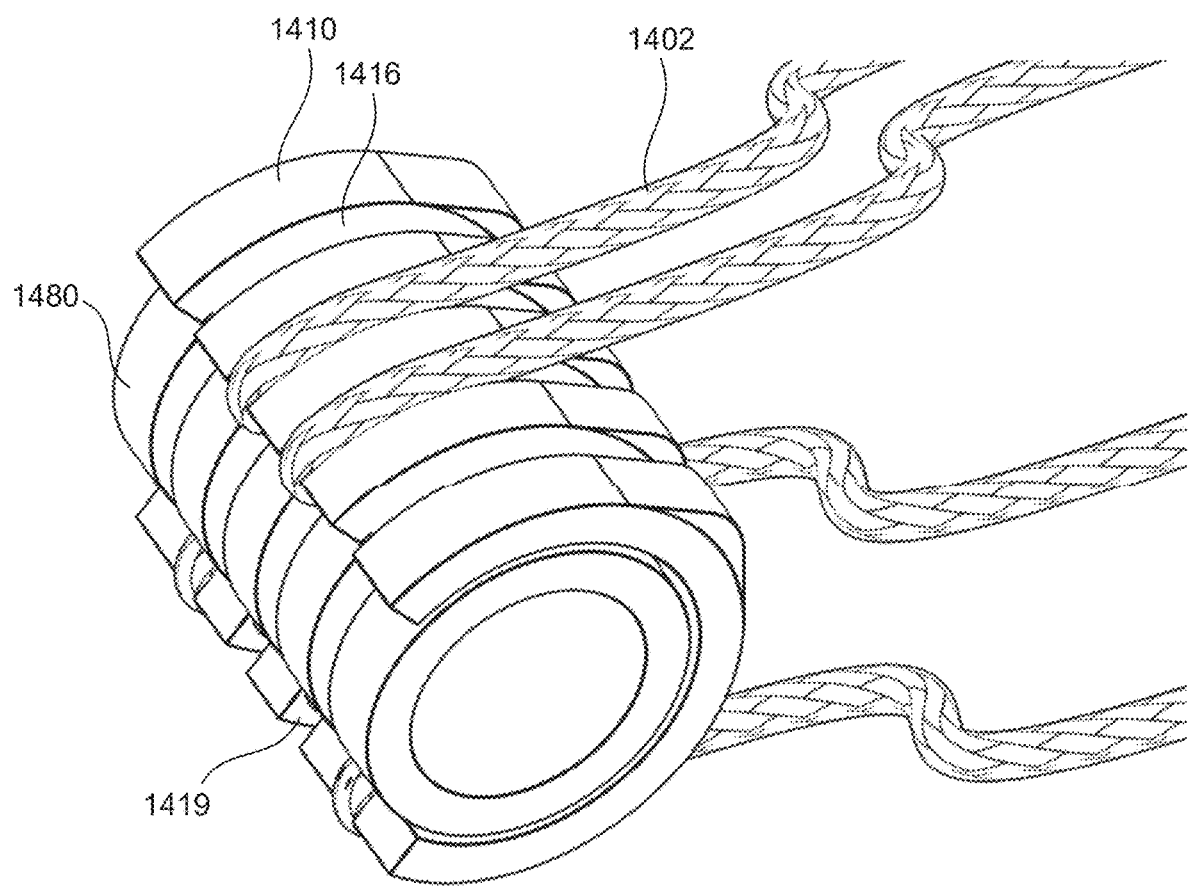
Figure 14E:
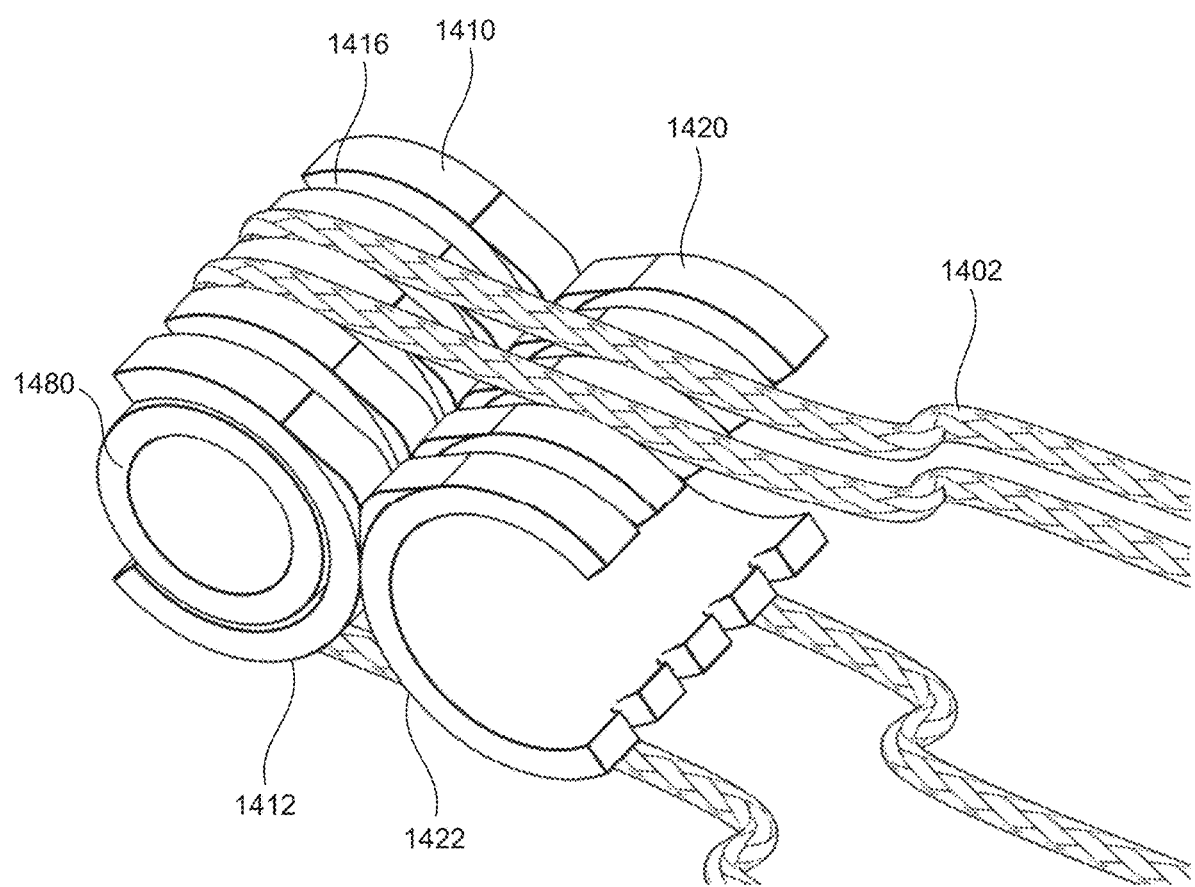
Figure 14F:
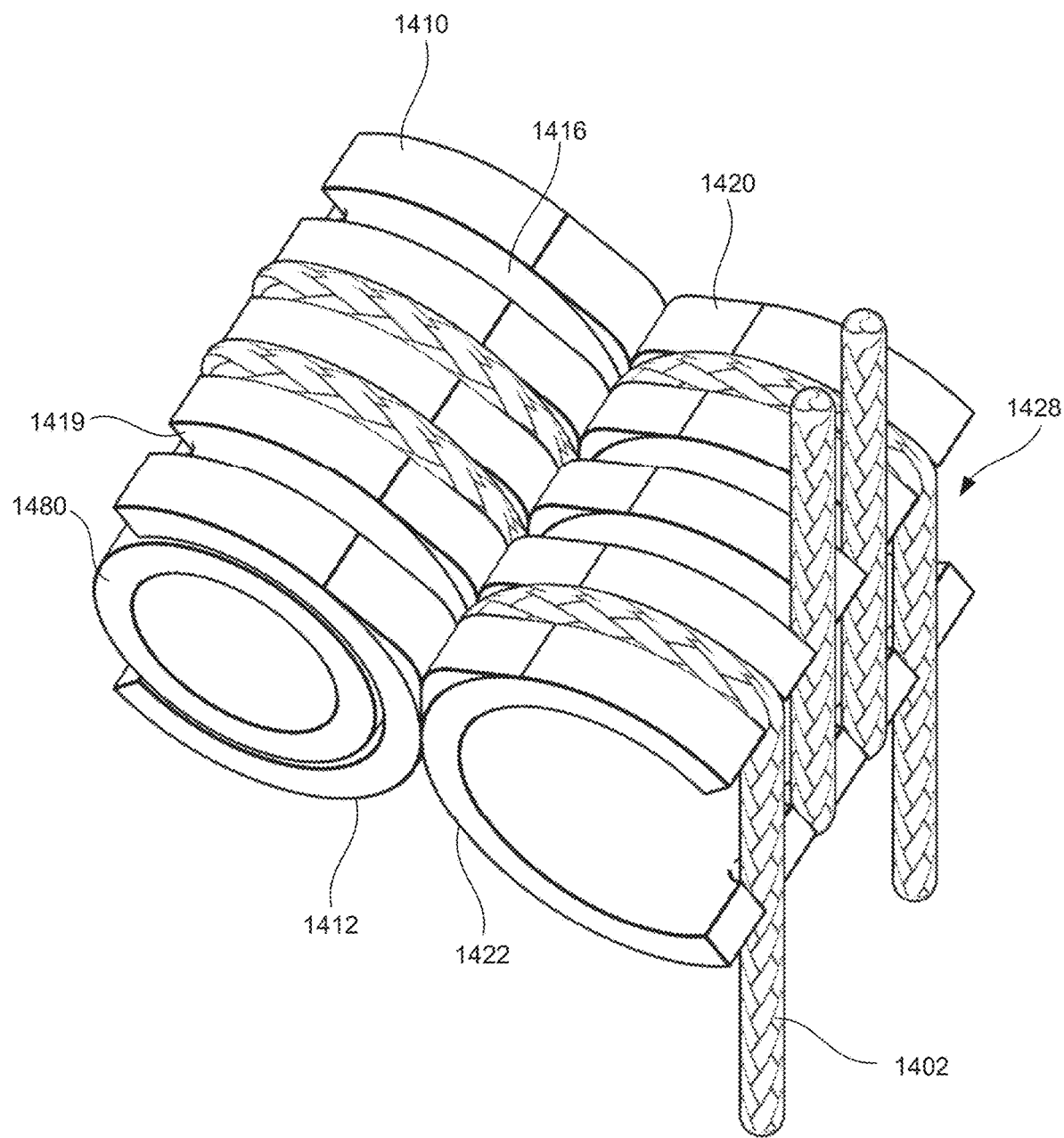
Figure 14G:
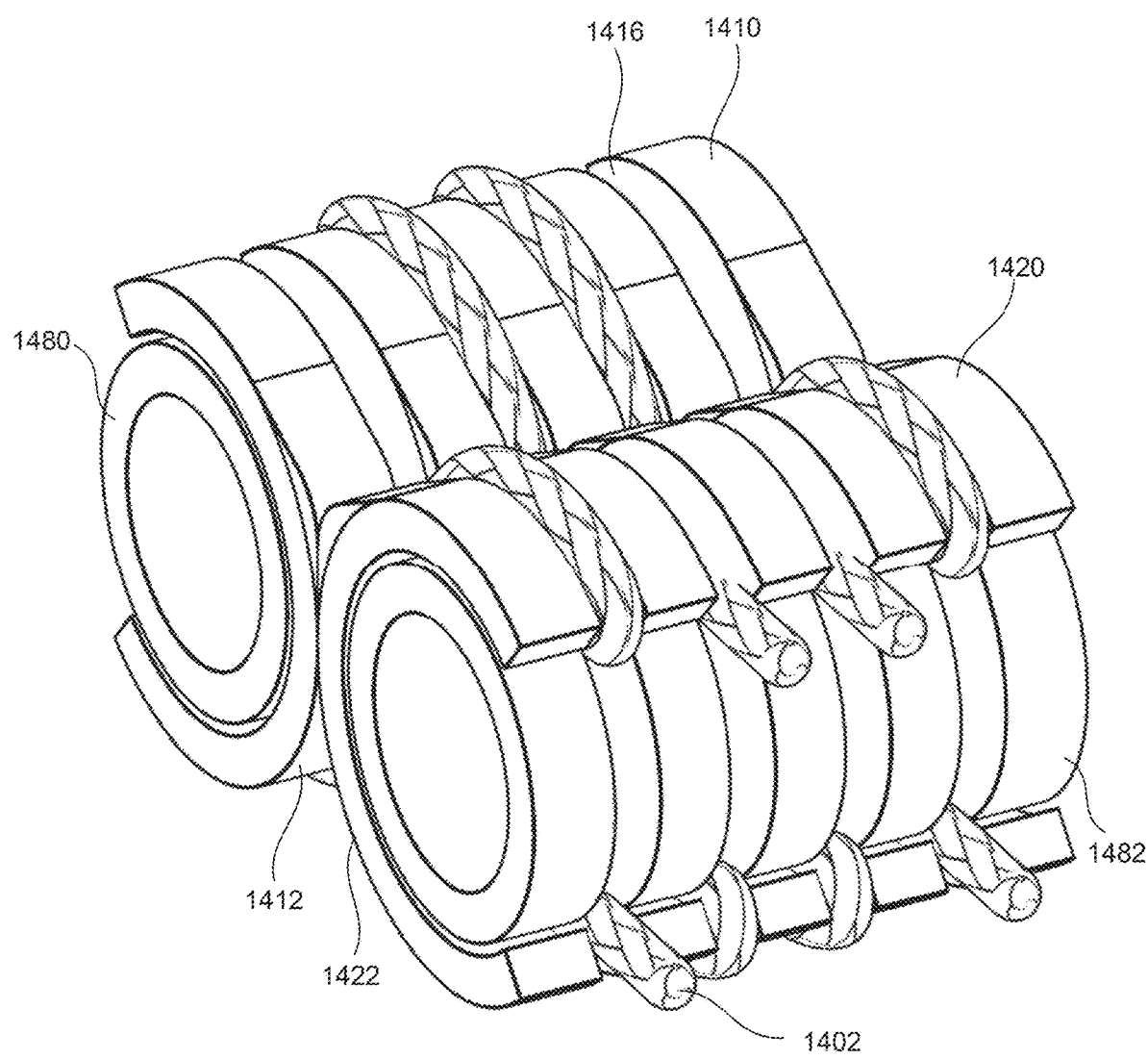
Figure 14H:
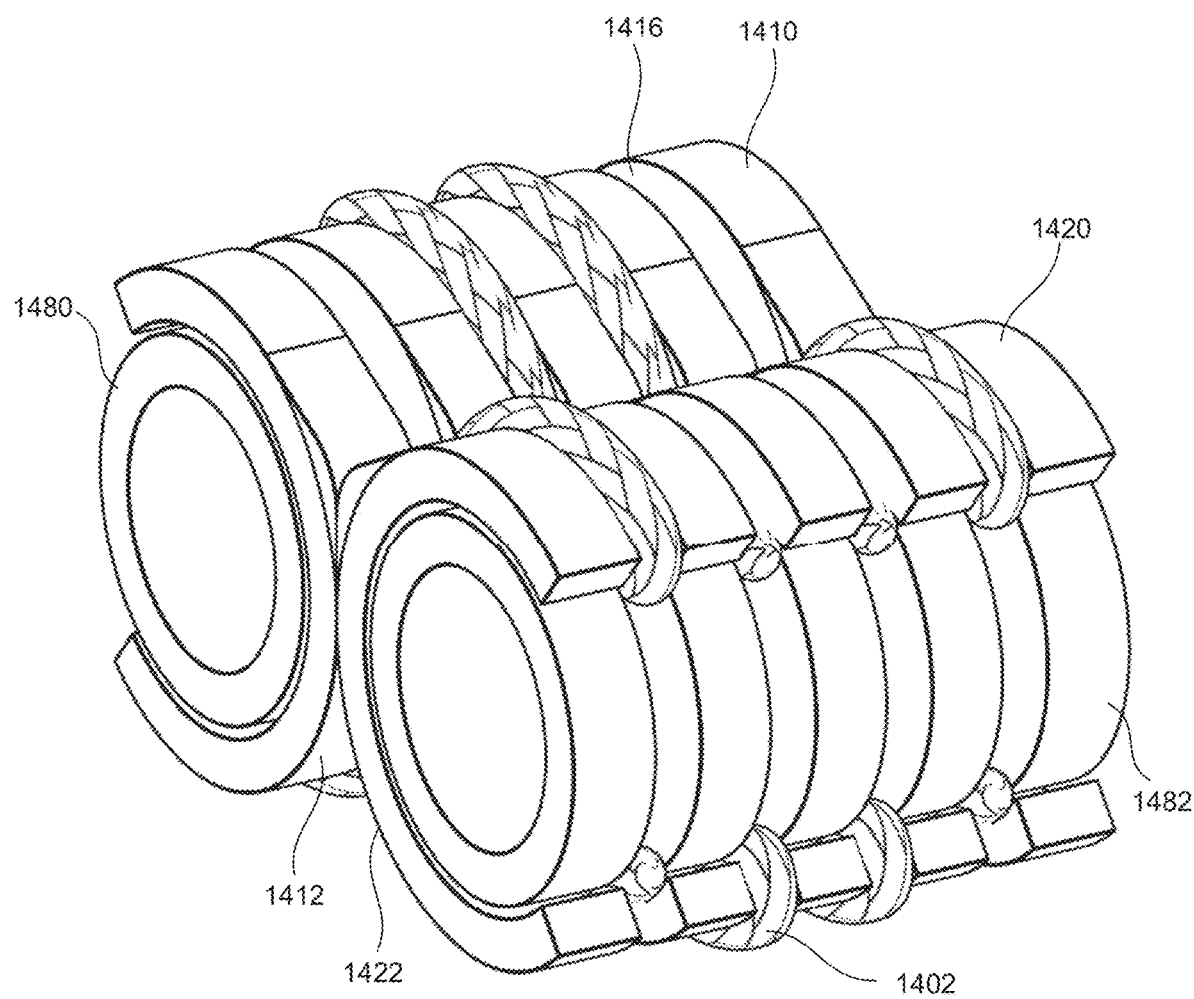

FIG. 14A shows a step in a different example method of making a joint implant. In this example, filaments 1402 are wrapped around a proximal tensioning element 1480. A proximal joint implant element 1410 with a gap 1418 leading to a hollow interior volume is also provided. FIG. 14B shows another step, in which the tensioning element 1480 is pressed into the hollow interior volume of the proximal joint implant element 1410. FIG. 14C shows the proximal joint implant element 1410 after the proximal tensioning element 1480 has been pressed in. This secures the ends of the filaments 1402. FIG. 14D shows how, after the proximal tensioning element 1480 has been pressed into place in the proximal joint implant element 1410, the filaments 1402 can be wrapped around the proximal joint implant element and positioned in proximal grooves 1416. These grooves can comprise the same or a different profile than the curved interface surfaces of the joint implant elements, in a similar manner as discussed above and taught herein with respect to other examples. This example includes notches 1419 cut in the edge of the proximal joint implant element 1410 leading to each of the proximal grooves 1416. These notches can be deep enough to accommodate the entire width of the filaments, or a partial width of the filaments. The notches can make is easier to guide the filaments into the proper grooves and also act to reduce the stress concentration on the filaments as they are folded over. FIG. 14E shows a distal joint implant element 1420 placed adjacent the proximal joint implant element 1410 with the distal curved interface surface 1422 facing the proximal curved interface surface 1412. The filaments 1402 are also positioned in the grooves on the distal joint implant element 1420. FIG. 14F shows the filaments 1402 wrapped around the distal joint implant element 1420 so the filaments cross the gap 1428 leading to the hollow interior of the distal joint implant element. FIG. 14G shows a distal tensioning element 1482 pressed into the hollow interior of the distal joint implant element 1420. The distal tensioning element 1482 applies tension to the filaments 1402 and secures the filaments inside the space between the distal tensioning element and the interior surface of the distal joint implant element 1420. FIG. 14H shows the filaments 1402 being cut off to remove loose ends of the filaments after the joint implant has been assembled. In some examples, the ends of the filaments can also be deformed by melting or cauterizing to form a bulging end that will prevent the filament from pulling through the space between the tensioning element and the interior surface of the joint implant element. Alternatively, knots can be tied at the ends of the filaments.

Figure 15:
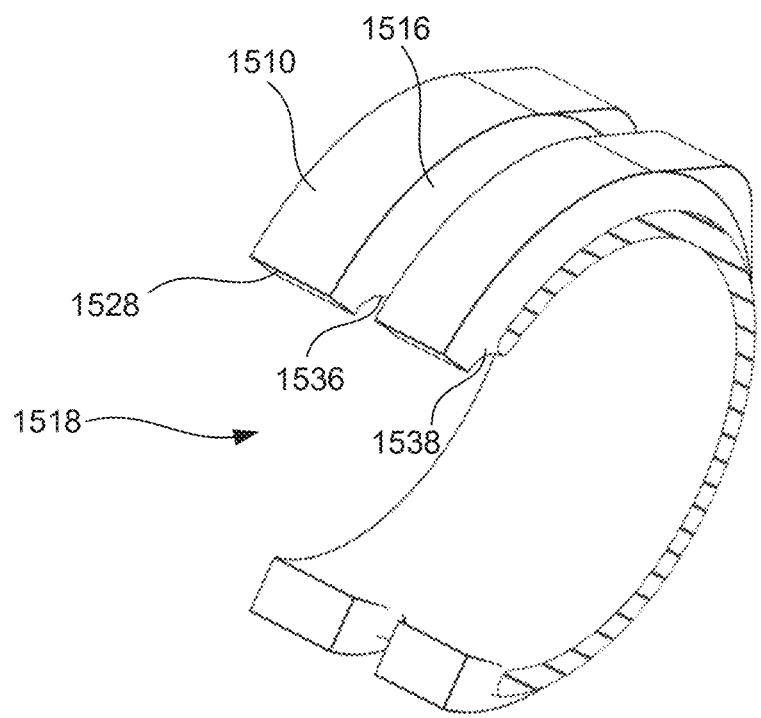
FIG. 15 is a perspective cross-sectional view of an example joint implant element in accordance with the present technology.

In some examples, the joint implant elements can include notches in the edge of the gap leading into the hollow interior of the joint implant elements. FIG. 15 shows a partial, perspective cross-sectional view of a proximal joint implant element 1510. The cross-section is taken in one of the grooves 1516. The grooves are designed for filaments to lie in the grooves on the curved interface surface 1512, and the filaments can extend from the curved interface surface around the edge 1528 of the gap 1518 leading into the hollow interior of the joint implant element 1510. The edge includes notches 1536 aligned with the grooves 1516. The filament can extend through these notches 1536 as the filament wraps around the edge and into the hollow interior. This figure shows one of the notches 1536 cut in half by the cross section. The notches 1536 have a curved surface so that the filaments do not wrap around a sharp edge, which could lead to breakage of the filaments over time. In this example, the notches have a surface that is curved in two orthogonal directions, i.e., a saddle curve 1538. It is noted that the grooves 1516 on the curved interface surface 1512 can also have a curved bottom surface to match the curve of a cord-shaped filament. The curve of the groove can transition smoothly to the saddle curve of the notch, which can transition smoothly to the interior surface of the joint implant element. It is contemplated that any of the grooves in any of the example joint implants discussed herein can be configured with notches and/or a curved bottom.

Figure 16:
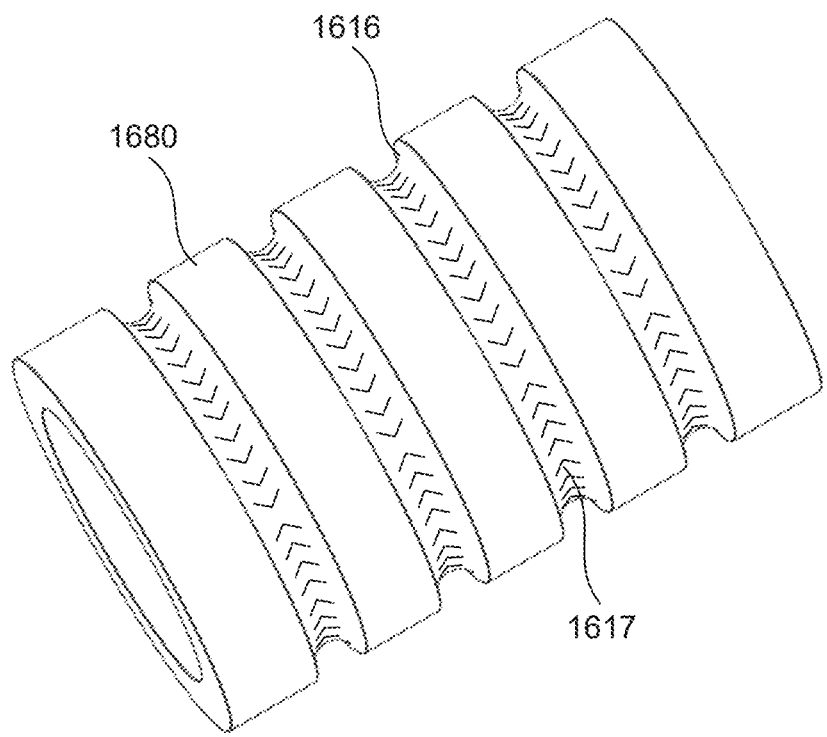
FIG. 16 is a perspective view of an example tensioning element in accordance with the present technology.

FIG. 16 shows a perspective view of another example tensioning element 1680. This tensioning element 1680 has the shape of a hollow cylinder with grooves 1616 formed in the outer surface. These grooves 1616 have a curved bottom surface to accommodate a cord-shaped filament. These grooves can comprise the same or a different profile than the outer surface of the tensioning element 1680, can comprise varying depths along their length, and can comprise elements or objects to enhance engagement with the filaments, in a similar manner as discussed above and taught herein with respect to other examples. As explained above, the filaments can be held in this groove 1616 under pressure between the tensioning element 1680 and an interior surface of a joint implant element. This example also includes a gripping texture 1617 inside the grooves. In this example, the gripping texture is a directional texture. This texture can be designed to allow filaments to slide over the texture in grooves in one direction but not in the opposite direction. The texture can be oriented so that when the tensioning element is inserted inside a joint implant element, the texture prevents the filaments from pulling out of the space between the tensioning element and the joint implant element. In this example, the directional gripping texture switches directions at a midpoint. The tensioning element can be inserted midpoint-first into the interior space of a joint implant element. This can be useful because the filaments can wrap around the tensioning element in either direction. No matter which direction a filament wraps around the tensioning element, at least a portion of the grooves can have a directional texture (or other surface objects or elements) that helps retain the filament in the groove. In other examples, a non-directional texture can be used to increase friction on the filaments in both directions.

Other variations of the tensioning element can also be used. In some examples, a tensioning element can have a cylindrical shape similar to the tensioning element shown in FIG. 16, but the tensioning element can have a smooth surface without grooves. In other examples, the tensioning element can have partial grooves that extend part way around the surface. In further examples, the tensioning element can be roughened on a leading edge to more positively grip the filaments. In another examples, the tensioning element can be split into two or more parts. The filaments can be placed between these parts and then the parts can be assembled together to sandwich the filaments within the tensioning element. The tensioning element can then be placed into the joint implant element as in the previous examples. The parts of the tensioning element can be assembled by fastening using a mechanical fastener, or adhering using an adhesive, or by any other suitable method of assembling. In yet another example, the tensioning element can include a shape memory alloy. The shape memory alloy can be configured to change shape upon a triggered phase change, such as by a change in temperature. The tensioning element can have an initial shape to allow assembly of the tensioning element with the filaments and the joint implant element, and then the shape memory alloy can be triggered after assembly to change to a different shape that applies tension to the filaments and secures the filaments. In another example, a shape memory alloy can be triggered by a phase change to relax and reduce force applied to the filaments, in order to more easily disassemble the joint implant for revision. In other examples, the tensioning element can have a C-shape, as opposed to a full cylinder shape. In certain examples, the C-shaped tensioning element can be sprung to have an outer diameter that is greater than the inner diameter of the joint implant element. The tensioning element can then be elastically compressed and placed into the hollow interior of the joint implant element with the filaments between the tensioning element and the interior surface of the joint implant element. Then the tensioning element can be allowed to spring back toward its original diameter, which can apply a controllable and uniform force to the filaments and the interior surface of the joint implant element, trapping the filaments. A C-shaped tensioning element can also be used with a pin that can slide into the hollow center of the tensioning element, or be inserted with a press fit. The pin can ensure that the C-shaped tensioning element keeps applying force to trap the filaments. In a further examples, the pin that is inserted into the C-shaped tensioning element can also include another pin that is designed to fit inside a bone anchor attached to it via a web of appropriate length to allow for lateral insertion into the bone anchor.

Figure 17A:
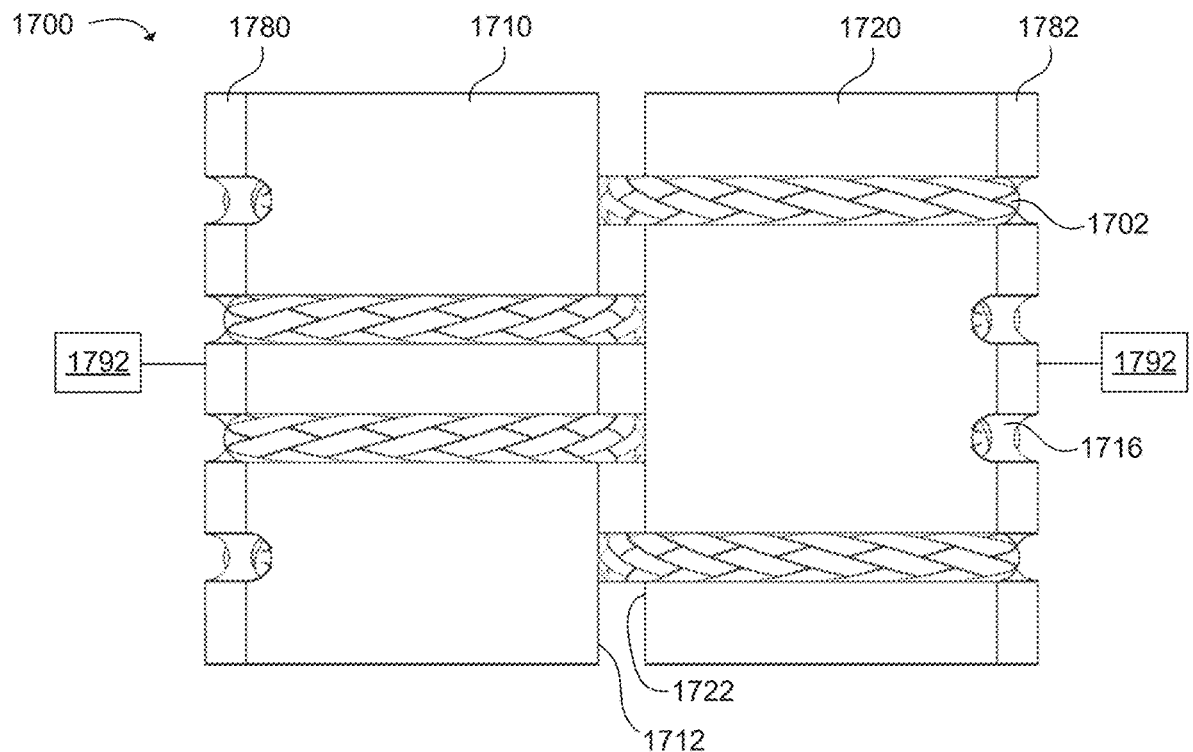
FIGS. 17A-17B illustrate another example joint implant in accordance with the present technology.
Figure 17B:
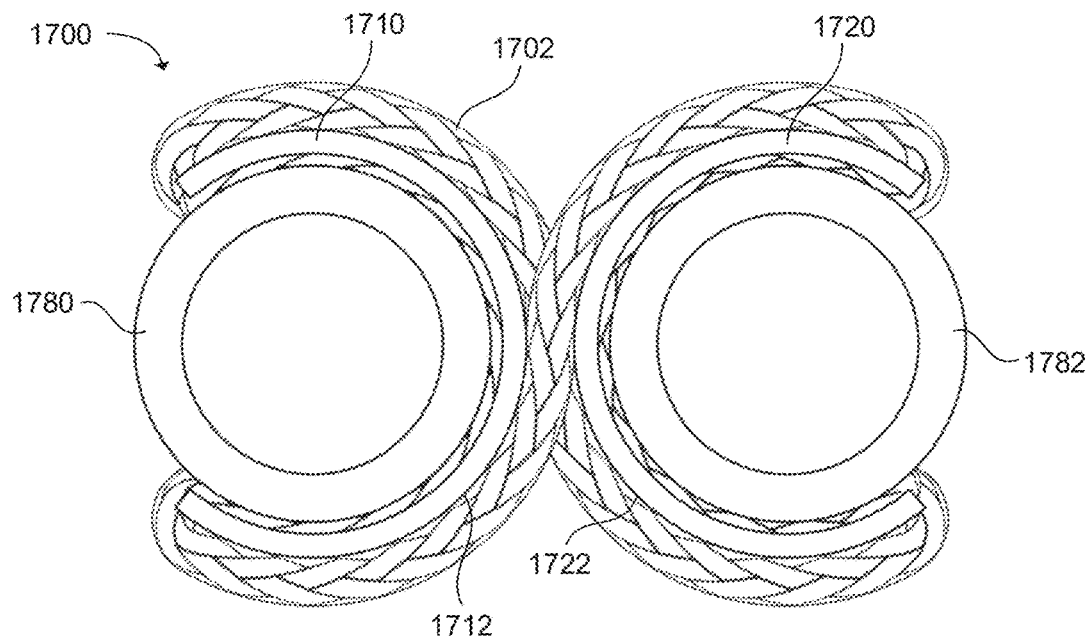

FIG. 17A shows a top-down view of another example joint implant. This example includes a proximal joint implant element 1710 and a distal joint implant element 1720. The proximal joint implant element has a proximal curved interface surface 1712 that is smooth, without any grooves or protrusions. Similarly, the distal joint implant element has a distal curved interface surface that is smooth. Filaments 1702 extend from the proximal joint implant element 1710 to the distal joint implant element 1720 as in other examples. In this example, the proximal curved interface surface 1712 does not directly contact the distal curved interface surface 1722. Instead, the filaments separate the curved interfaces surfaces from each other. When the joint implant elements rotate with respect to each other, each one rolls on the filaments. As in other examples, a proximal tensioning element 1780 is in the hollow interior of the proximal joint implant element 1710, and a distal tensioning element 1782 is in the hollow interior of the distal joint implant element 1720. The tensioning elements include grooves 1716 to partially accommodate the filaments. The tensioning elements hold the filaments in place. The tensioning elements can be pressed into the hollow interior spaces in the joint implant elements, and the act of pressing the tensioning elements in can automatically apply a tension force to the filaments because the filaments can be pulled along with the tensioning elements into the hollow interior spaces. FIG. 17A also shows boxes 1792, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. FIG. 17B shows a side view of the example shown in FIG. 17A.

Figure 18:
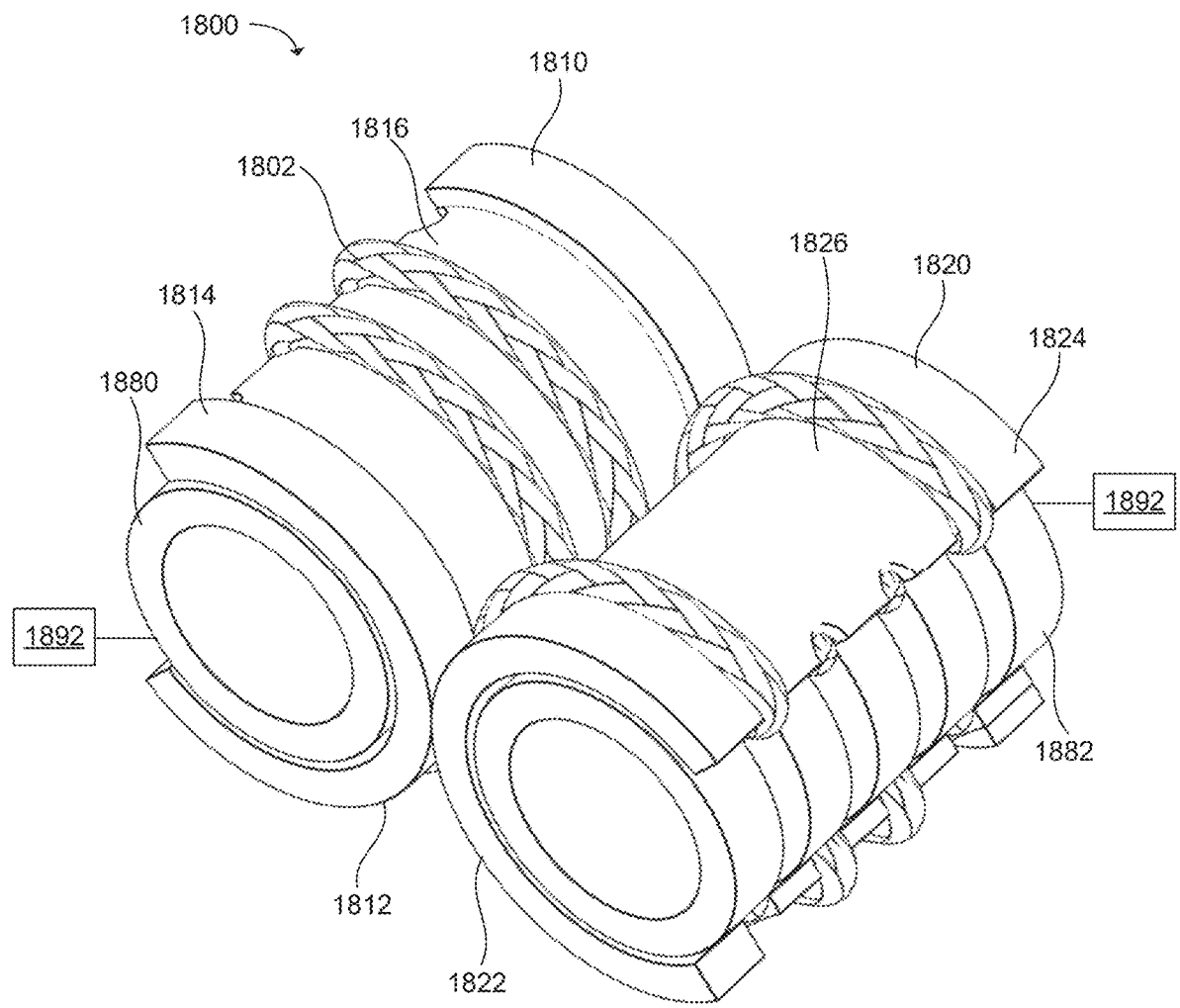
FIG. 18 is a perspective view of another example joint implant in accordance with the present technology.

FIG. 18 shows a perspective view of a different example joint implant 1800. This example includes tensioning elements 1880, 1882 similar to other examples above. However, instead of individual grooves, this example includes curved interface surfaces 1812, 1822 that have raised outer portions 1814, 1824 with a larger recessed area 1816, 1826 between the raised outer portions. The recessed areas 1816, 1826 act as a large groove that accommodates all the filaments 1802 while the raised outer portions 1814,1824 of the joint implant elements 1810, 1820 contact each other directly. FIG. 18 also shows boxes 1892, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

Figure 19A:
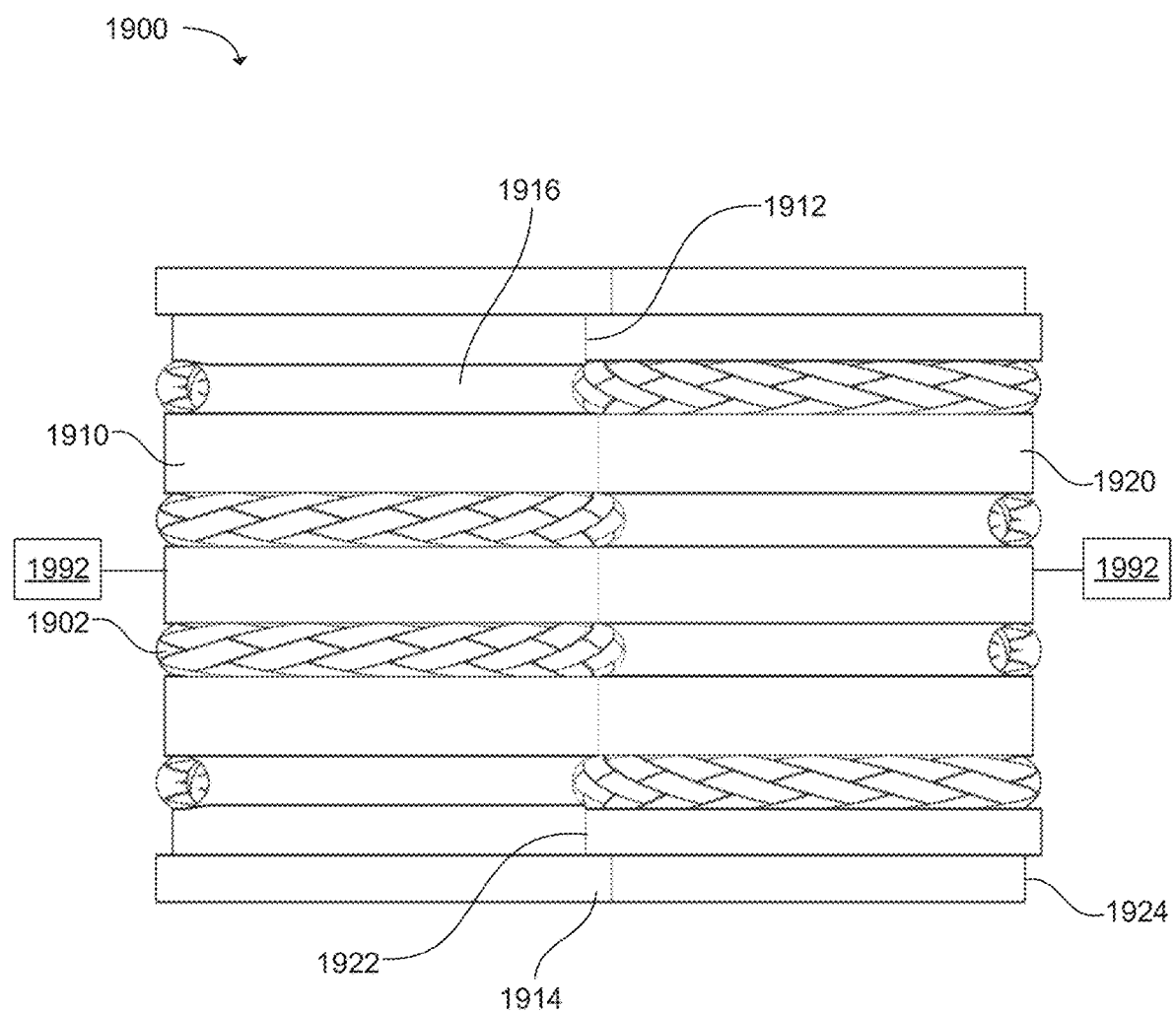
FIGS. 19A-19B illustrate another example joint implant in accordance with the present technology.
Figure 19B:
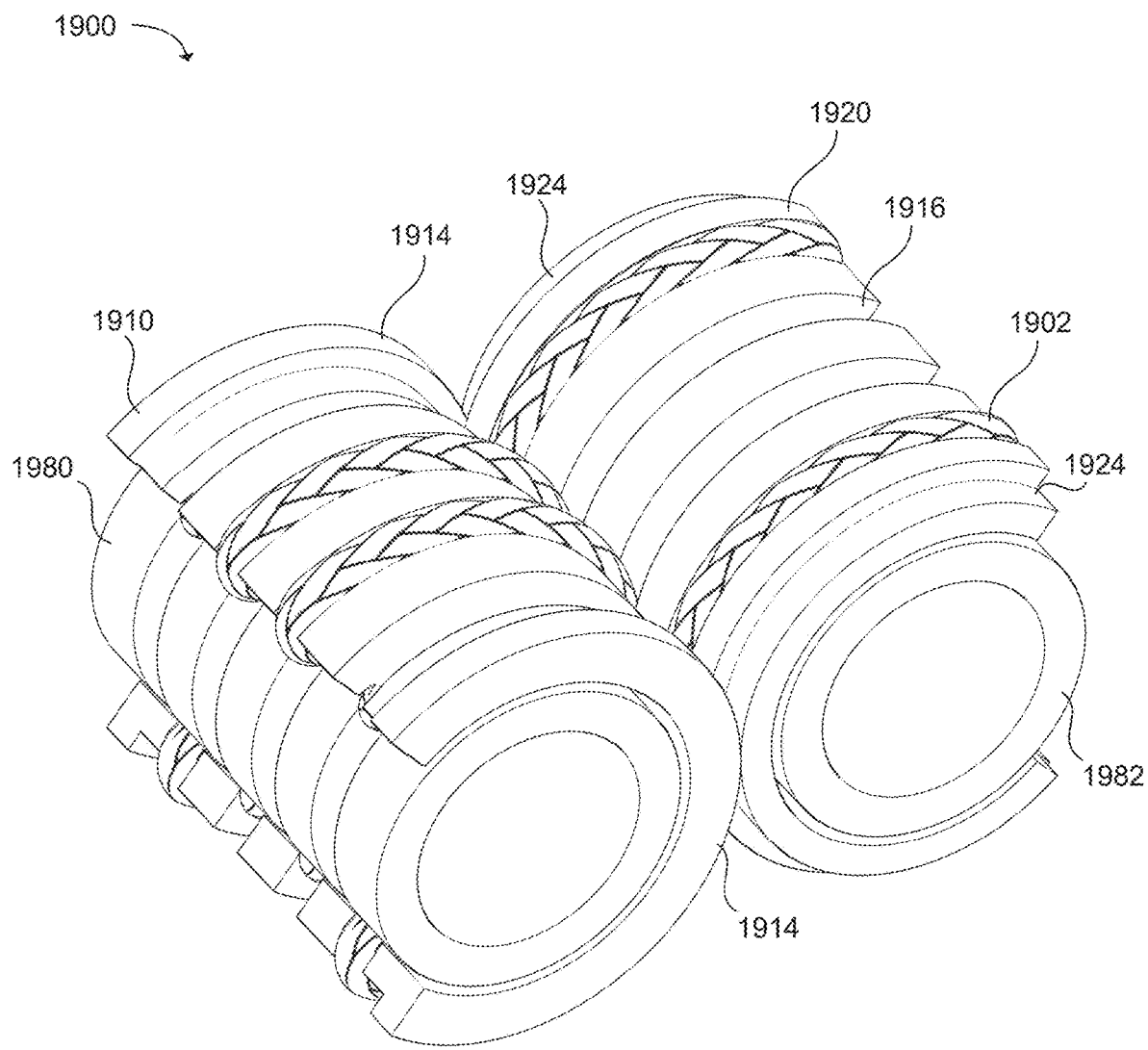

FIG. 19A shows a top-down view of another example joint implant 1900. This example includes interlocking features on the curved interfaces surfaces that can prevent shearing motion of the joint implant elements. In particular, the proximal joint implant element 1910 includes a proximal curved interface surface 1912 with a ridge 1914 at the sides of the proximal joint implant element. This ridge protrudes farther outward, radially, than other portions of the proximal curved interface surface. The distal joint implant element 1920 includes a distal curved interface surface 1922 with a recess 1924 at the sides of the distal joint implant element. The ridge fits into the recess. When both ridges 1914 on either side of the proximal joint implant element 1910 are interlocked with the recesses 1924 on either side of the distal joint implant element 1920, the ridges prevent any lateral shearing motion of the joint implant elements relative to each other. This example also includes filaments 1902 that are accommodated by grooves 1916 in the proximal and distal curved interfaces surfaces. FIG. 19A also shows boxes 1992, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. FIG. 19B shows a perspective view of this example. In this example, the proximal tensioning element 1980 and distal tensioning element 1982 are visible.

The joint implants described herein can also include bone interface connectors that function to facilitate implanting of the joint implant within a patient by directly or indirectly connecting with the bone of a patient. In some examples, the joint implant can comprise a proximal joint implant element having a proximal curved interface surface and a proximal base portion, and the joint implant can further comprise a proximal bone interface connector operable with (e.g., connected to) the proximal base portion. The joint implant can also include a distal joint implant element having a distal curved interface surface and a distal base portion, with a distal bone interface connector operable with (e.g., connected to) the distal base portion. The bone interface connectors can be an element that either is configured to connect directly to a bone of a patient, or is configured to connect to a bone anchor, where the bone anchor is a separate element that connects directly to a bone of a patient. In other words, in some examples the bone interface connector itself can be in direct contact with a bone when the joint implant is implanted. In other examples, a separate bone anchor element can be implanted in the bone, and the bone interface connector can connect to the bone anchor. As used here, a "bone interface connector operable with the base portion" can refer to a bone interface connector that is integrally formed with the base portion, such that the joint implant element is a single piece that includes the bone interface connector integrally formed therein; or this can refer to a bone interface connector that is a separate piece from the joint implant element, but which is directly connected in direct contact with the base portion of the joint implant element; or this can refer to a bone interface connector that is a separate piece from the joint implant element and which is indirectly connected to the base portion of the joint implant element. As used herein, "indirectly connected" refers to the bone interface connector being connected with one or more other elements or pieces located between the bone interface connector and the joint implant element. Thus, the joint implants described herein can have a variety of arrangements that allow the joint implants to be connected to the bones of a joint in which the joint implant is to be implanted.

The bone anchors can be permanently attached to bones of a patient in some examples. "Permanently attached" can mean that the bone anchors are not intended to be detachable to be removed or replaced at a later time. In some examples, the joint implant can be designed as a modular joint implant that includes one or two bone anchors that are permanently attached to bones of the patient, while other components of the joint implant can be designed to be detachable from the bone anchors. The detachable components can be removed and swapped with different components, or removed to be repaired or adjusted and then re-attached. In some examples, the components connected between the two bone anchors can be collectively referred to as the joint span. The joint span can include the proximal joint implant element, the distal joint implant element, and the filament segments coupling the joint implant elements together. Other components, such as tensioning elements and bone interface connectors can also be included as parts of the joint span. In some examples, the joint span can have a modular design such that the joint span is removable from the bone anchors.

Figure 20A:
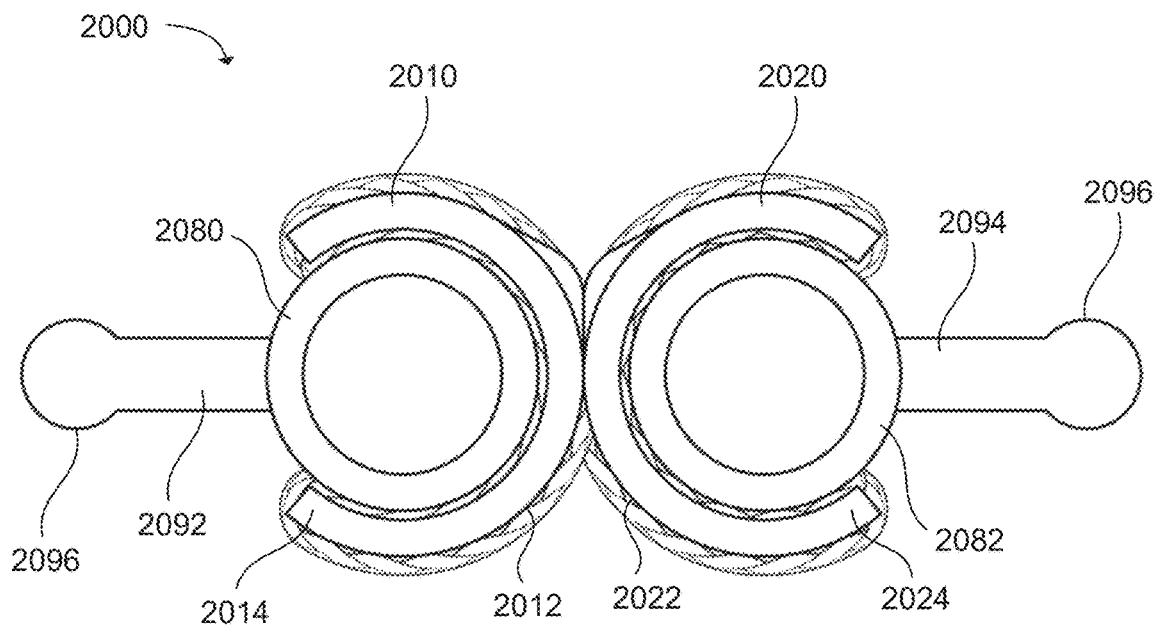
FIG. 20A is a side view of an example joint implant in accordance with the present technology.
Figure 20B:
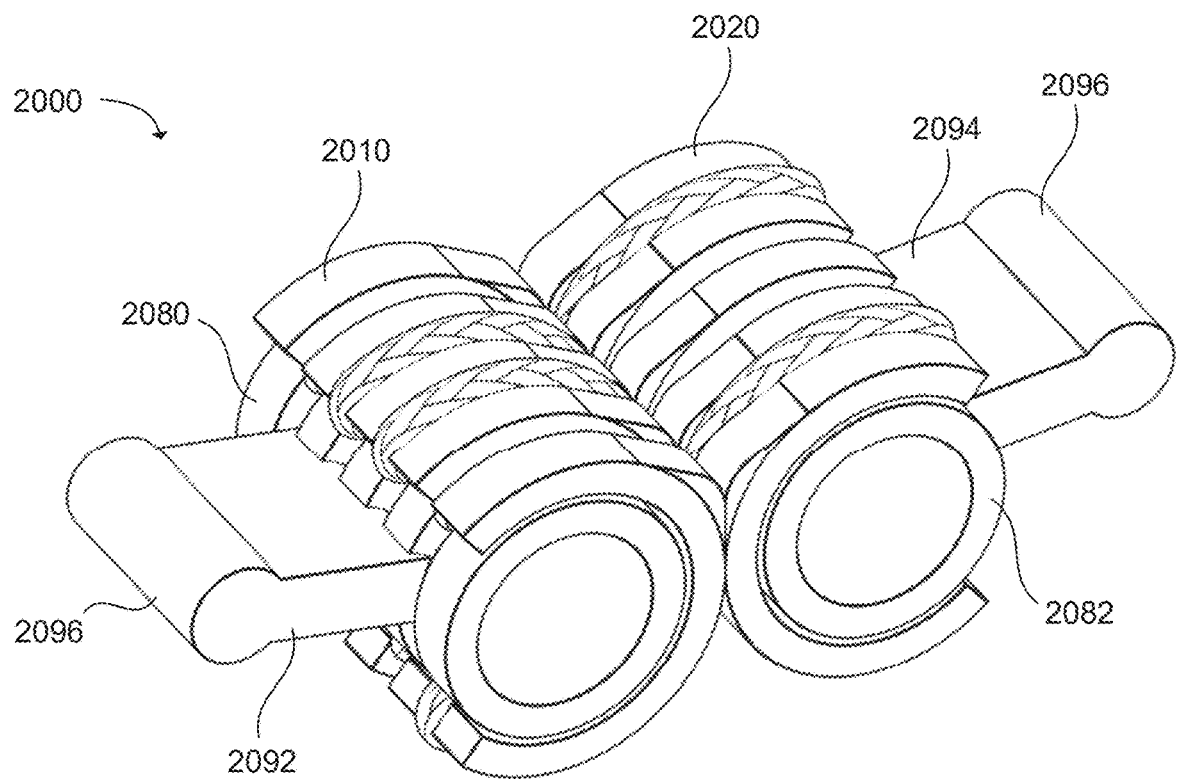
FIG. 20B is a perspective view of the example joint implant of FIG. 20A.

FIG. 20A shows a side view of an example joint implant 2000. FIG. 20B shows a perspective view of the same example. This example is similar to other examples above, including a proximal joint implant element 2010, a distal joint implant element 2020, a proximal tensioning element 2080, and a distal tensioning element 2082. This example also includes a proximal bone interface connector 2092 and a distal bone interface connector 2094. In this example, the proximal bone interface connector 2092 is integrally formed with the proximal tensioning element 2080. Thus, the proximal tensioning element 2080 and the proximal bone interface connector 2092 are a single piece that can be pressed into the hollow interior of the proximal joint implant element 2010 to apply tension to the filaments. The distal bone interface connector 2094 is similarly integrally formed with the distal tensioning element 2082. This shows one example of how the bone interface connector can be indirectly connected to the base portions 2014,2024 of the joint implant elements 2010,2020. The proximal base portion 2014 includes all parts of the proximal joint implant element 2010 other than the proximal curved interface surface 2012. Thus, the proximal base portion includes the interior surface of the hollow interior of the proximal joint implant element 2010. The distal base portion 2024 includes all parts of the distal joint implant element other than the distal curved interface surface 2022. The bone interface connector can be integrally formed with a tensioning element that is connected to the base portion of the joint implant element, as in this example. The proximal and distal bone interface connectors 2092,2094 each include a direct bone interface surface 2096 with a bulged profile at the end of the bone interface connectors. A bone can be prepared by forming a slot in the bone that has a bore of sized slightly larger than the bulged profile. The bone interface connector can then slide into the slot laterally, so that the bulged portion is retained in the slot. In other examples, a similar bulged shape can be used together with a separate bone anchor. The bone anchor can be a separate part that is fixed to the bone, and the bone anchor can have a slot that corresponds to the shape of the bone interface connector. The bulged portion can be retained in the slot of the bone anchor. The proximal and distal bone interface connectors with their respective direct bone interface surfaces having a bulged profile can comprise any size, shape, or configuration.

Figure 20C:
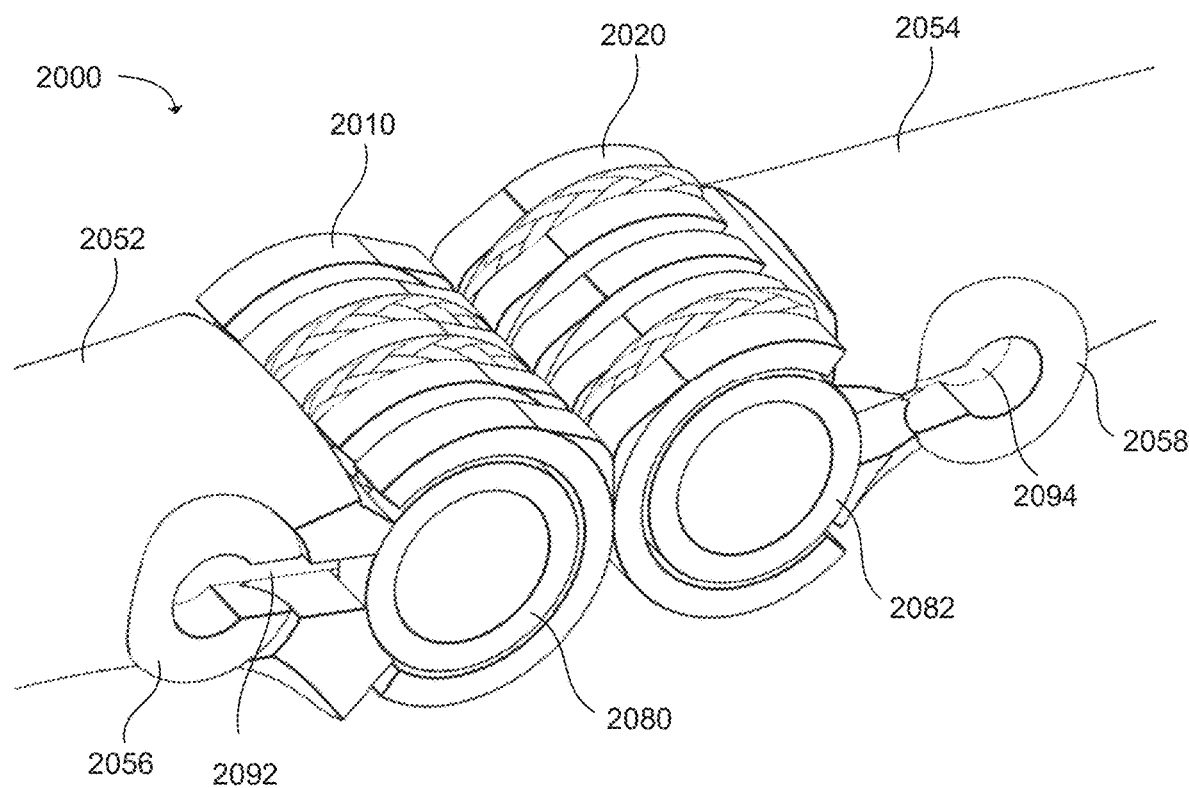
FIG. 20C is a perspective view of the example joint implant implanted into bones of a joint in accordance with the present technology.

FIG. 20C shows the example joint implant 2000 implanted into two bones 2052, 2054 of a human subject. The bones have been prepared by forming bores and slots in the bones, and a proximal anchor 2056 is implant into one bone, while a distal anchor 2058 is implanted into the other bone. The proximal bone interface connector 2092 fits into the proximal anchor and the distal bone interface connector 2094 fits into the distal anchor. This allows the joint implant 2000 to be connected to both bones 2052,2054 of the joint being repaired, forming a working repaired joint.

In some examples, the bone interface connectors can be configured to be secured to bone anchors through interference fit or by an adhesive such as cement. Revision of the joint can be facilitated by using an interference fit because this can make it easier to remove the bone interface connector from the bone anchor later. In other examples, the bone interface connectors can be configured to be secured directly to a bone through interference fit or by cement.

Figure 20D:
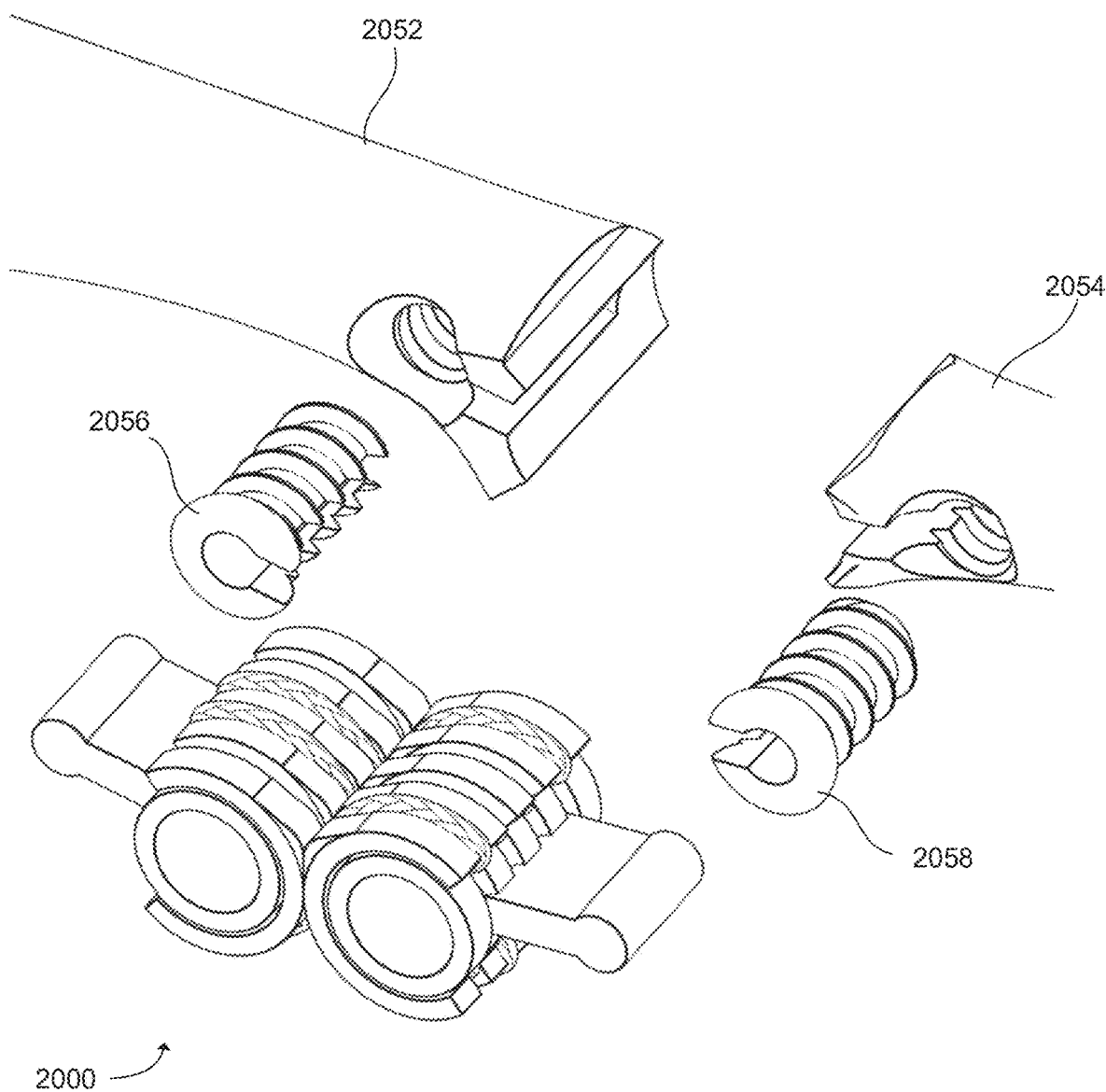
FIG. 20D is a perspective exploded view of the example joint implant and the bones into which it is implanted in accordance with the present technology.

FIG. 20D shows an exploded view of the bones 2052, 2054 with the proximal anchor 2056 and, distal anchor 2058, and the joint implant 2000. In this example, the anchors 2056,2058 have threads on their exterior surfaces, allowing the anchors to be screwed into the bones 2052,2054. In other examples, anchors can be made without threads such that the anchors can be press-fit into bores formed in the bones instead of being screwed into the bones. The anchors can be formed with any profile that allows them to be press-fit into the bones in this way. The anchors in these examples can be implanted laterally, entering the bone from the side. In some cases, this can be beneficial because the anchors and the joint implant can be implanted through a transverse incision on the side of a finger joint or other joint in the body.

In some examples, the bone interface connectors can have a narrow insertion end adapted to be inserted longitudinally into a bone. In other examples, a separate bone anchor can be used and the bone anchor can have a narrow insertion end adapted to be inserted longitudinally into a bone. In further examples, the bone interface connector or the bone anchor can be adapted to be inserted along a transition from a diaphysis to an epiphysis of a bone, such as a phalanx bone. In certain examples, the bone interface connector or the bone anchor does not extend farther into the bone than the transition from the diaphysis to the epiphysis. In other examples, the bone interface connector or bone anchor can extend into the diaphysis.

The examples described above involve a joint implant to be used in a finger or toe joint, such as a distal interphalangeal joint, a proximal interphalangeal joint, or a metacarpophalangeal joint. In other examples, the joint implants described herein can be used to repair a variety of other joints, such as an elbow, knee, wrist, ankle, or other single-bend axis joints (i.e., hinge joints). The size of the joint implant can be selected depending on the size of the joint in which the joint implant is to be implanted. The size can also vary between different patients even when the same joint is being repaired. In some examples, the joint implant can have an overall width that is about the same as the width of bones at the joint to be repaired. In other examples, the joint implant can have an overall width that is less than the width of the bones. The overall width of the joint implant can be the greatest lateral distance between any components of the joint implant. In some examples, the joint implant elements can be the widest components, and therefore the overall width can be the width of the joint implant elements. In other examples, some other component such as screws, caps, or others can extend out laterally farther than the joint implant elements. In various examples, the overall width of the joint implant can be from about 5 mm to about 10 cm, or from about 5 mm to about 5 cm, or from about 5 mm to about 2 cm, or from about 5 mm to about 15 mm, or from about 5 mm to about 12 mm, or from about 10 mm to about 15 mm.

FIG. 21 shows a perspective view of another example joint implant 2100 that includes a proximal bone interface connector 2192 and a distal bone interface connector 2194. The proximal bone interface connector is integrally formed with the proximal tensioning element 2180 and the distal bone interface connector is integrally formed with the distal tensioning element 2182. The proximal and distal bone interface connectors 2192,2194 taper to a narrow end 2196 that can be inserted longitudinally into a prepared bone. The bone interface connectors 2192,2194 also include a transverse hole 2198. A screw or pin can be inserted into the bone through this transverse hole 2198 after the bone interface connector 2192,2194 has been inserted into the bone. The screw or pin can help retain the bone interface connector 2192,2194 in the bone and provide a strong connection to the bone. In other examples, a separate bone anchor can have similar features, including a narrow end for longitudinal insertion into a bone and a transverse hole to allow a screw or pin to hold the anchor in the bone.

The bone anchor can then be attachable to a bone interface connector of the joint implant. This example also includes interlocking features on the curved interface surfaces 2112, 2122 that can prevent shearing (lateral motion) of the joint implant elements 2110, 2120. The proximal joint implant element 2110 includes a ridge 2114 at the outer edge of the proximal curved interface surface 2112. The distal joint implant element 2120 includes a recess 2124 at the outer edge of the distal curved interface surface 2122. The ridge can fit into the recess so that the curved interface surfaces 2112,2122 interlock one with another. The curved interface surfaces 2112,2122 can still roll on each other throughout the whole range of motion of the joint implant, but the interlocking features can prevent lateral movement of the joint implant elements. It is contemplated that such interlocking features can be present on any of the example joint implant elements discussed herein, or in other words, that any of the joint implant elements discussed herein can comprise interlocking features, such as shown here.

Figure 22:
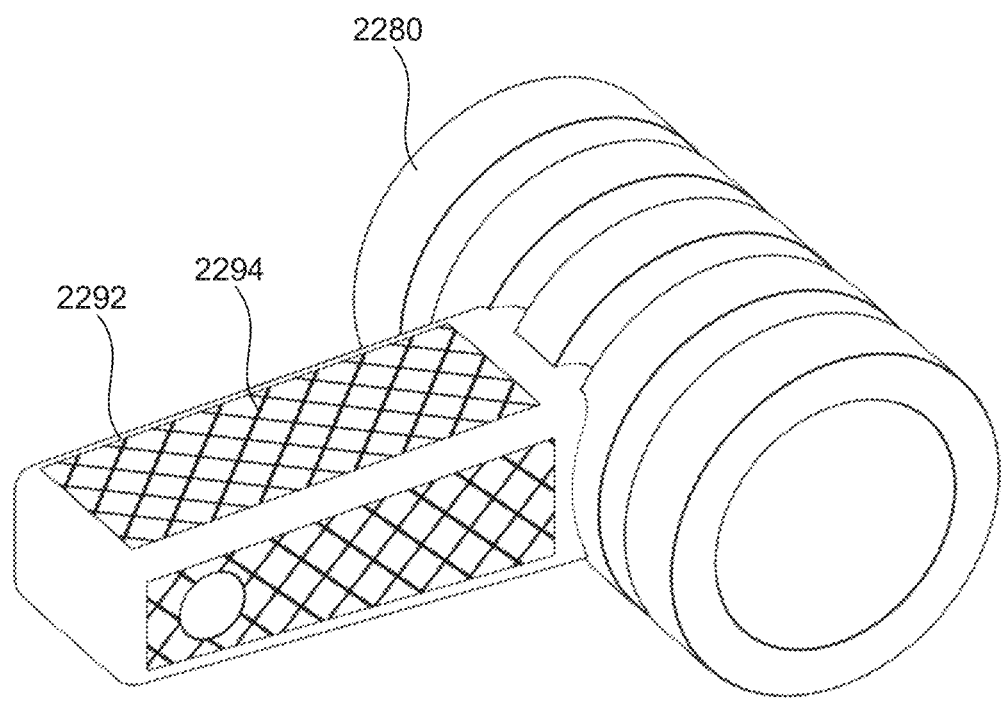
FIG. 22 is a perspective view of an example bone interface connector and tensioning element in accordance with the present technology.

FIG. 22 shows a perspective view of another example bone interface connector 2292 that is integrally formed with a tensioning element 2280. This bone interface connector has a feature in the form of a surface texture 2294 designed to facilitate and increase osseointegration (compared to a similar design without such a feature). A variety of textures having small raised or recessed patterns can be useful for helping form a stronger bond between the bone interface connector and the bone into which it is implanted. Other features that can be included on the bone interface connector to increase osseointegration include, but are not limited to, an osseointegration coating, a sintered surface texture, barbs, flanges, protrusions or recesses to allow bone in-growth, and combinations of these. Still further, the bone interface connector itself can be configured to comprise an open lattice structural configuration having a plurality of apertures or passageways defined by a plurality of intersecting structural members, the open lattice structural configuration being sized and configured to facilitate and increase osseointegration. FIG. 22 can be referred to as alternatively showing an open lattice configuration. The open lattice configuration can further facilitate insertion of a lateral or transverse screw, pin or other fastener to help secure the bone interface connector to a prepared bone once implanted therein. In other examples, a separate bone anchor can be implanted into the bone and the bone anchor can have any of these surface features or structural configurations to increase osseointegration. It is contemplated that any of the example bone interface connectors or bone anchors discussed herein can comprise one or more features or configurations to facilitate and increase osseointegration.

Figure 23:
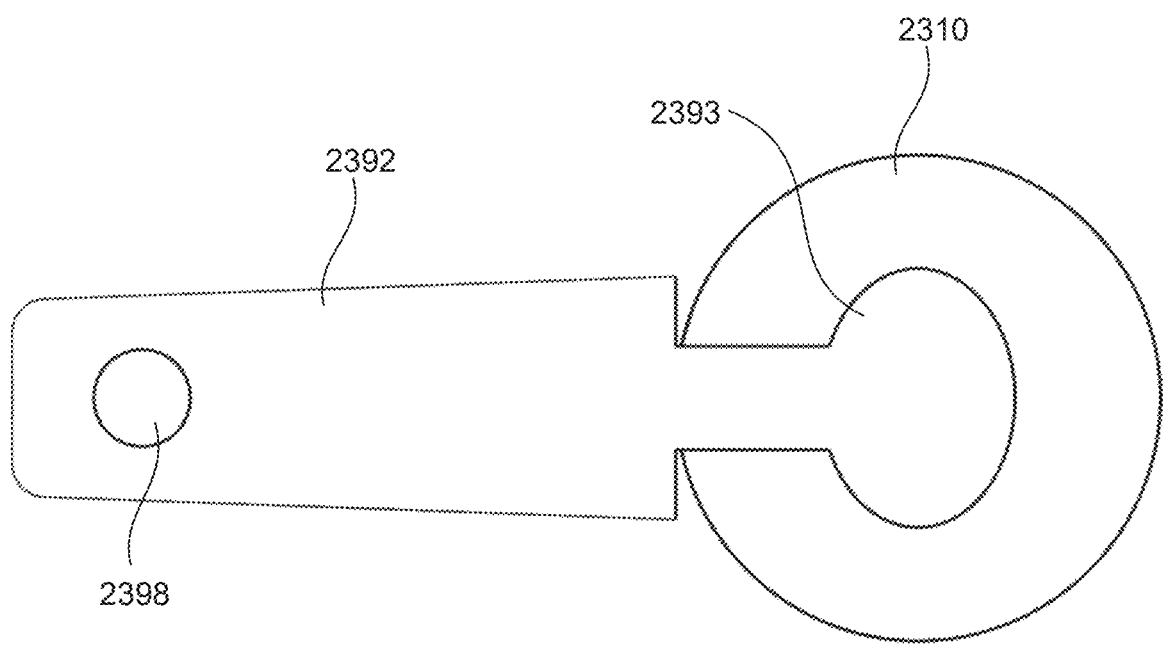
FIG. 23 is a side view of an example bone interface connector and joint implant element in accordance with the present technology.

FIG. 23 shows a side view of a different example of a bone interface connector 2392 connected to a joint implant element 2310. In this example, the bone interface connector has a connector 2393 that can slide laterally into a matching slot in the joint implant element. The bone interface connector also includes a transverse hole 2398 in this example, wherein a screw or pin can be inserted to secure the bone interface connector to a prepared bone once implanted therein.

Figure 24A:
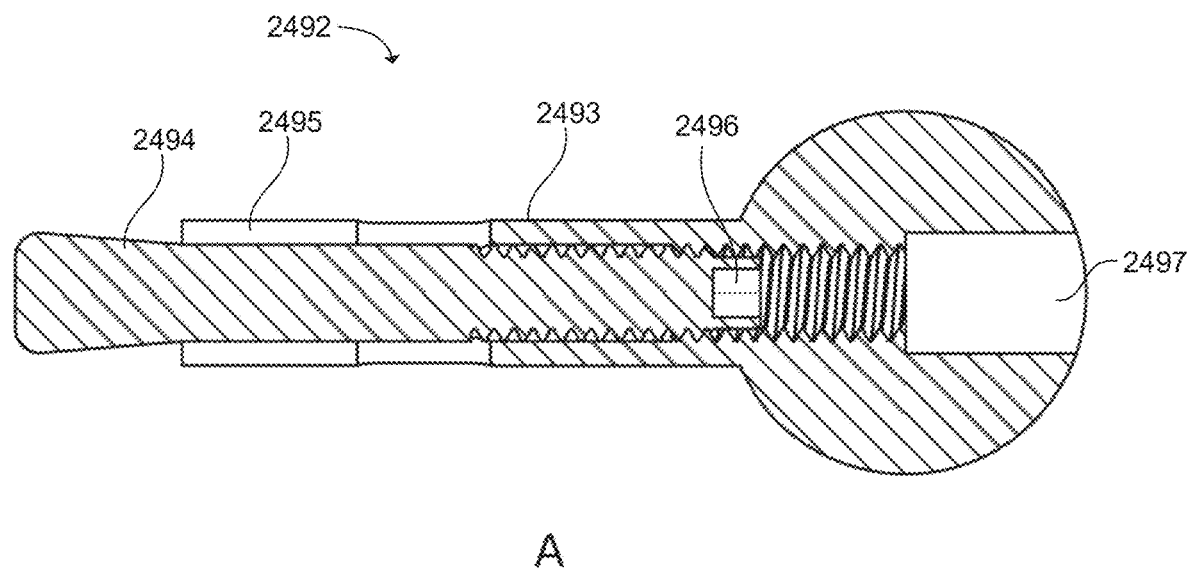
FIGS. 24A-24B illustrate cross-sectional views of an example bone interface connector in accordance with the present technology.
Figure 24B:
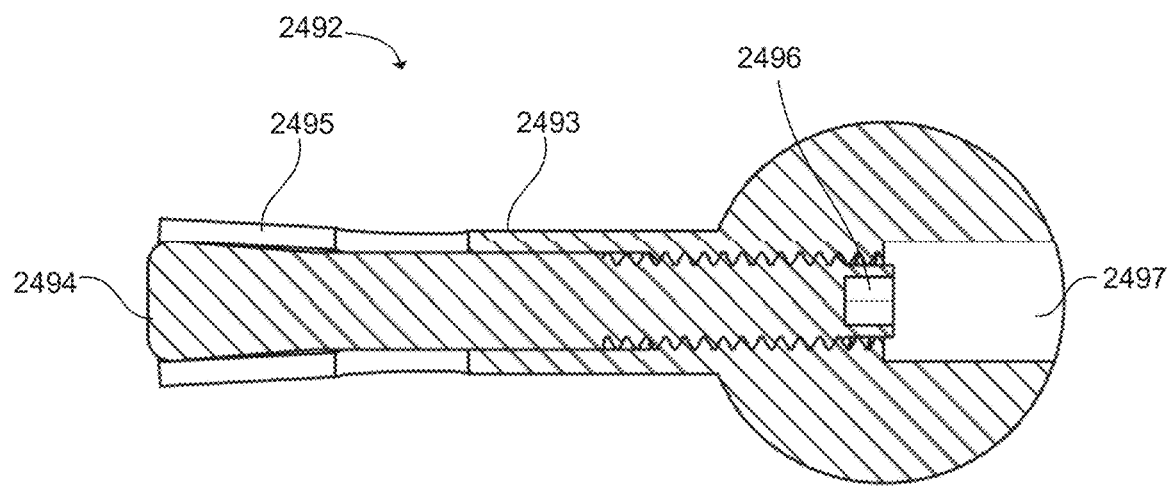

FIGS. 24A and 24B show cross-sectional views of an example bone interface connector 2492 with an expanding stem 2493. The expanding stem includes a screw 2494 inside a sleeve 2495. The screw includes a hex socket 2496 accessible through an opening 2497 that allows the screw to be turned by a hex key. The expanding stem 2493 of this bone interface connector 2492 can be inserted longitudinally into a hole drilled in a bone, while the screw 2494 is extended as shown in FIG. 24A. After being inserted into the bone, a hex key can be used to twist the screw 2494, which causes the screw to retract into the sleeve 2495 as shown in FIG. 24B. The screw has a larger diameter at one end, so that the screw causes the sleeve to expand outward as the screw is retracted. This can place pressure on the bone surrounding the sleeve to hold the bone interface connector 2492 in place.

Figure 25:
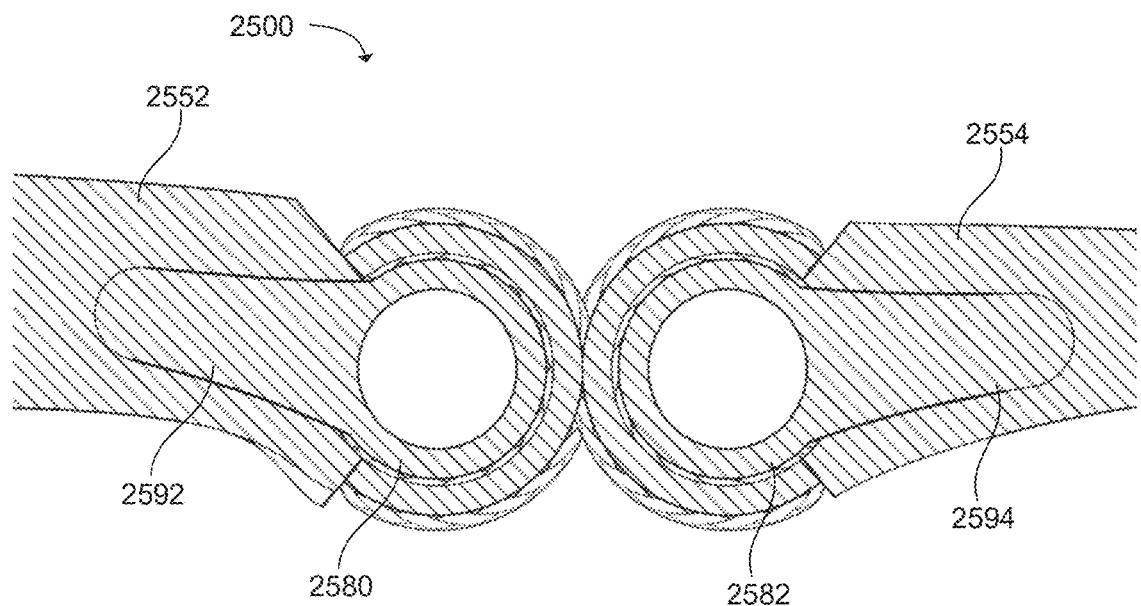
FIG. 25 is a side cross-sectional view of an example joint implant implanted into bones of a joint in accordance with the present technology.

FIG. 25 shows a cross-sectional view of another example joint implant 2500 that has been implanted into bones 2552, 2554. In this example, the bone interface connectors 2592, 2594 are also integrally formed with the tensioning elements 2580, 2582. The bone interface connectors 2592,2594 have a tapered rounded end in this example.

Figure 26:
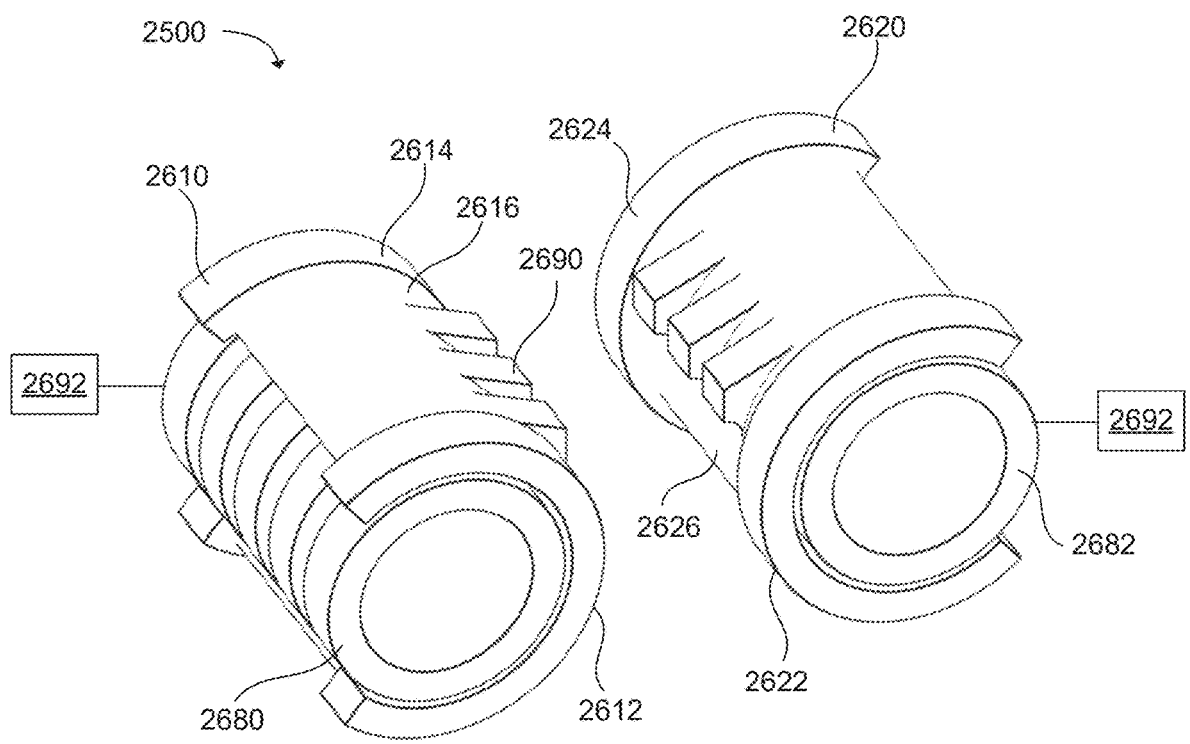
FIG. 26 is a perspective view of another example joint implant in accordance with the present technology.

FIG. 26 shows a perspective view of another example joint implant 2600 with the filaments omitted for the sake of clarity. This example has a proximal joint implant element 2610 with a proximal curved interface surface 2612 and a distal joint implant element 2620 with a distal curved interface surface 2622. The curved interface surfaces 2612, 2622 include raised outer portions 2614, 2624 with large recessed areas 2616, 2626, respectively, between the raised outer portions. The recessed areas 2616,2626 can accommodate all the filament segments in the joint implant. The curved interface surfaces 2612,2622 also include protrusions 2690 that can act as stoppers to stop or limit rotation of the joint implant elements. The protrusions 2690 are separated by spaces that can accommodate the filament segments, which can help keep the filament segments aligned within the large recessed area. This example also includes tensioning elements 2680, 2682 inside the hollow interiors of the joint implant elements. It is contemplated that any of the example joint implants discussed herein can comprise one or more of the features shown here. FIG. 26 also shows boxes 2692, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

Figure 27:
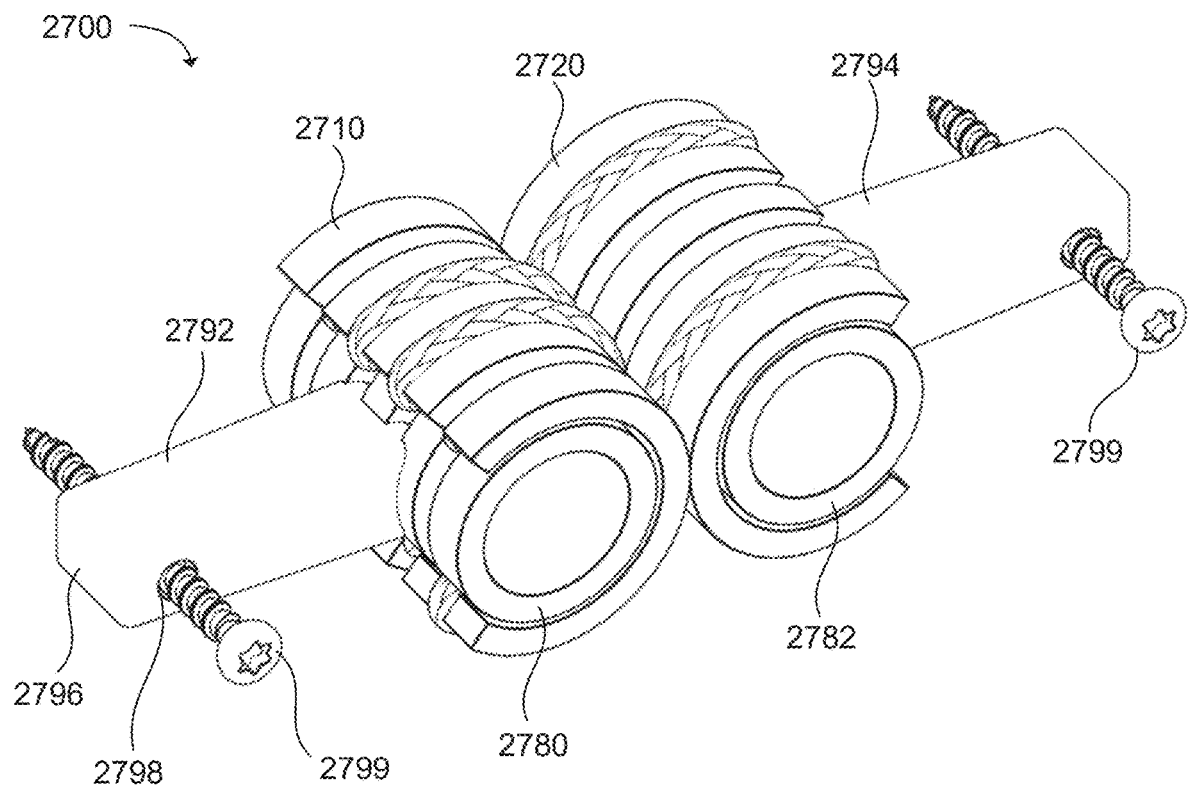
FIG. 27 is a perspective view of another example joint implant in accordance with the present technology.

Another example joint implant 2700 is shown in FIG. 27. This example includes a proximal bone interface connector 2792 and a distal bone interface connector 2794. The proximal bone interface connector is integrally formed with the proximal tensioning element 2780 and the distal bone interface connector is integrally formed with the distal tensioning element 2782. The proximal tensioning element 2780 is retained inside the proximal joint implant element 2710, and the distal tensioning element 2782 is retained inside the distal joint implant element 2720. The proximal and distal bone interface connectors 2792,2794 taper to a narrow end 2796 that can be inserted longitudinally into a prepared bone. The bone interface connectors 2792,2794 also include transverse holes 2798. A screw 2799 or a pin can be inserted into the bone through this transverse hole 2798 after the bone interface connector 2792,2794 has been inserted into the bone. The screw 2799 or pin can help retain the bone interface connector 2792,2794 in the bone and provide a strong connection to the bone.

Figure 28:
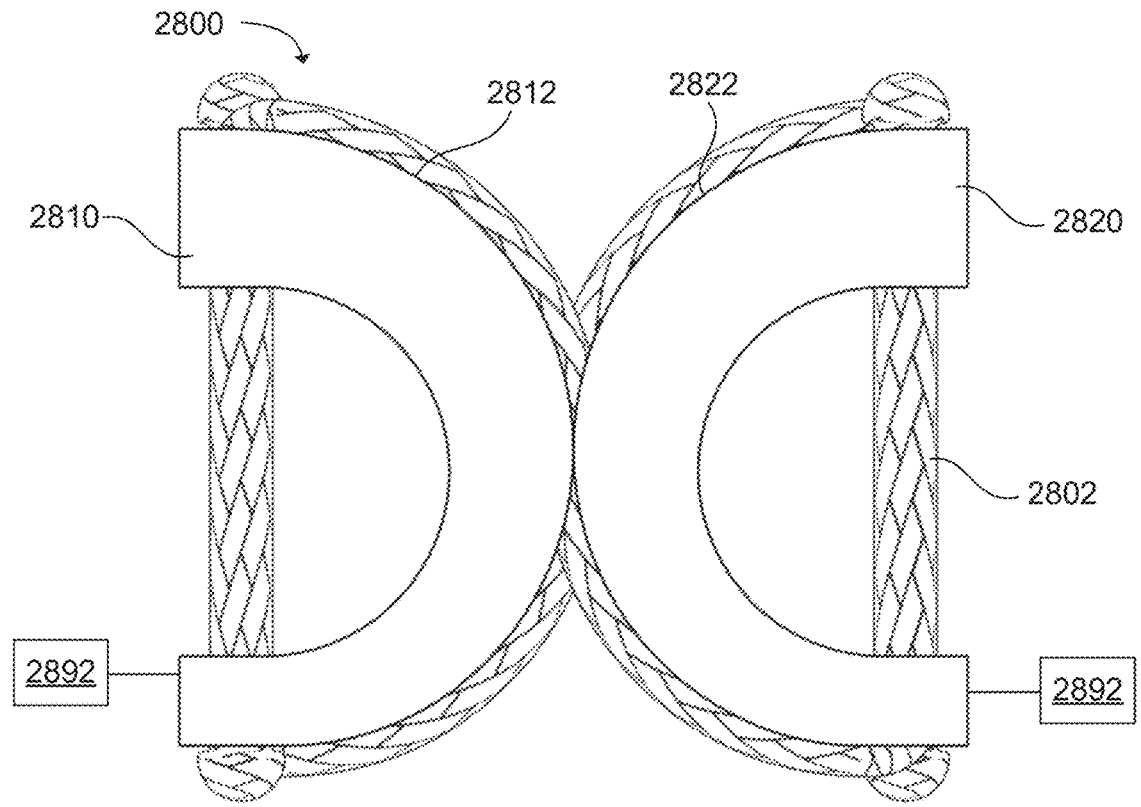
FIG. 28 is a side view of another example joint implant in accordance with the present technology.

FIG. 28 is a side view of another example joint implant 2800. This example includes a proximal joint implant element 2810 with a proximal curved interface surface 2812 and a distal joint implant element 2820 with a distal curved interface surface 2822. The curved interface surfaces have a radius of curvature that gradually increases in the upward direction, in the orientation shown in this figure. The gradually increasing radius of curvature can cause tension in the filaments 2802 to increase gradually as the joint implant elements 2810,2820 rotate. In effect, when the curved interface surfaces 2812,2822 contact each other at a location where the radius is larger, then the tension in the filaments 2802 is greater than when the curved interface surfaces contact each other at a location where the radius is smaller. In this example, the increase tension can create a restoring force that tends to return the joint implant 2800 from an extended position to a flexed position. In other examples, the curved interface surfaces 2812,2822 can have a radius of curvature that is larger at the contact locations of the curved interface surfaces when the joint implant 2800 is in a flexed position. This can create a force that tends to return the joint implant 2800 from the flexed position to the extended position. FIG. 28 also shows boxes 2892, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

It is noted that many of the example joint implants have been depicted without bone interface connectors. However, each of these examples are intended to be operable with one or more bone interface connectors. Indeed, the example joint implants can each comprise bone interface connectors that facilitate their attachment to a bone of a human subject, namely to allow the joint implants to connect to the bones of the joint of the human subject in which the joint implant is to be implanted.

The joint implants can be implanted by arthroplasty, or a surgery for replacing or repairing a joint. In one example, a method of replacing a joint can include preparing a first bone to receive a proximal bone anchor, preparing a second bone to receive a distal bone anchor, securing a proximal bone anchor in the first bone, securing a distal bone anchor in the second bone, and connecting the proximal bone anchor to the distal bone anchor using a joint implant. The joint implant can include any of the elements and features described herein.

In other examples, a method of replacing a joint can be performed with a joint implant that does not utilize separate bone anchors. In some examples, the method can include preparing a first bone to receive a proximal bone interface connector, preparing a second bone to receive a distal bone interface connector, and then implanting the proximal bone interface connector of a joint implant into the first bone and implanting the distal bone interface connector into the second bone.

In some examples, the surgical methods can include making a transverse incision in a finger to implant the joint implant laterally. In further examples, the methods can include inserting a screw or pin into the bone and through a transverse hole in a bone anchor or bone interface connector that has been implanted in the bone. In certain examples, a Huene jig can be used to stabilize at least one of the bones during the surgery.

It is noted that the joint implants described herein can have design characteristics that can simplify surgical methods used to implant the joint implants. For example, some of the joint implant designs described herein can be implanted laterally through a transverse incision. This can be simpler than many previous surgical methods for arthroplasty, because the transverse incision can be made without involving extensor tendons and flexor tendons in some cases. Additionally, modular joint implants as described herein can be implanted in multiple parts, which can generally be done with a smaller incision and less impact on the surrounding bones and tissue. For example, a modular joint implant can include two bone anchors and a joint span. The bone anchors can have any of the designs described herein. The joint span can include any of the joint implant components described herein, and can be designed to be connectable to the two bone anchors. To implant the joint implant, the two bone anchors can be first be attached to the bones of the patient. The joint span can then be connected to each of the bone anchors after the bone anchors have been attached to the bones. In other examples, it may be useful to partially assemble the joint implant before implantation. For example, one bone anchor can be attached to one bone on its own, and then the second bone anchor can be assembled with the joint span before attaching the second bone anchor to a second bone. The joint span can then be connected to the first bone anchor to finish the implantation process. In further examples, the joint implant can be initially provided in an assembled state and then a surgeon can fully or partially disassemble the implant before the implantation surgery. Thus, the modular designs described herein can provide flexibility to the surgeon to use any desired order in implanting the components and assembled the components together.

Figure 29A:
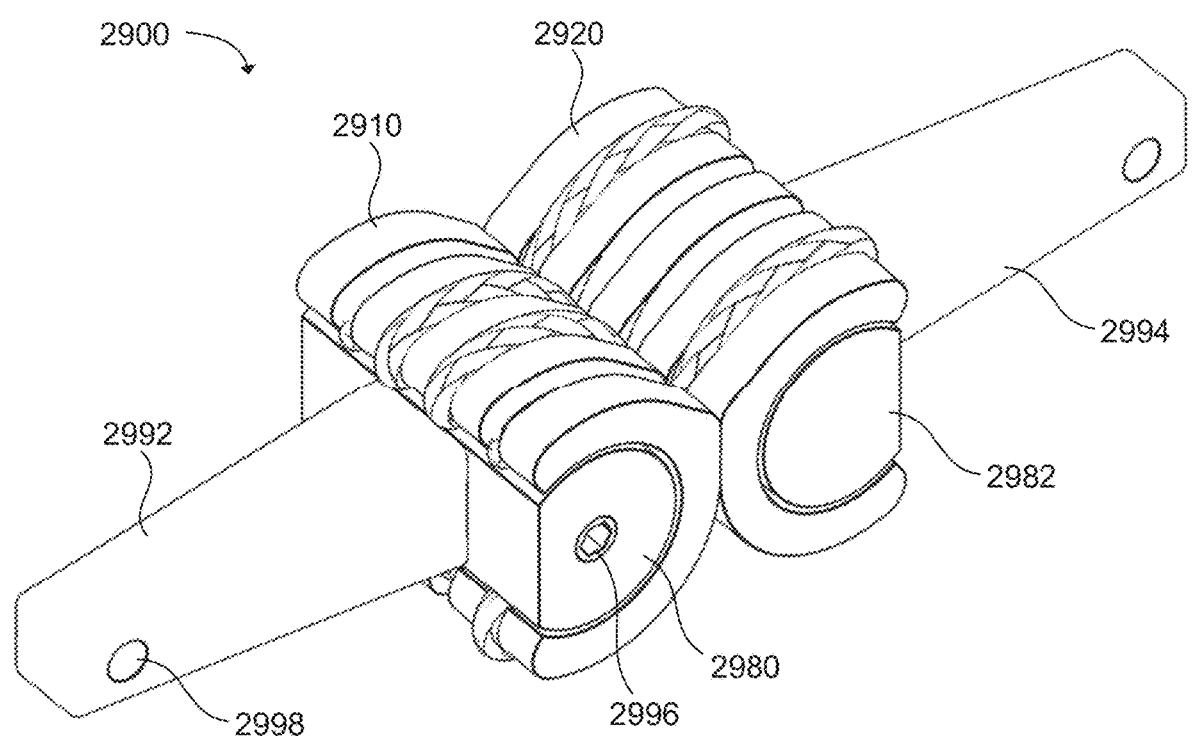
FIGS. 29A-29C illustrate another example joint implant in accordance with the present technology.
Figure 29B:
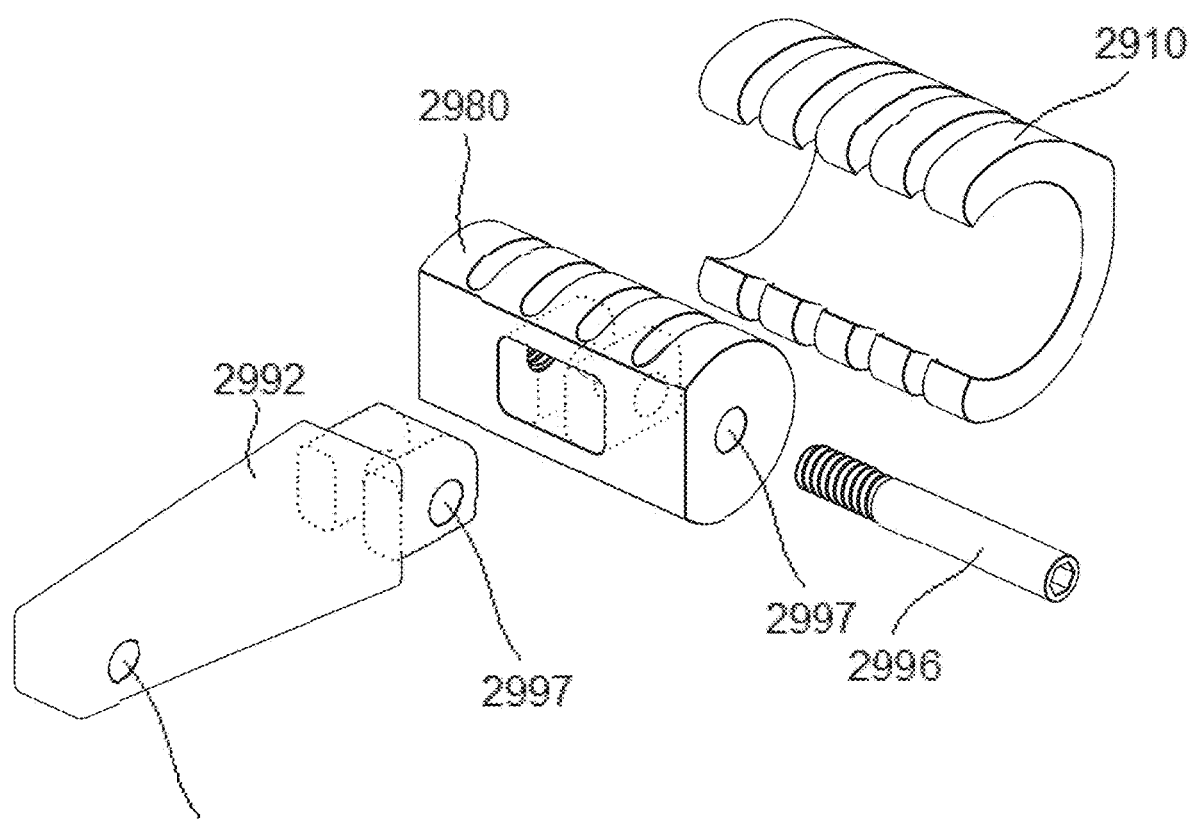
Figure 29C:
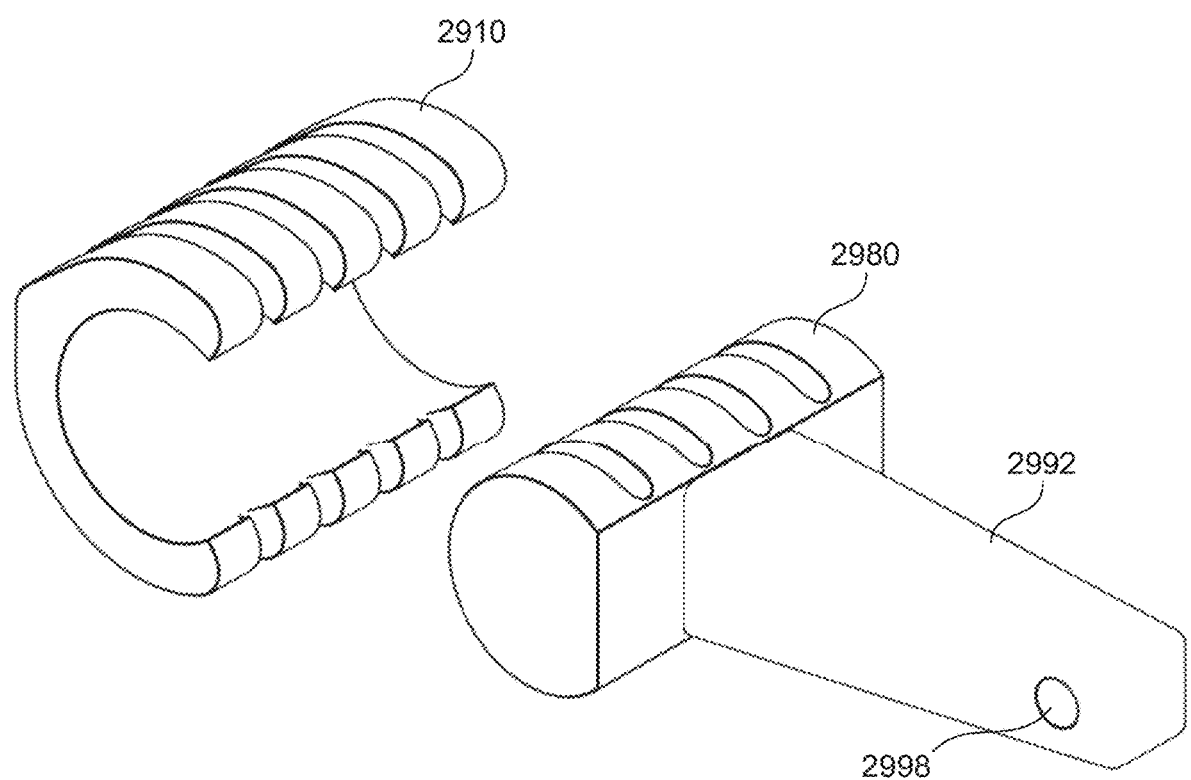

Another example joint implant 2900 is shown in FIGS. 29A-29C. FIG. 29A shows a perspective view of the joint implant 2900. This example includes a proximal joint implant element 2910 and a distal joint implant element 2920 similar to several of the above examples. The joint implant elements 2910, 2920 include hollow interiors that accommodate a proximal tensioning element 2980 and a distal tensioning element 2982. A proximal bone interface connector 2992 is a separate part from the proximal tensioning element, but these parts are assembled together using a bolt 2996. In particular, the proximal bone interface connector 2992 can be attached to the proximal tensioning element 2980 by inserting a protruding portion of the proximal bone interface connector into a recess formed in the proximal tensioning element and screwing a bolt 2996 through a bolt hole 2997 in the proximal tensioning element and the proximal bone interface connector. The proximal bone interface connector 2992 includes a transverse hole 2998 that can be used to secure the proximal bone interface connector in a bone using a screw or pin. A distal bone interface connector 2994 is also separate part from the distal tensioning element 2982 (i.e., not integrally formed as a single piece). The distal bone interface connector can be similarly be secured in the distal tensioning element using a fastener, such as a bolt, that can be inserted from the opposite side, not visible in this figure. FIG. 29B shows an exploded view of a portion of the joint implant. The proximal joint implant element 2910, the proximal tensioning element 2980, the bolt 2996, and the proximal bone interface connector 2992 are all separate parts that can be assembled as shown in FIG. 29A. FIG. 29C shows a perspective view from a different angle, in which the proximal bone interface connector 2992 has been assembled with the proximal tensioning element 2980 and the bolt (not visible from this angle), but the proximal tensioning element has not yet been assembled with the proximal joint implant element 2910.

Figure 29D:
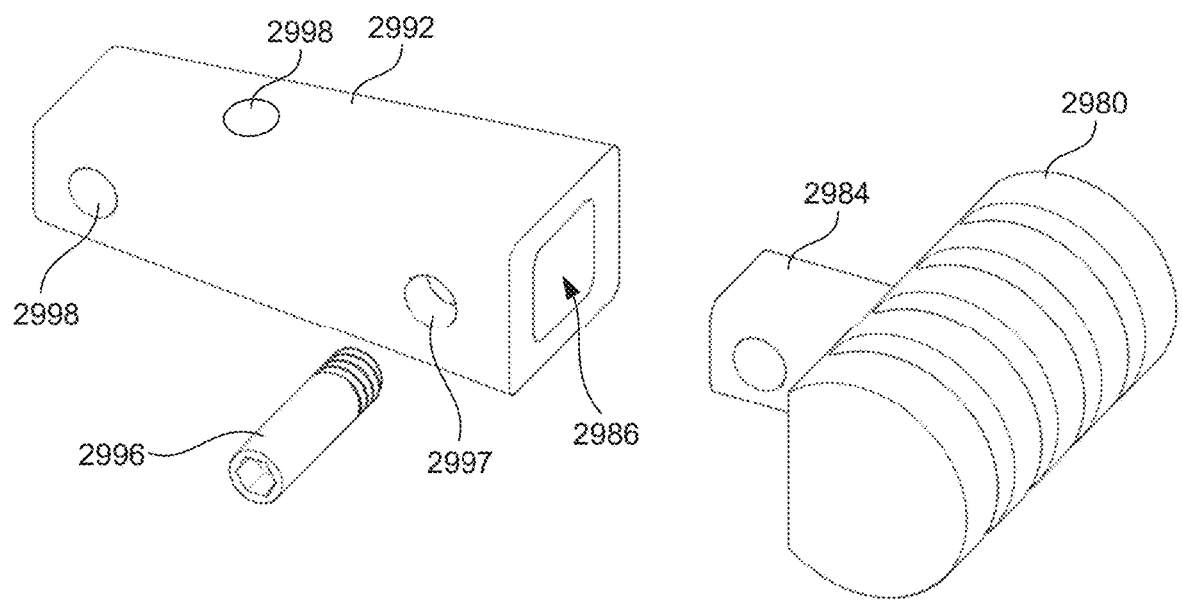
FIG. 29D illustrates another example joint implant in accordance with the present technology.

A similar example is shown in FIG. 29D. This example includes a proximal bone interface connector 2992 with two transverse holes 2998 and a bolt hole 2997. In this example, the bone interface connector includes multiple transverse holes at different angles to allow a transverse screw or pin to be inserted at multiple different angles. In some cases, it can be useful to have multiple options of the angle for a screw for securing the bone interface connector in a bone. In this example, two transverse holes are oriented at a 90° angle one to another. This can allow a surgeon to select either or both transverse holes to use for screwing a screw or inserting a pin through the bone to secure the bone interface connector. Any number of additional transverse holes at other angles can also be included in other examples. The proximal bone interface connector can be attached to the proximal tensioning element 2980 using a bolt 2996, as in the previous example. However, in this example, the proximal tensioning element has an insertion portion 2984 that fits into a slot 2986 in the proximal bone interface connector. The bolt 2996 can be inserted through a bolt hole in the insertion portion 2984.

Figure 29E:
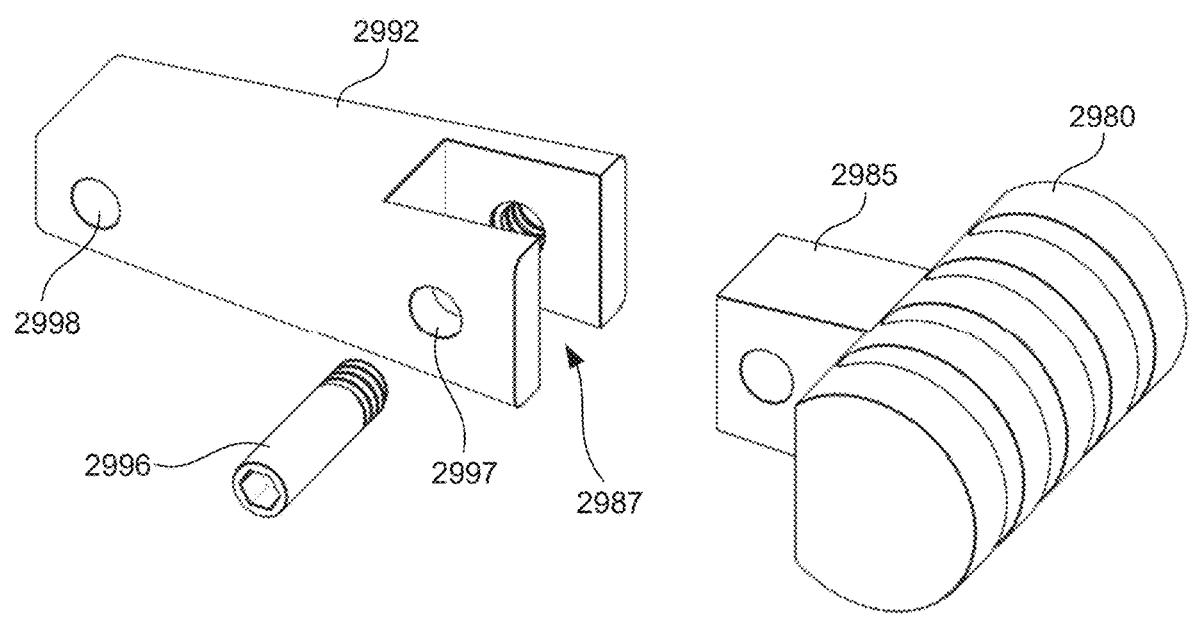
FIG. 29E illustrates another example joint implant in accordance with the present technology.

Another similar example is shown in FIG. 29E. This example also includes a proximal bone interface connector 2992 with a screw hole 2998 and a bolt hole 2997. The proximal tensioning element 2980 in this example includes a tongue 2985 that can fit into a groove 2987 formed in the proximal bone interface connector. The tongue includes a bolt hole so that the bolt 2996 can secure the proximal tensioning element to the proximal bone interface connector.

Although FIGS. 29A-29E illustrate the various bone interface connectors as comprising a single abutment interface between the bone interface connector and the tensioning element (e.g., a single protrusion on the bone interface connector that is inserted into a recess formed in the tensioning element (e.g., see FIGS. 29A-29C), a single insertion portion on the tensioning element that is inserted into a slot formed on the bone interface connector (e.g., see FIG. 29D), a single tongue formed on the tensioning element that fits within a groove formed in the bone interface connector (e.g., see FIG. 29E), etc.), this is not intended to be limiting in any way. Indeed, the interface between any of the bone interface connectors and any of the tensioning elements described herein can comprise any number of abutment interfaces. For example, the proximal bone interface connector 2992 of FIGS. 29A-29C can comprise a plurality of protrusions having holes 2997 therethrough, which holes can be coaxial with one another. The proximal tensioning element 2980 can comprise a plurality of corresponding recesses formed therein configured to receive the plurality of protrusions of the proximal bone interface connector. Once the proximal bone interface connector is inserted into the tensioning element, a single fastener, such as a bolt, can be inserted through the holes 2997 to assemble and secure the proximal bone interface connector to the tensioning element.

Figure 30A:
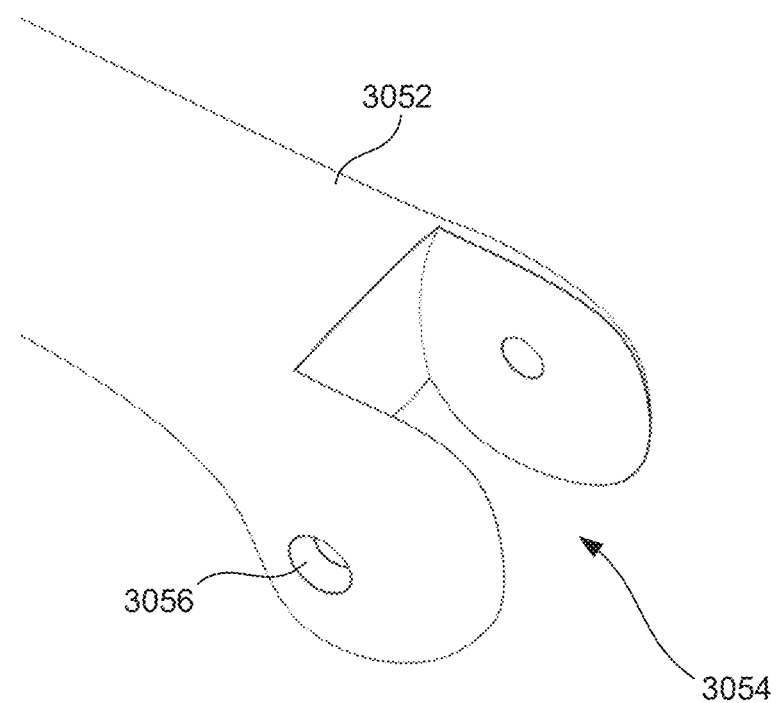
FIGS. 30A-30C illustrate yet another example joint implant in accordance with the present technology.
Figure 30B:
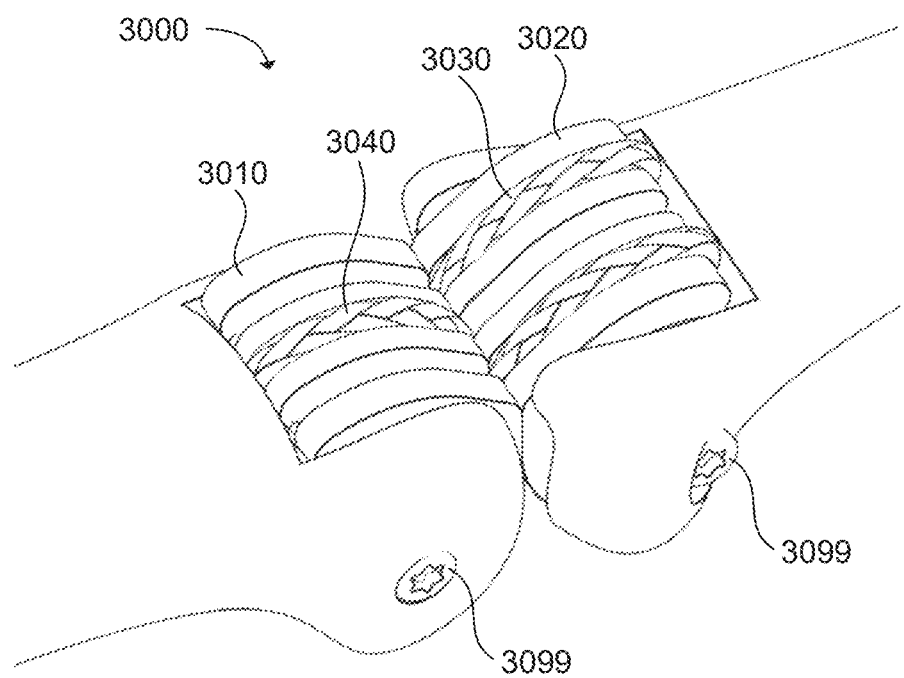
Figure 30C:
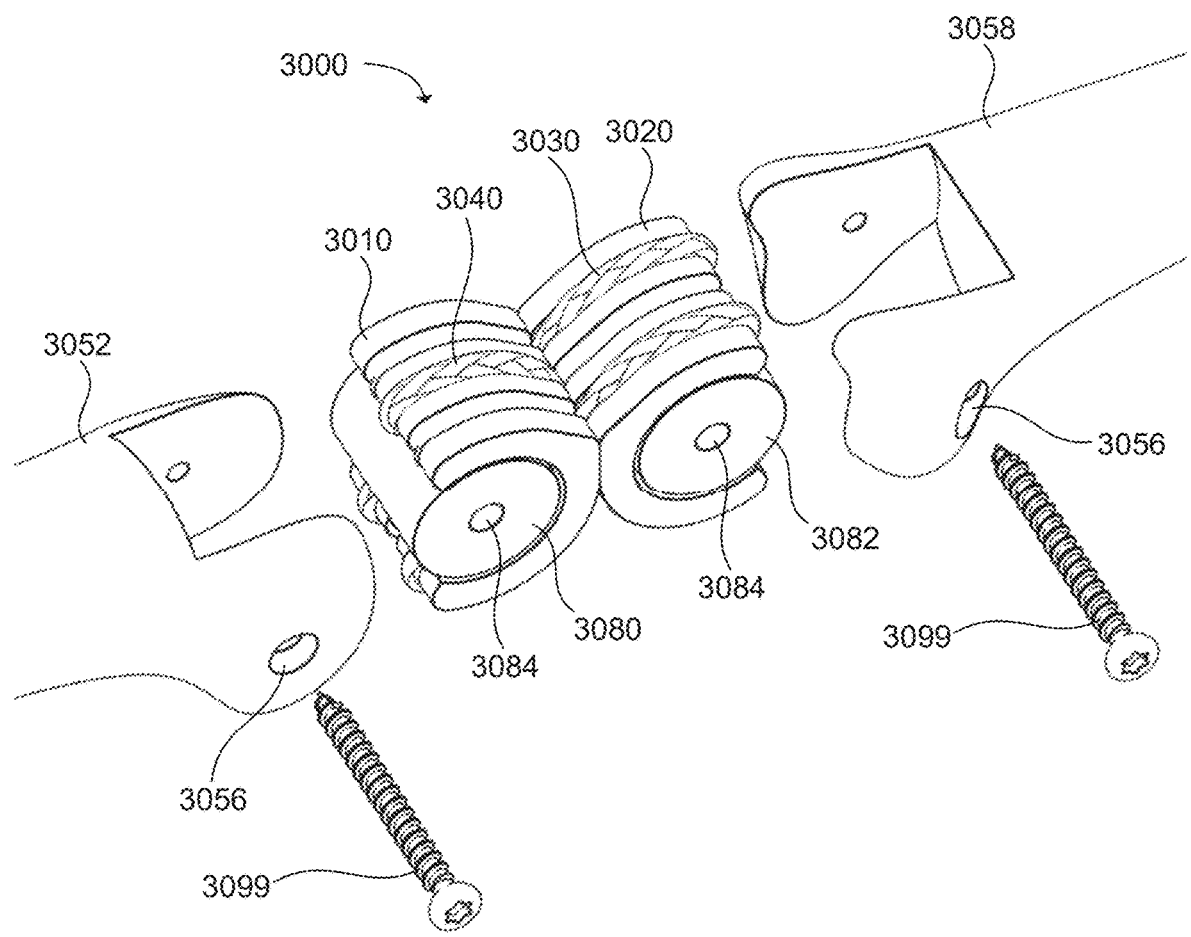

FIGS. 30A-30C illustrate another example joint implant 3000. FIG. 30A shows a bone 3052 that has been prepared for the joint implant. The bone includes a slot 3054 that has been cut to accommodate the width of the joint implant. and holes 3056 for a screw 3099 that can be used to secure the joint implant. FIG. 30B shows the joint implant 3000 after being implant in the bone 3052 and a second bone 3058 of a joint. The joint implant includes a proximal joint implant element 3010 and a distal joint implant element 3020. The joint implant elements are coupled together using filament segments, including a pair of outer filament segments 3030 and one inner filament segment 3040. The joint implant is secured in the bones using screws 3099. FIG. 30C shows an exploded view of the joint implant 3000 with the bones 3052,3058 and screws 3099. The joint implant includes proximal tensioning element 3080 retained in the hollow interior of the proximal joint implant element. A distal tensioning element 3082 is retained in the hollow interior of the distal joint implant element. The tensioning elements include screw holes 3084 through which the screws can be inserted.

As shown in FIG. 30A, a bone can be prepared by cutting a slot in the bone to accommodate the joint implant. In some examples, the slot can accommodate a bone anchor or a bone interface connector. The slot shown in FIG. 30A is a vertical slot cut through the entire height of the bone. In other examples, the slot can be a horizontal slot cut through the entire width of the bone. In further examples, a slot can be cut that does not extend through the entire width or the entire height of the bone. Such a slot can be cut from a top surface of the bone and can extend vertically part way through the bone, without reaching the bottom surface of the bone. In another examples, the slot can be cut from the bottom surface of the bone and can extend vertically part way through the bone, without reaching the top surface. In still other examples, a slot can be cut from one side of the bone and extend laterally part way through the bone without reaching the opposite side. In still further examples, a slot can be cut in a central portion of the front surface of the bone without reaching any of the top, bottom, or side surfaces. Thus, the slot can be open at a top surface of the bone, at a bottom surface of the bone, at one or both side surfaces of the bone, or the slot may not be open at the top surface, or the bottom surface, or the side surfaces of the bone.

Figure 31A:
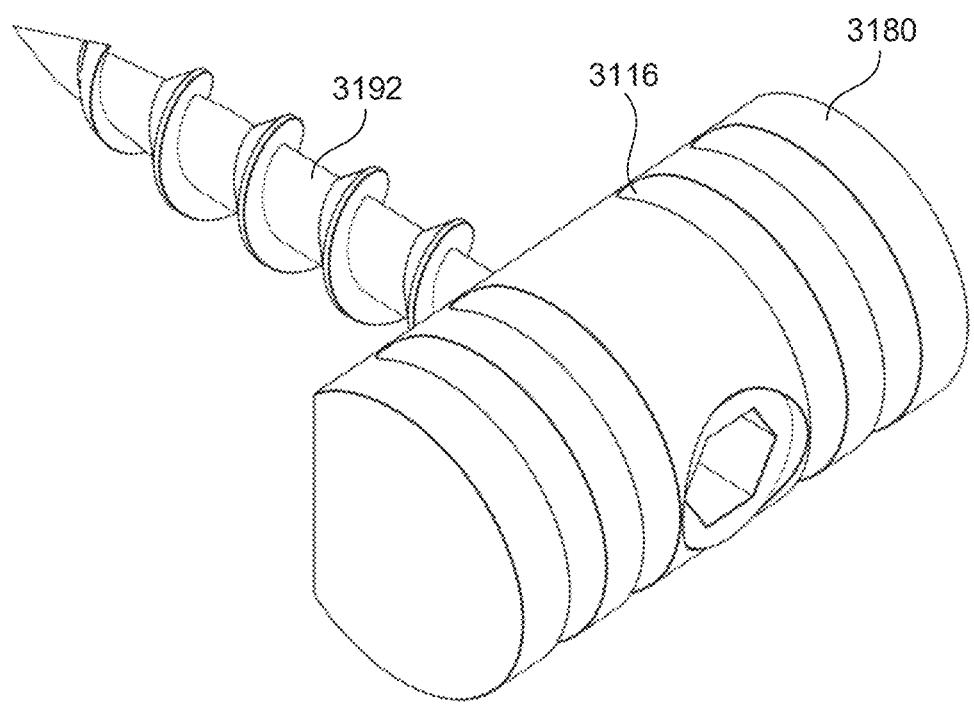
FIGS. 31A and 31B illustrate a tensioning element with a bone interface connector screw to be used in a joint implant in accordance with the present technology.
Figure 31B:
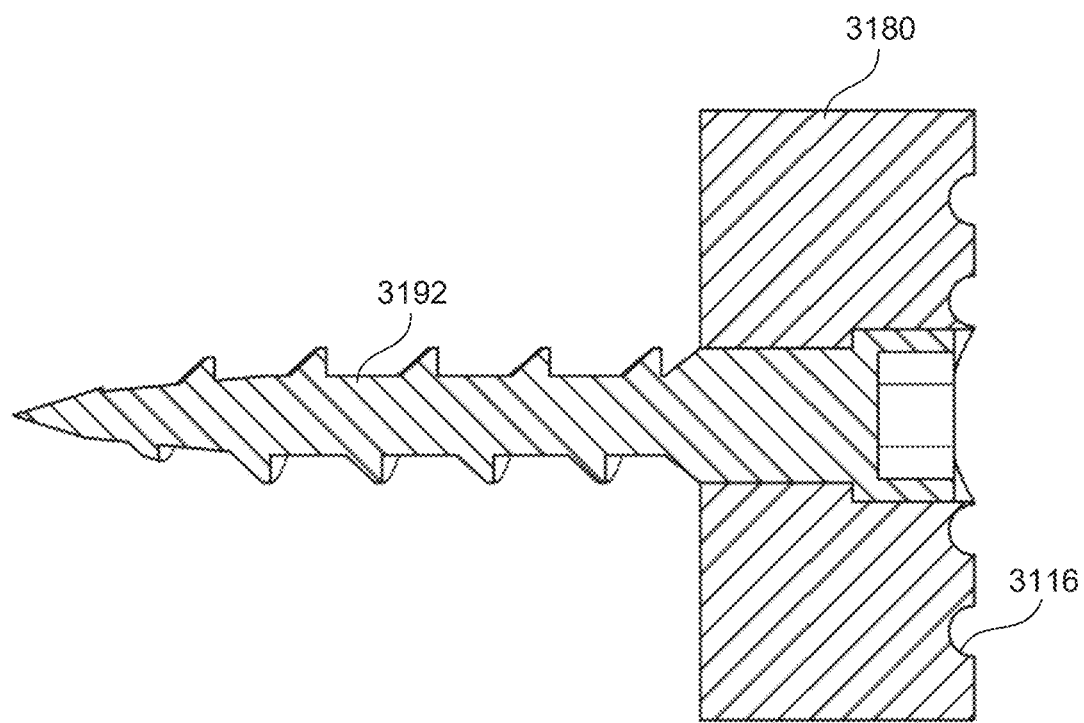

In further examples, the joint implant can include a bone interface connector that comprises a screw that is screwed longitudinally into a bone. FIGS. 31A and 31B shows one example that includes a longitudinal screw 3192 that is inserted through a tensioning element 3180 and screws longitudinally into a bone. FIG. 31A shows a perspective view and FIG. 31B shows a top-down cross-sectional view. The tensioning element can be inserted into a joint implant element as in many of the examples described above. The tensioning element also includes grooves 3116 for accommodating filaments. When the tensioning element is inserted into a joint implant element, the filaments can be secured between the joint implant element and the tensioning element as in many of the examples described above.

Figure 32A:
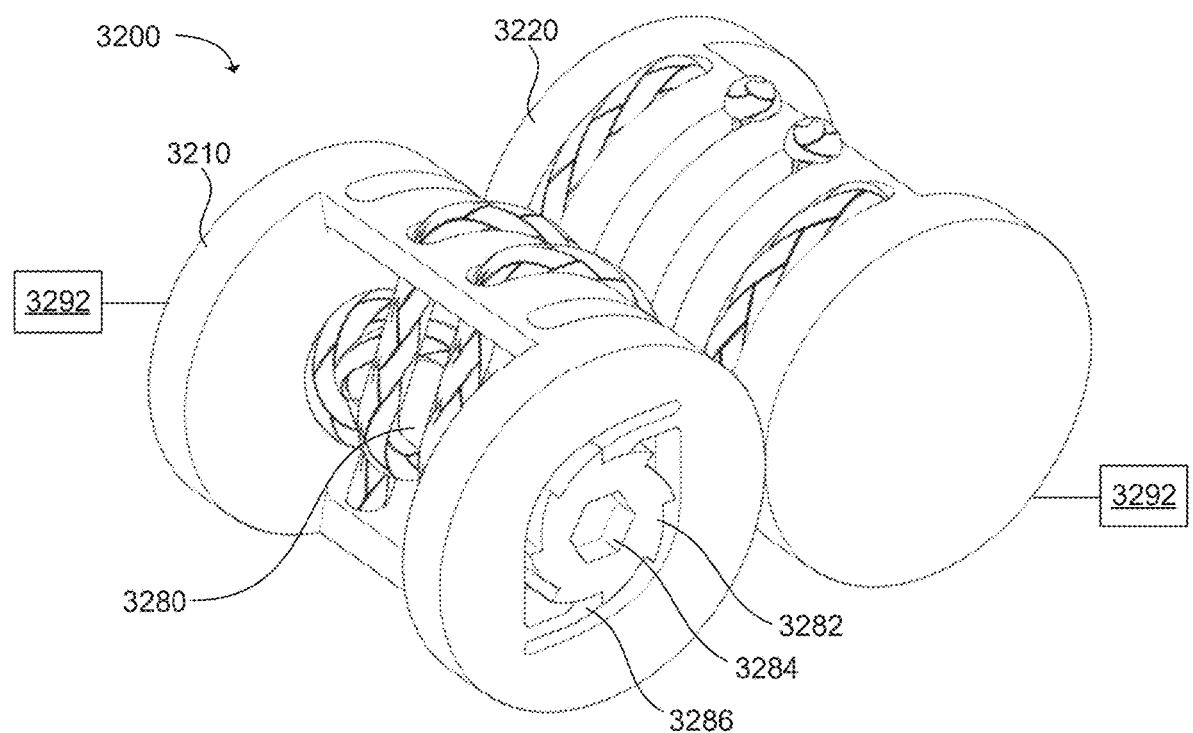
FIGS. 32A and 32B illustrate another example joint implant in accordance with the present technology.
Figure 32B:
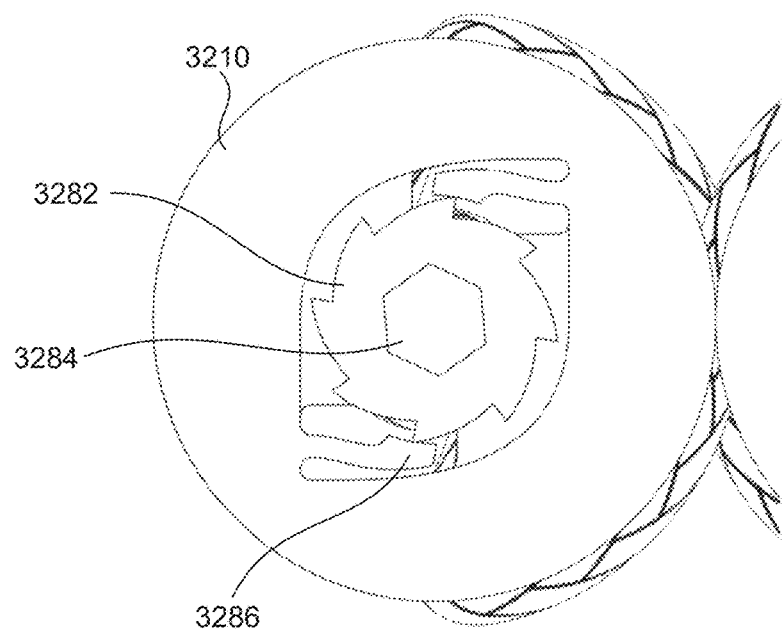

Another example joint implant 3200 is shown in FIGS. 32A-32B. FIG. 32A is a perspective view of the joint implant, which includes a proximal joint implant element 3210 and a distal joint implant element 3220. This example includes a tensioning element 3280 inside a hollow interior space of the proximal joint implant element. The tensioning element can be rotated to wind the filaments around the tensioning element, thereby applying tension to the filaments. In this example, the tensioning element includes a ratcheting portion 3282 with unidirectional teeth that allow the tensioning element to rotate in a counterclockwise direction but prevents the tensioning element from rotating in the clockwise direction. The tensioning element also includes a hexagonal recess 3284 to allow the tensioning element to be turned using a hex key. The proximal joint implant element 3210 also includes compliant catches 3286 that can bend slightly when the teeth of the ratcheting portion move in the counterclockwise direction, but which will catch the teeth to prevent rotation in the clockwise direction. FIG. 32B shows a side view of the proximal joint implant element 3210. In this figure, the ratcheting portion 3282 is positioned mid-turn to show how the compliant catches 3286 can bend to allow the teeth to move past. FIG. 32A also shows boxes 3292, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

Figure 33A:
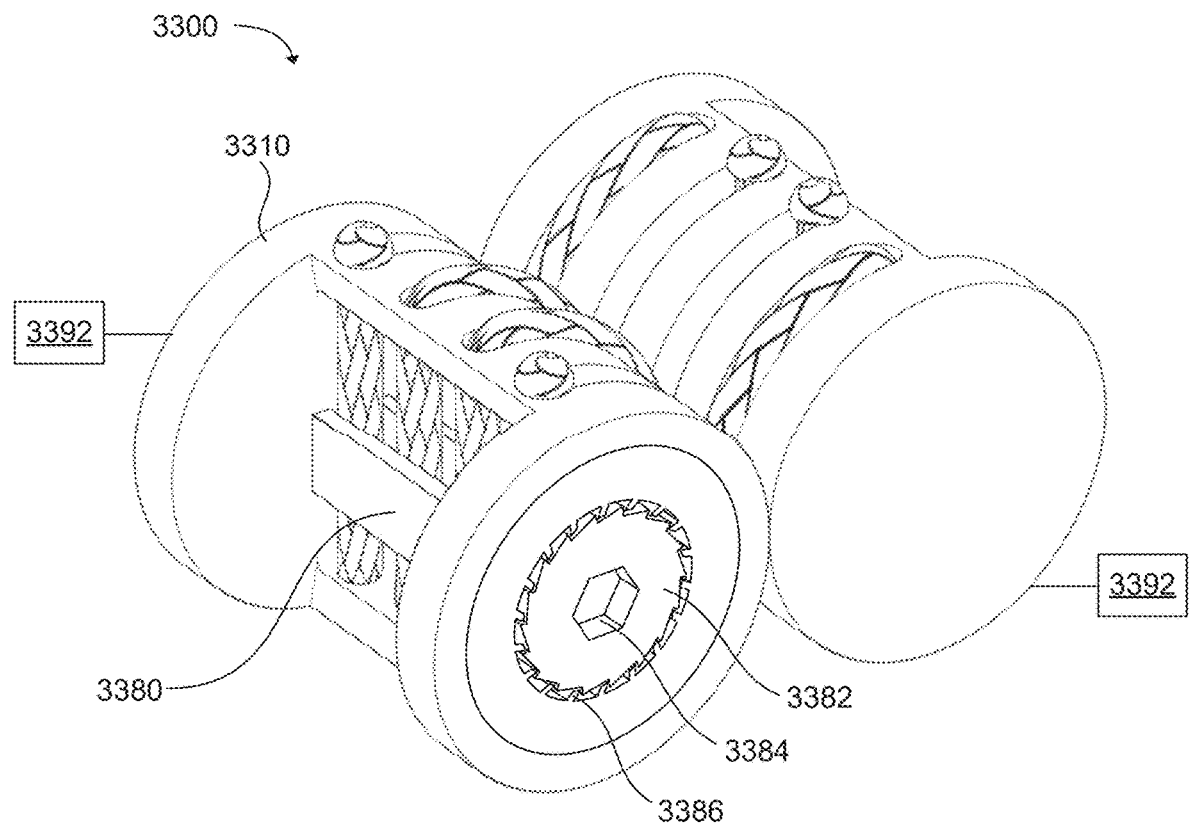
FIGS. 33A and 33B illustrate another example joint implant in accordance with the present technology.
Figure 33B:
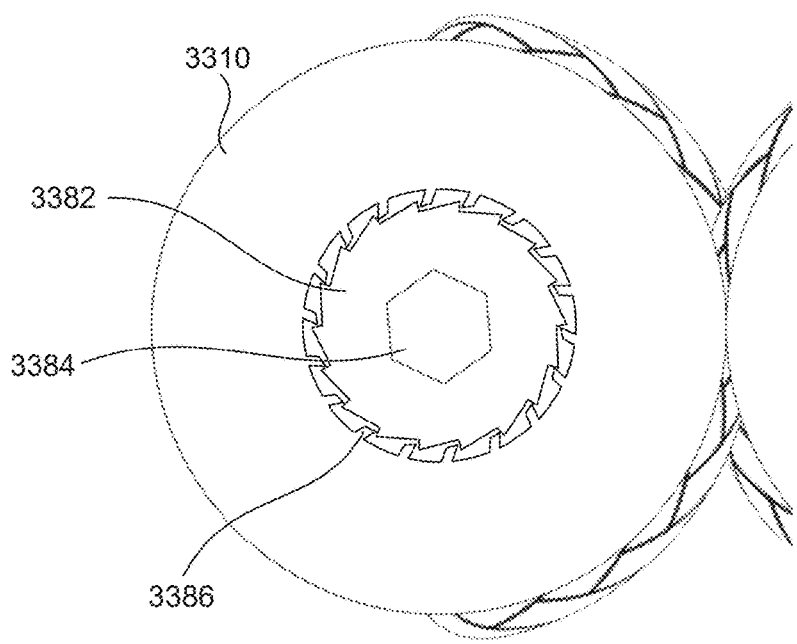

FIGS. 33A-33B illustrate another example joint implant 3300. This example is similar to the example shown in FIGS. 32A-32B in that that tensioning element 3380 has a ratcheting portion 3382 with unidirectional teeth. The proximal joint implant element 3310 has complementary teeth 3386 that can be flexible to allow the teeth of the tensioning element to pass over in one direction, but prevent the teeth from passing in the other direction. A hexagonal recess 3384 allows the tensioning element to be turned using a hex key. The teeth in this example are smaller, which can provide finer control over the amount that the tensioning element is turned, and thus finer control over the tension on the filaments. In this example, the tensioning element includes a slot that can accommodate the filaments. The filaments extend through the slot in the middle of the tensioning element, instead of wrapping around the tensioning element as in FIGS. 32A-32B. When the tension element is rotated, it can start to bend the filaments, which can apply tension to the filaments. In this example, the slot is open at the end opposite from the ratcheting portion. The filaments can be assembled with the proximal joint implant element 3310 first, and then the tensioning element can be inserted from the side. The slot with an open end can guide the tensioning element over the filaments and embed in a cylindrical pocket that is the same diameter as the tensioning element on the far side, so that the filaments become trapped in the slot. In other examples, the slot can be closed at both ends, in which case the filaments can be threaded through the slot after the tensioning element has been assembled with the proximal joint implant element. In another similar examples, two tensioning elements can be inserted from both sides of the proximal joint implant element. Each of the tensioning elements can have a half-slot with an open end. The two half-slots can slide over the filaments when the tensioning elements are inserted, and then connect together in the center, thus trapping the filaments in the slot. FIG. 33A also shows boxes 3392, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example.

In further examples, the joint implant can include a bone anchor, or a bone interface connector, or both that include a push-on locking feature. The push-on locking feature can allow the joint implant to be assembled by a surgeon during surgery, at least in part, by simply pushing components together and the components can automatically lock in place. The push-on locking feature can include unidirectional teeth on one component, such as a bone anchor, and complementary teeth on the other component, such as a bone interface connector. The unidirectional teeth and complementary teeth can allow the components to be pushed together, but not to be pulled apart. In some examples, the push-on lock feature can include a male component and a female component, where the male component fits inside the female component.

Figure 34A:
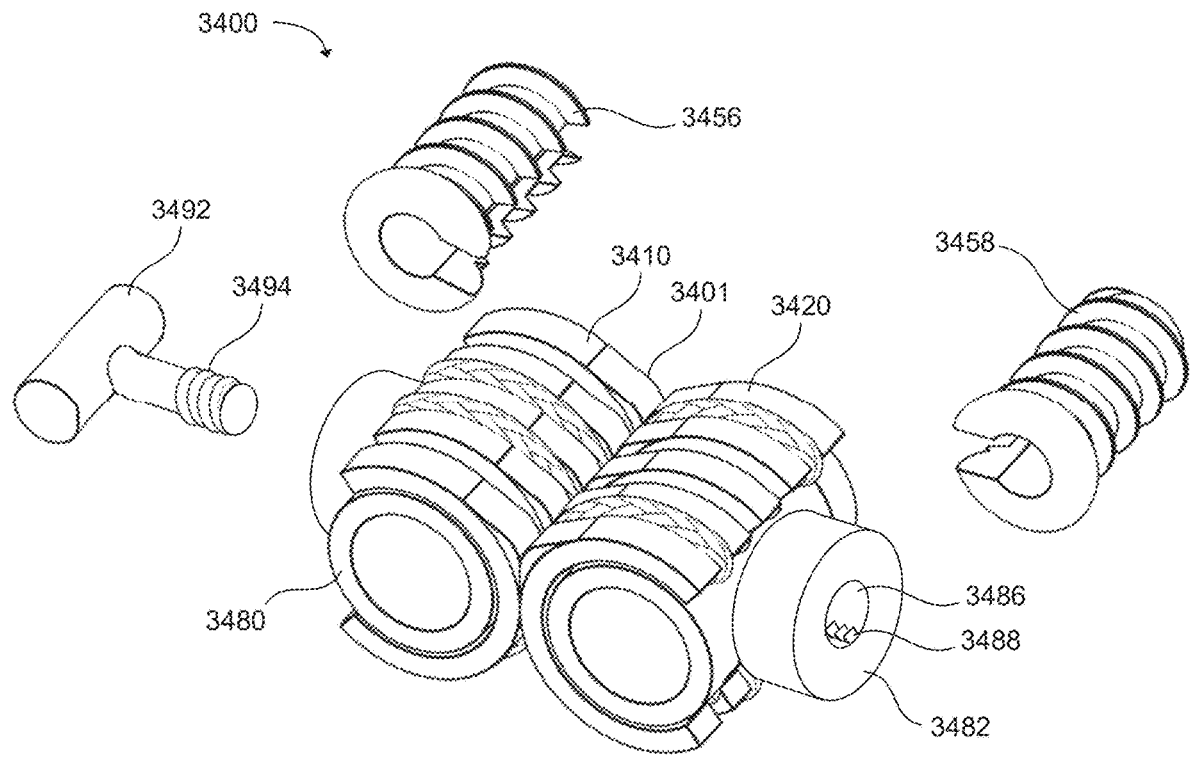
FIGS. 34A and 34B illustrate another example joint implant in accordance with the present technology.
Figure 34B:
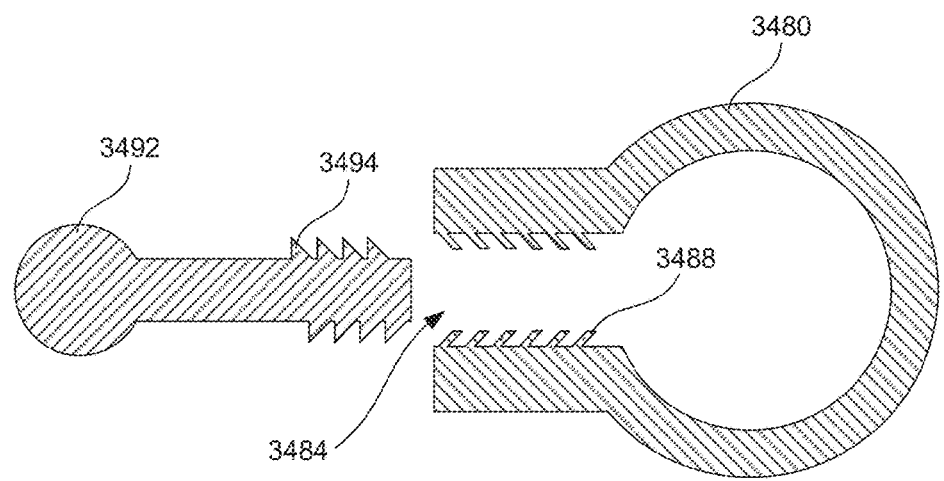

FIGS. 34A-34B illustrate one example joint implant 3400 that includes a push-on locking feature. FIG. 34A shows an exploded view of a joint span 3401 made up of joint implant elements 3410, 3420 and tensioning elements 3480, 3482 as in previous examples. This example also includes bone anchors 3456, 3458 as in some previous examples. A T-shaped bone interface connector 3492 is configured to slide laterally into the bone anchor. The T-shaped bone interface connector also includes a shaft with unidirectional teeth 3494. In this example, the unidirectional teeth are slanted in an opposite direction to the insertion direction in which the shaft is inserted into an opening 3484, 3486 in the tensioning elements. The unidirectional teeth are also in the shape of a corkscrew thread, which allows the bone interface connector to function as a screw. The opening 3484, 3486 includes internal teeth 3488 that are complementary to the unidirectional teeth of the bone interface connector. These internal teeth can be flexible to allow the bone interface connector shaft to be inserted into the opening, but the teeth can prevent the shaft being pulled back out of the opening. However, because the unidirectional teeth are in the form of threads, the bone interface connector can be removed by rotating either the bone interface connector or the tensioning element to unscrew the threads. This can allow these components to be separated at a later time if desired for revision of the implant. The unidirectional teeth can be pushed in to a desired depth in the opening and lock in place at any desired depth. This can allow the joint implant to be customizable to the individual anatomy of a subject, which may require longer or shorter connections depending on the individual.

Figure 35A:
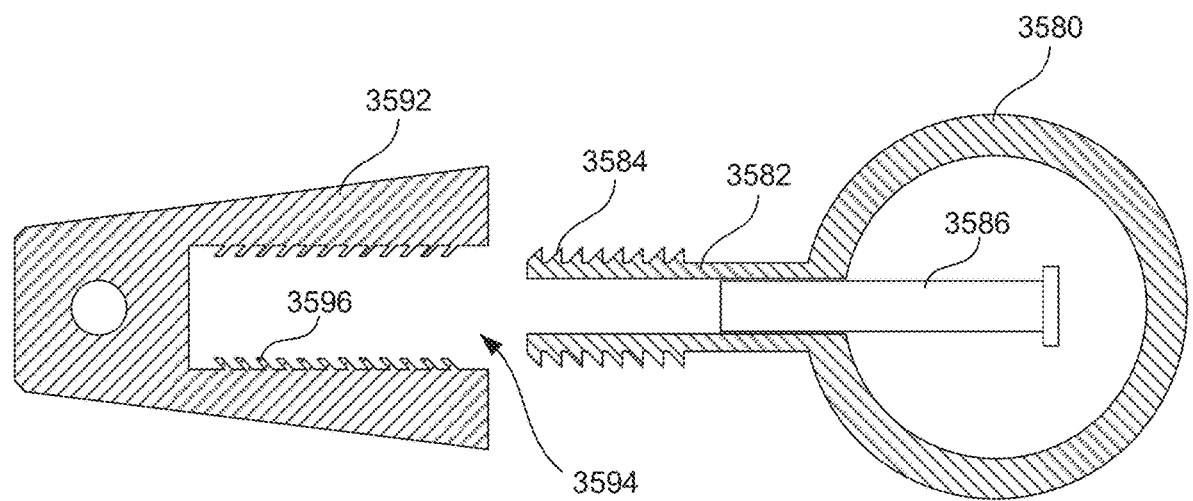
FIGS. 35A and 35B illustrate another example joint implant in accordance with the present technology.
Figure 35B:
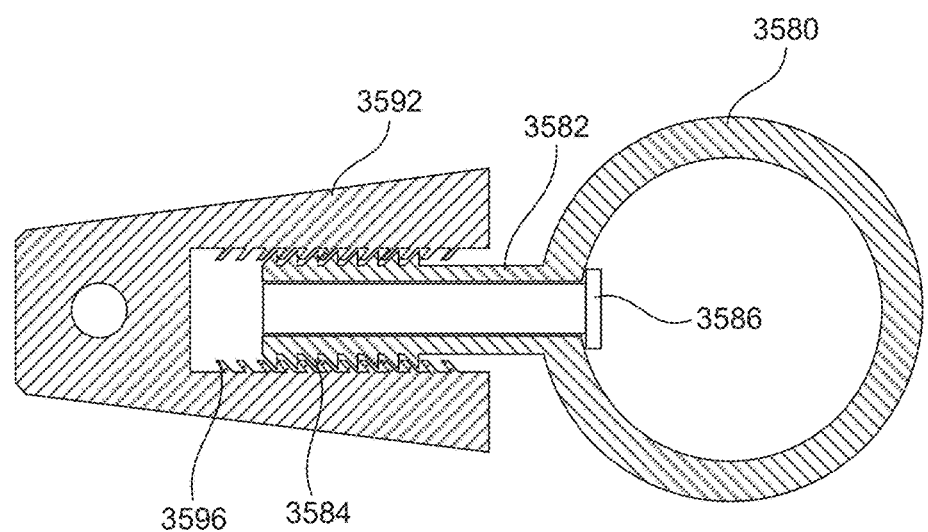

Another example with a push-on locking feature is shown in FIGS. 35A and 35B. These figures show a cross-sectional side view of a bone interface connector 3592 and a tensioning element 3580, with the cross-section taken at a plane at the center of these components. In this example, a tensioning element 3580 includes a male component of the push-on locking feature. In particular, the tensioning element includes a split shaft 3582 with unidirectional teeth 3584 on the top and bottom surfaces of the shaft. A bone interface connector 3592 includes an opening 3594 that has internal teeth 3596 on a top interior surface and bottom interior surface. The internal teeth are complementary to the unidirectional teeth of the tensioning element. The teeth can allow the split shaft of the tensioning element to be pushed into the opening in the bone interface connector, but not to be pulled back out. A pin 3586 is inserted in the center of the split shaft to ensure that the top and bottom halves of the split shaft are rigid so that the teeth are pressed against the complementary internal teeth of the bone interface connector. FIG. 35B shows the tensioning element 3580 after having been pushed into the bone interface connector 3592 and the pin 3586 has been pushed fully into the split shaft 3582. This design can allow the lock to be disengaged at a later time by removing the pin 3586. The top and bottom halves of the split shaft can be flexible and can flex inward when the pin is removed, which can disengage the teeth and allow the tensioning element to be separated from the bone interface connector. However, in a different example the shaft can be solid and the push-on lock feature can lock permanently, without providing a way to separate the components later.

Figure 36A:
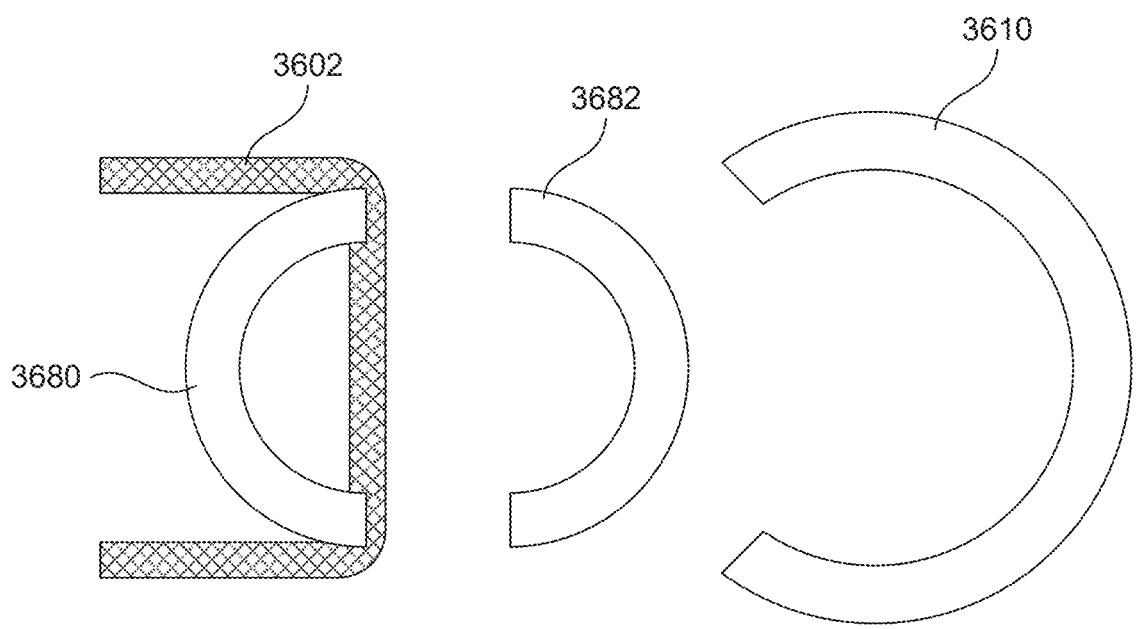
FIGS. 36A-36D illustrate another example joint implant in accordance with the present technology.
Figure 36B:
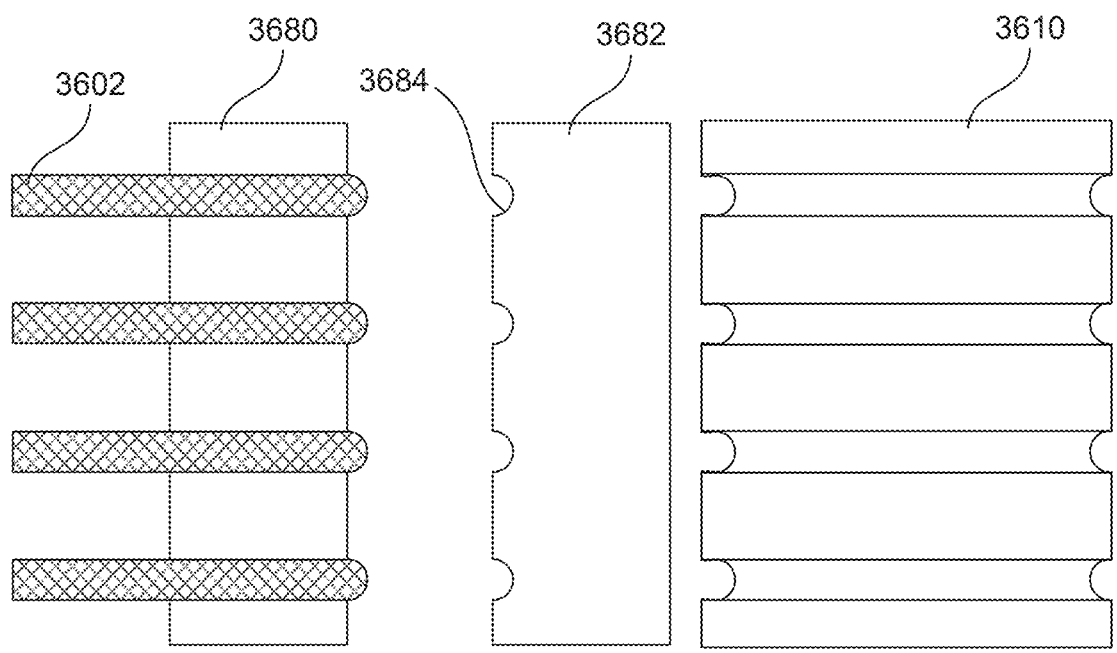
Figure 36C:
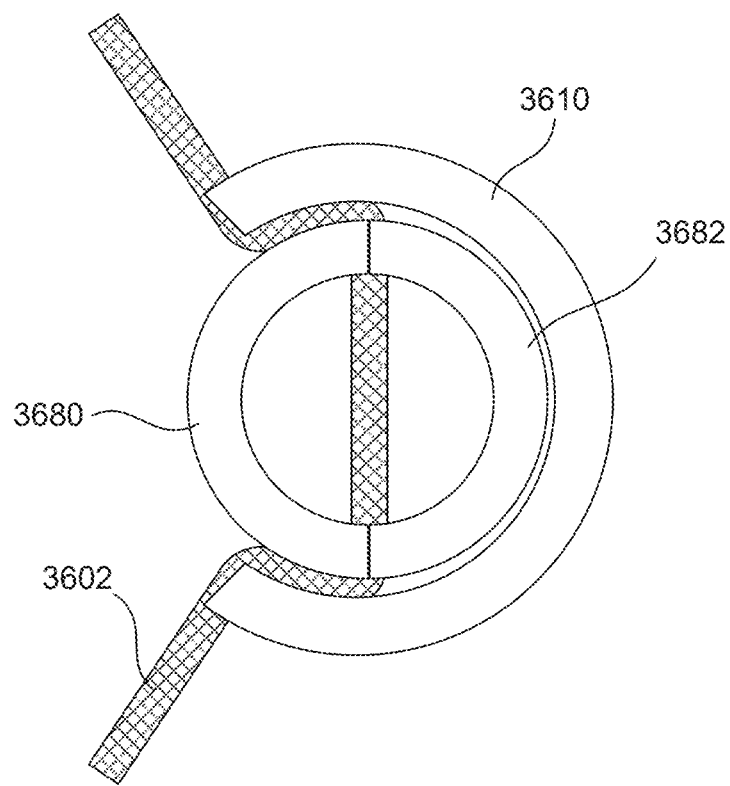
Figure 36D:
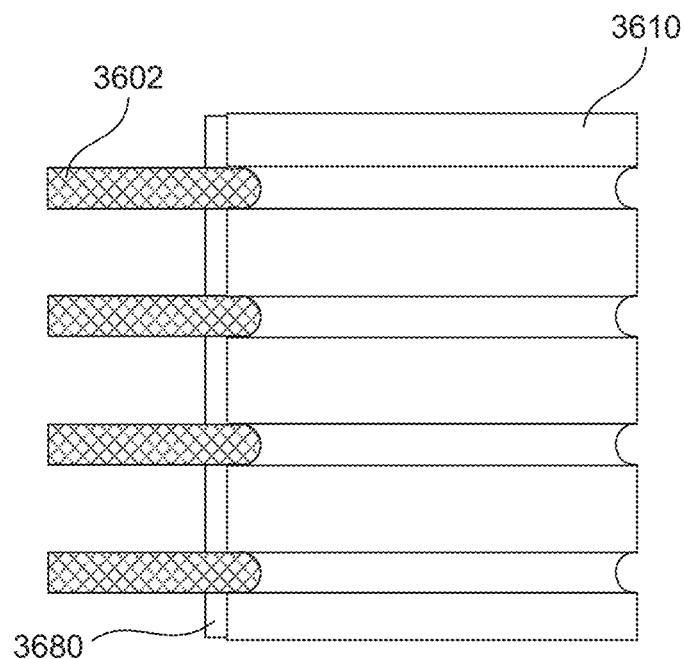

An alternate design for a tensioning element is shown in FIGS. 36A-36D. FIG. 36A shows a side exploded view of a joint implant element 3610 and a split tensioning element made up of two tensioning element halves 3680, 3682. The tensioning element halves include half-holes 3684 that allow the filaments 3602 to pass through the middle of the tensioning element. FIG. 36B shows a top-down exploded view in which the half-holes are visible. FIG. 36C shows a side view of these components after being assembled. The tensioning element halves 3680, 3682 are fastened together with the filaments trapped between the halves. The assembled tensioning elements can then be pressed into the hollow interior of the joint implant element 3610. These components can then be assembled together with another joint implant element to form a joint implant as in many of the previous examples. The half-holes 3684 form full holes when the tensioning element halves are fastened together. In some examples, the holes can have a diameter slightly smaller than the diameter of the filament, so that the holes exert pressure on the filament when the tensioning element halves are fastened together. In some examples, this pressure can be sufficient to prevent the filaments from pulling out of the holes. The tensioning element halves can be fastened together using any suitable fastening method, such as adhering with an adhesive, or bonding, welding, fastening using a mechanical fastener, or fastening using built in fastening features that may be incorporated in the tensioning element halves. In other examples, the tensioning element can be split in other ways besides splitting in half, such as splitting into tensioning element subparts that are different sizes.

Figure 37A:
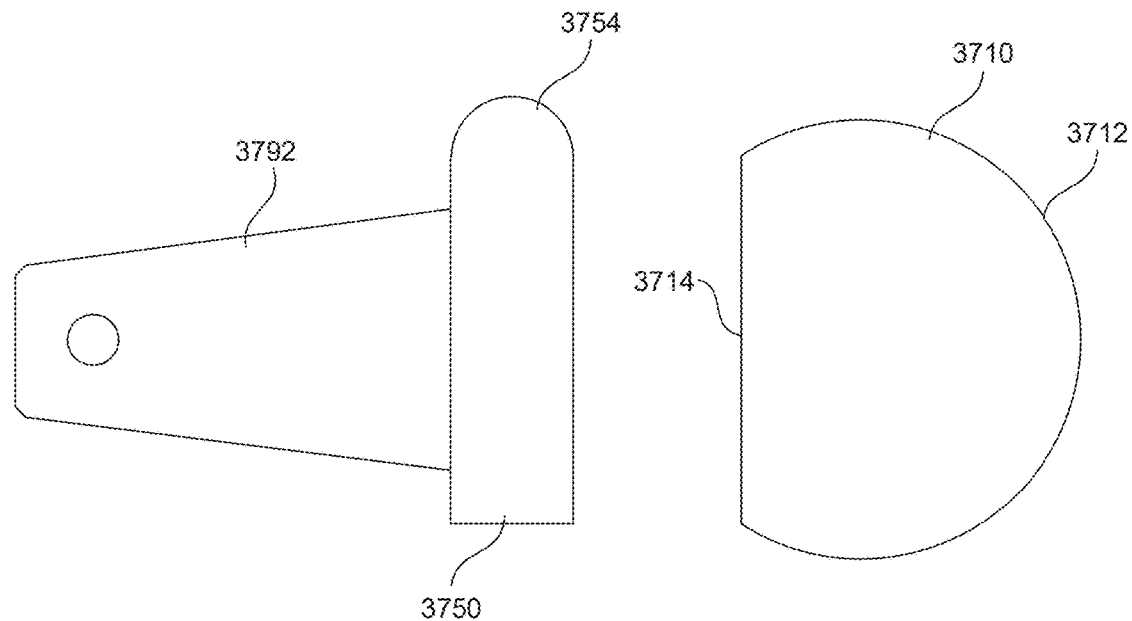
FIGS. 37A and 37B illustrate another example joint implant in accordance with the present technology.
Figure 37B:
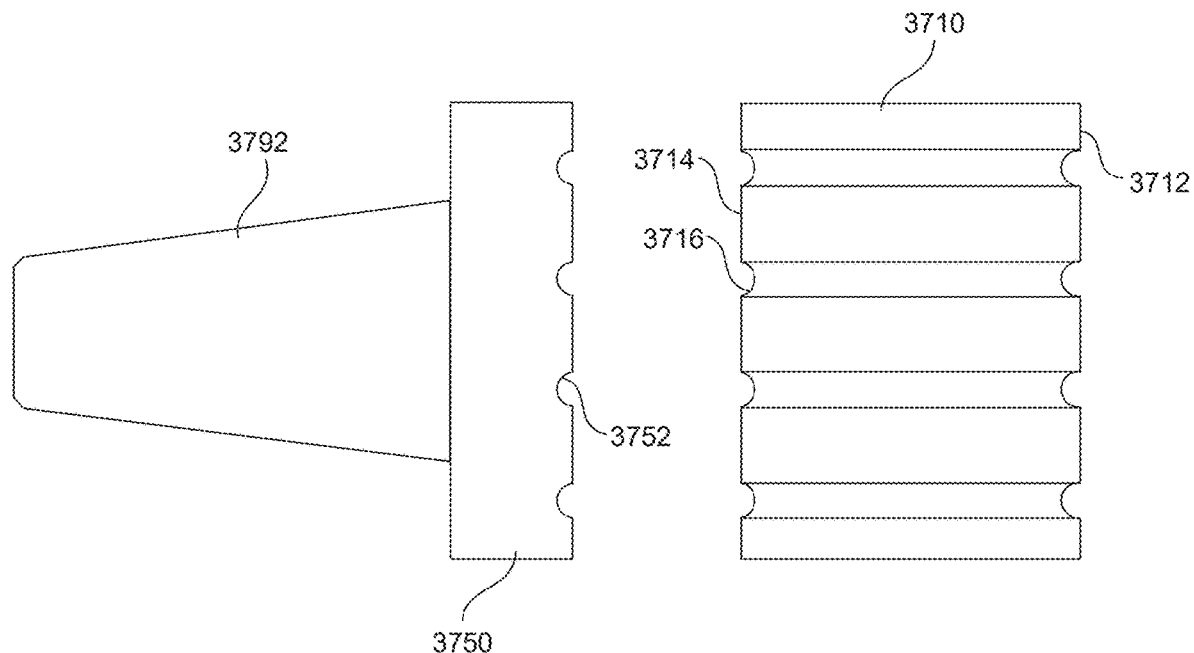

Another method of securing the filaments to the joint implant elements is illustrated in FIGS. 37A and 37B. FIG. 37A shows a side view of a joint implant element 3710 and a clamping element 3750. FIG. 37B shows a top-down view of these components. The joint implant element includes a curved interface surface 3712 as in previous examples. The joint implant element also includes a base surface 3714 opposite from the curved interface surface. The base surface in this example is flat with grooves 3716 formed in the base surface. In other examples, the base surface can be completely flat, or the base surface can have any other shape include ridges and other features. The clamping element 3750 is configured to be fastened to the base surface with the filaments clamped between the clamping element and the base surface. The clamping element also includes grooves 3752 that align with the grooves on the base surface. The filaments can be clamped in these grooves. The grooves can be configured, such that the groove depth and width create a situation where, even under the maximum locking pressure, the filaments are slightly proud of the surface and engaged directly on the internal surface of the associated joint implant element. In some examples, the depth of the grooves can be less than half the width of the filaments, so that the grooves apply pressure to the filaments when the clamping element is fastened to the joint implant element 3710. In other examples, additional features can be included to grip the filaments, such as textured surfaces on the base surface and/or the clamping element surface to increase friction, or ridges or other features designed to hold the filaments in place. The filaments can be placed between the clamping element and the base surface. Tension can then be applied to the filaments before fastening the clamping element to the base surface. The tension can be applied by an external tool or device. After the clamping element has been fastened to the base surface, the clamping element and the base surface can hold the filaments securely and maintain the tension. The filaments can be terminated by cutting or melting and a knot or melted portion can also be formed to help prevent the filaments from pulling out of the clamping element. In this example, the clamping element also includes a protrusion 3754 that can act as a stop to define an end point of the range of motion of the joint implant. A bone interface connector 3792 is also integrated as a part of the clamping element. The clamping element can be fastened to the joint implant element using any suitable fastening method, such as adhering with an adhesive, or bonding, welding, fastening using a mechanical fastener, or fastening using built in fastening features that may be incorporated in the clamping element and/or the joint implant element.

Figure 38A:
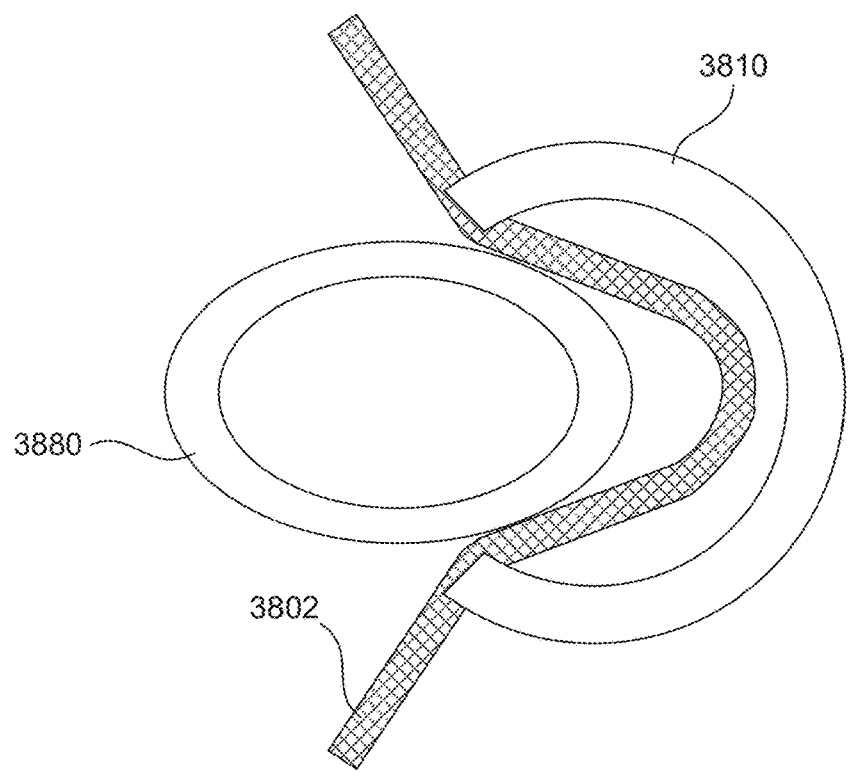
FIGS. 38A and 38B illustrate another example joint implant in accordance with the present technology.
Figure 38B:
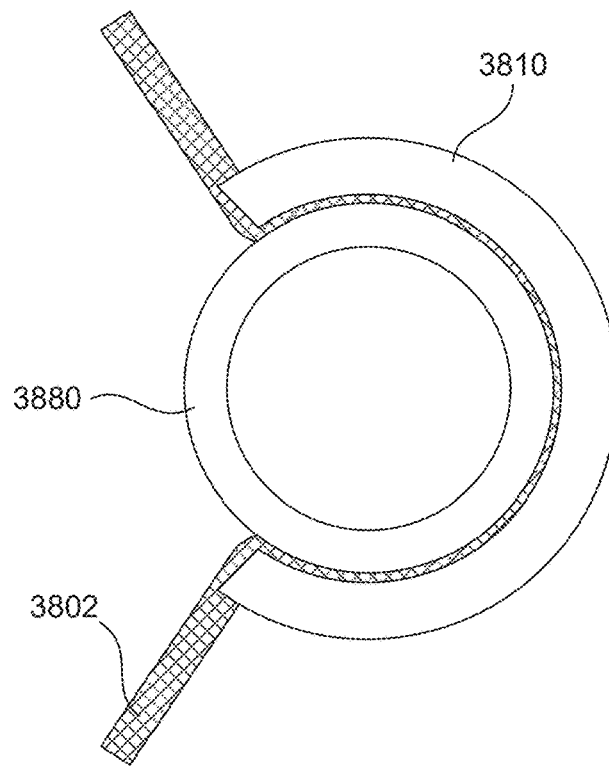

FIGS. 38A and 38B illustrate another type of tensioning element 3880. These figures both show a side view of a tensioning element 3880, a joint implant element 3810, and a filament 3802. In this example, the tensioning element is made of a shape memory alloy. In FIG. 38A, the tensioning element is deformed to reduce the height of the tensioning element so that it can fit through a gap in the joint implant element. The tensioning element is inserted through the gap, with the filament placed between the tensioning element and the interior surface of the joint implant element. After the tensioning element has been inserted into the joint implant element, a phase change can be triggered in the shape memory alloy to cause the tensioning element to change shape. FIG. 38B shows the tensioning element 3880 after this phase change, which causes the tensioning element to adopt a cylindrical shape. When the tensioning element changes shape, it presses against the interior surface of the joint implant element, trapping the filament 3802 between the tensioning element and the interior surface of the joint implant while simultaneously applying tension to the filament.

Figure 39:
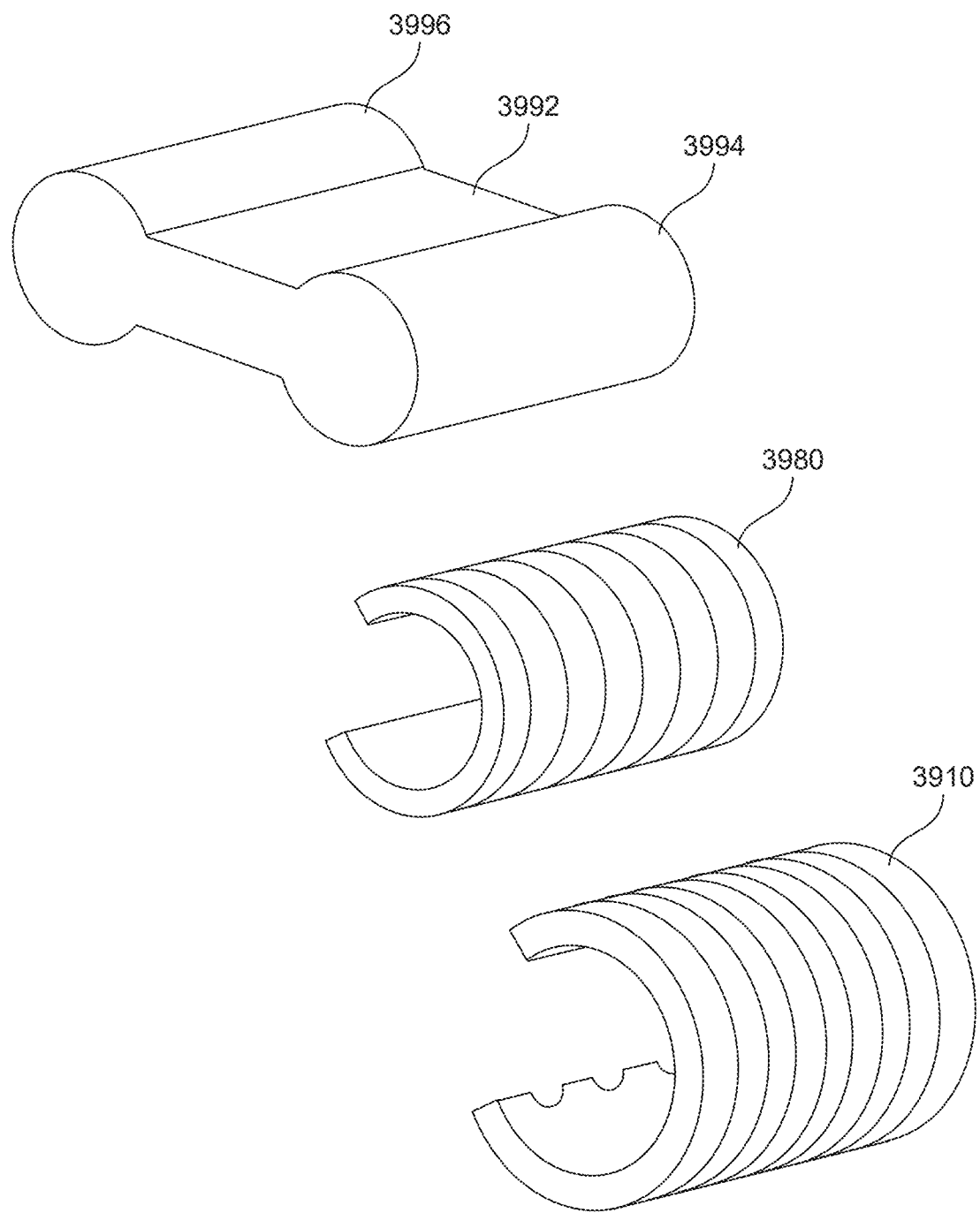
FIG. 39 illustrates another example joint implant in accordance with the present technology.

Another example is illustrated in FIG. 39. This figure shows an exploded view of a joint implant element 3910, a tensioning element 3980, and a bone interface connector 3992. In this example, the tensioning element is C-shaped. The tensioning element can be made of a springy material that allows the tensioning element to be elastically compressed slightly to help the tensioning element fit through the gap of the joint implant element. When the compression is released, the tensioning element can spring back to a larger diameter inside the joint implant element. In some examples, the uncompressed diameter of the tensioning element can be greater than the internal diameter of the joint implant element. Thus, the joint implant element can prevent the tensioning element from springing back to its original diameter and the tensioning element can exert a constant pressure against the interior surface of the joint implant element. This figure also shows a bone interface connector 3992 that has two bulged portions 3994, 3996. One bulged portion 3994 can slide laterally into the C-shaped tensioning element after the tensioning element has been placed inside the joint implant element. The other bulged portion 3996 can be inserted laterally into a bone anchor or a slot prepared directly in a bone, as described in previous examples.

Figure 40:
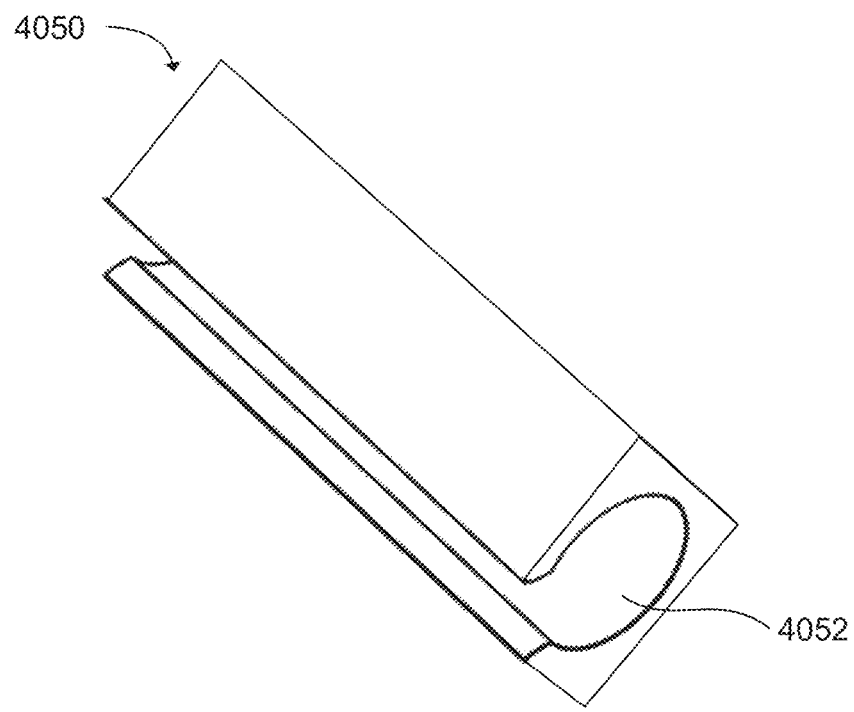
FIG. 40 illustrates an example bone anchor in accordance with the present technology.
Figure 41:
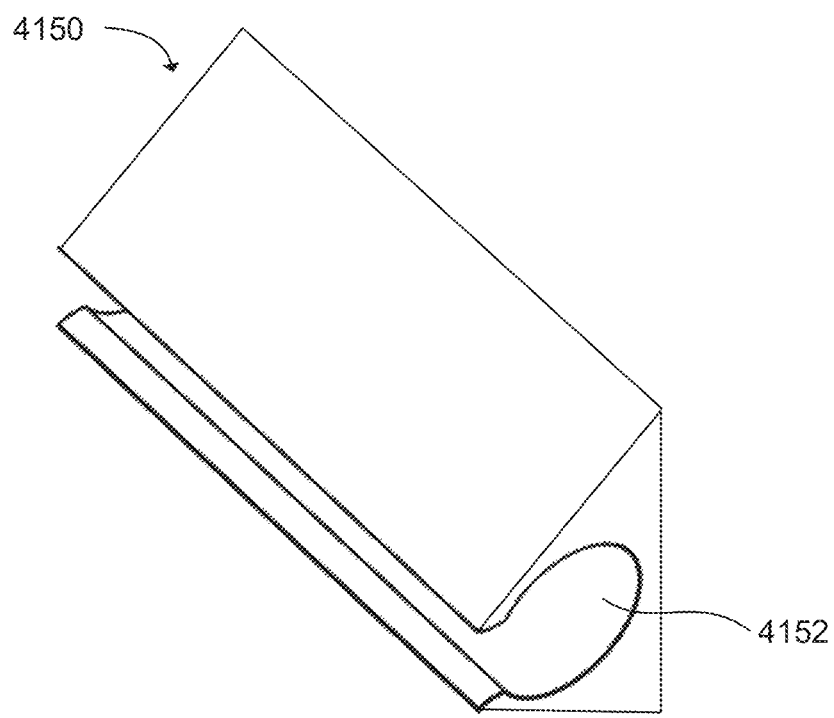
FIG. 41 illustrates another example bone anchor in accordance with the present technology.

Many of the examples described above have utilized slots formed in a bone to hold either a bone anchor or a bone interface connector. Many of the slots depicted in the figures have a cylindrical shape. However, a variety of other shapes can also be used. In some examples, it can be useful to use a non-circular hole in the bone because non-circular shapes can provide additional resistance to rotation of the bone anchor or bone interface connector in the bone. FIGS. 40 and 41 show examples of non-circular bone anchors. FIG. 40 shows a perspective view of a bone anchor 4050 with a square shape. The internal slot 4052 formed in the bone anchor has a circular profile. However, in other examples, the internal slot in the bone anchor can also have a non-circular profile. FIG. 41 shows a perspective view of a triangular bone anchor 4150. This example also includes an internal slot 4152 that has a circular profile. In further examples, any types of bone anchors and bone interface connectors described herein can have a profile that is square, rectangular, triangular, hexagonal, shaped as another polygon, elliptical, or a variety of other shapes.

Figure 42A:
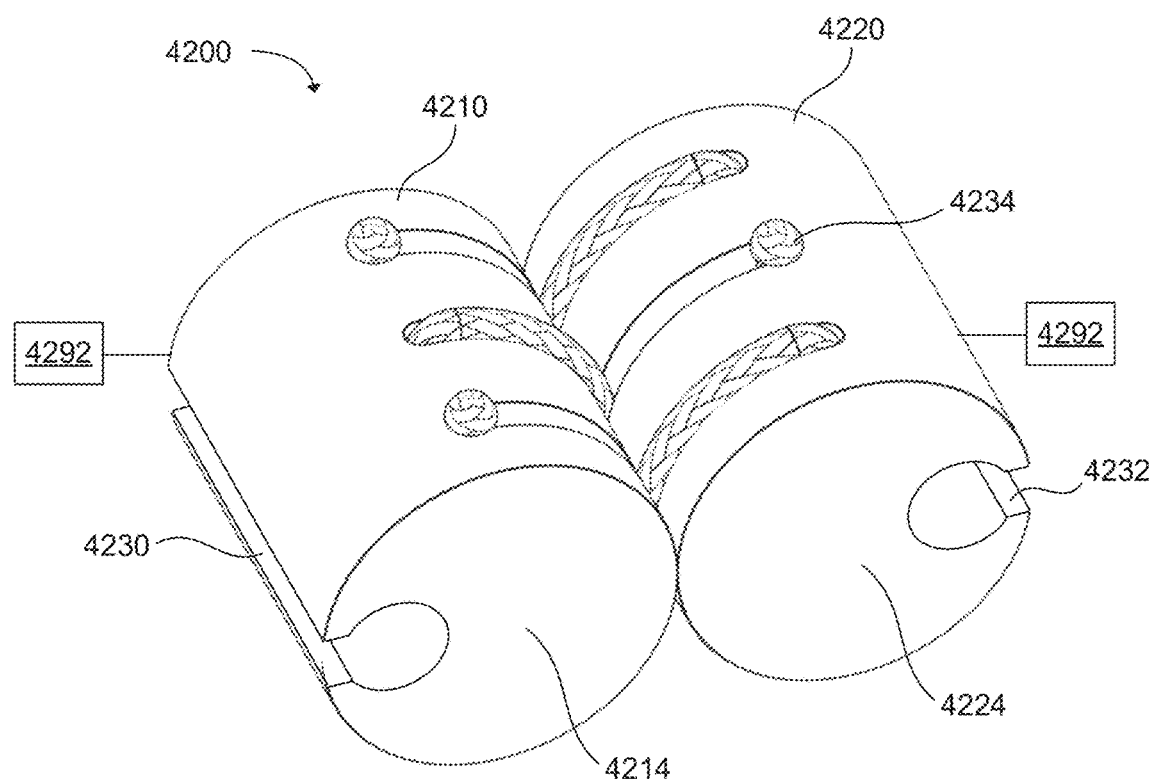
FIGS. 42A and 42B illustrate another example joint implant in accordance with the present technology.
Figure 42B:
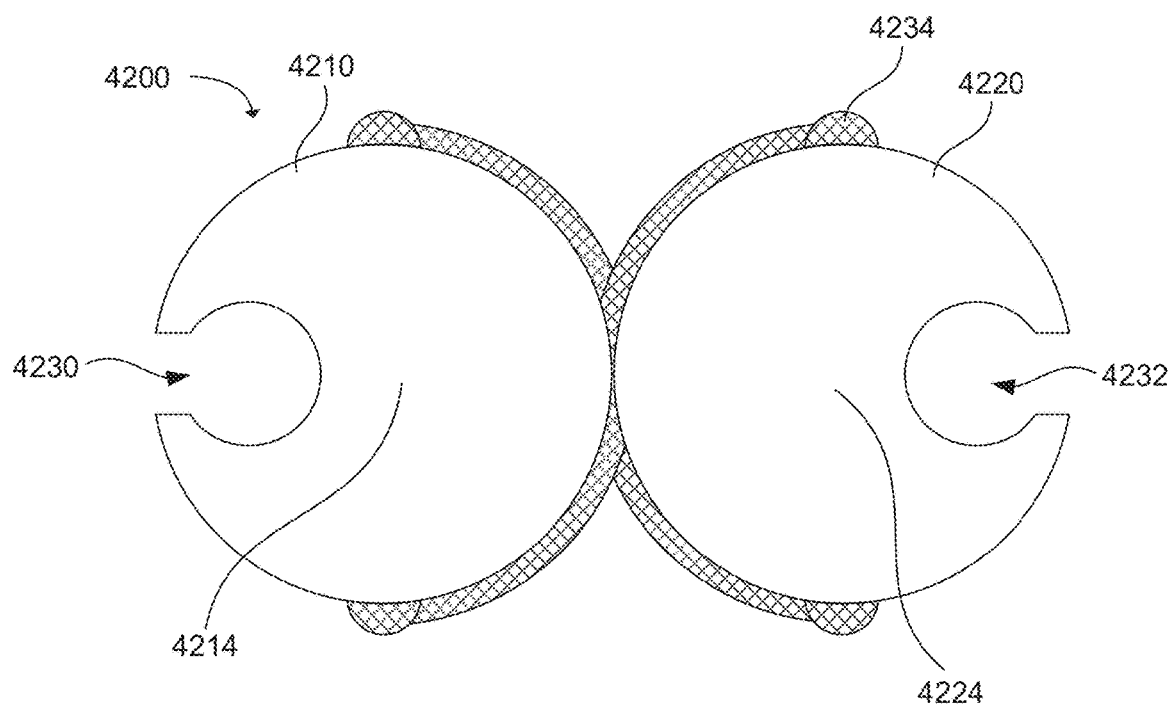

Another design for the joint implant elements is illustrated in FIGS. 42A and 42B. FIG. 42A shows a perspective view of an example joint implant 4200 that includes a proximal joint implant element 4210 and a distal joint implant element 4220. The proximal joint implant element includes a proximal solid central portion 4214. The distal joint implant element includes a distal solid central portion 4224. These solid central portions comprise solid material through the joint implant elements, except for holes that are formed for the filaments to be threaded through. In this example, holes are formed from the top surface of the joint implant elements to the bottom surface of the joint implant elements. The filaments can be threaded through these holes, and then terminated with a knot 4234 to prevent the filaments from pulling out of the holes. Tension can be applied to filaments during this process using an external tool or device. The knot can be tied while tension is maintained, so that the filament will be under tension after tying the knot and cutting off the excess filament. In other examples, a fused or melted portion of the filament can be used instead of a knot. Melting the filament can be used to terminate the filament and to form a melted portion with a width larger than the hole to prevent the filament from pulling out of the hole. In this particular example, the holes are formed across a diameter of the joint implant elements, from top to bottom. However, in other examples, the holes can be formed in other ways, such as across a cord of the circular profile of the joint implant element instead of across the whole diameter. The proximal joint implant element 4210 also includes a proximal slot 4230 with a bulged profile. This slot is configured to retain a dumbbell shaped bone interface connector that has a matching bulged profile. The bone interface connector can be pushed into the slot from the side. The distal joint implant element also includes a similar distal slot 4232. FIG. 42A also shows boxes 4292, which represent bone interface connectors or bone anchors, which can be connected to one or more components of, and be a part of, the joint implant. The bone interface connectors or bone anchors can be supported by a joint implant element or a tensioning element. A variety of different bone interface connectors and bone anchors are described herein, any of which can be used in this example. FIG. 42B shows a side view of the joint implant.

Figure 43A:
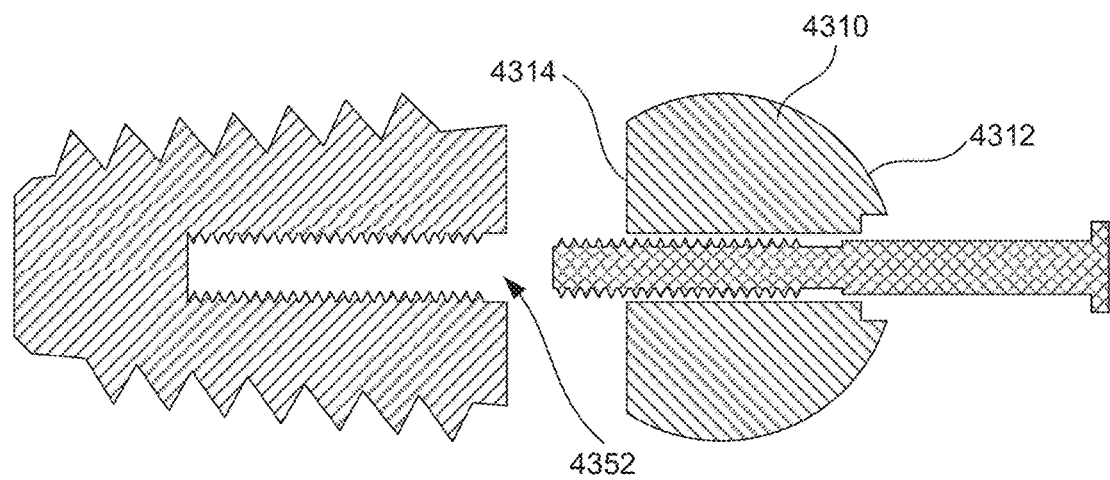
FIGS. 43A and 43B illustrate another example joint implant in accordance with the present technology.
Figure 43B:
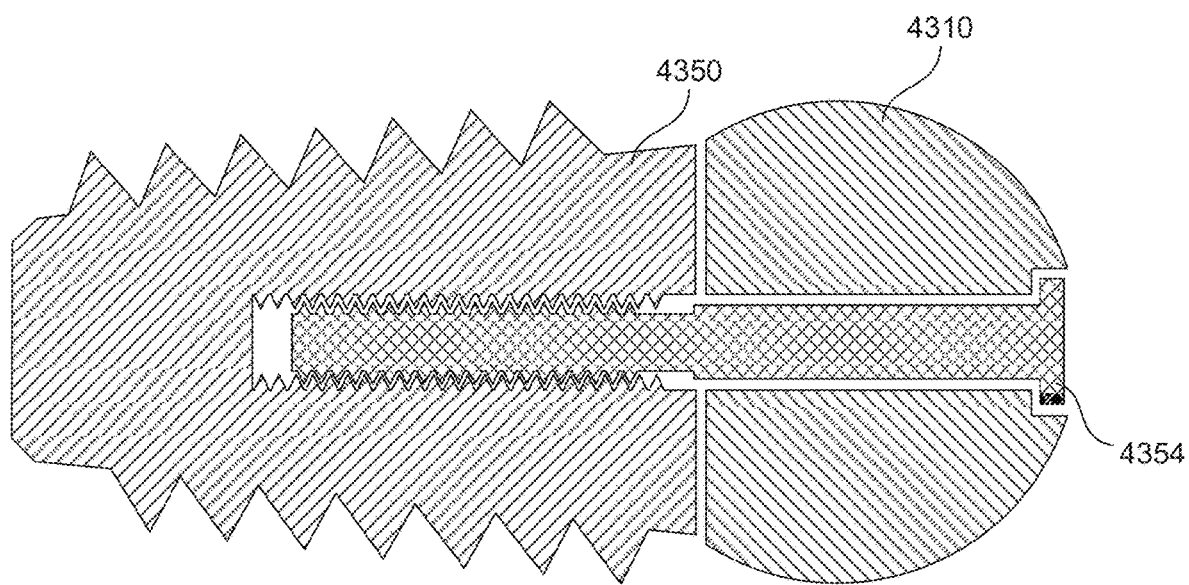

An additional option for securing a joint implant element to a bone anchor is shown in FIGS. 43A and 43B. FIG. 43A shows an exploded cross-sectional side view of a joint implant element 4310, a longitudinal screw-in bone anchor 4350, and a screw 4354 for attaching the joint implant element to the bone anchor. In this example, the bone anchor includes larger external threads configured to be screwed into a bone longitudinally. This type of bone anchor operates similarly to a dental implant, which also has an anchor that is screwed into bone longitudinally. The bone anchor includes an interior threaded recess 4352 that accepts the threaded end of the screw 4354. The joint implant element includes a screw hole that extends from the curved interface surface 4312 to a back surface 4314 to allow the screw to be inserted from the front and then screw into the bone anchor behind the joint implant element. The joint implant can also have filaments attached (not shown) as in previous examples, and grooves to accommodate the filaments in the curved interface surface. The screw hole can be positioned between the grooves so that the screw can be screwed in without interfering with the filaments. In certain examples, the bone anchor can also act as a clamping element to clamp the filaments behind the joint implant element. FIG. 43B shows the joint implant element 4310, bone anchor 4350, and the screw 4354 after they have been assembled.

Figure 44:
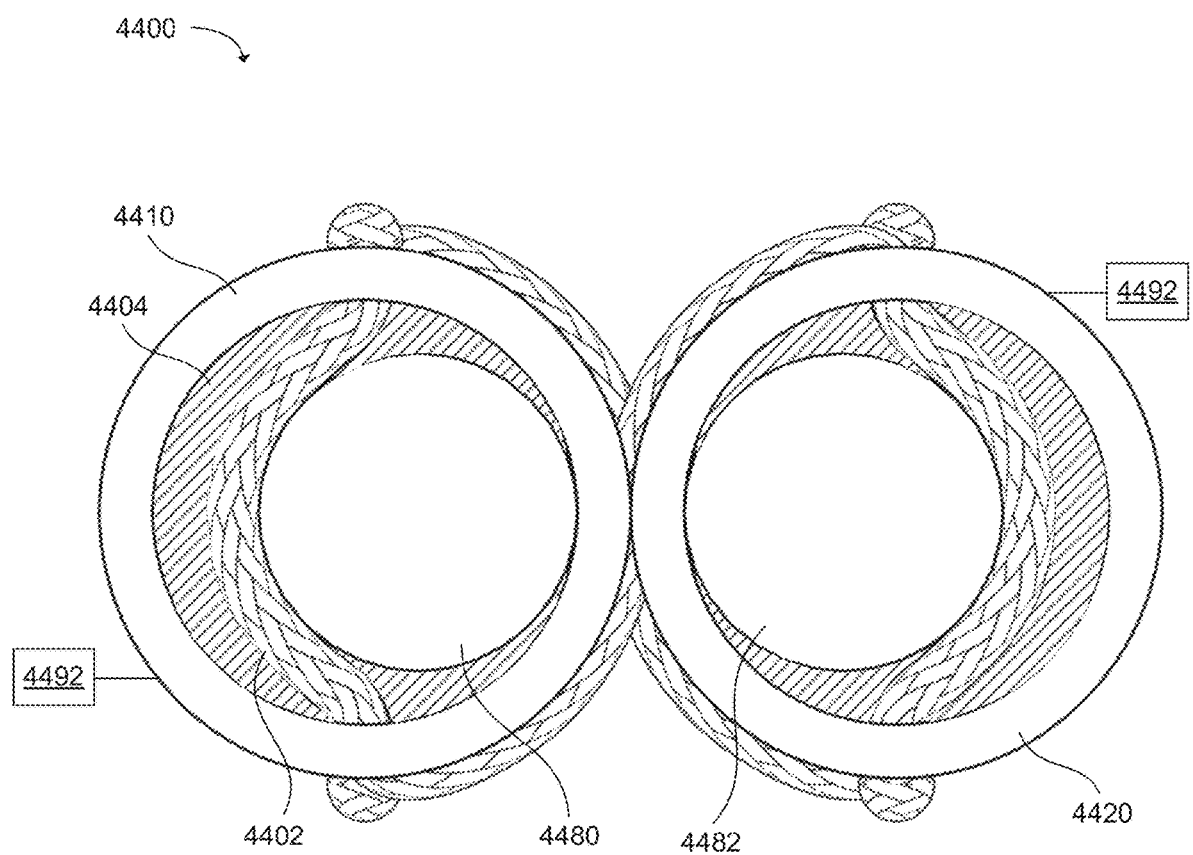
FIG. 44 illustrates another example joint implant in accordance with the present technology.

Many of the joint implant elements, tensioning elements, and other components described herein are cylindrical, partially cylindrical, or other shapes that have a hollow interior space. In some examples, it can be useful to fill the hollow interior space with a solid material before implanting the joint implants into a subject. In many cases, any hollow interior spaces or other voids in the joint implants described herein can be filled with a polymer by melting the polymer, filling the voids, and then allowing the polymer to solidify. Any biocompatible polymer can be used for this, as long as the polymer has a melting temperature that will not damage any of the other components of the joint implant. For example, if the filaments are made of a polymer, then the void space can be filled with a melted polymer that has a melting temperature below the melting temperature of the filaments. If the joint implant elements or other components are made of a polymer, then the melting temperature of the polymer used to fill the voids can also be less than the melting temperature of these components. FIG. 44 shows an example joint implant 4400 that includes a solid polymer 4404 filling void spaces inside the proximal joint implant element 4410 and the distal joint implant element 4420. As in previous examples, filaments 4402 are secured in the joint implant elements and a proximal tensioning element 4480 and distal tensioning element 4482 are placed inside the hollow interiors of the joint implant elements to apply tension to the filaments. These components would have void space remaining in the hollow interior of the joint implant elements. Therefore, a melted polymer is used to fill the remaining void space inside the joint implant elements. The polymer then solidifies, becoming a solid polymer 4404. According, the interior of the joint implant elements has solid material all the way through. This same process can be applied to any other joint implant designs described herein, when there are void spaces inside the joint implant elements or in other components of the joint implant. FIG. 44 also shows boxes 4492, which represent bone interface connectors or bone anchors, which can be connected to the joint implant. The bone interface connectors or bone anchors can be supported by a joint implant element or a tensioning element. A variety of different bone interface connectors and bone anchors are described herein, any of which can be used in this example.

As explained above, the joint implant can be constrained by filament segments, which can function as a registration features, or by other types of registration features, or a combination thereof. Many of the example joint elements described above utilize filament segments to couple joint implant elements together in a way that allows the joint implant elements to rotate relative to each other in a rolling motion without slipping. This can be useful because the filaments constrain the motion of the joint implant elements to prevent the joint implant elements from sliding on (i.e., relative to) each other. In particular, the motion of the joint implant elements in the sagittal plane is constrained and limited to the rolling motion of one joint implant on the other. Without such a constraint, the joint implant would potentially be subject to dislocation because one joint implant element would be able to slide above or below the other joint element. The constraint provided by the filament segments makes the joint implant much more stable and helps the motion of the joint to be predictable.

In other examples, other types of registration features can be used to constrain the motion of the joint implant instead of, or in addition to, filament segments. In certain examples, a joint implant can include a proximal joint implant element having a proximal curved interface surface and a distal joint implant element having a distal curved interface surface. The proximal curved interface surface and the distal curved interface surface can each include registration features that interface (e.g., mate) together to achieve and maintain registration between the proximal and distal joint implant elements. As used herein, "maintain registration" means that the proximal and distal joint implant elements rotate as if rolling against each other without sliding. The registration of joint implant elements prevents the joint implant elements from rotating freely independently from each other.

The registration features can include any features that constrain the motion of the proximal and distal joint implant elements. In some examples, the registration features can include protrusions from the curved interface surfaces or recesses into the curved interface surfaces, or both, where the protrusions and/or recesses are complementary. One example of this type of registration feature is a series of teeth on each of the interfacing joint implant elements operable to interface with one another upon rotation of the joint implant elements relative to one another, similar to the teeth of a gear. With a gear, the teeth of a gear can interface with the complementary teeth of another gear in a way that constrains the motion of both gears. When the teeth of two gears are interlocked, the gears cannot slide against each. Rather, the gears must move by a rolling motion without slipping.

Figure 45A:
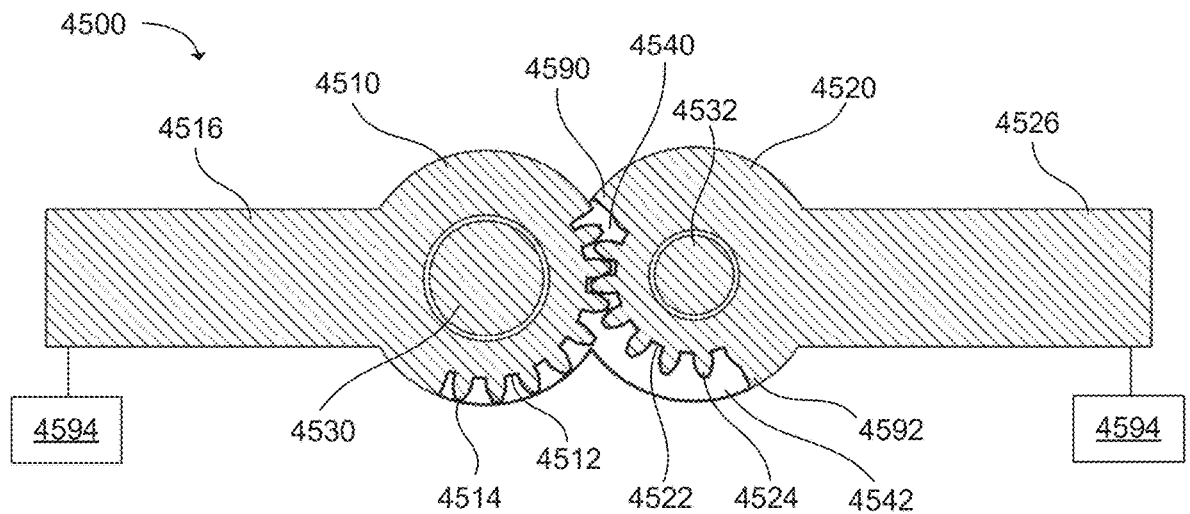
FIGS. 45A-45C show side cross-sectional views of another example joint implant in different rotational positions in accordance with the present technology.
Figure 45B:
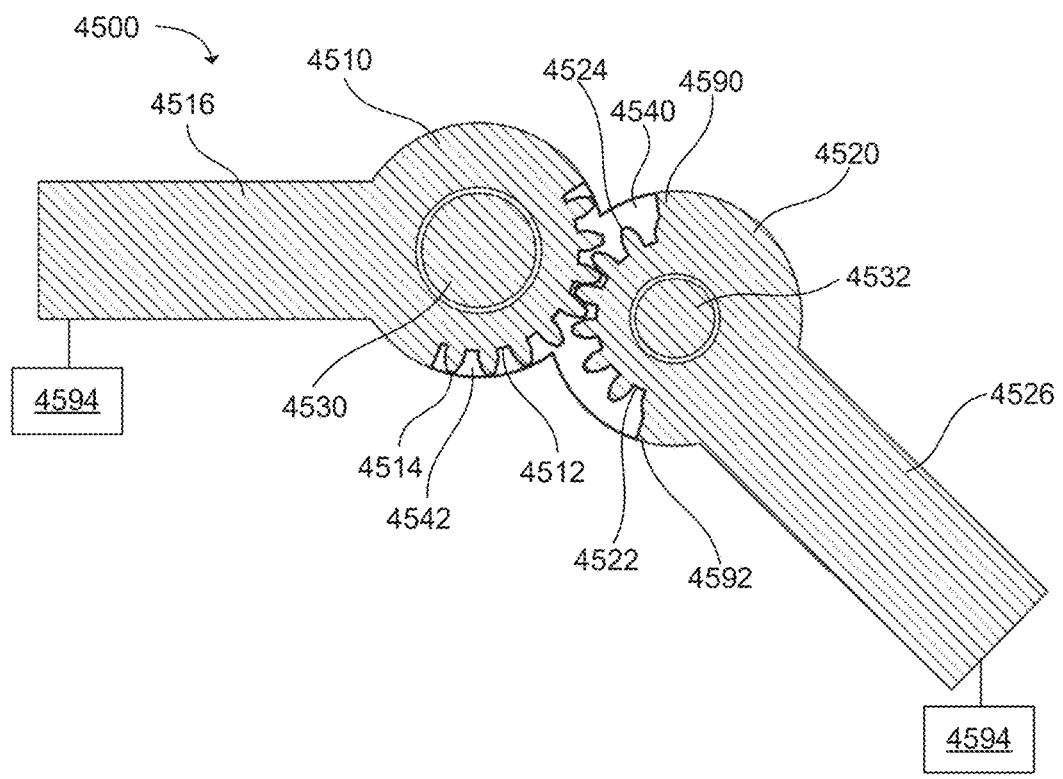
Figure 45C:
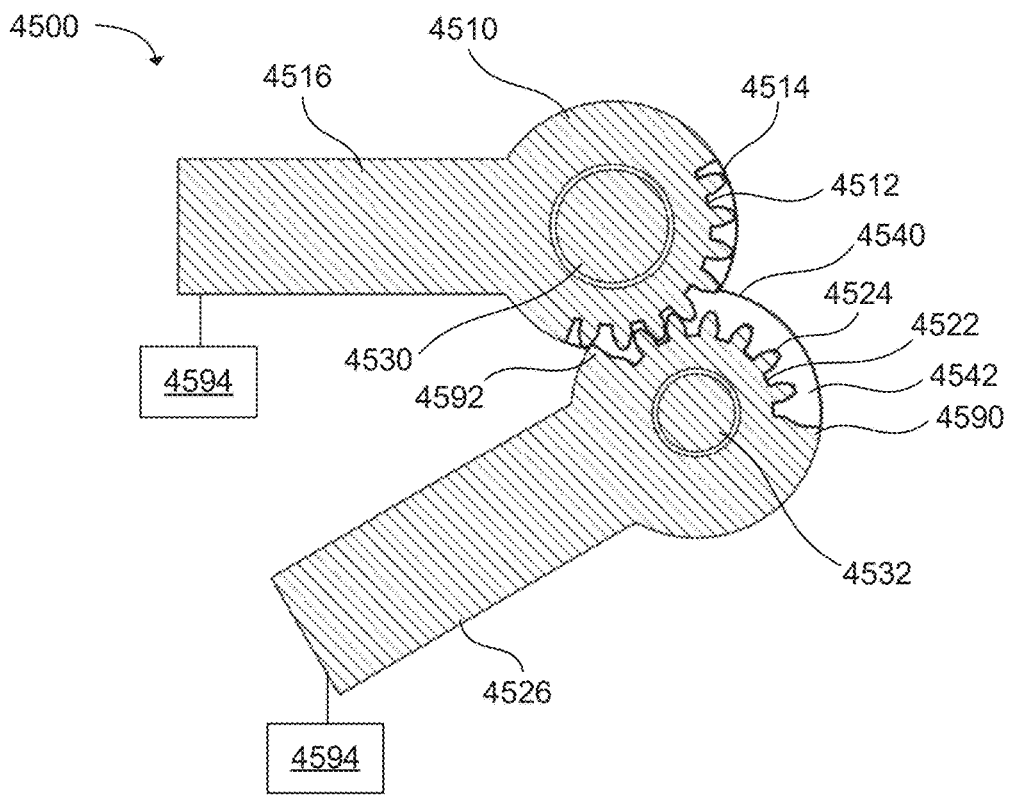

FIG. 45A shows a side cross-sectional view of one example joint implant 4500 that includes a proximal joint implant element 4510 having a proximal curved interface surface 4512 and proximal registration features 4514 on the proximal curved interface surface. The joint implant 4500 also includes a distal joint implant element 4520 having a distal curved interface surface 4522 and distal registration features 4524 on the distal curved interface surface. In this example, the registration features comprise a series of teeth, which can be referred to as gear teeth. The proximal registration features interface with the distal registration features by engaging, or intermeshing, the gear teeth together at a contact location where the proximal joint implant element contacts the distal joint implant element. These registration features 4514, 4524 maintain registration between the proximal and distal joint implant elements 4510, 4520 by preventing either of the joint implant elements from slipping or sliding on the surface of the other joint implant element. This constrains the motion of the joint implant elements to a rolling motion. FIG. 45B shows the same example joint implant 4500 after the joint implant 4500 with its joint implant elements 4510, 4520 have moved to a partially flexed position. FIG. 45C shows the joint implant 4500 in a fully flexed position. The registration features 4514, 4524 maintain registration between the joint implant elements 4510, 4520 throughout the range of motion of the joint implant 4500, from the fully extended position to the fully flexed position.

The example joint implant 4500 shown in FIGS. 45A-45C also includes a first protrusion 4590 and a second protrusion 4592 formed in the distal curved interface surface 4522 of the distal joint implant element 4520. These protrusions can define the range of motion of the joint implant by acting as stopping points to stop rotation of the proximal and distal joint implant elements 4510, 4520 relative to one another. In this example, the protrusions 4590, 4592 extend radially outward from a rotational axis of the distal joint implant element 4520. The protrusions 4590, 4592 protrude radially farther than the tips of the distal registration features 4524. In other words, the protrusions 4590, 4592 protrude to a radial distance that is farther than the radial distance from the axis to the distal registration features 4524 (i.e., gear teeth). Because these protrusions extend farther outward than the gear teeth on the distal joint implant element 4520, the protrusions do not mesh with the gear teeth on the proximal joint implant element 4510. When the joint implant elements 4510, 4520 rotate far enough that the first protrusion 4590 or second protrusion 4592 is at the contact point between the joint implant elements 4510, 4520, then the protrusion will block the joint implant elements 4510, 4520 from rotating any further. FIGS. 45A-45C also shown a proximal pin 4530 about which the proximal joint implant element 4510 rotates. The proximal pin 4530 extends along the rotational axis of the proximal joint implant element. A distal pin 4532 similarly extends along the rotational axis of the distal joint implant element 4520 such that the distal joint implant element 4520 rotates about the distal pin 4530. The proximal pin 4530 and distal pin 4532 are part of a joint implant element connector 4540 that also includes a connector base 4542 that can be partially seen behind the joint implant elements 4510, 4520 in these figures. The joint implant element connector 4540 can hold the proximal and distal joint implant elements 4510, 4520 at a constant center-to-center distance. The pins also provide rotational axes for the proximal and distal joint implant elements 4510, 4520. Thus, the pins acts as axles about which the joint implant elements 4510, 4520 can rotate. The proximal joint implant element 4510 also includes a proximal base portion 4516 located on an opposite end of the proximal joint implant element 4510 from the proximal curved interface surface 4512. The distal joint implant element 4520 similarly includes a distal base portion 4526 located on an opposite end of the distal joint implant element 4520 from the distal curved interface surface 4522. The proximal base portion and/or the distal base portion can connect to a bone interface connector 4594. The bone interface connector 4594 is represented by a box in these figures, and any of the types of bone interface connectors described herein can be used.

As mentioned above, the joint implant can include protrusions that protrude radially farther than a tip of the registration features so that the protrusions act as a stopping point for the joint implant. In various examples, the joint implant can include at least one protrusion that protrudes radially farther than a tip of at least one of the proximal registration features or the distal registration features. The protrusion or protrusions can be part of the proximal joint implant element or the distal joint implant element. In some examples, the protrusion or protrusions can protrude past the tips of the registration features by a distance from about 0.1 mm to about 3 mm, or from about 0.1 mm to about 2 mm, or from about 0.1 mm to about 1 mm, or from about 0.1 mm to about 0.5 mm, or from about 0.5 mm to about 3 mm, or from about 0.5 mm to about 2 mm, or from about 0.5 mm to about 1 mm, or from about 1 mm to about 3 mm, or from about 1 mm to about 2 mm, or from about 2 mm to about 3 mm.

The protrusion described above can define an end point of the range of motion of motion of the joint implant. As explained above, when the proximal and distal joint implant elements rotate so that the protrusion is at a contact point between the joint implant elements, then the protrusion can prevent further rotation of the joint implant elements. Thus, the protrusion defines and end point of the range of the range motion at that rotational position. In some examples, the protrusion can define a first end point of the range of motion. A second end point of the range of motion can be defined by a second protrusion. In certain examples, at least one of the proximal curved interface surface or the distal curved interface surface can also include a second protrusion that defines the second end point of the range of motion. In alternative examples, the second end point of the range of motion can be defined by soft tissue in the joint where the joint implant is implanted, and not by a feature of the joint implant itself.

As used herein, the term "teeth" or "gear teeth" can refer to a series of protruding and receding areas in a curved interface surface of one joint implant element that can interface with a complementary series of protruding and receding areas (i.e., teeth or gear teeth) on another curved interface surface of another joint implant element. The term "gear teeth" does not imply any particular shape or dimensions of these protruding and receding areas. In some examples, gear teeth can include flat surfaces, curved surfaces, sharp edges, rounded edges, or any combination thereof. For example, the gear teeth shown in FIGS. 45A-45C include curved side surfaces shaped such that each tooth tapers from a wider width at a base of the tooth to a narrower width at a tip of the tooth. These curved side surfaces can be designed to minimize rubbing between the proximal gear teeth and the distal gear teeth when the joint implant elements rotate.

Figure 46:
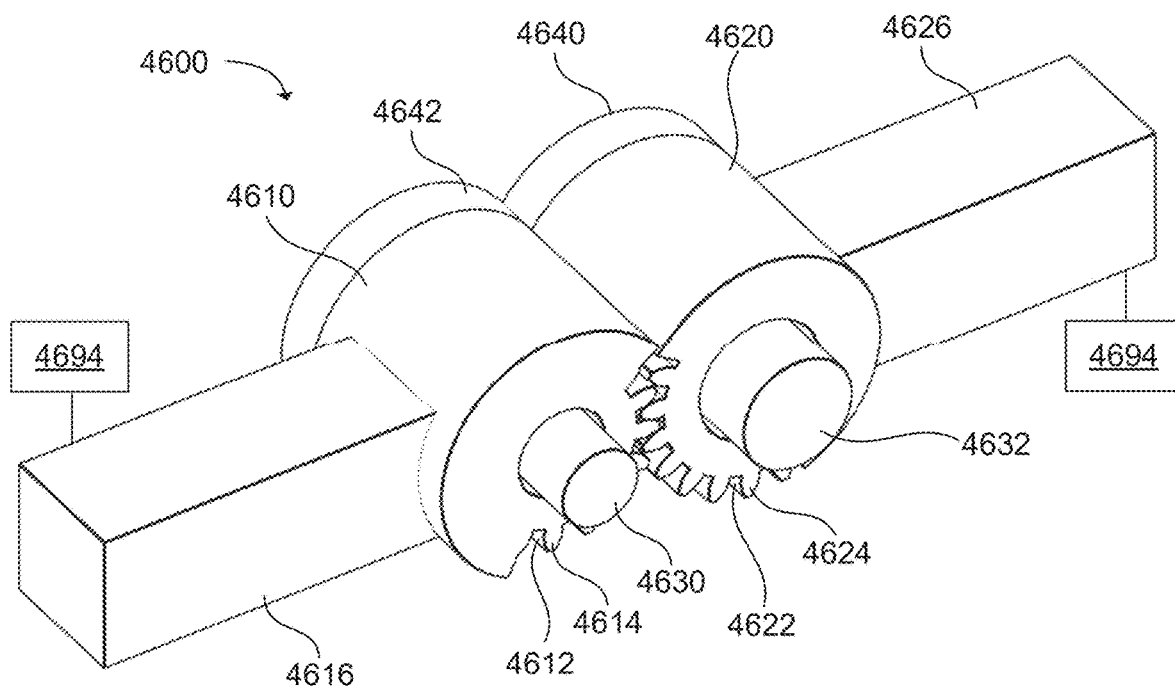
FIG. 46 shows a perspective view of another example joint implant in accordance with the present technology.

FIG. 46 is a perspective view of an example joint implant 4600 similar to the example shown in FIGS. 45A-45C. This example also includes a proximal joint implant element 4610 having a proximal curved interface surface 4612 with proximal registration features 4614. The proximal joint implant element 4610 also includes a proximal base portion 4616 connected to a bone interface connector 4694. The joint implant 4600 also includes a distal joint implant element 4620 having a distal curved interface surface 4622 with distal registration features 4624. The distal joint implant element 4620 also includes a distal base portion 4626 connected to a bone interface connector 4694. The proximal registration features 4614 interface with the distal registration features 4624 to maintain registration between the proximal joint implant element 4610 and the distal joint implant element 4620. The joint implant 4600 also includes a joint implant element connector 4640. The joint implant element connector 4640 is a part that is separate from the proximal and distal joint implant elements 4610, 4620, and which includes a proximal pin 4630 and distal pin 4632. The proximal pin 4630 and distal pin 4632 are attached to a connector base 4642. The proximal pin 4630 extends through the proximal joint implant element 4610 to provide a rotational axis for the proximal joint implant element 4610. The distal pin 4632 extends through the distal joint implant element 4620 to provide a rotational axis for the distal joint implant element 4620. The joint implant element connector 4640 couples the proximal joint implant element 4610 to the distal joint implant element 4620. The joint implant element connector 4640 maintains a set distance between the axis of rotation of the proximal joint implant element 4610 and the axis of rotation of the distal joint implant element 4620. Therefore, the joint implant element connector 4640 keeps the joint implant elements 4610, 4620 together so that the registration features can be engaged and prevents the joint implant elements 4610, 4620 from pulling apart.

Figure 47:
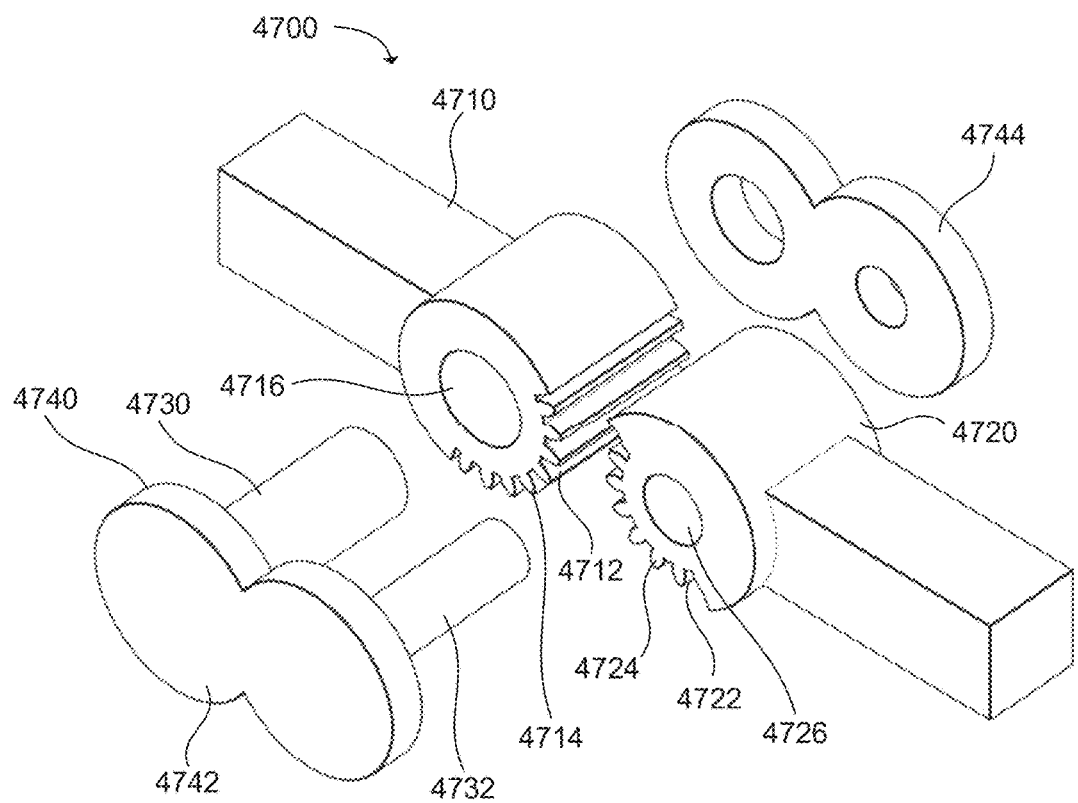
FIG. 47 shows an exploded view of another example joint implant in accordance with the present technology.

FIG. 47 shows an exploded view of another example joint implant element 4700. This example includes a proximal joint implant element 4710 and a distal joint implant element 4720. The proximal joint implant element 4710 includes a proximal curved interface surface 4712 with proximal registration features 4714. The distal joint implant element 4720 includes a distal curved interface surface 4722 with distal registration features 4724. The distal curved interface surface 4722 also includes protrusions 4790, 4792 that act as stops when the joint implant 4700 is assembled. These protrusions 4790, 4792 protrude radially farther than the tips of the distal registration features. The proximal joint implant element 4710 also includes a proximal pin hole 4716 that can accommodate a proximal pin 4730 such that the proximal joint implant element 4710 can rotate around the proximal pin 4730. The distal joint implant element 4720 includes a distal pin hole 4726 that can accommodate a distal pin 4732 and the distal joint implant element 4720 can rotate around the distal pin 4732. The proximal pin 4730 and distal pin 4732 are part of a joint implant element connector 4740. The pins extend from a connector base 4742. In this example, the connector base 4742 has a profile and configuration that aligns with the profile and configuration of the proximal joint implant element 4710 and distal joint implant element 4720. In this example, the profile and configuration is shaped as two joined circles. A connector cap 4744 can be connected to the pins 4730, 4732 on the opposite side of the proximal and distal joint implant elements 4710, 4720. The connector cap 4744 can retain the proximal and distal joint implant elements 4710, 4720 on the proximal and distal pins 4730, 4732, respectively. The connector cap 4744 in this example has two holes into which the ends of the proximal and distal pins 4730, 4732, can be inserted. In other examples, the proximal and distal pints 4730, 4732, can connect to the connector cap 4744 in other ways, such as by holes that extend partially through the thickness of the connector cap 4744 instead of penetrating all the way through the thickness. Once the pins are inserted into the connector cap 4744, these can be secured using clips that clip onto the pins, or by adhesive, or by welding, or by screwing a screw through the connector cap 4744 and into the pins, or other methods.

Figure 48A:
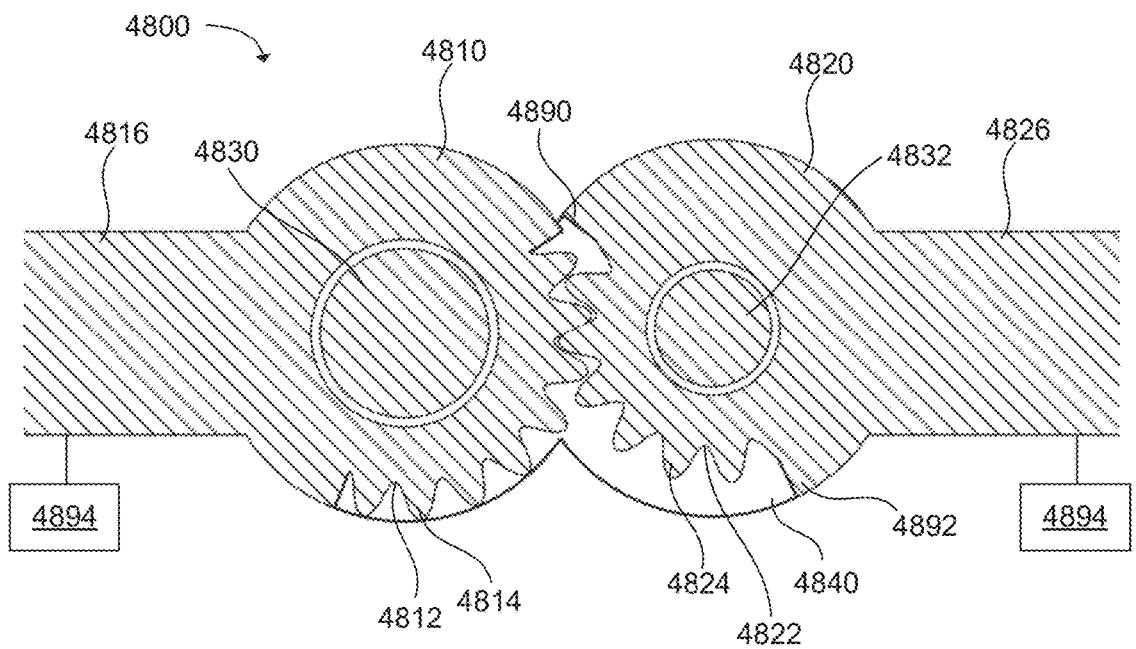
FIGS. 48A and 48B show cross-sectional views of additional example joint implants in accordance with the present technology.
Figure 48B:
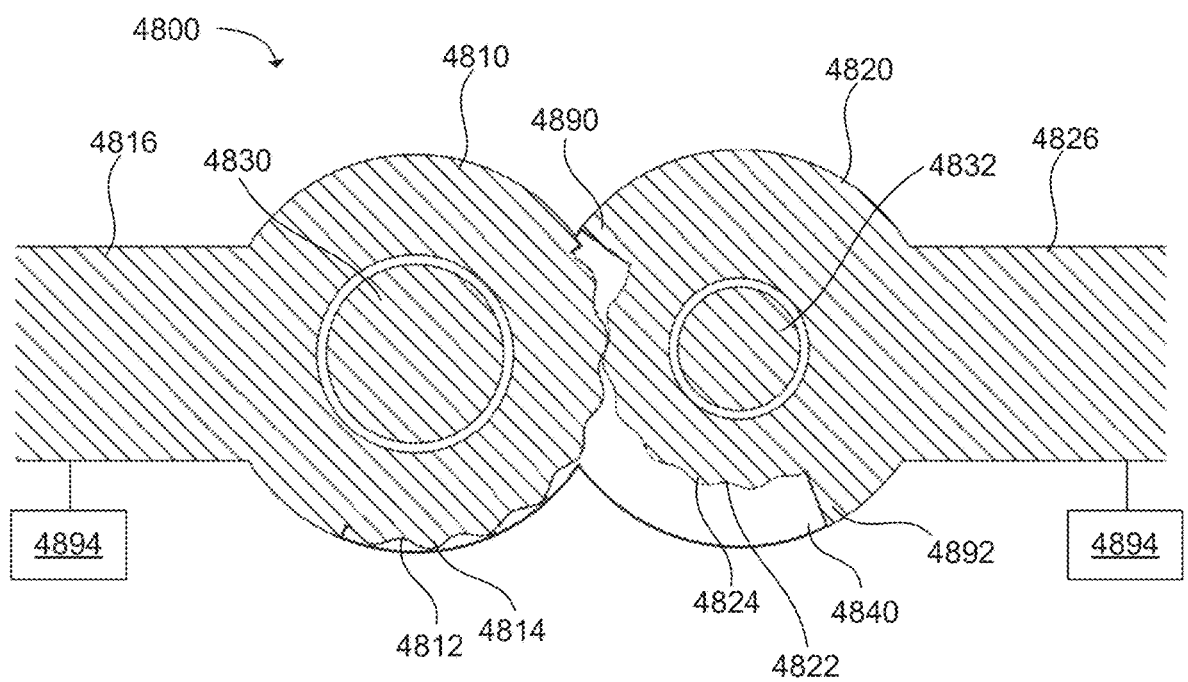

FIG. 48A shows another cross-sectional side view of an example joint implant 4800. This example includes differently shaped gear teeth than the previous examples. In particular, this example includes proximal registration features 4814 and distal registration features 4824 that are both shaped as sinusoidal curved gear teeth. These gear teeth do not include any sharp edges or flat surfaces. Instead, the proximal and distal registration features 4814, 4824 both include sinusoidal wave shapes that can interface together as the joint implant 4800 rotates. As in previous examples, the registration features 4814, 4824 are formed in the proximal curved interface surface 4812 of the proximal joint implant element 4810 and the distal curved interface surface 4822 of the distal joint implant element 4820, respectively. Additionally, the distal curved interface surface 4822 includes protrusions 4890, 4892 that act as stops to stop rotation of the joint implant elements 4810, 4820 when the joint implant 4800 is in a fully flexed position or a fully extended position. A joint implant element connector 4840 includes a proximal pin 4830 and a distal pin 4832. The proximal pin 4830 extends through a pin hole in the proximal joint implant element 4810 and the distal pin 4832 extends through a hole in the distal joint implant element 4820. This example also includes a proximal base portion 4816 connected to a proximal bone interface connector 4892 and a distal base portion 4826 connected to a distal bone interface connector 4894. FIG. 48B shows another example that is almost identical to the example in FIG. 48A, except that the registration features 4814, 4824 have a shorter height. Therefore, the registration features 4814, 4824 have a smaller height to period ratio in the example of FIG. 48B. In some examples, it can be useful to use a smaller height to period ratio like this to reduce the effects of the registration features on surrounding tissue.

As explained above, and generally speaking with reference to any of the examples herein, the registration features can have a variety of sizes, configurations, and shapes. As mentioned above, the example of FIG. 48 includes registration features having a sinusoidal profile. In other examples, the registration features can be shaped as gear with other profiles, such as an involute profile, a spur profile, a helical profile, a double helical profile, a sinusoidal profile, or a combination thereof.

In some examples, the registration features can have a height measured in a radial direction (i.e., along a radius of the joint implant element with an origin at the rotational axis of the joint implant element) where the height can be a distance from the tips of the registration features to the lowest point of the recesses between the tips. The height of the registration features can also be referred to as an amplitude. When the registration features are in the form of a wave such as the sinusoidal gear teeth in FIG. 48, the amplitude is measured from the peak of a wave to a trough between two peaks. In some examples, the height or amplitude of the registration features can be from about 0.1 mm to about 5 mm, or from about 0.1 mm to about 3 mm, or from about 0.1 mm to about 2 mm, or from about 0.1 mm to about 1 mm, or from about 0.1 mm to about 0.5 mm, or from about 0.5 mm to about 5 mm, or from about 0.5 mm to about 3 mm, or from about 0.5 mm to about 2 mm, or from about 0.5 mm to about 1 mm, or from about 1 mm to about 5 mm, or from about 1 mm to about 3 mm, or from about 1 mm to about 2 mm, or from about 2 mm to about 5 mm, or from about 2 mm to about 3 mm, or form about 3 mm to about 5 mm.

The registrations features can also have a width. The width can include a width of a protruding registration feature and also a width of a recess between protruding portions. For wave-shaped registration features, this can also be the period of the wave, measured as the distance from one peak to an adjacent peak. For registration features having other shapes, the period can refer to the width of one protruding portion plus one adjacent recessed portion. In some examples, the period of the of the registration features can be from about 0.1 mm to about 5 mm, or from about 0.1 mm to about 3 mm, or from about 0.1 mm to about 2 mm, or from about 0.1 mm to about 1 mm, or from about 0.1 mm to about 0.5 mm, or from about 0.5 mm to about 5 mm, or from about 0.5 mm to about 3 mm, or from about 0.5 mm to about 2 mm, or from about 0.5 mm to about 1 mm, or from about 1 mm to about 5 mm, or from about 1 mm to about 3 mm, or from about 1 mm to about 2 mm, or from about 2 mm to about 5 mm, or from about 2 mm to about 3 mm, or form about 3 mm to about 5 mm.

A ratio of the amplitude, or height, of the registration features to a period of the registration features, or a height-to-period ratio, can be from about 1:20 to about 2:1, or from about 1:20 to about 1:1, or from about 1:20 to about 1:2, or from about 1:20 to about 1:4, or from about 1:20 to about 1:10, or from about 1:10 to about 2:1, or from about 1:10 to about 1:1, or from about 1:10 to about 1:2, or from about 1:10 to about 1:4, or from about 1:4 to about 2:1, or from about 1:4 to about 1:1, or from about 1:4 to about 1:2, or from about 1:2 to about 2:1, or from about 1:2 to about 1:1, or from about 1:1 to about 2:1. In some cases, smaller ratios can be useful to avoid soft tissue in a joint of a subject from being caught between the proximal and distal registration features. In some examples, the registration features can have a low aspect ratio, which can refer to registration features that have an amplitude to period ratio of less than 1:1, or less than 1:2, or less than 1:4, or less than 1:10, or less than 1:20. The registration features can be located at a radial distance from the rotational axis of the joint implant element. In some examples, the proximal registration features can be located at a radial distance from the rotation axis of the proximal joint implant element, and the distal registration features can be located at the same radial distance from the rotational axis of the distal joint implant element. In other examples, the proximal and distal registration features can be located at different radial distances from their respective rotational axes (e.g., see the example shown in FIG. 45A, wherein the proximal registration features 4514 are located at a greater radial distance from the rotational axis of the proximal joint implant element 4510 than the radial distance of the distal registration features 4524 from the rotational axis of the distal joint implant element 4520. In this example, the proximal joint implant element 4510 and the distal joint implant element 4520 both have a portion with a cylindrical shape, and the registration features 4514, 4524 are formed as recesses in the respective cylindrical surfaces. In the proximal joint implant element 4510, the registration features 4514 have tips that extend outward to the same radius as the remainder of the cylindrical surface. The distal joint implant element 4520 is different in that the distal registration features 4524 do not extend outward to the same radius as the cylindrical portion of the distal joint implant element 4520. Instead, all the distal registration features 4524 are recessed with their tips below the cylindrical surface of the cylindrical portion. The distal registration features 4524 are present around a little less than half a circumference of the cylindrical portion. The distal registration features 4524 are bounded by the protrusions that act as stops to limit the rotation of the joint implant 4500. In this example, the protrusions extend outward to the cylindrical surface. The cylindrical surface of the cylindrical portion of the distal joint implant element 4520 has the same radius as the cylindrical portion of the proximal joint implant element 4510 in this example, although in other examples these radii can be different.).

In some examples, the registration features can be bounded by two protrusions that act as stops to limit the range of motion of the joint implant. In certain examples, the protrusions can be located on the joint implant element at angular locations with respect to the rotational axis of the joint implant element. For example, if the two protrusions are on directly opposite sides of the rotation axis then the angular locations are separated by 180°. In other examples, the protrusions can be located at angular locations separated by less than 180°. For example, the protrusions can be separated by an angle from about 90° to 180°, or from about 90° to about 170°, or from about 90° to about 160°, or from about 90° to about 150°, or from about 90° to about 140°, or from about 90° to about 130°, or from about 90° to about 120°. In further examples, the angle between the protrusions can be approximately equal to the angular range of motion of the joint implant.

The joint implant element connector can include pins that provide rotational axes for the proximal and distal joint implant elements, as explained above. In some examples, the pins can each have the same diameter, while in other examples, the pins can have different diameters. It can be useful during assembly to have pins with different diameters, as this will ensure that the joint implant element connector is assembled in the correct direction with the other components of the joint implant. In certain examples, one of the joint implant elements can have registration features that are located closer to the rotational axis than in the other joint implant element. The joint implant element that has the registration features located closer to the rotational axis can also have a smaller pin hole than the other joint implant element. Therefore, the joint implant element connector can have a smaller pin that is inserted into the smaller pin hole, and a larger pin that is inserted into a larger pin hole in the other joint implant element.

Figure 49A:
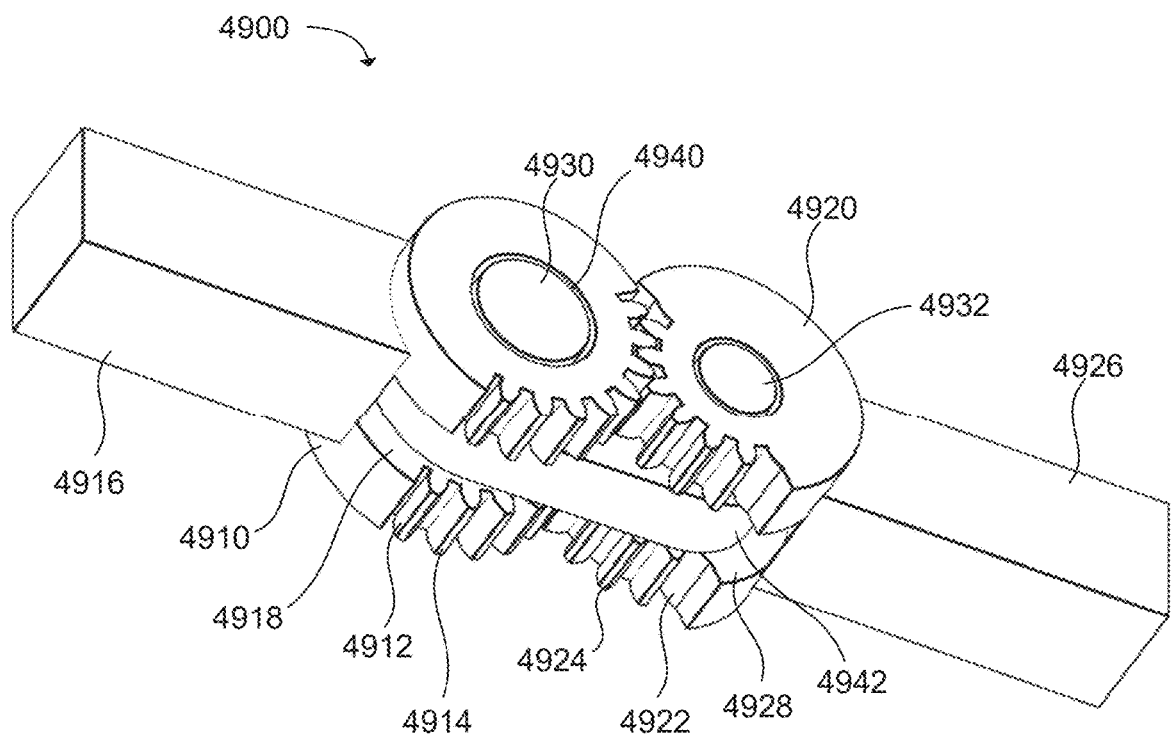
FIG. 49A shows a perspective view of another example joint implant in accordance with the present technology.

In various examples, the joint implant element connector can have a connector base and two pins extending from the connector base. The pins can be inserted into a proximal joint implant element and a distal joint implant element. After the pins have been inserted into the joint implant elements, the connector body can be positioned along the side of the joint implant elements. In certain examples, a connector cap can be placed on the ends of the pins that extend through the joint implant elements. In other examples, the joint implant element connector can have other designs. In certain examples, the joint implant element connector can have a connector base that is designed to be in a central portion of the joint implant instead of on one side. The proximal and distal join implant elements can be designed with slots in a central portion, and the connector base can fit in the slots. Pins can then secure the proximal and distal joint implant elements to the connector such that the pins provide the rotational axes of the proximal and distal joint implant elements. FIG. 49A shows a bottom perspective view of one such example joint implant 4900.

As shown in FIG. 49A, the joint implant 4900 includes a proximal joint implant element 4910 that includes a proximal base portion 4916 and a proximal curved interface surface 4912. Proximal registration features 4914 are formed in the proximal curved interface surface 4912. The proximal joint implant element also includes a slot 4918 formed in a central portion of the proximal joint implant element 4910. A joint implant element connector 4940 is partially held in the slot 4918 of the proximal joint implant element 4910. The joint implant 4900 also includes a distal joint implant element 4920 with a distal curved interface surface 4922 and a distal base portion 4926. The distal curved interface surface 4922 has distal registration features 4924 that interface with the proximal registration features 4914 to maintain registration between the proximal joint implant element 4910 and the distal joint implant element 4920. The distal joint implant element 4920 also includes a slot 4928 in a central portion. The joint implant element connector 4940 is partially held in the slot 4928 of the distal joint implant element 4920. The joint implant element connector 4940 also includes two pins 4930, 4932 that extend through pin holes in the proximal and distal joint implant elements 4910, 4920 to provide rotational axes for the proximal and distal joint implant elements 4910, 4920. In this example, the joint implant element connector 4940 can be made up of multiple parts that are assembled together. Specifically, the joint implant element connector 4940 can include a connector base 4942 that has holes for the pins 4930, 4932 to pass through. To assemble the joint implant 4900, the connector base 4942 can be positioned in the slots 4918, 4928 of the proximal and distal joint implant elements 4910, 4920, respectively, and then the pins 4930, 4932 can be inserted through the holes in the proximal and distal joint implant elements 4910, 4920 and the connector base 4942.

Figure 49B:
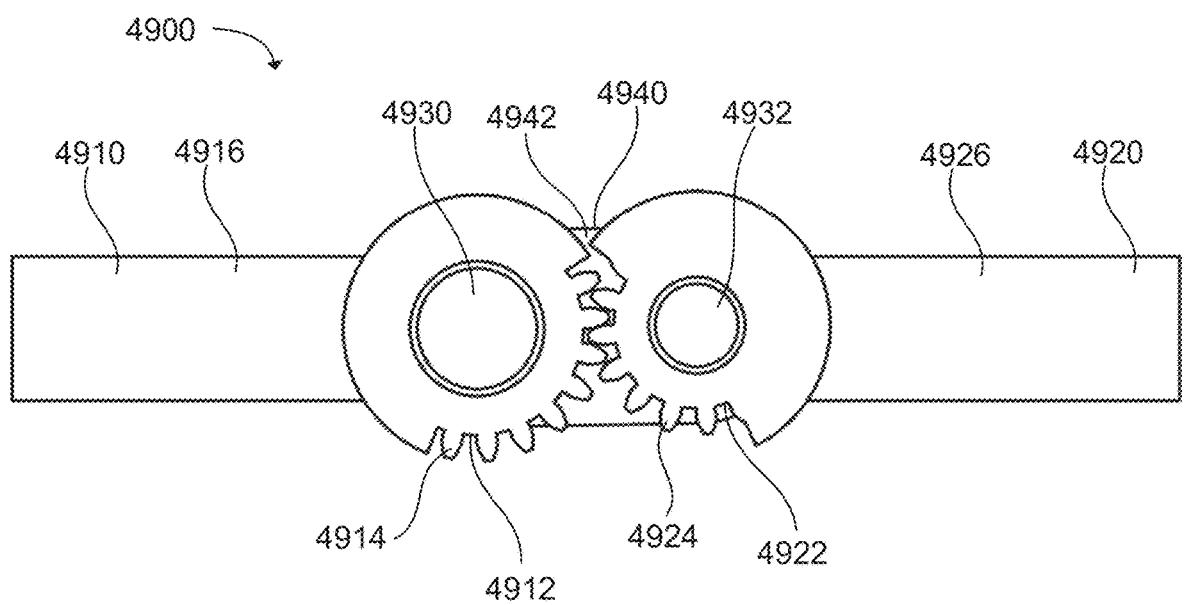
FIG. 49B shows a side view of the example joint implant of FIG. 49A.
Figure 49C:
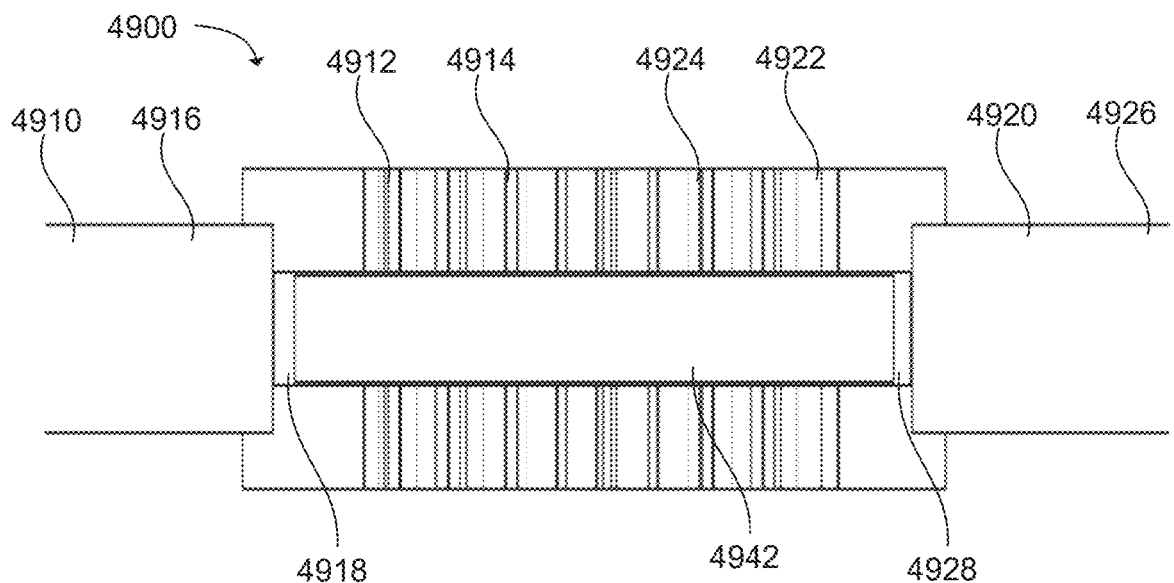
FIG. 49C shows a bottom view of the example joint implant of FIG. 49A.
Figure 49D:
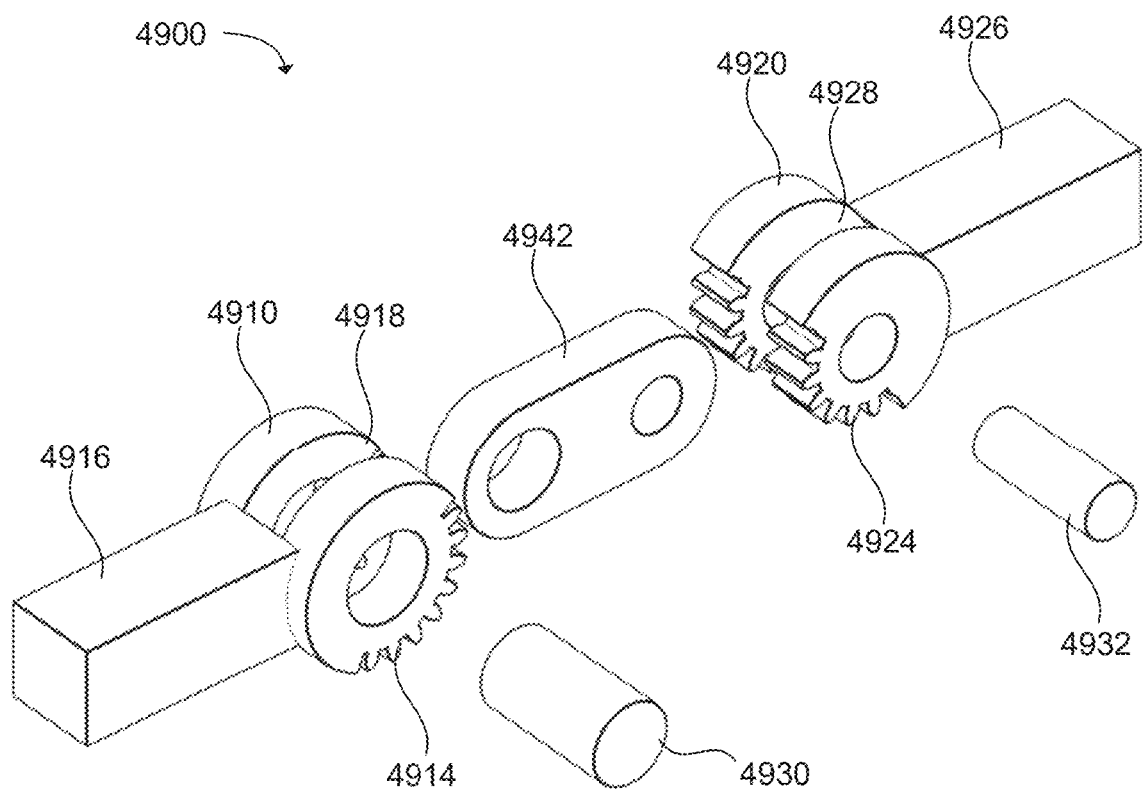
FIG. 49D shows an exploded view of the example joint implant of FIG. 49A.

FIG. 49B shows the same example joint implant 4900 from a side view. In this view, the connector base 4942 is partially visible between the proximal joint implant element 4910 and the distal joint implant element 4920. A bottom view of the same example is shown in FIG. 49C. This view shows how the slots 4918, 4928 are located in a central portion of the proximal and distal joint implant elements 4910, 4920. The connector base 4942 can be paced into these slots 4918, 4928 from below. This view also shows the edges of the registration features 4914, 4924 as vertical lines. FIG. 49D shows an exploded view of this example joint implant 4900. This view shows that the proximal joint implant element 4910 is formed as a single part, the distal joint implant element 4920 is formed as a single part, the connector base 4942 is formed as another part, and the pins 4930, 4932 are two separate parts. These components can be assembled by positioning the proximal and distal joint implant elements 4910, 4920 in contact so that the registration features 4914, 4924 interface together (i.e., the gear teeth mesh together). The connector base 4942 can be positioned in the slots 4918, 4928 so that the pin holes of the proximal and distal joint implant elements 4910, 4920 align with the holes of the connector base 4942. The pins 4930, 4932 can then be inserted through the holes. The pins 4930, 4932 together with the connector base 4942 can together make up the joint implant element connector 4940.

Figure 50:
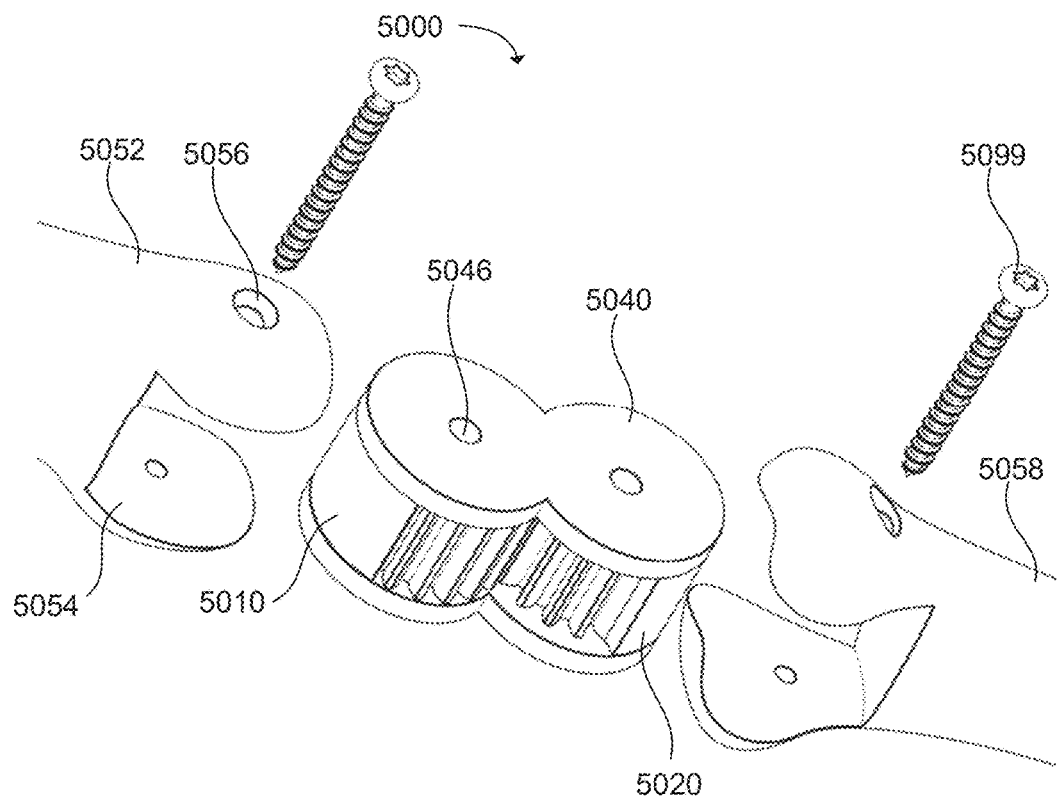
FIG. 50 shows an exploded view of another example joint implant in accordance with the present technology.

FIG. 50 shows an example joint implant 5000 to be implanted into bones 5052, 5058 of a subject. The bones have been prepared by cutting a slot 5054 that can accommodate the width of the joint implant. The bones also have holes 5056 for allowing screws 5099 to be inserted through the holes. The joint implant 5000 also includes holes 5046 for the screws. The joint implant 5000 includes a proximal joint implant element 5010 and a distal join implant element 5020 and a joint implant element connector 5040. The joint implant elements 5010, 50220 and the joint implant element connector 5040 include the holes 4046 for the screws to be inserted through. Although not visible in the figure, the joint implant element connector 5040 includes pins that extend through the proximal and distal joint implant elements 5010,

5020. The holes for the screws are formed through a central portion of the pins, so the screws go through the pines when the screws are inserted.

Figure 51:
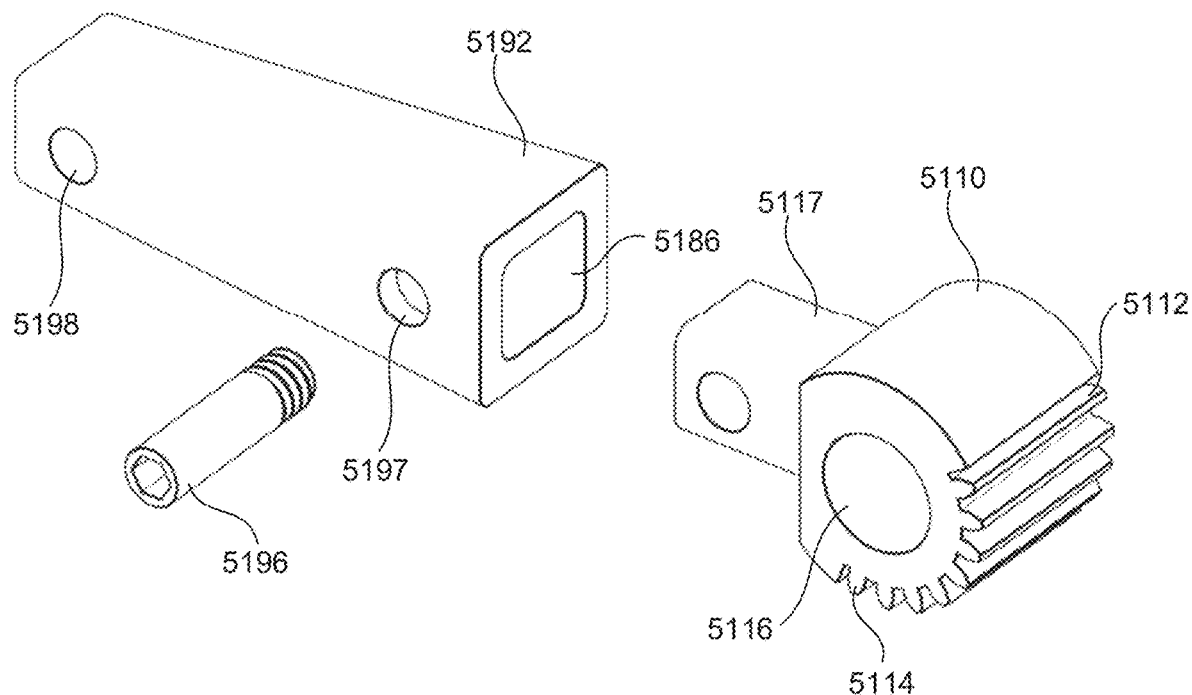
FIG. 51 shows an exploded view of another example joint implant in accordance with the present technology.

FIG. 51 shows an exploded view of an example proximal joint implant element 5110 and a bone interface connector 5192. The proximal joint implant element 5110 includes a proximal curved interface surface 5112 with proximal registration features 5114 shaped as gear teeth. The proximal joint implant element 5110 also includes a pin hole 5116. A joint implant element connector (not pictured in this figure) can have a pin that is inserted into this pin hole. As in the previous examples, a distal joint implant element (not shown) can also be assembled with the joint implant element connector and the proximal joint implant element so that the registration features of each joint implant element interface together to maintain registration of the joint implant elements. The proximal joint implant element 5110 in this example also includes a base portion 5117 that can be inserted into a slot 5186 formed in the proximal bone interface connector 5192. The proximal bone interface connector 5192 also includes a bolt hole 5197 that aligns with a bolt hole on the proximal joint implant element 5110. A bolt 5196 can be inserted through the bolt holes to attach the proximal bone interface connector 5192 to the proximal joint implant element 5110. The proximal bone interface connector 5192 also includes a transverse hole 5198. The proximal bone interface connector 5192 can be implanted into a bone of a joint and then a transverse screw or pin can be driven through the bone and the transverse hole to secure the proximal bone interface connector 5192 in and to the bone. Although not shown, the distal joint implant element can comprise the same or a similar configuration and function.

Two examples of securing to a bone in a joint example joint implants having registration features are shown in FIG. 50 and FIG. 51 above. In further examples, joint implants that utilize registration features (such as a series of teeth or gear teeth) can be secured to bones in a joint using any of the various examples of bone interface connectors, bone anchors, screws, stems, and so on as described herein. For example, many joint implants are described above that utilize filament segments to couple the proximal joint implant element to the distal joint implant element. The filament segments can also be and function as registration features to constrain the motion of the joint implant elements to a rolling motion, and therefore the filament segments can maintain registration between the proximal and distal joint implant elements. The use of registration features, such as a series of teeth or gear teeth, can provide an alternate way to maintain registration between the proximal and distal joint implant elements, or these can be used in conjunction with filaments. The joint implant elements connectors described above can provide an alternative way to couple the proximal and distal joint implant elements together rather than using filaments. Therefore, it is specifically noted herein, and those skilled in the art will recognize, that any of the example joint implants described herein that utilize filament segments can be modified by using a proximal and distal joint implant element with registration features, and/or by adding a joint implant element connector to couple the joint implant elements together.

In some examples, a joint span can include a proximal joint implant element having registration features as shown in FIG. 45A and a distal joint implant element having registration features as shown in FIG. 45A. The joint span can also include a joint implant element connector that couples the proximal and distal joint implant elements together. This joint span can be used in place of a joint span without registration features, such as the proximal joint implant element, distal joint implant element, and filament segments as in many of the examples described above. In certain examples, a joint span comprising registration features can be used in place of these components in the examples shown in FIG. 5, FIGS. 6A-6D, FIGS. 7A-7B, FIG. 8, FIG. 9, FIGS. 10A-10C, FIGS. 11A-11E, FIG. 12, FIG. 13, FIGS. 14A-14H, FIGS. 17A-17B, FIG. 18, FIGS. 19A-19B, FIGS. 20A-20D, FIG. 21, FIG. 22, FIG. 23, FIGS. 24A-24B, FIG. 25, FIG. 26, FIG. 27, FIG. 28, FIGS. 29-A-29E, FIGS. 30A-30C, FIGS. 31A-31B, FIGS. 32A-32B, FIGS. 33A-33B, FIGS. 34A-34B, FIGS. 35A-35B, FIGS. 36A-36D, FIGS. 37A-37B, FIGS. 38A-38B, FIG. 39, FIGS. 42A-42B, FIGS. 43A-43B, or FIG. 44. Or, stated differently, each of the examples in these figures can be modified to include registration features as taught herein. Alternatively, the examples described above that include registration features can be used together with any of the bone interface connectors and/or bone anchors described herein, and in particular the bone interface connectors and bone anchors shown in the above-listed figures or in FIG. 40 or FIG. 41.

Joint implants can also utilize a combination of both registration features and filament segments. Joint implants can include filament segments arranged in any of the ways described herein. As explained above, the filament segments can extend across a portion of the proximal and distal curved interface surfaces of the joint implant elements. The joint implant elements can also include registration features, such as a series of teeth or gear teeth or any of the other types of registration features described above, that interface and maintain registration of the proximal and distal joint implant elements. In some examples, the registration features can be located on a portion of the curved interfaces surfaces where the filament segments do not contact the curved interface surface. This can prevent the filament segments from interfering with the meshing of the registration features. In certain examples, the filament segments can be arranged with a gap between two or more of the filament segments. A portion of the curved interface surfaces within this gap can have registration features, where the proximal registration features interface with the distal registration features. Additionally, the curved interface surfaces can have an area near one or both sides of the joint implant that is free of filament segments. The registration features can be located in this area by one or both sides of the joint implant.

Figure 52:
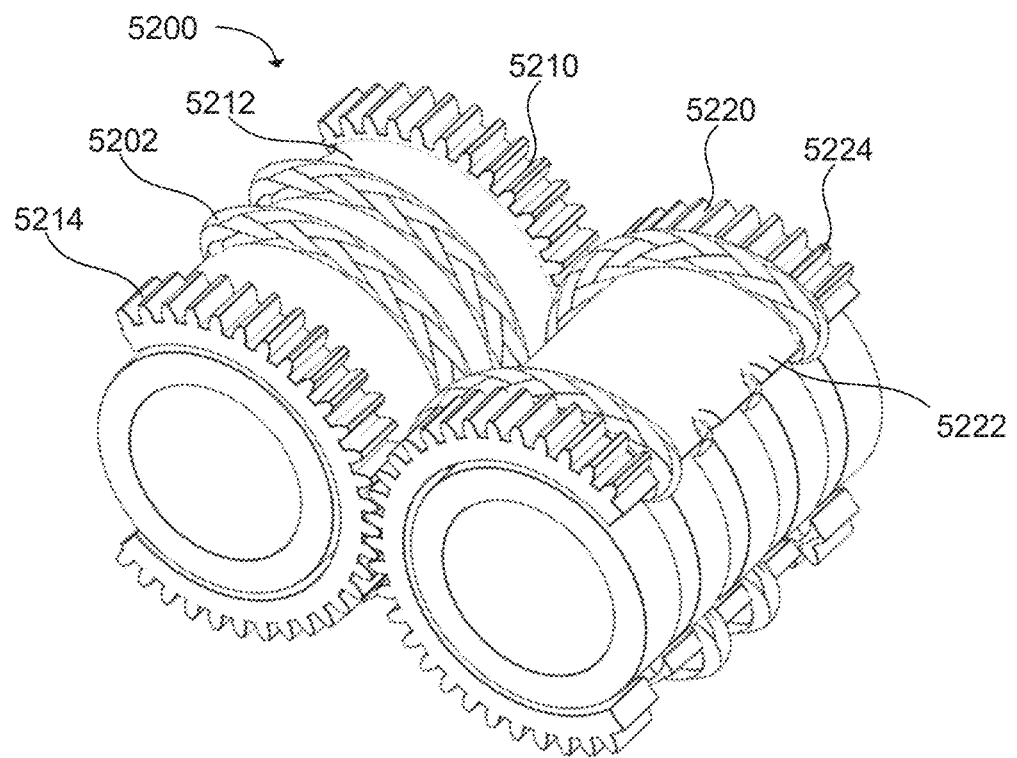
FIG. 52 shows a perspective view of another example joint implant in accordance with the present technology.

FIG. 52 shows a perspective view of an example joint implant 5200 that includes both filament segments 5202 and registration features 5214, 5224. The joint implant 5200 includes a proximal joint implant element 5210 having a proximal curved interface surface 5212 and a distal joint implant element 5220 having a distal curved interface surface 5222. A central portion of the curved interface surfaces 5212, 5222, respectively, are smooth, which allows the filament segments 5202 to wind and unwind on these curved interface surfaces 5212, 5222 as the joint implant elements 5210, 5220 rotate. The curved interface surfaces 5212, 5222 also include side portions where the registration features 5214, 5224, respectively, are formed. The curved interfaces surfaces 5212, 5222 in this example have a cylindrical profile, and the registration features 5214, 5224 are located on an outer surface of the cylindrical profile. The registration features 5214, 5224 are shaped as gear teeth that mesh together at a location where the proximal joint implant element 5210 contacts the distal joint implant element 5222. This example does not include a joint implant element connector, because the filament segments 5202 are utilized to couple the proximal joint implant element 5210 to the distal joint implant element 5220. Therefore, generally speaking, joint implants as taught herein can be designed with a combination of filament segments and registration features without including any joint implant element connector.

Figure 53:
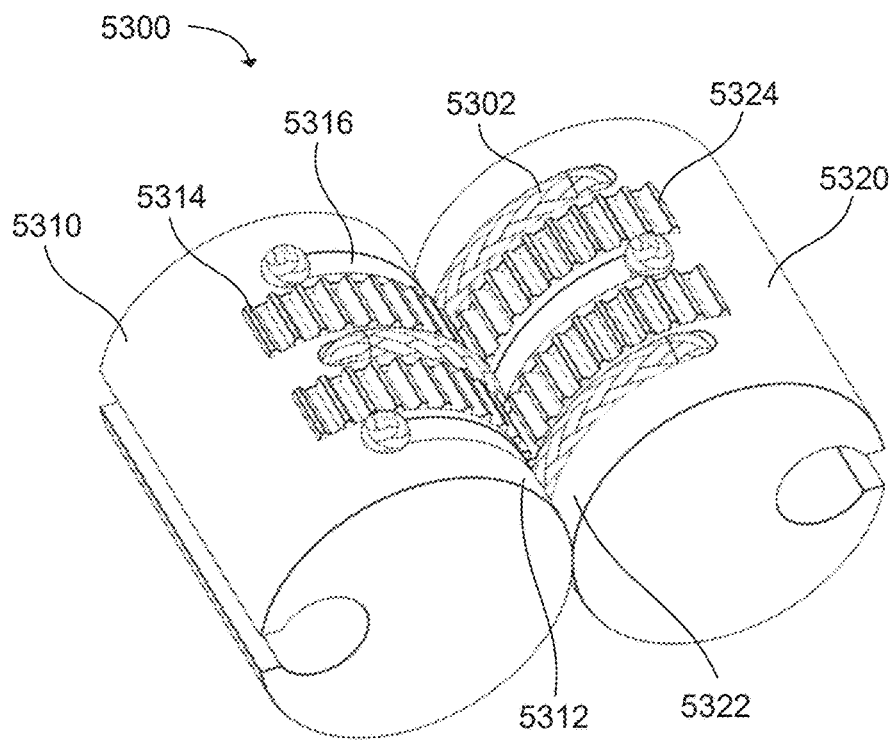
FIG. 53 shows a perspective view of another example joint implant in accordance with the present technology.

FIG. 53 shows a perspective view of another joint implant 5300 that includes a combination of filament segments 5302 and registration features 5314, 5324. In this example, the proximal joint implant element 5310 includes a proximal curved interface surface 5312 with grooves 5316 for the filament segments. In spaces between the grooves 5316, proximal registration features 5314 are formed. The distal joint implant element 5320 has a distal curved interface surface 5322 that also includes grooves for the filaments. Distal registration features 5324 are formed in areas between the grooves. In this example, the curved interface surfaces 5312, 5322 have a cylindrical profile, and the registration features 5314, 5324 are located on an outer surface of the cylindrical profile.

FIGS. 52 and 53 show two examples of joint implants that incorporate a combination of filaments and registration features. Any of the other joint implant examples described herein can also be modified to include a combination of filaments and registration features. This can be accomplished by forming registration features on any area of the curved interface surfaces of the respective joint implant elements where the registration features will not interfere with the filament segments.

In certain examples, a joint span can include a proximal joint implant element that has a proximal curved interface surface with proximal registration features. The joint span can also include a distal joint implant element with a distal curved interface surface with distal registration features that interface with the proximal registration features. The joint span can also include a first filament segment that extends from the proximal joint implant element to the distal joint implant element and a second filament segment that extends from the distal joint implant element to the proximal joint implant element. The first and second filament segments can cross each other at a location between the proximal and distal curved interface surfaces. This type of joint span can be used in place of a joint span comprising a proximal joint implant element, distal joint implant element, and filament segments devoid of registration features formed on the curved interface surfaces in any of the examples described above. In certain examples, this joint span can be used in place of these components in the examples shown in FIG. 5, FIGS. 6A-6D, FIGS. 7A-7B, FIG. 8, FIG. 9, FIGS. 10A-10C, FIGS. 11A-11E, FIG. 12, FIG. 13, FIGS. 14A-14H, FIGS. 17A-17B, FIG. 18, FIGS. 19A-19B, FIGS. 20A-20D, FIG. 21, FIG. 22, FIG. 23, FIGS. 24A-24B, FIG. 25, FIG. 26, FIG. 27, FIG. 28, FIGS. 29-A-29E, FIGS. 30A-30C, FIGS. 31A-31B, FIGS. 32A-32B, FIGS. 33A-33B, FIGS. 34A-34B, FIGS. 35A-35B, FIGS. 36A-36D, FIGS. 37A-37B, FIGS. 38A-38B, FIG. 39, FIGS. 42A-42B, FIGS. 43A-43B, or FIG. 44. Alternatively, this joint span can be used with any of the bone interface connectors and/or bone anchors described herein, and in particular the bone interface connectors and bone anchors shown in the above-listed figures or in FIG. 40 or FIG. 41.

It is noted that any of the example joint implant designs described herein can be adapted to be modular or non-modular. Providing the joint implants in a modular form can include designing the joint implant to use bone anchors or bone interface connectors that can be detachable and attachable to a joint span. Any of the various designs for bone anchors, bone interface connectors, and joint spans described above can be used. The joint spans can include the joint implant elements, filaments, tensioning elements, and any components and characteristics thereof that are described above.

Additionally, the joint implants can have a symmetrical design or an asymmetrical design. In particular, symmetrical joint implants can have the same components on the proximal end of the joint implant as on the distal end of the joint implant. In a certain example, the joint implant can have a detachable bone anchor on the proximal end and on the distal end. In other examples, the joint implant can include a fixed bone anchor or bone interface connector on both the proximal and distal ends. On the other hand, asymmetrical joint implants can have different components on the proximal and distal ends. In one example, an asymmetrical joint implant can have a detachable bone anchor on one end and a fixed bone anchor or bone interface connector on the other end. Any of the other components can also be different in the proximal end of the joint implant compared to the distal end, such as different joint implant elements, different tensioning elements, different types of bone interface connectors, different types of bone anchors, and so on.

It is to be understood that the examples of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular examples only and is not intended to be limiting.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various examples of the present invention can be referred to herein along with alternatives for the various components thereof. It is understood that such examples and alternatives are not to be construed as de facto equivalents of one another, but are to be considered as separate and autonomous representations of the present technology.

Furthermore, the described features, structures, or characteristics can be combined in any suitable manner in one or more examples. In the description, numerous specific details are provided, such as examples of lengths, widths, shapes, etc., to provide a thorough understanding of examples of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description. Reference throughout this specification to "one example" or "an example" means that a particular feature, structure, or characteristic described in connection with the example is included in at least one example of the present invention. Thus, appearances of the phrases "in one example" or "in an example" in various places throughout this specification are not necessarily all referring to the same example.

Although the disclosure may not expressly disclose that some examples or features described herein may be combined or interchanged with other examples or features described herein, this disclosure should be read to describe any such combinations that would be practicable by one of ordinary skill in the art no matter the specific examples that were described. Indeed, unless a certain combination of elements or functions not expressly disclosed would conflict with one another, such that the combination would render the resulting example inoperable or impracticable as would be apparent to those skilled in the art, this disclosure is meant to contemplate that any disclosed element or feature or function in any example described herein can be incorporated into any other example described herein (e.g., the elements or features or functions combined or interchanged with other elements or features or functions across examples) even though such combinations or interchange of elements or features or functions and resulting examples may not have been specifically or expressly disclosed and described. Indeed, the following examples are further illustrative of several embodiments of the present technology:

Example 1. A joint implant, comprising:
- a proximal joint implant element having a proximal curved interface surface;
- a distal joint implant element rotatably coupled to the proximal joint implant element, and having a distal curved interface surface facing the proximal curved interface surface, the distal joint implant element being supported such that the distal curved interface surface interfaces with the proximal curved interface surface through a range of motion of the proximal and distal joint implant elements relative to one another;
- a first filament segment extending from an attachment point on the proximal joint implant element to an attachment point on the distal joint implant element; and
- a second filament segment extending from an attachment point on the distal joint implant element to an attachment point on the proximal joint implant element,
- wherein the second filament segment crosses the first filament segment at a location between the proximal joint implant element and the distal joint implant element.

Example 2. The joint implant of example 1, wherein the proximal curved interface surface comprises a proximal contact portion adjacent to the at least one proximal groove and the distal curved interface surface comprises a distal contact portion adjacent to the at least one distal groove, wherein the proximal and distal contact portions are in direct contact.

Example 3. The joint implant of example 1-2, wherein the proximal joint implant element and the distal joint implant element are operable to roll relative to one another along their respective proximal and distal curved interface surfaces without slipping between the proximal and distal curved interface surfaces.

Example 4. The joint implant of any of examples 1-3, wherein the proximal curved interface surface comprises a circular profile and a radius of curvature.

Example 5. The joint implant of any of examples 1-4, wherein the distal curved interface surface comprises a circular profile and a radius of curvature.

Example 6. The joint implant of any of examples 1-5, wherein the proximal curved interface surface and the distal curved interface surface each comprise a circular profile having a radius of curvature, the radius of curvature of the proximal curved interface surface being different from the radius of curvature of the distal curved interface surface.

Example 7. The joint implant of any of examples 1-6, wherein the proximal and distal curved interface surfaces are congruent.

Example 8. The joint implant of any of examples 1-7, wherein at least one of the proximal curved interface surface or the distal curved interface surface comprises at least one of a circular profile, a non-circular profile, a profile having a linearly increasing radius through a range of motion of the joint implant, an elliptical profile, a parabolic profile, a hyperbolic profile, a piriform profile, or an oval profile.

Example 9. The joint implant of any of examples 1-8, wherein at least one of the proximal curved interface surface or the distal curved interface surface comprises a contact portion having a radius of curvature that increases from a minimum radius of curvature at a contact location when the joint implant is in an extended position to a maximum radius of curvature at the contact point when the joint implant is in a flexed position, to increase tension in at least one of the filament segments as the joint implant elements rotate relative to one another from the extended position to the flexed position.

Example 10. The joint implant of any of examples 1-9, wherein at least one of the proximal curved interface surface or the distal curved interface surface comprises a contact portion having a radius of curvature that decreases to decrease tension in at least one of the filament segments as the joint implant elements rotate relative to one another from an extended position to a flexed position.

Example 11. The joint implant of any of examples 1-10, wherein tension in the first and second filament segments remains constant when the proximal and distal joint implant elements rotate relative to each other.

Example 12. The joint implant of any of examples 1-11, wherein the proximal curved interface surface and the distal curved interface surface have a shape that allows the proximal joint implant element to roll against the distal curved interface surface with a ratio of rotation of the proximal joint implant element to rolling distance that is non-uniform throughout a range of motion of the joint implant.

Example 13. The joint implant of any of examples 1-112, wherein at least one of the first filament segment or the second filament segment comprises a ribbon.

Example 14. The joint implant of any of examples 1-13, wherein at least one of the first filament segment or the second filament segment comprises a cord.

Example 15. The joint implant of any of examples 1-14, wherein at least one of the first filament segment or the second filament segment comprises a braided polymeric cord.

Example 16. The joint implant of any of examples 1-15, wherein the first filament segment and the second filament segment are at least partially radiopaque Example 17. The joint implant of any of examples 1-16, further comprising a third filament segment extending from an attachment point on the proximal joint implant element, along the proximal curved interface surface, to an attachment point on the distal joint implant element, wherein the third filament segment is substantially parallel to the first filament segment such that the third filament segment crosses the second filament segment in the same direction as the first filament segment crosses the second filament segment, wherein the second filament segment is between the first and third filament segments.

Example 18. The joint implant of any of examples 1-17, further comprising a fourth filament segment extending from an attachment point on the distal joint implant element, along the distal curved interface surface, to an attachment point on the proximal joint implant element, wherein the fourth filament segment is substantially parallel to the second filament segment, wherein the second and fourth filament segments are both between the first and third filament segments.

Example 19. The joint implant of any of examples 1-18, wherein the first and second filament segments are members of a plurality of filament segments extending from attachment points on the proximal joint implant element to attachment points on the distal implant element, wherein the plurality of filament segments comprises a pair of outer filament segments nearest to sides of the joint implant that are substantially parallel, and wherein the plurality of filament segments also comprises at least one inner filament segment between the outer filament segments that crosses the outer filament segments at the location between the proximal joint implant element and the distal joint implant element.

Example 20. The joint implant of any of examples 1-19, wherein at least one of the proximal curved interface surface or the distal curved interface surface comprises one or more grooves configured to accommodate and receive therein at least one of the first filament segment or the second filament segment.

Example 21. The joint implant of any of examples 1-20, wherein the proximal curved interface surface comprises at least one proximal groove and the distal curved interface surface comprises at least one distal groove aligned with the at least one proximal groove to accommodate and receive therein at least one of the first filament segment or the second filament segment.

Example 22. The joint implant of any of examples 1-21, wherein the proximal curved interface surface comprises a proximal contact portion adjacent to the at least one proximal groove and the distal curved interface surface comprises a distal contact portion adjacent to the at least one distal groove, wherein the proximal and distal contact portions are in direct contact.

Example 23. The joint implant of any of examples 1-22, wherein the one or more grooves have a groove width that is greater than or equal to the width of the first filament segment or the second filament segment.

Example 24. The joint implant of any of examples 1-25, wherein the one or more grooves have a groove depth that is greater than or equal to 50% of the thickness of the first filament segment or the second filament segment.

Example 25. The joint implant of any of examples 1-24, wherein at least a portion of each of the proximal curved interface surface and the distal curved interface surface are in indirect contact with one with another, wherein at least one of the first or second filament segments separate the portion of the proximal curved interface surface from the portion of the distal curved interface surface.

Example 26. The joint implant of any of examples 1-25, wherein the proximal curved interface surface comprises a single proximal groove and raised areas on either side of the single proximal groove;

wherein the distal curved interface surface comprises a single distal groove and raised areas on either side of the single distal groove;
wherein the raised areas of the proximal curved interface surface and the distal curved interface surface are in direct contact; and
wherein the first and second filament segments are received and accommodated in the single proximal groove and the single distal groove.

Example 27. The joint implant of any of examples 1-26, wherein each filament is in direct contact with an adjacent filament.

Example 28. The joint implant of any of examples 1-27, wherein the attachment points are on the proximal and distal curved interface surfaces.

Example 29. The joint implant of any of examples 1-28, wherein the attachment point of the first filament segment on the proximal curved interface surface and the attachment point of the second filament segment on the proximal curved interface surface are located at angular positions on the proximal curved interface surface separated by an arc from about 45° to about 180°.

Example 30. The joint implant of any of examples 1-29, wherein the attachment point of the first filament segment on the distal curved interface surface and the attachment point of the second filament segment on the distal curved interface surface are located at angular positions on the distal curved interface surface separated by an arc from about 45° to about 180°.

Example 31. The joint implant of any of examples 1-30, wherein the attachment points are positioned to facilitate a range of motion of relative rotation of the proximal joint implant element and the distal joint implant element from about 30° to about 180°.

Example 32. The joint implant of any of examples 1-31, wherein the range of motion is from about 50° to about 110°.

Example 33. The joint implant of any of examples 1-32, wherein at least one of the proximal curved interface surface or the distal curved interface surface comprises a protrusion that prevents rotation of the proximal joint implant element with respect to the distal joint implant element upon the protrusion contacting the other of the proximal curved interface surface or the distal curved interface surface, wherein the protrusion restricts a range of motion of the relative rotation of the proximal joint implant element and the distal joint implant element.

Example 34. The joint implant of any of examples 1-33, wherein the range of motion is restricted to from about 30° to about 180°.

Example 35. The joint implant of any of examples 1-34, wherein the proximal curved interface surface and the distal curved interface surface comprise interlocking features operable to prevent lateral movement between the proximal and distal joint implant elements through the range of motion.

Example 36. The joint implant of any of examples 1-35, wherein the attachment points comprise holes in the proximal and distal joint implant elements and wherein the first and second filament segments are retained in the holes, respectively.

Example 37. The joint implant of any of examples 1-36, wherein the first and second filament segments are each part of one or more filaments having ends secured at the holes by one or more of knots, fused portions, or a combination thereof.

Example 38. The joint implant of any of examples 1-37, wherein the knots, fused portions, or combination thereof act as stopping points to define an end point of motion of the joint implant.

Example 39. The joint implant of any of examples 1-38, wherein at least one of the proximal or distal joint implant element has a solid central portion and the holes extend from one surface of the proximal or distal joint implant element through the solid central portion to another surface of the proximal or distal joint implant element.

Example 40. The joint implant of any of examples 1-39, wherein at least one of the proximal or distal joint implant element further comprises a slot having a bulged profile configured to retain a bone interface connector.

Example 41. The joint implant of any of examples 1-40, wherein the first and second filament segments are part of a single filament looped through the holes, the single filament extending between the proximal joint implant element and the distal joint implant element.

Example 42. The joint implant of any of examples 1-41, wherein at least one of the proximal joint implant element or the distal joint implant element comprises a hollow interior and wherein the holes lead from the curved interface surface into the hollow interior.

Example 43. The joint implant of any of examples 1-42, wherein at least one of the first or second filament segments is part of a filament that passes through one of the holes, through the hollow interior, and is secured at an opposite surface of the proximal or distal joint implant element.

Example 44. The joint implant of any of examples 1-43, wherein the proximal joint implant element further comprises a proximal base portion comprising a proximal base surface that is different from the proximal curved interface surface, and wherein the distal joint implant element further comprises a distal base portion comprising a distal base surface that is different from the distal curved interface surface.

Example 45. The joint implant of any of examples 1-44, wherein at least one of the attachment points is on at least one of the proximal base portion or the distal base portion.

Example 46. The joint implant of any of examples 1-45, wherein at least one of the proximal base portion or the distal base portion is modularly connectable to a bone anchor.

Example 47. The joint implant of any of examples 1-46, further comprising 1) a proximal clamping element attachable to the proximal base surface, wherein at least one of the first or second filament segments is part of a filament that is clampable between the proximal clamping element and the proximal base surface; or 2) a distal clamping element attachable to the distal base surface, wherein at least one of the first or second filament segments is part of a filament that is clampable between the distal clamping element and the distal base surface.

Example 48. A joint implant, comprising:
a proximal joint implant element having a proximal curved interface surface;
a distal joint implant element having a distal curved interface surface facing the proximal curved interface surface;
a first filament segment coupling the proximal joint implant element to the distal joint implant element; and
a second filament segment coupling the proximal joint implant element to the distal joint implant element;
wherein the proximal curved interface surface comprises at least one proximal groove and the distal curved interface surface comprises at least one distal groove aligned with the at least one proximal groove to accommodate and receive therein at least one of the first filament segment or the second filament segment;
wherein upon rotation of the proximal and distal joint implant elements relative to one another in a first direction, at least a portion of the first filament segment winds onto the proximal curved interface surface and unwinds from the distal curved interface surface, and at least a portion of the second filament segment winds onto the distal curved interface surface and unwinds from the proximal curved interface surface.

Example 49. The joint implant of any of examples 1-48, wherein upon rotation of the proximal and distal joint implant elements relative to one another in a second direction opposite from the first direction, at least a portion of the first filament winds onto the distal curved interface surface and unwinds from the proximal curved interface surface, and at least a portion of the second filament winds onto the proximal curved interface surface and unwinds from the distal curved interface surface.

Example 50. The joint implant of any of examples 1-49, wherein the first and second filament segments are members of a plurality of filament segments coupling the proximal joint implant element to the distal joint implant element, wherein the plurality of filament segments comprises a pair of outer filament segments nearest to sides of the joint implant that are substantially parallel, wherein the first filament segment is one of the outer filament segments, wherein the plurality of filament segments also comprises at least one inner filament segment between the outer filament segments, wherein the at least one inner filament segment includes the second filament segment.

Example 51. A joint implant, comprising:
a proximal joint implant element having a proximal curved interface surface;
a distal joint implant element having a distal curved interface surface facing the proximal curved interface surface;
a pair of substantially parallel outer filament segments coupling the proximal joint implant element to the distal joint implant element, wherein the outer filament segments are located near sides of the joint implant; and
at least one inner filament segment coupling the proximal joint implant element to the distal joint implant element, wherein the at least one inner filament segment is between the outer filament segments;
wherein the proximal curved interface surface comprises a pair of outer proximal grooves and an inner proximal groove for each inner filament segment, wherein the distal curved interface surface comprises a pair of outer distal grooves and an inner distal groove for each inner filament segment, wherein the proximal and distal grooves are aligned to accommodate and receive therein the outer filament segments and the at least one inner filament segment;
wherein upon rotation of the proximal and distal joint implant elements relative to one another in a first direction, at least a portion of the outer filament segments winds onto the proximal curved interface surface and unwinds from the distal curved interface surface, and at least a portion of the at least one inner filament segment winds onto the distal curved interface surface and unwinds from the proximal curved interface surface.

Example 52. A joint implant, comprising:
a proximal joint implant element having a proximal curved interface surface;

a distal joint implant element rotatably coupled to the proximal joint implant element, and having a distal curved interface surface facing the proximal curved interface surface, the distal joint implant element being supported such that the distal curved interface surface interfaces with the proximal curved interface surface through a range of motion of the proximal and distal joint implant elements relative to one another, wherein the proximal curved interface surface and the distal curved interface surface each comprise a circular profile having a radius of curvature, the radius of curvature of the proximal curved interface surface being different from the radius of curvature of the distal curved interface surface;

a first filament segment extending from an attachment point on the proximal joint implant element to an attachment point on the distal joint implant element; and a second filament segment extending from an attachment point on the distal joint implant element to an attachment point on the proximal joint implant element, wherein the second filament segment crosses the first filament segment at a location between the proximal joint implant element and the distal joint implant element.

Example 53. A joint implant, comprising:

a proximal joint implant element having a proximal curved interface surface;

a distal joint implant element rotatably coupled to the proximal joint implant element, and having a distal curved interface surface facing the proximal curved interface surface, the distal joint implant element being supported such that the distal curved interface surface interfaces with the proximal curved interface surface through a range of motion of the proximal and distal joint implant elements relative to one another;

a first filament segment extending from an attachment point on the proximal joint implant element to an attachment point on the distal joint implant element; and a second filament segment extending from an attachment point on the distal joint implant element to an attachment point on the proximal joint implant element, wherein the second filament segment crosses the first filament segment at a location between the proximal joint implant element and the distal joint implant element, wherein at least one of the proximal curved interface surface or the distal curved interface surface comprises a contact portion having a radius of curvature that either increases to increase tension or decreases to reduce tension in at least one of the filament segments as the joint implant elements rotate relative to one another between an extended position and a flexed position.

Example 54. A method of making a joint implant, comprising:

configuring a proximal joint implant element to comprise a proximal curved interface surface having at least one proximal groove;

configuring a distal joint implant element to comprise a distal curved interface surface having at least one distal groove;

rotatably coupling the proximal joint implant element to the distal joint implant element to cause the proximal and distal curved interface surfaces to face and interface with one another through a range of motion of the proximal and distal joint implant elements relative to one another, wherein the rotatably coupling of the proximal joint implant element to the distal joint implant element comprises attaching a first filament segment to the proximal joint implant element and to the distal joint implant element, and attaching a second filament segment to the proximal joint implant element and to the distal joint implant element, such that the first filament segment crosses the second filament segment at a location between the proximal and distal joint implant elements, wherein the at least one distal groove is aligned with the at least one proximal groove to accommodate and receive therein at least one of the first filament segment or the second filament segment.

Example 55. The method of example 54, further comprising configuring the attachment points of the first and second filament segments to facilitate rotation of the distal joint implant element relative to the proximal joint implant element through the range of motion.

Example 56. The method of any of examples 54-55, further comprising configuring at least a portion of the first filament segment to wind onto the proximal curved interface surface and unwind from the distal curved interface surface, and at least a portion of the second filament segment to wind onto the distal curved interface surface and unwind from the proximal curved interface surface upon rotation of the proximal and distal joint implant elements relative to one another in a first direction.

Example 57. The method of any of examples 54-56, wherein the first and second filament segments are members of a plurality of filament segments extending from the proximal joint implant element to the distal implant element, wherein the plurality of filament segments comprises a pair of outer filament segments nearest to sides of the joint implant that are substantially parallel, and wherein the plurality of filament segments also comprises at least one inner filament segment between the outer filament segments that crosses the outer filament segments at the location between the proximal joint implant element and the distal joint implant element.

Example 58. The method of any of examples 54-57, wherein the joint implant is a joint implant as in any of examples 1-53.

Example 59. A joint implant, comprising:

a proximal joint implant element having a proximal curved interface surface and a proximal base portion comprising a hollow interior;

a distal joint implant element rotatably coupled to the proximal joint implant element, and having a distal curved interface surface facing the proximal curved interface surface, the distal joint implant element being supported such that the distal curved interface surface interfaces with the proximal curved interface surface through a range of motion of the proximal and distal joint implant elements relative to one another, wherein the distal joint implant element further comprises a distal base portion comprising a hollow interior;

a first filament segment extending from an attachment point on the proximal joint implant element to an attachment point on the distal joint implant element;

a second filament segment extending from an attachment point on the distal joint implant element to an attachment point on the proximal joint implant element, wherein the second filament segment crosses the first filament segment at a location between the proximal joint implant element and the distal joint implant element and wherein the first filament segment and the second filament segment are portions of at least one tensioned filament that extends into at least one of the hollow interior of the proximal base portion or the hollow interior of the distal base portion; and at least one tensioning element positioned in at least one of the hollow interior of the proximal base portion or the hollow interior of the distal base portion applying a tension force to the at least one tensioned filament.

Example 60. The joint implant of any of examples 1-53 or 59, wherein the proximal joint implant element and the distal joint implant element are operable to roll relative to one another along their respective proximal and distal curved interface surfaces without slipping between the proximal and distal curved interface surfaces.

Example 61. The joint implant of any of examples 1-53 or 59-60, wherein at least one of the first filament segment or the second filament segment comprises a cord.

Example 62. The joint implant of any of examples 1-53 or 59-61, wherein the cord is a braided polymeric cord.

Example 63. The joint implant of any of examples 1-53 or 59-62, further comprising a third filament segment extending from an attachment point on the proximal joint implant element, along the proximal curved interface surface, to an attachment point on the distal joint implant element, wherein the third filament segment is substantially parallel to the first filament segment such that the third filament segment crosses the second filament segment in the same direction as the first filament segment crosses the second filament segment, wherein the second filament segment is between the first and third filament segments.

Example 64. The joint implant of any of examples 1-53 or 59-63, further comprising a fourth filament segment extending from an attachment point on the distal joint implant element, along the distal curved interface surface, to an attachment point on the proximal joint implant element, wherein the fourth filament segment is substantially parallel to the second filament segment, wherein the second and fourth filament segments are both between the first and third filament segments.

Example 65. The joint implant of any of examples 1-53 or 59-64, wherein the first and second filament segments are members of a plurality of filament segments extending from attachment points on the proximal joint implant element to attachment points on the distal implant element, wherein the plurality of filament segments comprises a pair of outer filament segments nearest to sides of the joint implant that are substantially parallel, and wherein the plurality of filament segments also comprises at least one inner filament segment between the outer filament segments that crosses the outer filament segments at a location between the proximal joint implant element and the distal joint implant element.

Example 66. The joint implant of any of examples 1-53 or 59-65, wherein the tension force is from zero to 100% of a rated working load of the at least one tensioned filament.

Example 67. The joint implant of any of examples 1-53 or 59-66, wherein the first filament segment and the second filament segment have a modulus of elasticity from 1 GPa to 200 GPa.

Example 68. The joint implant of any of examples 1-53 or 59-67, wherein the tension force is not sufficient to cause plastic deformation of the at least one tensioned filament.

Example 69. The joint implant of any of examples 1-53 or 59-68, wherein the tension force causes plastic deformation of the at least one tensioned filament to reduce creep deformation.

Example 70. The joint implant of any of examples 1-53 or 59-69, wherein at least one of the proximal curved interface surface or the distal curved interface surface comprises one or more grooves configured to accommodate and receive therein at least one of the first filament segment or the second filament segment.

Example 71. The joint implant of any of examples 1-53 or 59-70, wherein the one or more grooves have a groove width that is greater than or equal to the width of the first filament segment or the second filament segment.

Example 72. The joint implant of any of examples 1-53 or 59-71, wherein the one or more grooves have a groove depth that is greater than or equal to 50% of the thickness of the first filament segment or the second filament segment.

Example 73. The joint implant of any of examples 1-53 or 59-72, wherein the one or more grooves are present on both the proximal curved interface surface and the distal curved interface surface, wherein the grooves are aligned so that the first and second filament segments fit within the grooves on the proximal curved interface surface and in the grooves on the distal curved interface surface.

Example 74. The joint implant of any of examples 1-53 or 59-73, wherein the proximal curved interface surface and the distal curved interface surface each comprise:
  a single groove configured to accommodate and receive therein each of the first and second filament segments, and
  raised areas on either side of the single wide groove, wherein the raised areas of the proximal curved interface surface directly contact the raised areas of the distal curved interface surface.

Example 75. The joint implant of any of examples 1-53 or 59-74, wherein the attachment points comprise holes in the proximal and distal joint implant elements and wherein the first and second filament segments are retained in the holes, respectively.

Example 76. The joint implant of any of examples 1-53 or 59-75, wherein at least one of the attachment points is on at least one of the proximal base portion or the distal base portion.

Example 77. The joint implant of any of examples 1-53 or 59-76, wherein the tensioning element is wedged between the tensioned filament and an interior surface of the hollow interior such that the tensioning element presses on the tensioned filament in a direction transverse to a longitudinal axis of the tensioned filament.

Example 78. The joint implant of any of examples 1-53 or 59-77, wherein the tensioning element comprises a spool having the at least one tensioned filament wrapped at least partially around the spool.

Example 79. The joint implant of any of examples 1-53 or 59-78, wherein the tensioning element further comprises a lock configured to prevent the spool from rotating relative to the hollow interior to maintain the tension force.

Example 80. The joint implant of any of examples 1-53 or 59-79, wherein the tensioning element comprises a slot configured to accommodate the at least one tensioned filament through the slot, wherein the tensioning element is configured to rotate to apply tension to the at least one tensioned filament.

Example 81. The joint implant of any of examples 1-53 or 59-80, wherein the tensioning element comprises a ratcheting portion comprising unidirectional teeth configured to allow the tensioning element to rotate in one direction but not in another direction.

Example 82. The joint implant of any of examples 1-53 or 59-81, wherein at least one of the proximal base portion or the distal base portion comprises a gap leading into the hollow interior, wherein the at least one tensioned filament extends through the gap and into the hollow interior.

Example 83. The joint implant of any of examples 1-53 or 59-82, wherein at least one of the proximal base portion or the distal base portion further comprises notches formed in an edge of the gap, wherein the at least one tensioned filament extends through at least one of the notches and into the hollow interior.

Example 84. The joint implant of any of examples 1-53 or 59-83, wherein the tensioned filament is held between the at least one tensioning element and an interior surface of the hollow interior.

Example 85. The joint implant of any of examples 1-53 or 59-84, wherein at least one of the tensioning element or the interior surface of the hollow interior comprises grooves to accommodate the tensioned filament.

Example 86. The joint implant of any of examples 1-53 or 59-85, wherein the tensioning element, the interior surface of the hollow interior, or both comprise a textured surface to grip the tensioned filament.

Example 87. The joint implant of any of examples 1-53 or 59-86, wherein the tensioning element is sized to be pressed through the gap into the hollow interior.

Example 88. The joint implant of any of examples 1-53 or 59-87, wherein the tensioning element has a diameter larger than the gap, and wherein the proximal base portion or distal base portion having the gap is formed from a resilient material capable of elastically deforming to allow the tensioning element to be pressed through the gap and then returning to an original form to retain the tensioning element within the hollow interior.

Example 89. The joint implant of any of examples 1-53 or 59-88, wherein the tensioning element has a cylindrical shape with grooves from on an exterior surface thereof, wherein the interior surface of the hollow interior also comprises grooves aligned with the grooves of the tensioning element to accommodate the tensioned filament.

Example 90. The joint implant of any of examples 1-53 or 59-89, wherein the tensioning element and the interior surface each comprise from 3 to 6 grooves, wherein the at least one tensioned filament comprises 3 to 6 tensioned filaments that are retained in the grooves.

Example 91. The joint implant of any of examples 1-53 or 59-90, wherein the tensioning element splits into subparts configured to be fastened together with the at least one tensioned filament held between the subparts.

Example 92. The joint implant of any of examples 1-53 or 59-91, wherein the tensioning element comprises a shape memory alloy configured to change shape upon a phase change of the shape memory alloy to change a force applied to the at least one tensioned filament.

Example 93. The joint implant of any of examples 1-53 or 59-92, wherein the tensioning element has a C-shape with an uncompressed diameter that is greater than an internal diameter of at least one of the hollow interior of the proximal base portion or the hollow interior of the distal base portion.

Example 94. The joint implant of any of examples 1-53 or 59-93, wherein remaining void space in at least one of the hollow interior of the proximal joint implant element or the hollow interior of the distal joint implant element is filled with a melted biocompatible polymer that is subsequently solidified.

Example 95. A method of making a joint implant, comprising:
    configuring a proximal joint implant element to comprise a proximal curved interface surface and a proximal base portion comprising a hollow interior;
    configuring a distal joint implant element to comprise a distal curved interface surface and a distal base portion comprising a hollow interior;
    rotatably coupling the proximal joint implant element to the distal joint implant element to cause the proximal and distal curved interface surfaces to face and interface with one another through a range of motion of the proximal and distal joint implant elements relative to one another, wherein the rotatably coupling of the proximal joint implant element to the distal joint implant element comprises attaching a first filament segment to the proximal joint implant element and to the distal joint implant element, and attaching a second filament segment to the proximal joint implant element and to the distal joint implant element, such that the first filament segment crosses the second filament segment at a location between the proximal and distal joint implant elements, wherein the first filament segment and the second filament segment are portions of at least one tensioned filament that extends into at least one of the hollow interior of the proximal base portion or the hollow interior of the distal base portion; and
    configuring at least one tensioning element in at least one of the hollow interior of the proximal base portion or the hollow interior of the distal base portion such that the at least one tensioning element applies a tension force to the at least one tensioned filament.

Example 96. The method of any of examples 54-58 or 95, wherein the proximal base portion or the distal base portion comprises a gap leading into the hollow interior.

Example 97. The method of any of examples 54-58 or 95-96, wherein configuring the at least one tensioning element comprises pressing the at least one tensioning element through the gap into the hollow interior.

Example 98. The method of any of examples 54-58 or 95-97, further comprising wrapping the at least one tensioned filament around the at least one tensioning element before pressing the at least one tensioning element through the gap.

Example 99. The method of any of examples 54-58 or 95-98, further comprising positioning the at least one tensioned filament across the gap before pressing the at least one tensioning element through the gap, wherein pressing the at least one tensioning element through the gap simultaneously wraps the at least one tensioned filament around the at least one tensioning element and applies tension to the at least one tensioned filament.

Example 100. The method of any of examples 54-58 or 95-99, wherein the at least one tensioning element comprises a proximal tensioning element and a distal tensioning element, wherein the at least one tensioned filament comprises a first tensioned filament comprising the first filament segment and a second tensioned filament comprising the second filament segment, wherein the method further comprises:
    wrapping the first and second tensioned filaments around the proximal tensioning element;
    pressing the proximal tensioning element through the gap into the hollow interior of the proximal joint implant element to hole the first and second tensioned filaments between the proximal tensioning element and the interior surface of the hollow interior of the proximal joint implant element;

wrapping free ends of the first and second tensioned filaments around the proximate joint implant element and the distal joint implant element in opposite directions such that the first and second tensioned filaments cross at a location between the proximate joint implant element and the distal joint implant element;

positioning the free ends of the first and second tensioned filaments across the gap of the distal joint implant element;

pressing the distal tensioning element through the gap into the hollow interior of the distal joint implant element to simultaneously wrap the first and second tensioned filaments around the distal tensioning element and apply tension to the first and second tensioned filaments.

Example 101. The method of any of examples 54-58 or 95-100, further comprising configuring a third tensioned filament parallel to the first tensioned filament and configuring a fourth tensioned filament parallel to the second tensioned filament, wherein the first and third tensioned filaments are outer filaments near sides of the joint implant and wherein the second and fourth tensioned filaments are inner filaments between the outer filaments.

Example 102. The method of any of examples 54-58 or 95-101, wherein the at least one tensioning element comprises a proximal tensioning element and a distal tensioning element, wherein the at least one tensioned filament comprises a first tensioned filament comprising the first filament segment and a second tensioned filament comprising the second filament segment, wherein the method further comprises:

positioning a portion of the first and second tensioned filaments across the gap of the proximal joint implant element;

wrapping free ends of the first and second tensioned filaments around the proximate joint implant element and the distal joint implant element in opposite directions such that the first and second tensioned filaments cross at a location between the proximate joint implant element and the distal joint implant element;

positioning another portion of the first and second tensioned filaments across the gap of the distal joint implant element;

pressing the proximal tensioning element through the gap into the hollow interior of the proximal joint implant element to simultaneously wrap the first and second tensioned filaments around the distal tensioning element and apply tension to the first and second tensioned filaments; and pressing the distal tensioning element through the gap into the hollow interior of the distal joint implant element to simultaneously wrap the first and second tensioned filaments around the distal tensioning element and apply tension to the first and second tensioned filaments.

Example 103. A joint implant, comprising:
a proximal joint implant element having a proximal curved interface surface and a proximal base portion;
a distal joint implant element rotatably coupled to the proximal joint implant element, and having a distal curved interface surface facing the proximal curved interface surface, the distal joint implant element being supported such that the distal curved interface surface interfaces with the proximal curved interface surface through a range of motion of the proximal and distal joint implant elements relative to one another, wherein the distal joint implant element further comprises a distal base portion;
a first filament segment extending from an attachment point on the proximal joint implant element to an attachment point on the distal joint implant element;
a second filament segment extending from an attachment point on the distal joint implant element to an attachment point on the proximal joint implant element, wherein the second filament segment crosses the first filament segment at a location between the proximal joint implant element and the distal joint implant element;
a proximal bone interface connector connected to the proximal base portion; and
a distal bone interface connector connected to the distal base portion.

Example 104. The joint implant of any of examples 1-53 or 59-94 or 103, wherein the proximal joint implant element and the distal joint implant element are operable to roll relative to one another along their respective proximal and distal curved interface surfaces without slipping between the proximal and distal curved interface surfaces.

Example 105. The joint implant of any of examples 1-53 or 59-94 or 103-104, wherein at least one of the first filament segment or the second filament segment comprises a cord.

Example 106. The joint implant of any of examples 1-53 or 59-94 or 103-105, wherein the cord is a braided polymeric cord.

Example 107. The joint implant of any of examples 1-53 or 59-94 or 103-106, further comprising a third filament segment extending from an attachment point on the proximal joint implant element, along the proximal curved interface surface, to an attachment point on the distal joint implant element, wherein the third filament segment is substantially parallel to the first filament segment such that the third filament segment crosses the second filament segment in the same direction as the first filament segment crosses the second filament segment, wherein the second filament segment is between the first and third filament segments.

Example 108. The joint implant of any of examples 1-53 or 59-94 or 103-107, further comprising a fourth filament segment extending from an attachment point on the distal joint implant element, along the distal curved interface surface, to an attachment point on the proximal joint implant element, wherein the fourth filament segment is substantially parallel to the second filament segment, wherein the second and fourth filament segments are both between the first and third filament segments.

Example 109. The joint implant of any of examples 1-53 or 59-94 or 103-108, wherein the first and second filament segments are members of a plurality of filament segments extending from attachment points on the proximal joint implant element to attachment points on the distal implant element, wherein the plurality of filament segments comprises a pair of outer filament segments nearest to the sides of the joint implant that are substantially parallel, and wherein the plurality of filament segments also comprises at least one inner filament segment between the outer filament segments that crosses the outer filament segments at a location between the proximal joint implant element and the distal joint implant element.

Example 110. The joint implant of any of examples 1-53 or 59-94 or 103-109, wherein the attachment points comprise holes in the proximal and distal joint implant elements and wherein the first and second filament segments are retained in the holes, respectively.

Example 111. The joint implant of any of examples 1-53 or 59-94 or 103-110, wherein at least one of the attachment points is on at least one of the proximal base portion or the distal base portion.

Example 112. The joint implant of any of examples 1-53 or 59-94 or 103-111, wherein the proximal bone interface connector is integrally formed as a part of the proximal base portion or wherein the distal bone interface connector is integrally formed as a part of the distal base portion.

Example 113. The joint implant of any of examples 1-53 or 59-94 or 103-112, wherein the proximal bone interface connector is detachable from the proximal base portion or wherein the distal bone interface connector is detachable from the distal base portion.

Example 114. The joint implant of any of examples 1-53 or 59-94 or 103-113, wherein at least one of the proximal bone interface connector or the distal bone interface connector comprises a direct bone interface surface to be retained in direct contact with a bone of a subject.

Example 115. The joint implant of any of examples 1-53 or 59-94 or 103-114, wherein the direct bone interface surface comprises a bulged profile adapted to be retained in a slot formed in the bone.

Example 116. The joint implant of any of examples 1-53 or 59-94 or 103-115, further comprising a proximal anchor adapted to be fixed in a bone of a subject, wherein the proximal bone interface connector is attachable to the proximal anchor, or further comprising a distal anchor adapted to be fixed in a bone of a subject, wherein the distal bone interface connector is attachable to the distal anchor.

Example 117. The joint implant of any of examples 1-53 or 59-94 or 103-116, wherein the proximal or distal bone interface connector comprises a bulged profile adapted to be retained in a slot of the proximal or distal anchor.

Example 118. The joint implant of any of examples 1-53 or 59-94 or 103-117, wherein at least one of the proximal or distal anchor comprises exterior threads adapted to be screwed into the bone.

Example 119. The joint implant of any of examples 1-53 or 59-94 or 103-118, wherein at least one of the proximal or distal anchor has a profile adapted to be press-fit into the bone.

Example 120. The joint implant of any of examples 1-53 or 59-94 or 103-119, wherein at least one of the proximal or distal anchor has a narrow insertion end adapted to be inserted longitudinally into the bone.

Example 121. The joint implant of any of examples 1-53 or 59-94 or 103-120, wherein at least one of the proximal or distal anchor is adapted to extend along a transition from a diaphysis to an epiphysis of a bone.

Example 122. The joint implant of any of examples 1-53 or 59-94 or 103-121, wherein at least one of the proximal or distal anchor comprises a transverse hole adapted to receive a transverse screw or pin to lock the anchor in the bone.

Example 123. The joint implant of any of examples 1-53 or 59-94 or 103-122, wherein at least one of the proximal or distal anchors comprises an osseointegration coating, an osseointegration surface texture, a sintered surface, barbs, flanges, protrusions for bone in-growth, recesses for bone in-growth, an open lattice configuration, or a combination thereof.

Example 124. The joint implant of any of examples 1-53 or 59-94 or 103-123, wherein at least one of the proximal or distal anchor is adapted to extend into a diaphysis of a bone.

Example 125. The joint implant of any of examples 1-53 or 59-94 or 103-124, wherein at least one of the proximal or distal anchor is a longitudinal bone anchor having external threads configured to be screwed into a bone longitudinally, and further comprises an internal threaded recess configured to accept a screw to attach the proximal or distal joint implant element to the longitudinal bone anchor.

Example 126. The joint implant of any of examples 1-53 or 59-94 or 103-125, wherein at least one of the proximal or distal bone interface connector has a narrow insertion end adapted to be inserted longitudinally into the bone.

Example 127. The joint implant of any of examples 1-53 or 59-94 or 103-126, wherein at least one of the proximal or distal bone interface connector is adapted to extend along a transition from a diaphysis to an epiphysis of a bone.

Example 128. The joint implant of any of examples 1-53 or 59-94 or 103-127, wherein at least one of the proximal or distal bone interface connector is adapted to extend into a diaphysis of a bone.

Example 129. The joint implant of any of examples 1-53 or 59-94 or 103-128, wherein at least one of the proximal or distal bone interface connector comprises a transverse hole adapted to receive a transverse screw or pin to lock the anchor in the bone.

Example 130. The joint implant of any of examples 1-53 or 59-94 or 103-129, wherein at least one of the proximal or distal bone interface connector further comprises one or more additional transverse holes oriented at different angles to receive a transverse screw or pin at the different angles.

Example 131. The joint implant of any of examples 1-53 or 59-94 or 103-130, wherein at least one of the proximal or distal bone interface connectors comprises an osseointegration coating, an osseointegration surface texture, a sintered surface, barbs, flanges, protrusions for bone in-growth, recesses for bone in-growth, an open lattice configuration, or a combination thereof.

Example 132. The joint implant of any of examples 1-53 or 59-94 or 103-131, wherein the proximal base portion and the distal base portion each comprises a hollow interior, further comprising a proximal tensioning element in the hollow interior of the proximal base portion and a distal tensioning element in the hollow interior of the distal base portion, wherein the proximal bone interface connector is integrally formed with the proximal tensioning element, and wherein the distal bone interface connector is integrally formed with the distal tensioning element.

Example 133. The joint implant of any of examples 1-53 or 59-94 or 103-132, wherein at least one of the proximal or distal bone interface connector comprises a push-on locking feature comprising unidirectional teeth configured to lock with complementary teeth on another component.

Example 134. The joint implant of any of examples 1-53 or 59-94 or 103-133, wherein at least one of the proximal or distal bone interface connector comprises a non-circular profile.

Example 135. A joint replacement system, comprising:
a joint implant comprising:
   a proximal joint implant element having a proximal curved interface surface,
   a distal joint implant element rotatably coupled to the proximal joint implant element, and having a distal curved interface surface facing the proximal curved interface surface, the distal joint implant element being supported such that the distal curved interface surface interfaces with the proximal curved interface surface through a range of motion of the proximal and distal joint implant elements relative to one another,
a first filament segment extending from an attachment point on the proximal joint implant element, along the proximal curved interface surface, to an attachment point on the distal joint implant element, and
a second filament segment extending from an attachment point on the distal joint implant element, along the distal curved interface surface, to an attachment point on the proximal joint implant element,
wherein the second filament segment crosses the first filament segment at a location between the proximal joint implant element and the distal joint implant element;
a proximal bone anchor operable with the proximal joint implant element and configured to connect to a first bone; and
a distal bone anchor operable with the distal joint implant element and configured to connect to a second bone.

Example 136. The system of example 135, wherein the proximal joint implant element further comprises a proximal base portion, wherein the distal joint implant element further comprises a distal base portion, wherein the system further comprises a proximal bone interface connector connectable to the proximal base portion and a distal bone interface connector connectable to the distal base portion, wherein the proximal and distal bone interface connectors are also connectable to the proximal and distal bone anchors.

Example 137. The system of any of examples 135-136, wherein the proximal joint implant element further comprises a proximal base portion comprising a proximal bone interface connector integrally formed as a part of the proximal base portion, wherein the distal joint implant element further comprises a distal base portion comprising a distal bone interface connector integrally formed as a part of the distal base portion, wherein the proximal and distal bone interface connectors are connectable to the proximal and distal bone anchors.

Example 138. The system of any of examples 135-137, wherein at least one of the proximal or distal bone anchor comprises a push-on locking feature comprising unidirectional teeth configured to lock with complementary teeth on another component.

Example 139. The system of any of examples 135-138, wherein at least one of the proximal or distal bone anchor comprises a non-circular profile.

Example 140. The system of any of examples 135-139, wherein the joint implant is a joint implant of any of examples 1-53 or 59-94 or 103-134.

Example 141. A method of replacing a joint, comprising:
preparing a first bone to receive a proximal bone anchor;
preparing a second bone to receive a distal bone anchor;
securing the proximal bone anchor in the first bone;
securing the distal bone anchor in the second bone;
connecting the proximal bone anchor to the distal bone anchor using a joint implant, the joint implant comprising:
a proximal joint implant element connected to the proximal bone anchor, wherein the proximal joint implant element comprises a proximal curved interface surface,
a distal joint implant element connected to the distal bone anchor, wherein the distal joint implant element is rotatably coupled to the proximal joint implant element, and having a distal curved interface surface facing the proximal curved interface surface, the distal joint implant element being supported such that the distal curved interface surface interfaces with the proximal curved interface surface through a range of motion of the proximal and distal joint implant elements relative to one another,
a first filament segment extending from an attachment point on the proximal joint implant element, along the proximal curved interface surface, to an attachment point on the distal joint implant element, and
a second filament segment extending from an attachment point on the distal joint implant element, along the distal curved interface surface, to an attachment point on the proximal joint implant element,
wherein the second filament segment crosses the first filament segment at a location between the proximal joint implant element and the distal joint implant element.

Example 142. The method of example 141, wherein the proximal joint implant element further comprises a proximal base portion, wherein the distal joint implant element further comprises a distal base portion, wherein the joint implant further comprises a proximal bone interface connector connected to the proximal base portion and a distal bone interface connector connected to the distal base portion, wherein the proximal joint implant element is connected to the proximal bone anchor through the proximal bone interface connector, and wherein the distal joint implant element is connected to the distal bone anchor through the distal bone interface connector.

Example 143. The method of any of examples 141-142, wherein the proximal bone interface connector is integrally formed as a part of the proximal base portion, and wherein the distal bone interface connector is integrally formed as a part of the distal base portion.

Example 144. The method of any of examples 141-143, further comprising using a jig to stabilize the first bone or the second bone.

Example 145. The method of any of examples 141-144, wherein preparing the first bone or the second bone comprises forming a slot in the bone, wherein the slot extends fully or partially across a width of the bone, wherein the slot extends fully or partially through a height of the bone, wherein the slot opens at a top surface of the bone, at a bottom surface of the bone, at one or both side surfaces of the bone, or any combination thereof, or wherein the slot does not open at a top surface, bottom surface, or side surface of the bone.

Example 146. The method of any of examples 141-145, wherein the joint implant is a joint implant of any of examples 1-53 or 59-94 or 103-134.

Example 147. A joint implant, comprising:
a proximal joint implant element having a proximal curved interface surface, wherein the proximal curved interface surface comprises a plurality of proximal registration features;
a distal joint implant element rotatably coupled to the proximal joint implant element, and having a distal curved interface surface facing the proximal curved interface surface, wherein the distal curved interface surface comprises a plurality of distal registration features that are complementary to the proximal registration features such that the distal registration features and the proximal registration features interface together to maintain registration between the proximal and distal joint implant elements through a range of motion of the proximal and distal joint implant elements relative to one another; and a joint implant element connector comprising a proximal pin supporting the proximal joint implant element and a distal pin supporting the distal joint implant element such that the distal curved interface surface interfaces with the proximal curved interface surface through the range of motion of the proximal and distal joint implant elements relative to one another;

wherein at least one of the proximal curved interface surface or the distal curved interface surface comprises a protrusion that prevents rotation of the proximal joint implant element with respect to the distal joint implant element upon the protrusion contacting the other of the proximal curved interface surface or the distal curved interface surface, such that the protrusion restricts a range of motion of the relative rotation of the proximal joint implant element and the distal joint implant element.

Example 148. The joint implant of any of examples 1-53 or 59-94 or 103-133 or 147, wherein the proximal registration features, the distal registration features, or both are shaped as gear teeth.

Example 149. The joint implant of any of examples 1-53 or 59-94 or 103-133 or 147-148, wherein the gear teeth have an involute profile, a spur profile, a helical profile, a double helical profile, a sinusoidal profile, or a combination thereof.

Example 150. The joint implant of any of examples 1-53 or 59-94 or 103-133 or 147-149, wherein the registration features have a height-to-period ratio from about 1:20 to about 2:1.

Example 151. The joint implant of any of examples 1-53 or 59-94 or 103-133 or 147-150, wherein the proximal registration features are located at a different radial distance from a rotational axis of the proximal joint implant element than a radial distance of the distal registration features from a rotational axis of the distal joint implant element.

Example 152. The joint implant of any of examples 1-53 or 59-94 or 103-133 or 147-151, wherein the protrusion protrudes radially farther than a tip of at least one of the proximal registration features or the distal registration features.

Example 153. The joint implant of any of examples 1-53 or 59-94 or 103-133 or 147-152, the protrusion defines a first end point of the range of motion and wherein the at least one of the proximal curved interface surface or the distal curved interface surface further comprises a second protrusion that defines a second end point of the range of motion.

Example 154. The joint implant of any of examples 1-53 or 59-94 or 103-133 or 147-153, wherein the range of motion is from about 50° to about 180°.

Example 155. The joint implant of any of examples 1-53 or 59-94 or 103-133 or 147-154, wherein the proximal pin and the distal pin have different diameters.

Example 156. The joint implant of any of examples 1-53 or 59-94 or 103-133 or 147-155, wherein the joint implant element connector further comprises a connector base, wherein the proximal pin extends from the connector base along a rotational axis of the proximal joint implant element, and wherein the distal pin extends from the connector base along a rotational axis of the distal joint implant element.

Example 157. The joint implant of any of examples 1-53 or 59-94 or 103-133 or 147-156, wherein the connector base is positioned on a first side of the proximal joint implant element and the distal joint implant element.

Example 158. The joint implant of any of examples 1-53 or 59-94 or 103-133 or 147-157, further comprising a connector cap attached to the proximal pin and the distal pin on a second side of the proximal joint implant element and the distal joint implant element.

Example 159. The joint implant of any of examples 1-53 or 59-94 or 103-133 or 147-158, wherein the connector base is positioned in slots formed in central portions of the proximal joint implant element and the distal joint implant element.

Example 160. A joint implant, comprising:
a proximal joint implant element having a proximal curved interface surface and a proximal base portion, wherein the proximal curved interface surface comprises a plurality of proximal registration features;
a distal joint implant element rotatably coupled to the proximal joint implant element, and having a distal curved interface surface facing the proximal curved interface surface, wherein the distal curved interface surface comprises a plurality of distal registration features that are complementary to the proximal registration features such that the distal registration features and the proximal registration features interface together to maintain registration between the proximal and distal joint implant elements through a range of motion of the proximal and distal joint implant elements relative to one another, wherein the distal joint implant element further comprises a distal base portion;
a proximal bone interface connector connected to the proximal base portion; and
a distal bone interface connector connected to the distal base portion.

Example 161. The joint implant of any of examples 1-53 or 59-94 or 103-133 or 147-160, further comprising a joint implant element connector comprising a proximal pin supporting the proximal joint implant element and a distal pin supporting the distal joint implant element such that the distal curved interface surface interfaces with the proximal curved interface surface through the range of motion of the proximal and distal joint implant elements relative to one another.

Example 162. The joint implant of any of examples 1-53 or 59-94 or 103-133 or 147-161, further comprising:
a first filament segment extending from an attachment point on the proximal joint implant element, across a second area of the proximal curved interface surface without overlapping the proximal registration features, to an attachment point on the distal joint implant element; and
a second filament segment extending from an attachment point on the distal joint implant element, across a second area of the distal curved interface surface without overlapping the distal registration features, to an attachment point on the proximal joint implant element, wherein the second filament segment crosses the first filament segment at a location between the proximal joint implant element and the distal joint implant element.

Example 163. The joint implant of any of examples 1-53 or 59-94 or 103-133 or 147-162, wherein the proximal bone interface connector is integrally formed as a part of the proximal base portion or wherein the distal bone interface connector is integrally formed as a part of the distal base portion.

Example 164. The joint implant of any of examples 1-53 or 59-94 or 103-133 or 147-163, wherein the proximal bone interface connector is detachable from the proximal base portion or wherein the distal bone interface connector is detachable from the distal base portion.

Example 165. The joint implant of any of examples 1-53 or 59-94 or 103-133 or 147-164, wherein at least one of the proximal bone interface connector or the distal bone interface connector comprises a direct bone interface surface to be retained in direct contact with a bone of a subject.

Example 166. The joint implant of any of examples 1-53 or 59-94 or 103-133 or 147-165, wherein the direct bone interface surface comprises a bulged profile adapted to be retained in a slot formed in the bone.

Example 167. The joint implant of any of examples 1-53 or 59-94 or 103-133 or 147-166, further comprising a proximal anchor adapted to be fixed in a bone of a subject, wherein the proximal bone interface connector is attachable to the proximal anchor, or further comprising a distal anchor adapted to be fixed in a bone of a subject, wherein the distal bone interface connector is attachable to the distal anchor.

Example 168. The joint implant of any of examples 1-53 or 59-94 or 103-133 or 147-167, wherein the proximal or distal bone interface connector comprises a bulged profile adapted to be retained in a slot of the proximal or distal anchor.

Example 169. The joint implant of any of examples 1-53 or 59-94 or 103-133 or 147-168, wherein at least one of the proximal or distal anchor comprises exterior threads adapted to be screwed into the bone.

Example 170. The joint implant of any of examples 1-53 or 59-94 or 103-133 or 147-169, wherein at least one of the proximal or distal anchor has a profile adapted to be press-fit into the bone.

Example 171. The joint implant of any of examples 1-53 or 59-94 or 103-133 or 147-170, wherein at least one of the proximal or distal anchor has a narrow insertion end adapted to be inserted longitudinally into the bone.

Example 172. The joint implant of any of examples 1-53 or 59-94 or 103-133 or 147-171, wherein at least one of the proximal or distal anchor is adapted to extend along a transition from a diaphysis to an epiphysis of a bone.

Example 173. The joint implant of any of examples 1-53 or 59-94 or 103-133 or 147-172, wherein at least one of the proximal or distal anchor comprises a transverse hole adapted to receive a transverse screw or pin to lock the anchor in the bone.

Example 174. The joint implant of any of examples 1-53 or 59-94 or 103-133 or 147-173, wherein at least one of the proximal or distal anchors comprises an osseointegration coating, an osseointegration surface texture, a sintered surface, barbs, flanges, protrusions for bone in-growth, recesses for bone in-growth, an open lattice configuration, or a combination thereof.

Example 175. The joint implant of any of examples 1-53 or 59-94 or 103-133 or 147-174, wherein at least one of the proximal or distal anchor is adapted to extend into a diaphysis of a bone.

Example 176. The joint implant of any of examples 1-53 or 59-94 or 103-133 or 147-175, wherein at least one of the proximal or distal anchor is a longitudinal bone anchor having external threads configured to be screwed into a bone longitudinally, and further comprises an internal threaded recess configured to accept a screw to attach the proximal or distal joint implant element to the longitudinal bone anchor.

Example 177. The joint implant of any of examples 1-53 or 59-94 or 103-133 or 147-176, wherein at least one of the proximal or distal bone interface connector has a narrow insertion end adapted to be inserted longitudinally into the bone.

Example 178. The joint implant of any of examples 1-53 or 59-94 or 103-133 or 147-177, wherein at least one of the proximal or distal bone interface connector is adapted to extend along a transition from a diaphysis to an epiphysis of a bone.

Example 179. The joint implant of any of examples 1-53 or 59-94 or 103-133 or 147-178, wherein at least one of the proximal or distal bone interface connector is adapted to extend into a diaphysis of a bone.

Example 180. The joint implant of any of examples 1-53 or 59-94 or 103-133 or 147-179, wherein at least one of the proximal or distal bone interface connector comprises a transverse hole adapted to receive a transverse screw or pin to lock the anchor in the bone.

Example 181. The joint implant of any of examples 1-53 or 59-94 or 103-133 or 147-180, wherein at least one of the proximal or distal bone interface connector further comprises one or more additional transverse holes oriented at different angles to receive a transverse screw or pin at the different angles.

Example 182. The joint implant of any of examples 1-53 or 59-94 or 103-133 or 147-181, wherein at least one of the proximal or distal bone interface connectors comprises an osseointegration coating, an osseointegration surface texture, a sintered surface, barbs, flanges, protrusions for bone in-growth, recesses for bone in-growth, an open lattice configuration, or a combination thereof.

Example 183. The joint implant of any of examples 1-53 or 59-94 or 103-133 or 147-182, wherein at least one of the proximal base portion or the distal base portion comprises a hollow interior and a tensioning element in the hollow interior, wherein at least one of the proximal bone interface connector or the distal bone interface connector is integrally formed with the tensioning element.

Example 184. The joint implant of any of examples 1-53 or 59-94 or 103-133 or 147-183, wherein at least one of the proximal or distal bone interface connector comprises a push-on locking feature comprising unidirectional teeth configured to lock with complementary teeth on another component.

Example 185. The joint implant of any of examples 1-53 or 59-94 or 103-133 or 147-184, wherein at least one of the proximal or distal bone interface connector comprises a non-circular profile Example 186. A joint implant, comprising:
- a proximal joint implant element having a proximal curved interface surface, wherein the proximal curved interface surface comprises a first area having a plurality of proximal registration features;
- a distal joint implant element rotatably coupled to the proximal joint implant element, and having a distal curved interface surface facing the proximal curved interface surface, the distal joint implant element being supported such that the distal curved interface surface interfaces with the proximal curved interface surface through a range of motion of the proximal and distal joint implant elements relative to one another, wherein the distal curved interface surface comprises a first area having a plurality of distal registration features that are complementary to the proximal registration features such that the distal registration features and the proximal registration features interface together to maintain registration between the proximal and distal joint implant elements through the range of motion;
- a first filament segment extending from an attachment point on the proximal joint implant element, across a second area of the proximal curved interface surface without overlapping the proximal registration features, to an attachment point on the distal joint implant element; and
a second filament segment extending from an attachment point on the distal joint implant element, across a second area of the distal curved interface surface without overlapping the distal registration features, to an attachment point on the proximal joint implant element, wherein the second filament segment crosses the first filament segment at a location between the proximal joint implant element and the distal joint implant element.

Example 187. The joint implant of any of examples 1-53 or 59-94 or 103-133 or 147-186, wherein the proximal registration features, the distal registration features, or both are shaped as gear teeth.

Example 188. The joint implant of any of examples 1-53 or 59-94 or 103-133 or 147-187, wherein the gear teeth have an involute profile, a spur profile, a helical profile, a double helical profile, a sinusoidal profile, or a combination thereof.

Example 189. The joint implant of any of examples 1-53 or 59-94 or 103-133 or 147-188, wherein the registration features have a height-to-period ratio from about 1:20 to about 2:1.

Example 190. The joint implant of any of examples 1-53 or 59-94 or 103-133 or 147-189, wherein the proximal registration features are located at a different radial distance from a rotational axis of the proximal joint implant element than a radial distance of the distal registration features from a rotational axis of the distal joint implant element.

Example 191. The joint implant of any of examples 1-53 or 59-94 or 103-133 or 147-190, wherein at least one of the proximal curved interface surface or the distal curved interface surface comprises a protrusion that prevents rotation of the proximal joint implant element with respect to the distal joint implant element upon the protrusion contacting the other of the proximal curved interface surface or the distal curved interface surface, wherein the protrusion restricts a range of motion of the relative rotation of the proximal joint implant element and the distal joint implant element, wherein the protrusion protrudes radially farther than a tip of at least one of the proximal registration features or the distal registration features.

Example 192. The joint implant of any of examples 1-53 or 59-94 or 103-133 or 147-191, wherein the protrusion defines a first end point of the range of motion and wherein the at least one of the proximal curved interface surface or the distal curved interface surface further comprises a second protrusion that defines a second end point of the range of motion.

Example 193. The joint implant of any of examples 1-53 or 59-94 or 103-133 or 147-192, wherein the range of motion is from about 50° to about 180°.

Example 194. The joint implant of any of examples 1-53 or 59-94 or 103-133 or 147-193, wherein the proximal curved interface surface comprises at least one proximal groove and the distal curved interface surface comprises at least one distal groove aligned with the at least one proximal groove to accommodate and receive therein at least one of the first filament segment or the second filament segment.

Example 195. The joint implant of any of examples 1-53 or 59-94 or 103-133 or 147-194, wherein at least one of the first filament segment or the second filament segment comprises a ribbon.

Example 196. The joint implant of any of examples 1-53 or 59-94 or 103-133 or 147-195, wherein at least one of the first filament segment or the second filament segment comprises a cord.

Example 197. The joint implant of any of examples 1-53 or 59-94 or 103-133 or 147-196, wherein at least one of the first filament segment or the second filament segment comprises a braided polymeric cord.

Example 198. The joint implant of any of examples 1-53 or 59-94 or 103-133 or 147-197, wherein the first filament segment and the second filament segment are at least partially radiopaque.

Example 199. The joint implant of any of examples 1-53 or 59-94 or 103-133 or 147-198, wherein at least one of the proximal curved interface surface or the distal curved interface surface has a cylindrical profile and wherein at least one of the proximal registration features or the distal registration features are located on an outer surface of the cylindrical profile.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention.

The term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the present technology have been described in the context of those embodiments, other embodiments can also exhibit such advantages, and not all embodiments need necessarily exhibit such advantages to fall within the scope of the technology. Accordingly, the disclosure and associated present technology can encompass other embodiments not expressly shown or described herein.

Moreover, unless the word "or" is expressly limited to mean only a single item exclusive from other items in reference to a list of two or more items, then the use of "or" in such a list is to be interpreted as including (a) any single item in the list, (b) all of the items in the list, or (c) any combination of the items in the list. In other words, the use of "or" in this disclosure should be understood to mean non-exclusive "or" (i.e., "and/or") unless otherwise indicated herein.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described present technology.

What is claimed is:
1. An interphalangeal joint implant, comprising:
a proximal joint implant element having a proximal curved interface surface and a proximal base portion, wherein the proximal curved interface surface comprises a plurality of proximal registration features;

a distal joint implant element rotatably coupled to the proximal joint implant element, the distal joint implant element having a distal curved interface surface facing the proximal curved interface surface and having a distal base portion, wherein the distal curved interface surface comprises a plurality of distal registration features that are complementary to the proximal registration features such that the distal registration features and the proximal registration features directly interface with one another to maintain registration between the proximal and distal joint implant elements through a range of rolling motion of the proximal and distal joint implant elements relative to one another;

a proximal bone interface connector connected to the proximal base portion, the proximal bone interface connector sized and configured to be implanted into a phalanx bone;

a distal bone interface connector connected to the distal base portion, the distal bone interface connector sized and configured to be implanted into a phalanx bone; and a joint implant element connector comprising a connector base positioned in slots formed in central portions of the proximal joint implant element and the distal joint implant element, a proximal pin supporting the proximal joint implant element, and a distal pin supporting the distal joint implant element such that the distal curved interface surface interfaces with the proximal curved interface surface through the range of motion of the proximal and distal joint implant elements relative to one another;

wherein at least one of the proximal curved interface surface or the distal curved interface surface comprises a protrusion that prevents rotation of the proximal joint implant element with respect to the distal joint implant element upon the protrusion contacting the other of the proximal curved interface surface or the distal curved interface surface, such that the protrusion restricts a range of motion of the relative rotation of the proximal joint implant element and the distal joint implant element;

wherein the proximal pin extends transversely through the proximal curved interface surface and through the connector base along the rotational axis of the proximal joint implant element, and wherein the distal pin extends transversely through the distal curved interface surface and through the connector base along the rotational axis of the distal joint implant element.

2. The interphalangeal joint implant of claim 1, wherein the proximal registration features, the distal registration features, or both are configured as gear teeth.

3. The interphalangeal joint implant of claim 2, wherein the gear teeth have an involute profile, a spur profile, a helical profile, a double helical profile, a sinusoidal profile, or a combination thereof.

4. The interphalangeal joint implant of claim 1, wherein the registration features have a height-to-period ratio from about 1:20 to about 2:1.

5. The interphalangeal joint implant of claim 1, wherein the proximal registration features are located at a different radial distance from a rotational axis of the proximal joint implant element than a radial distance of the distal registration features from a rotational axis of the distal joint implant element.

6. The interphalangeal joint implant of claim 1, wherein the protrusion protrudes radially farther than a tip of at least one of the proximal registration features or the distal registration features.

7. The interphalangeal joint implant of claim 1, wherein the protrusion defines a first end point of the range of motion and wherein the at least one of the proximal curved interface surface or the distal curved interface surface further comprises a second protrusion that defines a second end point of the range of motion.

8. The interphalangeal joint implant of claim 7, wherein the range of motion is from about 50° to about 180°.

9. The interphalangeal joint implant of claim 1, wherein the proximal pin and the distal pin have different diameters.

10. The interphalangeal joint implant of claim 1, wherein the proximal bone interface connector is integrally formed as a part of the proximal base portion or wherein the distal bone interface connector is integrally formed as a part of the distal base portion.

11. The interphalangeal joint implant of claim 1, wherein the proximal bone interface connector is detachable from the proximal base portion or wherein the distal bone interface connector is detachable from the distal base portion.

12. The interphalangeal joint implant of claim 1, wherein at least one of the proximal bone interface connector or the distal bone interface connector comprises a direct bone interface surface to be retained in direct contact with a bone of a subject.

13. The interphalangeal joint implant of claim 12, wherein the direct bone interface surface comprises a bulged profile adapted to be retained in a slot formed in the bone.

14. The interphalangeal joint implant of claim 1, further comprising a proximal anchor adapted to be fixed in a bone of a subject, wherein the proximal bone interface connector is attachable to the proximal anchor, and a distal anchor adapted to be fixed in a bone of a subject, wherein the distal bone interface connector is attachable to the distal anchor.

15. The interphalangeal joint implant of claim 14, wherein the proximal or distal bone interface connector comprises a bulged profile adapted to be retained in a slot of the proximal or distal anchor.

16. The interphalangeal joint implant of claim 14, wherein at least one of the proximal or distal anchor comprises exterior threads adapted to be screwed into the bone.

17. The interphalangeal joint implant of claim 14, wherein at least one of the proximal or distal anchor has a profile adapted to be press-fit into the bone.

18. The interphalangeal joint implant of claim 14, wherein at least one of the proximal or distal anchor has a narrow insertion end adapted to be inserted longitudinally into the bone.

19. The interphalangeal joint implant of claim 18, wherein at least one of the proximal or distal anchor is adapted to extend along a transition from a diaphysis to an epiphysis of a bone.

20. The interphalangeal joint implant of claim 18, wherein at least one of the proximal or distal anchor comprises a transverse hole adapted to receive a transverse screw or pin to lock the anchor in the bone.

21. The interphalangeal joint implant of claim 14, wherein at least one of the proximal or distal anchors comprises an osseointegration coating, an osseointegration surface texture, a sintered surface, barbs, flanges, protrusions for bone in-growth, recesses for bone in-growth, an open lattice configuration, or a combination thereof.

22. The interphalangeal joint implant of claim 14, wherein at least one of the proximal or distal anchor is adapted to extend into a diaphysis of a bone.

23. The interphalangeal joint implant of claim 14, wherein at least one of the proximal or distal anchor is a longitudinal bone anchor having external threads configured to be screwed into a bone longitudinally, and further comprises an internal threaded recess configured to accept a screw to attach the proximal or distal joint implant element to the longitudinal bone anchor.

24. The interphalangeal joint implant of claim 1, wherein at least one of the proximal or distal bone interface connector has a narrow insertion end adapted to be inserted longitudinally into the bone.

25. The interphalangeal joint implant of claim 24, wherein at least one of the proximal or distal bone interface connector is adapted to extend along a transition from a diaphysis to an epiphysis of a bone.

26. The interphalangeal joint implant of claim 24, wherein at least one of the proximal or distal bone interface connector is adapted to extend into a diaphysis of a bone.

27. The interphalangeal joint implant of claim 24, wherein at least one of the proximal or distal bone interface connector comprises a transverse hole adapted to receive a transverse screw or pin to lock the anchor in the bone.

28. The interphalangeal joint implant of claim 27, wherein at least one of the proximal or distal bone interface connector further comprises one or more additional transverse holes oriented at different angles to receive a transverse screw or pin at the different angles.

29. The interphalangeal joint implant of claim 1, wherein at least one of the proximal or distal bone interface connectors comprises an osseointegration coating, an osseointegration surface texture, a sintered surface, barbs, flanges, protrusions for bone in-growth, recesses for bone in-growth, an open lattice configuration, or a combination thereof.

* * * * *